US007361472B2

(12) United States Patent
Yguerabide et al.

(10) Patent No.: US 7,361,472 B2
(45) Date of Patent: Apr. 22, 2008

(54) METHODS FOR PROVIDING EXTENDED DYNAMIC RANGE IN ANALYTE ASSAYS

(75) Inventors: Juan Yguerabide, La Jolla, CA (US); Evangelina Yguerabide, La Jolla, CA (US); Laurence Warden, Poway, CA (US); Todd Peterson, Coronado, CA (US)

(73) Assignee: Invitrogen Corporation, Carlsbad, CA (US)

( * ) Notice: Subject to any disclaimer, the term of this patent is extended or adjusted under 35 U.S.C. 154(b) by 410 days.

(21) Appl. No.: 10/084,844

(22) Filed: Feb. 25, 2002

(65) Prior Publication Data

US 2003/0096302 A1    May 22, 2003

Related U.S. Application Data

(60) Provisional application No. 60/271,089, filed on Feb. 23, 2001.

(51) Int. Cl.
*G01N 33/53* (2006.01)

(52) U.S. Cl. .................. 435/7.1; 435/283.1; 435/288.7; 435/288.4; 435/305.1; 356/300; 356/341; 356/342; 356/337; 436/501; 436/518

(58) Field of Classification Search .................... 435/4, 435/7.1, 6, 283.1, 288.7, 288.4, 288.3, 305.1; 356/300, 341, 342, 337; 422/50, 55, 61, 422/68.1; 436/501, 518, 164
See application file for complete search history.

(56) References Cited

U.S. PATENT DOCUMENTS 3,939,350 A    2/1976  Kronick et al.
3,975,084 A    8/1976  Block
4,157,498 A    6/1979  Johnson
4,245,031 A    1/1981  Chambers
4,313,734 A    2/1982  Leuvering
4,420,558 A    12/1983 De Mey et al.
4,446,238 A    5/1984  De Mey
4,480,042 A    10/1984 Craig et al.
4,575,399 A    3/1986  Tanaka et al.
4,597,944 A    7/1986  Cottingham
4,624,923 A    11/1986 Margel (Continued)

FOREIGN PATENT DOCUMENTS

EP    0479345 A2    4/1992

(Continued)

OTHER PUBLICATIONS

Allara, et al., "Spontaneously Organized Molecular Assemblies. 1. Formation, Dynamics, and Physical Properties of n-Alkanoic Acids Adsorbed from Solution on an Oxidized Aluminum Surface," Langmuir 1:45-52 (1984).

(Continued)

*Primary Examiner*—Long V. Le
*Assistant Examiner*—Melanie J. Yu
(74) *Attorney, Agent, or Firm*—Sughrue Mion PLLC

(57) ABSTRACT

Methods for enhancing the dynamic range for specific detection of one or more analytes in assays using scattered-light detectable particle labels. The methods involve utilizing variations in detection technique and/or signal processing to extend the dynamic range to either or both of lower and higher concentrations.

16 Claims, 31 Drawing Sheets

U.S. PATENT DOCUMENTS

| | | | |
|---|---|---|---|
| 4,647,544 A | 3/1987 | Nicoli et al. | |
| 4,752,567 A | 6/1988 | De Brabander | |
| 4,806,583 A | 2/1989 | Battaglia et al. | |
| 4,837,168 A | 6/1989 | de Jaeger et al. | |
| 4,851,329 A | 7/1989 | Cohen et al. | |
| 4,876,208 A | 10/1989 | Gustafson et al. | |
| 4,877,647 A | 10/1989 | Klabunde | |
| 4,886,360 A | 12/1989 | Finlan | |
| 4,904,525 A | 2/1990 | Taniguchi et al. | |
| 4,929,400 A | 5/1990 | Rembaum et al. | |
| 4,983,834 A | 1/1991 | Lindmayer et al. | |
| 5,015,580 A | 5/1991 | Christou et al. | |
| 5,017,009 A | 5/1991 | Schutt | |
| 5,079,172 A | 1/1992 | Hari et al. | |
| 5,100,805 A | 3/1992 | Ziege et al. | |
| 5,110,727 A | 5/1992 | Oberhardt | |
| 5,120,135 A | 6/1992 | Ullman | |
| 5,137,827 A | 8/1992 | Mroczkowski et al. | |
| 5,145,748 A | 9/1992 | Gaidis et al. | |
| 5,151,956 A | 9/1992 | Bloemer | |
| 5,202,231 A | 4/1993 | Drmanac et al. | |
| 5,248,772 A | 9/1993 | Siiman et al. | |
| 5,257,087 A | 10/1993 | Furuya | |
| 5,274,431 A | 12/1993 | Kuroda | |
| 5,286,452 A | 2/1994 | Hansen | |
| 5,294,369 A | 3/1994 | Shigekawa et al. | |
| 5,305,073 A | 4/1994 | Ford | |
| 5,311,275 A | 5/1994 | Taniguchi et al. | |
| 5,338,353 A | 8/1994 | Uchino et al. | |
| 5,350,697 A | 9/1994 | Swope | |
| 5,350,922 A * | 9/1994 | Bartz | 250/338.5 |
| 5,403,706 A | 4/1995 | Wilk et al. | |
| 5,432,099 A | 7/1995 | Ekins | |
| 5,451,525 A | 9/1995 | Shenkin et al. | |
| 5,485,250 A | 1/1996 | Kashimura et al. | |
| 5,498,875 A | 3/1996 | Obremski et al. | |
| 5,501,949 A | 3/1996 | Marshall | |
| 5,516,670 A | 5/1996 | Kuehnle et al. | |
| 5,518,887 A | 5/1996 | Parsons et al. | |
| 5,552,086 A | 9/1996 | Siiman et al. | |
| 5,567,628 A | 10/1996 | Tarcha et al. | |
| 5,571,726 A | 11/1996 | Brooks et al. | |
| 5,576,827 A * | 11/1996 | Strickland et al. | 356/336 |
| 5,585,241 A | 12/1996 | Lindmo | |
| 5,728,590 A | 3/1998 | Powell | |
| 5,734,498 A | 3/1998 | Krasieva et al. | |
| 5,784,162 A * | 7/1998 | Cabib et al. | 356/456 |
| 5,807,522 A | 9/1998 | Brown et al. | |
| 5,822,073 A * | 10/1998 | Yee et al. | 356/445 |
| 5,830,623 A | 11/1998 | Maruyama et al. | |
| 5,841,534 A | 11/1998 | Lorenz | |
| 5,843,651 A | 12/1998 | Stimpson | |
| 5,851,777 A | 12/1998 | Hunter et al. | |
| 5,856,018 A | 1/1999 | Chen et al. | |
| 6,122,042 A | 9/2000 | Wunderman et al. | |
| 6,159,748 A | 12/2000 | Hechinger | |
| 6,165,798 A | 12/2000 | Brooks | |
| 6,171,793 B1 * | 1/2001 | Phillips et al. | 435/6 |
| 6,180,415 B1 | 1/2001 | Schultz | |
| 6,207,263 B1 | 3/2001 | Takematsu et al. | |
| 6,214,560 B1 | 4/2001 | Yguerabide | |
| 6,215,549 B1 | 4/2001 | Suzuki et al. | |
| 6,287,768 B1 * | 9/2001 | Chenchik et al. | 435/6 |
| 6,294,241 B1 | 9/2001 | Kaule et al. | |
| 6,294,327 B1 | 9/2001 | Walton et al. | |
| 6,309,822 B1 | 10/2001 | Fodor et al. | |
| 6,312,901 B2 | 11/2001 | Virtanen | |
| 6,326,605 B1 * | 12/2001 | Modlin et al. | 250/214 SW |
| 6,528,323 B1 * | 3/2003 | Thayer et al. | 436/518 |
| 6,551,710 B1 | 4/2003 | Chen et al. | |
| 6,586,193 B2 | 7/2003 | Yguerabide et al. | |
| 6,775,427 B2 | 8/2004 | Evans | |
| 6,934,022 B1 | 8/2005 | Engelhardt | |
| 6,974,669 B2 | 12/2005 | Mirkin et al. | |
| 6,982,431 B2 | 1/2006 | Modlin et al. | |
| 6,985,664 B2 | 1/2006 | Caracci et al. | |
| 2001/0002315 A1 | 5/2001 | Schultz et al. | |
| 2002/0028519 A1 * | 3/2002 | Yguerabide et al. | 436/518 |
| 2002/0028547 A1 * | 3/2002 | Ryu et al. | 438/200 |
| 2002/0045276 A1 | 4/2002 | Yguerabide et al. | |
| 2003/0049866 A1 | 3/2003 | Bushway | |
| 2003/0089899 A1 | 5/2003 | Lieber et al. | |
| 2003/0096302 A1 | 5/2003 | Yguerabide et al. | |
| 2003/0124733 A1 | 7/2003 | Bushway | |
| 2003/0127609 A1 * | 7/2003 | El-Hage et al. | 250/574 |
| 2004/0004982 A1 | 1/2004 | Eisler et al. | |
| 2005/0117157 A1 | 6/2005 | Tarsa | |
| 2005/0194896 A1 | 9/2005 | Sugita et al. | |
| 2005/0243321 A1 | 11/2005 | Cohen et al. | |
| 2006/0234248 A1 | 10/2006 | Sun et al. | |

FOREIGN PATENT DOCUMENTS

| | | |
|---|---|---|
| WO | 9106036 A1 | 5/1991 |
| WO | 9740181 A1 | 10/1997 |
| WO | 9837417 A1 | 8/1998 |
| WO | 9920789 A1 | 4/1999 |

OTHER PUBLICATIONS

Bain, et al., "Formation of Monolayer Films by Spontaneous Assembly of Organic Thiols from Solution onto Gold," Journal of the American Chemical Society 111:321-335 (1989).

Bohren et al., Absorption and Scattering of Light by Small Particles, John Wiley & Sons, pp. 316-319, pp. 356-357, and pp. 368-375 (1983).

Eversole and Broida, "Size and Shape Effects in Light Scattering From Small Silver, Copper and Gold Particles," Physical Review B 15:1644-1654 (1977).

Jarvik et al., "CD-Tagging: A New Approach to Gene and Protein Discovery and Analysis," BioTechnioues 20:896-904 (1996).

Chee et al., "Accessing Genetic Information with High-Density DNA Arrays," Science 274:610-614 (1996).

Heller and Pugh, "Steric'Stablilization of Colloidal Solutions by Adsorption of Flexible Macromolecules," Journal of Polymer Science 47:203-217 (1960).

Hiemenz, "Ch. 5-Light Scattering," in Principles of Colloid and Surface Chemistry, 2nd Edition, Marcel Dekker, Inc., pp. 223-286 (1986).

Wiegel, "Uber die Farben des kolloiden Silbers und die Miesche Theorie," Zietschrift fur Physik, Bd., 136:642-653 (1954).

Klein and Metz, "Color of Colloidal Silver Sols in Gelatin," Photographic Science and Engineering 5:5-11 (1961).

Kreibig and Zacharias, "Surface Plasma Resonances in Small Spherical Silver and Gold Particles," Z. Physik 231:128-143 (1970).

Nuzzo and Allara, "Adsorption of Bifunctional Organic Disulfides on Gold Surfaces," Journal of the American Chemical Society 105:4481-4483 (1983).

Vener et al., "A Novel Approach to Nonradioactive Hybridization Assay of Nucleic Acids Using Stained Latex Particles," Analytical Biochemistry 198:308-311 (1991).

Stolz, Time-Resolved Light Scattering from Excitons, SpringerTracts, vol. 130, pp. 72-85.

Yguerabide & Yguerabide, "Light-Scattering submicroscopic Particles as Highly Fluorescent Analogs and Their Use as Tracer Labels in Clinical and Biological Applications: II. Experimental Characterization" Anal. Biochem. 262:157-176 (San. 28, 1998).

Stimpson et al., "Real-Time Detection of DNA Hybridization and Melting on Oligonucleotide Arrays by Using Optical Wave Guides," Proc. Natl. Acad. Sci., USA, 92:6379-6383 (Feb. 3, 1995).

Shaw et al., in Introduction to Colloid and Surface Chemistry, 2nd edition, pp. 41, 46-54 (1970).

Schafer et al., "Transcription by single molecule of RNA polymerase observed by light microscopy," Nature 352:444-448 (1991).

Roth, The Colloidal Gold Marker System for Light and Electron Microscopic Cytochemistry, Immunocytochemistry 2:217-284 (1983).

Okano et al., "Using Microparticle Labeling and Counting for Attomole-Level Detection in Heterogeneous Immunoassay," Analytical Biochemistry 202:120.125 (1992).

Elghanian et al., "Selective Colorimetric Detection of Polynucleotides Based on the Distance-Dependent Optical Properties of Gold Nanoparticles," Science 1078-1081 (Aug. 22, 1997).

Shalon et al., "A DNA Microarray System for Analyzing Complex DNA Samples Using Two-Color Fluorescent Probe Hybridization," Genome Research 639-645 (1996).

Horisberger, "Colloidal Gold; A Cytochemical Marker for Light and Fluorescent Microscopy and for Transmission and Scanning Electron Microscopy," Scanning Electron Microscopy 2:9-31 (1981).

Geoghegan et al., "The Detection of Human B Lymphocytes by Both Light and Electron Microscopy Utilizing Colloidal Gold Labeled Anti-Immunoglobulin," Immunological Communications 7:1-12 (1978).

Geerts et al., "Nanovid microscopy," Nature 351:765-766 (1991).

Kaneta et al., "Theory of Optical Chromatography," Anal. Chem. 69:2701-2710 (1997).

Hatano et al., "Application of Optical Chromatography to Immunoassay," Anal. Chem. 69:2711 2715.

DeBrabander et al., "The Use of Submicroscopic Gold Particles Combined with Video Contrast Enhancement as a Simple Molecular Probe for the Living Cell," Cell Motility and the Cytoskeleton. 6:105-113 (1986).

Silva, "A scanning near-field optical microscope with magneto-optic kerr effect contrast for the imaging of magnetic domains with 200 A resolution," Dissertation (1994).

Bohmer and King, "Immuno-Gold Labeling for Flow Cytometric Analysis," Journal of Immunological Methods 74:49-57 (1984).

Bloemer et al, "Optical properties of submicrometer-size silver needles," Physical Review B 37:8015-8021 (1988).

* cited by examiner

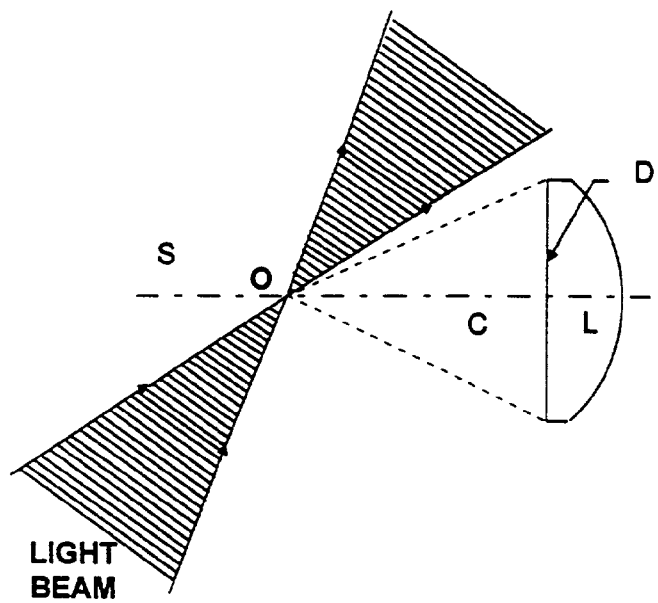
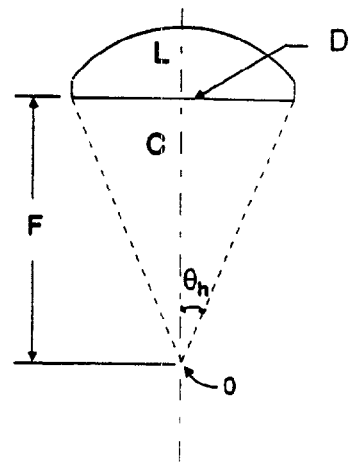
FIGURE 1                FIGURE 2
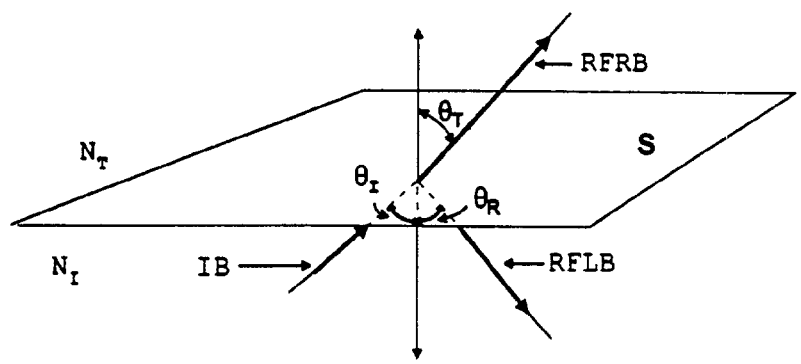
FIGURE 3

NOT TO SCALE

METHODS FOR PROVIDING EXTENDED DYNAMIC RANGE IN ANALYTE ASSAYS

CROSS REFERENCE TO RELATED APPLICATIONS

This application claims benefit of prior U.S. provisional application No. 60/271,089, titled "Methods For Providing Extended Dynamic Range In Analyte Assays", filed on Feb. 23, 2001, by inventors Juan Yguerabide, Evangelina Yguerabide, Laurence Warden, and Todd Peterson, which is hereby incorporated by reference in its entirety, including drawings.

1. FIELD OF THE INVENTION

The following application relates to methods of extending the dynamic range in detection of signals in analyte assays.

2. BACKGROUND OF THE INVENTION

The following is a brief description of some existing detection methods. It is also a summary of relevant science to aid the reader in understanding the details of the claimed invention. It should not be taken as an admission that any of the cited art is prior art to the claims. The cited art is hereby incorporated herein by reference so that the general procedures and methods in that art that are of use to practice of the present invention need not be rewritten herein. In particular, applicant incorporates those sections related to general methods of "binding-pair" methodology, and methods for measurement of light scattering herein.

Sensitive Analyte Assays

Binding-pair (also known as ligand-receptor, molecular recognition binding and the like) techniques play an important role in many applications of biomedical analysis and are gaining importance in the fields of environmental science, veterinary medicine, pharmaceutical research, food and water quality control and the like. For the detection of analytes at low concentrations (less than about 1 picomole analyte/sample volume analyzed) fluorescent, luminescent, chemiluminescent, or electrochemiluminescent labels and detection methods are often used.

For the detection of low concentrations of analytes in the field of diagnostics, the methods of chemiluminescence and electrochemiluminescence are gaining wide-spread use. These methods of chemiluminescence and electro-chemiluminescence provides a means to detect low concentrations of analytes by amplifying the number of luminescent molecules or photon generating events many-fold, the resulting "signal amplification" then allowing for detection of low concentration analytes.

In addition, the method of Polymerase Chain Reaction (PCR) and other related techniques have gained wide use for amplifying the number of nucleic acid analytes in the sample. By the addition of appropriate enzymes, reagents, and temperature cycling methods, the number of nucleic acid analyte molecules are amplified such that the analyte can be detected by most known detection means. The high level of commercial activity in the development of new signal generation and detection systems, and the development of new types of test kits and instruments utilizing signal and analyte molecule amplification attests to the importance and need for sensitive detection methods.

However, the above mentioned methods of signal and analyte molecule amplification have associated limitations which makes the detection of analytes by these methods complicated, not easy to use, time consuming, and costly. Problems of interference of chemical or enzymatic reactions, contamination, complicated and multi-step procedures, limited adaptability to single step "homogeneous" (non-separation) formats, and the requirement of costly and sophisticated instrumentation are areas that those in the art are constantly trying to improve.

Thus, there is a tremendous need for easy to use, quantitative, multi-analyte, and inexpensive procedures and instruments for the detection of analytes. Such procedures, test kits, and instruments would overcome the disadvantages and limitations of the current methods of signal and analyte molecule amplification, and would be useful in research, individual point of care situations (doctor's office, emergency room, out in the field, etc.), and in high throughput testing applications.

It is the object of the present invention to provide a new means to more easily detect one or more analytes in a sample to low concentrations than was previously possible. The present invention can detect low concentrations of analytes without the need for signal or analyte molecule amplification.

The present invention provides a signal and detection system for the detection of analytes where the procedures can be simplified and the amount and types of steps and reagents reduced. The present invention provides for the quantitative detection of single or multiple analytes in a sample. The present invention also provides for substantial reductions in the number of different tests and amounts of sample material that are analyzed. Such reduction in the number of individual tests leads to reduced cost and waste production, especially medically-related waste that must be disposed of.

Light Scattering Detection Methods and Properties of Light Scattering Particles

There is a large body of information concerning the phenomenon of light scattering by particles, the use of particulate labels in diagnostic assays, and the use of light scattering methods in diagnostic assays which are now presented in the following discussion of relevant art none of which is admitted to be prior art to the pending claims. This art is provided as a background for understanding of the novelty and utility of the claimed invention.

The general study of light scattering comprises a very large field. The phenomena of light scattering has been studied intensely for about the last one hundred or so years and the applications of the knowledge of light scattering to different aspects of human endeavor are wide and varied.

The classical theory of light scattering by small, homogeneous, non light absorbing, spherical particles of a size of about 1/20 or less the wavelength of the incident radiation was initially developed by Rayleigh. Later a more general phenomenological theory of light scattering by homogeneous, spherical particles of any size and composition was developed by Mie. The Mie theory applies both to light absorbing and non-absorbing particles. It has also been shown from Mie theory that the expressions of Rayleigh can easily be generalized so as to apply to particles which absorb light as long as the particles are much smaller than the wavelength of incident light. For these small diameter particles, Mie theory and the generalized Rayleigh theory give similar results. Light scattering (elastic) can be viewed from a classical or quantum mechanical point of view. An excellent quantitative description can be obtained through the classical point of view.

A historical background as well as a description of the basic theories of scattered light and other electromagnetic radiation is provided in the following references; *Absorption and Scattering of Light By Small Particles* (1983), C. F. Bohren, D. R. Huffman, John Wiley and Sons; *The Scattering of Light and Other Electromagnetic Radiation* (1969), M. Kerker, Academic Press.

Further background information of the phenomenon of light scattering can be found in the following publications.

Zsigmondy, *Colloids and the Ultramicroscope—A Manual of Colloid Chemistry and Ultramicroscopy,* 1914, John Wiley & Sons, Inc. is described various light scattering properties of gold particles and other types of particles.

Hunter, *Foundation of Colloid Science*, Vol, I, 105, 1991, describes use of optical microscopes, ultramicroscopes, and electron microscopes in observation of particles.

Shaw et al., *Introduction to Colloid and Surface Chemistry,* 2nd ed., 41, 1970, describe optical properties of colloids and the use of electron microscopy, and dark field microscopy e g., the ultramicroscope.

Stolz, SpringerTracts, Vol. 130, describes time resolve light scattering methodologies.

Klein and Metz, 5 *Photographic Science and Engineering* 5-11, 1961, describes the color of colloidal silver particles in gelatin.

Eversole and Broida, 15 *Physical Review* 1644-1654, 1977, describes the size and shape effects on light scattering from various metal particles such as silver, gold, and copper.

Kreibig and Zacharias, 231 *Z. Physik* 128-143, 1970, describe surface plasma resonances in small spherical silver and gold particles.

Bloemer et al., 37 *Physical Review* 8015-8021, 1988, describes the optical properties of submicrometer—sized silver needles and the use of such needles is described in Bloemer, U.S. Pat. No. 5,151,956,where a surface plasmon resonance of small particles of metal to polarize light propagating in a wave guide is described.

Wiegel., 136 *Zeitschrift fur Physik*, Bd., 642-653, 1954, describes the color of colloidal silver and the use of electron microscopy.

Use of Particles, Light Scattering and Other Methods for Detection of Analytes

For about the last thirty-five years, metal particles including gold and silver have been used as both contrast enhancement agents or light absorption labels in many different types of analytic and/or diagnostic applications. The great majority of these applications fall under the category of cytoimmunochemistry studies which have used gold or silver enhanced gold particles as markers to study structural aspects of cellular, subcellular, or tissue organization. In these studies, metal particles are usually detected and localized by electron microscopy, including scanning, transmission, and BEI (backscattered electron imaging). These methods take advantage of the electron dense nature of metals or the high atomic number of metals to facilitate the detection of the gold particles by virtue of the large numbers of secondary and backscattered electrons generated by the dense metal (see; Hayat, Immunogold-silver staining reference Page 1 and Chapters 1, 6, 15; and Hayat, Colloid Gold reference Chapters 1, 5, 7 and others).

There have been a few reports of the use of gold and silver enhanced gold particles in light microscopic studies. For example, in 1978 gold particles were used as an immunogold stain with detection by light microscopy. A review of the use of gold particles in light microscopy (See, Hayat, Immunogold-Silver Staining Reference Page 3) published in 1995 discusses this 1978 work and presents the following analysis:

"Geoghehan et al. (1978) were the first to use the red or pink color of colloidal gold sols for light microscopic immunogold staining using paraffin sections. In semi-thin resin sections red color of light scattered from gold particles as small as 14 nm was seen in cell organelles containing high concentrations of labeled antigens in the light microscope (Lucocq and Roth, 1984). Since the sensitivity of immunogold staining in light microscopy is inferior in comparison with other immunocytochemical techniques, the former did not gain general acceptance; the pinkish color of the gold deposit is difficult to visualize."

This paragraph is an indication of the state of understanding of the light scattering properties of gold and other metal particles for diagnostic and analytic studies. The paragraph specifically states "In semi-thin resin sections red color of light scatter from gold particles as small as 14 nm was seen in organelles containing high concentrations of labeled antigens in the light microscope."

However, with white light illumination, the scattered light from 14 nm gold particles is predominantly green. Since the particles appear red in the light microscope this indicates that some interactions other than pure light scattering are being detected. It is probable that the red color observed in the light microscope is predominantly transmitted light and not scattered light. When the gold particles accumulate sufficiently at the target site in cells, tissue sections or some other surface the red color due to transmitted light will be seen (see also; J. Roth (1983) *Immunocytochemistry* 2: 217; and Dewaele et al (1983) in *Techniques in Immunochemistry* Vol 2 p1, Eds. Bullock and Petrusz, Academic Press).

As mentioned in the above quote, it appears that the sensitivity of immunogold staining in light microscopy was believed to be inferior to that of other methods, and the use of gold particles as markers for light microscope detection did not gain general acceptance. In the 1995 review book in Chapter 12, p198 by Gao and Gao is the following quote on the same subject.

"Colloidal gold was initially used only as a marker for electron microscopy (EM), because of its electron dense nature and secondary electron emission feature (Horisberger, 1979). Direct visualization of colloidal gold in light microscopy (LM) was limited. The size of colloidal gold is too small to be detected at the light microscope level, although using highly concentrated immunogold cells may be stained red by this reagent (Geoghegan et al., 1978; Roth, 1982; Holgate et al., 1983)."

As mentioned in both of the above, the sensitivity of detection of colloidal gold with light microscopy was believed to be low. The method of silver enhancement of gold particles was developed to overcome this perceived drawback. The following is another quote from the 1995 review book.

"The real breakthrough for immunogold staining for light microscopy came with the introduction of silver-enhancement of colloidal gold particles (20 nm) bound to immunoglobin in paraffin sections 5 microns (Holgate et al., 1983). This approach significantly enhanced the sensitivity, efficiency, and accuracy of antigen detectability in the light microscope. Using IGSS, gold particles as small as 1 nm in diameter can be visualized in the light microscope. Thin section subjected to IGSS can also be viewed with the light microscope, especially by using phase contrast or epi-polarization illumination (Stierhof et al., 1992)."

The method of silver enhancement of gold particles is widely used. The enhancement method transforms the marker gold particle into a larger metal particle or an even larger structure which is microns or greater in dimensions. These structures are composed primarily of silver, and such enlarged particles can be more readily detected visually in the bright field optical microscope. Individual enlarged particles have been visualized by high resolution laser confocal and epipolarization light microscopy. *Id.* at 26 and 203.

However, even with the use of silver enhancement techniques, those in the art indicate that this will not achieve the sensitivity and specificity of other methods. For example, in the publication of Vener, T. I. et. al., *Analytical Biochemistry* 198: 308-311 (1991) the authors discuss a new method of sensitive analyte detection called Latex Hybridization Assay (LHA). In the method they use large polymer particles of 1.8 microns in diameter that are filled with many highly fluorescent dye molecules as the analyte tracer, detecting the bound analytes by the fluorescent signal. The following excerpt is from this publication:

"To assess the merits of LHA we have compared our technique with two other indirect non-radioactive techniques described in the literature. The most appropriate technique for comparison is the streptavidin colloid gold method with silver enhancement of a hybridization signal, since this is a competing corpuscular technique. However, this method is not very sensitive even with the additional step of silver enhancement: 8pg of λ-phage DNA is detected by this method as compared to 0.6 pg or $2 \times 10^4$ molecules of λ DNA detected by LHA on the nylon membrane."

Stimpson et al., *Proc. Natl. Acad. Sci. USA*, 92: 6379-6383, July 1995, a real time detection method for detection of DNA hybridization is described. The authors describe use of a particulate label on a target DNA which acts as a "light-scattering source when illuminated by the evanescent wave of the wave guide and only the label bound to the surface generates a signal. . . . The evanescent wave created by the wave guide is used to scatter light from a particulate label adsorbed at multiple DNA capture zones placed on the wave guide surface. Since an evanescent wave only extends a few hundred nanometers from the wave guide surface, the unbound/ dissociated label does not scatter light and a wash step is not required. The signal intensity is sufficient to allow measurement of the surface binding and desorption of the light-scattering label can be studied in real time; i.e., detection is not rate limiting. The hybridization pattern on the chip can be evaluated visually or acquired for quantitative analysis by using a standard CCD camera with an 8-bit video frame grabber in 1/30 of a second."

Experiments were performed with 70 nanometer diameter gold particles and 200 nanometer diameter selenium particles. More intense signals were observed with the selenium particles. The authors indicate "A wave guide signal sufficient for single-base discrimination has been generated between 4 and 40 nm DNA and is, therefore, comparable to a fluorescence signal system."

This method uses waveguides and evanescent type illumination. In addition, the method is about as sensitive as current fluorescence-based detection systems. Particles of 70 nm diameter and larger are said to be preferred. This is also described in Stimpson et al., U.S. Pat. No. 5,599,668.

Schutt et al., U.S. Pat. No. 5,017,009, describes an immunoassay system for detection of ligands or ligand binding partners in a heterogenous format. The system is based upon detection of "back scattered light from an evanescent wave disturbed by the presence of a colloidal gold label brought to the interface by an immunological reaction. . . . Placement of the detector at a back angle above the critical angle insures a superior signal-to-noise ratio."

The authors explain that the immunoassay system described utilizes scattered total internal reflectance, i.e., propagation of evanescent waves. They indicate that the presence of colloidal gold disrupts propagation of the evanescent wave resulting in scattered light, which may be detected by a photomultiplier or other light sensor to provide a responsive signal. They indicate that an important aspect of their invention is the physical location of the detector.

"The detector is ideally placed at an angle greater than the critical angle and in a location whereby only light scattered backward toward the light source is detected. This location thereby ideally avoids the detection of superior scattered light within the bulk liquid medium."

Total internal reflection of the incident beam is used to create the evanescent wave mode of illumination and the detection is performed on an optically-transmissive surface. The use of specialized apparatus is preferred.

Leuvering, U.S. Pat. No. 4,313,734, describes a method for detection of specific binding proteins by use of a labeled component obtained by coupling particles "of an aqueous dispersion of a metal, metal compound, or polymer nuclei coated with a metal or metal compound having a diameter of at least 5 nm." The process is said to be especially suited for estimation of immunochemical components such as haptens, antigens and antibodies. The metal particles are said to have already been used as contrast-enhancing labels in electron microscopy but their use in immunoassays had apparently "not previously been reported and has surprisingly proved to be possible.

The metal sol particle, immunochemical technique, according to the instant invention which has been developed can be not only more sensitive than the known radio- and enzyme-immunotechniques, but renders it furthermore possible to demonstrate and to determine more than one immunological component in the same test medium simultaneously by utilizing sol particles of different chemical compositions as labels."

Examples of metals include platinum, gold, silver, and copper or their salts.

"The measurement of the physical properties and/or the concentration of the metal and/or the formed metal containing agglomerate in a certain phase of the reaction mixture may take place using numerous techniques, which are in themselves known. As examples of these techniques there may be cited the calorimetric determination, in which use is made of the intense colour of some dispersions which furthermore change colour with physicochemical changes; the visual method, which is often already applicable to qualitative determinations in view of the above-noted fact that metal sols are coloured; the use of flame emission spectrophotometry or another plasma-emission spectrophotometric method which renders simultaneous determination possible, and the highly sensitive method of flame-less atomic absorption spectrophotometry."

Two or more analytes in a sample are preferably detected by using flame emission spectrophotometry or another plasma-emission spectrophotometric method. The preferred method of detection for greatest sensitivity is by flame-less atomic absorption spectrophotometry.

Swope et al., U.S. Pat. No. 5,350,697 describes apparatus to measure scattered light by having the light source located to direct light at less than the critical angle toward the sample. The detector is located to detect scattered light outside the envelope of the critical angle.

Craig et al., U.S. Pat. No. 4,480,042 describes use of high refractive index particle reagents in light scattering immunoassays. The preferred particles are composed of polymer materials. The concentration of compounds of biological interest was determined by measuring the change in turbidity caused by particle agglutination or inhibition of agglutination. The preferred particles are of a diameter less than approximately 0.1 μ and greater than 0.03 μ. "Shorter wavelengths, such as 340 nm, give larger signal differences than longer wavelengths, such as 400 nm."

Cohen et al., U.S. Pat. No. 4,851,329 and Hansen, U.S. Pat. No. 5,286,452, describe methods for detection of agglutinated particles by optical pulse particle size analysis or by use of an optical flow particle analyzer. These systems are said to be useful for determination of antigen or antibody concentrations. These methods use sophisticated apparatus and specialized signal processing means. Preferred particle diameters are of about 0.1 to 1 micron in diameter for the method of Cohen and about 0.5 to about 7.0 microns in diameter for the method of Hansen.

Okano et al., *Analytical Biochemistry* 202: 120, 1992, describes a heterogenous sandwich immunoassay utilizing microparticles which can be counted with an inverted optical microscope. The microparticles were of approximately 0.76 microns in diameter, and were carboxylated microparticles made from acrylate.

Other particle detection methods are described by Block, U.S. Pat. No. 3,975,084, Kuroda, U.S. Pat. No. 5,274,431, Ford, Jr., U.S. Pat. No. 5,305,073, Furuya, U.S. Pat. No. 5,257,087, and by Taniguchi et al., U.S. Pat. No. 5,311,275.

Geoghegan et al., *Immunological Communications* 7:1-12, 1978, describes use of colloidal gold to label rabbit anti-goat IgG for indirect detection of other antibodies. A light and electron microscope were used to detect labeled particles. The gold particles had an average size of 18-20 nanometers and bright field light microscopy was used. For electron microscopy, Araldite silver-gold thin sections were used. "Similar percentages of surface labeled cells were noted by immunofluorescence and the colloidal gold bright field method." 1-5 particles per cell could be detected by electron microscopy but the authors state that:

"Such small quantities of label were not detected by fluorescence or by brightfield microscopy and may represent either non-specific and Fc receptor bound GAD and GAM, where a low level of surface immunoglobulin (S.Ig) on the GAD and GAM treated cells."

Hari et al., U.S. Pat. No. 5,079,172, describes use of gold particles in antibody reactions and detection of those particles using an electron microscope. 15 nanometer gold particles were exemplified. In the preferred method, electron microscopy is used.

DeMey et al., U.S. Pat. No. 4,420,558, describes the use of a bright field light microscopic method for enumerating cells labeled with gold-labeled antibodies. The method uses a light microscope in the bright field arrangement and magnifications of 500 or greater with immersion oil lenses are used to count gold-labeled peroxidase negative cells. The visualization of the labeled-surfaces is based on the aggregate properties of the gold particles, which, under the indicated circumstances, undergo extensive patching, these patches on the cell surface being resolvable with the method described. 40 nanometer gold was found to give optimal results.

De Mey et al., U.S. Pat. No. 4,446,238, describes a similar bright field light microscopic immunocytochemical method for localization of colloidal gold labeled immunoglobulins as a red colored marker in histological sections. The method of Immuno Gold Staining (IGS) as described by the authors "In both procedures the end-product is an accumulation of large numbers of gold granules over antigen-containing areas, thus yielding the typical reddish colour of colloidal gold sols."

DeBrabander et al., U.S. Pat. No. 4,752,567 describes a method for detecting individual metal particles of a diameter smaller than 200 nm by use of bright field or epi-polarization microscopy and contrast enhancement with a vide camera is described. The inventors state:

"Typically, in the above mentioned procedures, the employed metal particles have a diameter of from about 10 to about 100 nm. This is well below the resolution limit of bright field microscopy, which is generally accepted to lie around 200 nm. It is therefore quite logical that all previously known visual light microscopic methods are limited in their applications to the detection of immobilized aggregates of metal particles. Individual particles could be observed with ultramicroscopic techniques only, in particular with electron microscopy.

It has now quite surprisingly been found that individual metal particles of a diameter smaller than 200 nm can be made clearly visible by means of bright field light microscopy or epi-polarization microscopy in the visible spectrum, provided that the resulting image is subjected to electronic contrast enhancement."

In subsequent sections the authors state:

"Compared with existing diagnostic methods based on sol particle immuno assays, the present method has a much greater sensitivity. Indeed, existing methods are in general based on light absorption or scattering by the bulk of absorbed or suspended metal particles. Obviously, the observation of colour, e.g. on a blotting medium, requires the presence of massive numbers of particles. In contrast therewith, the present method makes it possible to observe and count single particles. Hence, the present method will largely facilitate the development of diagnostic blots for applications where existing, e.g. visual or calorimetric, techniques are too less sensitive, e.g. for the detection of Hepatitis."

Schafer et al., *Nature* 352: 444-448, 1991, describes use of nanometer size particles of gold which could be observed using video enhanced differential interference contrast microscopy. A 40 nanometer diameter gold particle was used.

DeBrabander et al., *Cell Motility and the Cytoskeleton* 6: 105-113, 1986, (and U.S. Pat. No. 4,752,567) describe use of submicroscopic gold particles and bright field video contrast enhancement. Specifically, the cells were observed by bright field video enhanced contrast microscopy with gold particles of 5-40 nanometers diameters. They also state that "individual gold particles, having a size smaller than plus or minus 100 nanometers, adsorbed under glass or cells or microinjected in cells are not visible in the light microscope. They are, however, easily visualized when using the capacity of a video camera to enhance contrast electronically."

The authors describe use of epi-illumination, with polarized light and collection of reflected light or by use of a "easier and apparently more sensitive way" with a transmitted bright field illumination using monochromatic light and a simple camera. The authors indicate that the gold particles can be easily detected with phase contrast microscopy.

"Unlike that which is possible with larger gold (usually 20-40 nm), even dense accumulations of 5-nm gold, e.g., on structures such as microtubules, are not visible in the light microscope. They do not produce a detectable red colour. Recently, this has been corrected by a physical development with silver salts, which increases the size of the particles to produce all easily visible black stain.

We have described a method for localizing ligands almost at the molecular level. The method is new because it enables one for the first time to do this in the light microscope with discrete individual markers that are unambiguously discernible from background structures. Because it is applicable even in living cells, one can thus follow the dynamic behaviour of individual proteins. The method is because it combines two well developed techniques: gold labelling and video microscopy. Most of the applications can be done with inexpensive video equipment the price of which is less than most good 100× oil objectives. Still, many more possibilities arise when combining this with modern digital image manipulations. Some additional advantages are worth noting. Because the label consists of individual discrete markers, both manual and automatic (computer assisted) counting is easy and reliable. The small size of the marker minimizes problems of penetration and diffusion. The possibility of changing the charge of the marker almost at will is helpful in diminishing non-specific binding in any particular application."

This method was termed by the authors "nanoparticle video ultramicroscopy or short nanovid ultramicroscopy." A similar technology is described in "Geerts et al., *Nature* 351: 765-766, 1991.

Analyte detection using light scattering particles as labels is described in Yguerabide et al. PCT/US/97/06584 (WO 97/40181 and Yguerabide et al., PCT/US98/23160 (WO 99/20789). Elements of the technology are also described in two related articles by Yguerabide & Yguerabide, (1998) *Anal. Biochem.* 261:157-176; and (1998) *Anal. Biochem.* 262:137-156.

Methods utilizing light scattering (referred to as "plasmon resonance") labels for assays are also described in Schultz, et al, PCT/US98/02995 (WO 98/37417). The methods described in Schultz et al. are generally based on detection of individual plasmon resonant particles or entities.

Phillips et al. (U.S. Pat. No. 6,171,793 B1) describes a method of extending the dynamic range of a detector for gene probe arrays labeled with fluorescent reporter groups. The method involves the collection of light signals from multiple sites on the array at two different wavelengths, where the signal intensity at one wavelength can exceed the dynamic range of the detector for some sites of the array, while the signal intensity at the other wavelength is within the range of the detector. A scale factor correlation function is calculated based on a functional fit to a plot of the detector response at the two different wavelengths for all of the sites on the array. For sites that generated a signal which saturated the detector at one wavelength, the scale factor correlation function is applied to the signal at the other wavelength where it is within the dynamic range of the detector, such that the signal at the wavelength where the detector is saturated can be extrapolated.

The preceding discussions of the state of the art of light scattering methods, and the use of light scattering particles and methods in the field of diagnostics clearly shows the limits of current methods of analyte detection and the novelty and great utility of the present invention. It is the purpose of this invention not only to overcome the present day limitations and disadvantages of light scattering-based diagnostic assays, but to also overcome the limitations and disadvantages of other non-light scattering methods such as signal and analyte molecule amplification. This invention as described herein is easier to use, has greater detection sensitivity, and is capable of measuring analytes across wider analyte concentration ranges than was previously possible. The present invention is broadly applicable to most sample types and assay formats as a signal generation and detection system for analyte detection.

3. SUMMARY OF THE INVENTION

The present invention provides advantageous methods for the detection and measurement of one or more analytes in a sample in methods utilizing light collected from light scattering particles. In particular, the methods are used in conjunction with resonance light scattering (RLS) particle labels. The use of RLS labels is described in WO 97/40181 and WO 99/20789, which are incorporated herein by reference in their entireties, including drawings. The methods of the invention provide enhanced dynamic range to an analyte assay, and are particularly advantageous for assays conducted with in formats that comprise a plurality of separately addressable sites. Assays that employ such formats typically uses microtiter plates, slide arrays, and microarrays.

As described in Yguerabide et al., WO 97/40181 and WO 99/20789, in methods using RLS particles as labels, the detection and/or measurement of the light-scattering properties of the particle is correlated to the presence, and/or amount, or absence of one or more analytes in a sample. Such methods include detection of one or more analytes in a sample by binding those analytes to at least one detectable light scattering particle, with a size preferably smaller than the wavelength of the illumination light. This particle is illuminated with a light beam under conditions where the light scattered from the beam by the particle can be detected by the human eye with less than 500 times magnification. The light that is scattered from the particle is then detected under those conditions as a measure of the presence of those one or more analytes. By simply ensuring appropriate illumination, and ensuring maximal detection of specific scattered light, an extremely sensitive method of detection can result.

In the performance of many assays, it is highly advantageous to have a broad dynamic range over which the detection is substantially linear, also referred to as the "preferred range" of the detector. That is, the signals from various samples can be detected and the analyte presence quantitated over at least several orders of magnitude of variation in analyte concentration or density. Preferably the signal is proportional to the number of label particles present over a broad range, preferably at least 4, 5, 6, 7, or even more orders of magnitude. That is, a quantifiable, preferably linear, relationship is present between label concentration or density and signal intensity. Such broad dynamic ranges, preferably linear dynamic ranges, can be provided in various ways, for example, by various techniques in signal detection and or signal processing. As explained below, the various techniques can be used alone or in combination. The enhancements to dynamic range are particularly suitable for electronic detection of scattered light from light scattering particulate labels, but can also be applied to other types of particulate labels. For example, the methods described herein for providing extended dynamic range can be applied to fluorescent labels, though for small fluorophores, it is generally highly advantageous to use beads, e.g., polystyrene beads, loaded with the fluorophore.

Many detection devices, especially electronic detection devices have a finite range in which the detection device responds linearly to detected light, typically being restricted to about 3 or 3.5 orders of magnitude with a single exposure, and/or a limited range in which the signal-to-noise ratio of the instrument is acceptable. For example, at very weak signal levels, electronic noise from a system may significantly interfere with the precision of the quantitation. Certain of the techniques are directed primarily at compensating or overcoming the inherent limitations of the sensor, thereby increasing the range in which a detector can provide accurate quantifications. Other techniques are primarily directed to overcoming dynamic range limitations inherent in the characteristics of the labels themselves.

In the context of analyte assays, the term "dynamic range" refers to the range in density or concentration or absolute numbers of analyte entities that can be detected in an assay based on the presence of specific label attached directly or indirectly to the analyte or a surrogate thereof (or released therefrom)). Most preferably the dynamic range is the range that can be quantitated in a single performance of an assay, not requiring new sample.

Preferably the dynamic range is a linear portion of the correlation between label concentration or density, and signal intensity (i.e., the response curve), in which case it can be referred to as the "linear dynamic range". For the present methods, typically dynamic range is demonstrated by the concentration or density range of particles, preferably light scattering particles that can be quantitated in an assay. In general, dynamic range depends on label characteristics and the limitations of the sensor, though other factors can have an effect. In connection with dynamic range, the term "extended" refers to a dynamic range that encompasses at least 4 orders of magnitude. In the methods of this invention, an extended dynamic range is preferably greater than the dynamic range obtained under the same assay conditions using the same detector with a single exposure, without particle counting or the use of other dynamic range increasing techniques.

In a first aspect, the present invention concerns a method for providing an extended dynamic range, preferably linear dynamic range, in an analyte assay using light emitting particles, preferably light scattering particles, as labels, in assay formats with a plurality of sites. The method includes detecting integrated light scattered from the labels at the plurality of sites with a sensor, where the response of the sensor may become non-linear at high or low label counts or both. That is, the accumulated light produces a signal that becomes non-linear and eventually not quantifiable at high light accumulations. Such high light accumulations (integrated signal) will, of course, occur more rapidly with high intensity signals (corresponding to high particle densities) than with low intensity signals. The detection is performed using a plurality of different exposure times, which are selected to provide signals from at least some of the sites within the response range, preferably a linear response range, for the detection device. At least two different exposure times are used, and the results are selected to provide results (i.e., readings from the determinations) corresponding to the individual sites that are within the quantifiable response range for the detector.

Preferably the resulting extended linear dynamic range is at least 4 orders of magnitude, more preferably at least 5, 6, 7, or more orders of magnitude.

In preferred embodiments, the results from two or more different exposure times for each of the sites are combined to form a combined image of a given site. Scaling is used to normalize the values for different exposure times. Such combining can be performed pairwise on two or more sets of results. Alternatively the combining can be done by evaluating all corresponding readings (e.g., pixels) and selecting a value in a preferred range.

In preferred embodiments, the plurality of different exposure times is two different exposure times. Alternatively, 3, 4, 5, or even more different exposure times can be utilized.

A number of different detectors, with different types of light sensors can be utilized. Preferably, the sensor is in a camera, and preferably an electronic, preferably a digital sensor. Preferably the sensor is an imaging sensor. In particular applications, it may be desirable to utilize 2, 3, or more sensors, e.g., to detect signals with different intensities and/or other different characteristics. In preferred embodiments, the detection device utilizes a CCD sensor, a CID sensor, or a CMOS sensor. In preferred embodiments, the sensor is a non-blooming or blooming resistant sensor.

As is also described for other aspects herein, in preferred embodiments, the plurality of separately addressable sites are on a slide, on a chip, on a membrane, in a gel, in an array, in a microarray, in a cell, on a cell, in a tissue section.

As described in the Detailed Description, the extended dynamic range, preferably linear dynamic range, is preferably at least 4 orders of magnitude, more preferably at least 5, 6, 7, or more orders of magnitude. In preferred embodiments, the method increases the dynamic range, preferably the linear dynamic range, by at least one order of magnitude over the dynamic range, preferably linear dynamic range, as compared to when a single exposure time is utilized. More preferably the dynamic range is increased by at least 2, 3, or more orders of magnitude.

In preferred embodiments, the different exposure times are selected to provide signals within the linear response range for the detection device. Preferably the different exposure times are selected and/or controlled by computer to optimize exposure conditions.

In this, as well as in other aspects described herein, detection of multiple sites can be performed in a variety of ways. For example, multiple sites can be scanned one at a time; one or more individual sites can be scanned; multiple sites can be read together with an imaging sensor or arrangement of multiple individual sensors; or contiguous subsets of sites can be read with an imaging sensor or an arrangement of individual sensors; among other site reading possibilities. Where an imaging sensor is used to read a plurality of different sites, preferably the sensor has a resolution sufficient to image each site individually with at least one pixel, and preferably a plurality of pixels per-site.

The technique of multiple exposure times can be combined with other dynamic range enhancement techniques, e.g., with particle counting at sites with weak signals and/or by deconvolution of the signals for sites in a non-linear range of strong signals in which the light scattered from at least one site is not directly proportional to the number of label particles at the site. Various embodiments, e.g., as described herein, of those other techniques can be utilized herein.

The term "assay format" refers to the physical arrangement or layout of the assay components which employs various physical forms in or on which label is detected and/or from which label is released for detection. The assay format is also referred to as "sample format". Different assay formats employ different physical forms which include, for example, slide, chip, membrane, microtiter plate, flow cell, cuvette, test tube, gel (e.g., polyacrylamide and agarose gels) formats, as well as channels and reservoirs in small volume devices (with volume in the micro- to picoliter range).

In connection with methods for extending dynamic range, the term "sites" refers to physically discrete spaces, areas or locations in a single assay. The sites are associated with a physical form which is determined by the assay format. Preferably, the sites are "addressable sites" wherein the discrete sites can be separately identified by an operator or a machine. The addresses of the sites can be used for a variety of purposes, such as but not limited to delivery and/or retrieval of samples and reagents, detection of signals, data analysis, etc. Typically, without limitation the sites correspond to the presence of different samples, analytes, dilution ratios, sampling and/or different process treatments. Also typically, the different sites will have a physical separation between sites, e.g., a portion of a plate or chip to which analyte does not bind. Non-limiting examples of such sites and addressable sites include array spots (including microarray spots), microtiter wells, spots or bands in a gel, spots or bands on a membrane or filter, channels and reservoirs in small volume devices, as well as chromosome preparations, chromosomes or segments thereof, distinguishable cellular-compartments, components, organelles, or distinguishably different types of cells in a viewable field, in a cell culture, or in a tissue section.

The terms "spots" and "features" are also used interchangeably to refer to sites. In connection with multiple site assay formats, the term "spot" will be used to refer to a site (i.e., spot) on an array. Often the term "feature" will be used in this manner, but also can be used to refer to other formats.

As used herein, the term "array" refers to a plurality of sites in or on a single physical form, e.g., a slide, chip, or membrane. The arrangement of the plurality of sites on the physical form is also referred to as sample format or assay format. Preferably the sample format is a solid phase material with a flat sample-bearing or sample-binding surface. Preferably, an array includes at least 4, 6, 8, 10, 20, 50, 100, 200, 400, 800, or 1000, 5000, or 10,000 separate sites.

In the context of analyte assay labels and the present methods, the term "light emitting particles" refers to particles that give off light under the conditions of the assay. It does not mean that the light need be generated by the particle. The light may, for example, be emitted due to scattering of incident light or fluorescence.

Likewise, the term "light scattering particles" refers to particles that scatter light of visible wavelengths sufficiently strongly to be useful as labels in analyte assays. For example, such particles include metal or metal-like materials as described herein. It is recognized that all particles will scatter light to some extent.

As used herein, the terms "integrated intensity", "integrated light", "integrated signal" and like terms refer to the light collected over a period of time, rather than to the instantaneous light intensity or the light intensity detected at the minimum collection period of the detector or sensor. Thus, the amount of integrated light collected will depend on the collection period, the average light intensity over that period, and the collection efficiency of the collector or sensor.

The invention also provides a method for providing an extended dynamic range, preferably linear dynamic range, in an analyte assay using particulate labels. Preferably the particulate labels are light scattering particles where the scattered light is detected. The assay is performed with a plurality of sites, preferably separately addressable sites. The method includes determining the signals at the plurality of separately addressable sites with a plurality of different signal accumulation times with an imaging sensor providing non-destructive signal readings corresponding to separate pixels. The signals from the separately addressable sites are normalized arid the normalized signals corresponding to the various sites provide an indication of the numbers of label particles present at those sites.

Preferably, the separate pixels in the imaging sensor are random access pixels. Preferably, the separate pixels, or groups of pixels are separately re-settable. Preferably the imaging sensor is a Charge Injection Device sensor (CID sensor). Highly preferably, the sensor is a camera.

In preferred embodiments of the method, the pixels or groups of pixels corresponding to strong signal sites are re-set on a time interval or accumulation threshold selected to maintain the signal within the linear response range for the sensor. Preferably the accumulated signal corresponding to at least one strong signal site is read and summed or averaged over a plurality of accumulation intervals. Summing over a plurality of accumulation intervals provides increased total exposure time for said at least one strong signal site, by adding up the signals all within the appropriate response range for the sensor. Likewise, averaging over multiple accumulation intervals provides increased statistical significance for the measurement.

The invention also provides a method for providing an extended dynamic range, in an analyte assay using filters, preferably light-intensity reducing filters. At sites which produce high intensity light, filtering reduces the amount of light that reaches the sensor which would otherwise saturate the sensor.

The invention also provides a method for providing an extended linear dynamic range in an analyte assay using particles, preferably light scattering particles, as labels with a plurality of separately addressable sites by determining the signals corresponding to those sites with an imaging sensor, where at least one high density site contains a sufficient number of label particles that the scattered light signal is not directly proportional to the number of label particles. Deconvolution of the integrated light signals for said at least one high density site is utilized, thereby correcting for particle-particle interactions in the at least one high density site and extending the quantifiable range for the assay. The deconvolution technique adjusts for the loss of proportional scattered light signal as the density or concentration of particles becomes great enough so that particles interfere significantly with each other. The deconvolution can be empirical, analytical, or a combination of the two.

Preferably the deconvolution provides at least one order of magnitude, more preferably at least two orders of magnitude, increase in the dynamic range for quantification in the assay.

The present techniques for providing extended dynamic range can also utilized in combination. For example, in certain embodiments, the method includes embodiments of the dual particle counting/integrated signal technique along with a multiple exposure time technique (or alternatively the use of sensors providing non-destructive accumulated signal reading), a filtering technique, and/or deconvolution. In certain embodiments, the method includes an embodiment of a multiple exposure time technique along with deconvolution. In certain embodiments, the method includes an embodiment of a technique utilizing a sensor providing non-destructive reading of accumulated signal along with a technique for deconvolution.

In a related aspect, the invention provides a system (apparatus) for performing an analyte assay using light emitting particles, preferably light scattering particles, as labels with a plurality of separately addressable sites. The system includes an illumination source providing light to the separately addressable sites, and an imaging sensor providing non-destructive reading of separate pixels or groups of pixels.

For systems involving light scattering labels, preferably the illuminating light is directed toward the array sites at an angle closer to the perpendicular than the critical angle for incident light (if a critical angle if designed for the configuration) or no critical angle for incident light is defined (i.e., incident light does not pass through an interface from a medium of higher refractive index to a medium of lower refractive index).

Preferably the system also includes a sample array that includes a plurality of separately addressable sites, e.g., an array or microarray slide, chip, membrane, gel, microtiter plate, or other format array.

Preferably the sensor allowing non-destructive reading of separate pixels or groups of pixels is a charge injection device (CID) sensor, preferably in a camera; preferably one allowing random pixel access. Preferably the sensor provides at least 512 pixels in each pixel array dimension, e.g., a 512×512 pixel array, more preferably at least 1024 pixels in each array dimension, e.g., a 1024×1024 or a 1024×512 pixel array. Higher resolutions in one or both dimensions is even more preferably for many applications, for example, for assay media with high spot or feature density.

In another aspect, the invention provides a system for performing an analyte assay using particles, preferably light scattering particles, as labels, with an assay medium that has a plurality of separately addressable sites. The system includes an illumination source providing light to the separately addressable sites; at least one sensor, preferably an imaging sensor, providing signal readings for the plurality of separately addressable sites, forming an image. The at least one sensor can provide signal readings at a plurality of different exposure times. The system also includes a computer adapted to receive signals from the sensor(s) and to combine signals (or to select signals) from the plurality of different exposure times by selecting non-saturated pixel values, thereby providing signals corresponding to the numbers of label particles present at a plurality of separately addressable sites.

Preferably the system also includes a sample array that includes a plurality of separately addressable sites, e.g., an array or microarray slide, chip, membrane, gel, microtiter plate, or other format array.

In yet another aspect, the invention provides a system for performing an analyte assay using particles, preferably light scattering particles, as labels with a plurality of separately addressable sites. The system includes an illumination source providing light to the separately addressable sites; at least one sensor, preferably an imaging sensor, providing signal readings for the plurality of separately addressable sites forming an image; and a computer adapted to receive signals from the sensor(s) and to deconvolute signals from sites with particles densities sufficient to result in non-linear light scattering response but within the correctable range of response. The deconvolution will thus provide signals corresponding to the numbers of label particles present at a plurality of separately addressable sites and extend the dynamic range of the assay beyond the linear light scattering response range.

Preferably the system also includes a sample array that includes a plurality of separately addressable sites, e.g., an array or microarray slide, chip, membrane, gel, microtiter plate, or other format array.

In order to perform the deconvolution, preferably the computer includes a storage medium that has embedded therein a set of software instructions to perform the deconvolution.

The systems described for providing extended dynamic range can also include components in combination that provide 2 or 3 of the above techniques. Thus, a system may include in combination, components for performing the dual mode technique (integrated signal and particle counting) along with a sensor providing non-destructive signal readings or components for providing multiple exposure times and/or components for performing deconvolution. Likewise, a system may include components for performing multiple exposures and components for performing deconvolution in combination. Similarly, a system may include components for the dual mode technique in combination with components for performing deconvolution.

While typically the multiple exposure technique (and related components) and the use of a sensor providing non-destructive signal reading are treated as alternatives, it is also suitable to include both in a single method or system.

The methods for providing enhanced dynamic range can be utilized in conjunction with many different embodiments of the analyte detection method utilizing RLS particle labels, e.g., as described herein, as well as with other particulate labels, and with light scattering particle methods using evanescent wave illumination.

The RLS-based method and associated apparatus described herein are designed to maximize detection of only scattered light from the particles and thus is many times more sensitive than use of fluorophores, or the use of such particles in methods described above. Such particles can be detected by using a low magnification microscope (magnifying at 2 to 500 times, e.g. 10 to 100 times) without the need for any electronic amplification of the signal. In addition, methods are provided in which no microscope or imaging system is necessary but rather one or more of the light scattering properties are detected of a liquid or solid-phase sample through which light is scattered. These scattered light properties can be used to determine the presence, absence or amount of analyte present in any particular sample.

The source of light in general need not be treated in any particular manner (e.g., polarized, or laser or high intensity) but need only be directed such that it allows scattered light from the particles to be detected. Spatial filtering can be used to ensure reduction of non-specific light scatter. Such filtering can be supplemented by other instrumental components and sample chambers which reduce stray light.

The direct light can be polychromatic or monochromatic, steady-state or pulsed, and coherent or not coherent light. It need not be polarized and can be generated from a low power light source such as a Light Emitting Diode (LED), or 12 watt filament light bulb and the like. The light is directed at a sample which may contain the particles at an angle such that the direct light itself will not be observed by the detector unless it is scattered by the particles. The method and apparatus differs from that of Swope, supra in that such scatter can be observed by eye within the critical angle, preferably within the angle of illumination. It can, however, also be detected at greater than the critical angle and outside of the intensity envelope of the forward direction of scattered light. When used with an imaging apparatus, e.g., a microscope, the present method preferably uses a detector perpendicular to the plane of the sample.

Specific types of particles can be detected and measured to very low concentrations, to a high degree of specificity, and across wide concentration ranges with easier to use and less costly methods and apparatus. Methods using RLS particulate labels provide for detection of analytes with greater ease of use, sensitivity, specificity, and is less costly than prior methods of analyte detection.

By theoretical modeling and physical experimentation, it was determined that coated metal-like particles have similar light scattering properties as compared to uncoated metal-like particles, both of which have superior light scattering properties as compared to non-metal-like particles.

By "metal-like" particles is meant any particle or particle-like substance that is composed of metal, metal compounds, metal oxides, semiconductor (SC), superconductor, or a particle that is composed of a mixed composition containing at least 0.1% by weight of metal, metal compound, metal oxide, semiconductor, or superconductor material.

By "coated" particle is meant a particle has on its surface a layer of additional material. The layer is there to chemically stabilize the particle in different sample environments, and/or to bind specific analytes by molecular recognition means. Such coatings are for example, inorganic and/or organic compounds, polymers, proteins, peptides, hormones, antibodies, nucleic acids, receptors, and the like.

By "non-metal-like" particles is meant particles that are not composed of metal, metal compounds, superconductor, metal oxides, semiconductor, or mixed compositions that are not composed of at least 0.1% by weight of metal, metal compound, metal oxide, superconductor, or semiconductor material.

It was also determined that:

(1) one or more analytes in a sample can be detected and measured by detection and/or measurement of one or more of the specific light scattering properties of metal-like particles. These light scattering properties include the intensity, wavelength, color, polarization, angular dependence, and the RIFSLIW (rotational individual fluctuations in the scattered light intensity and/or wavelengths) of the scattered light. One or more of these properties of particle scattered light can be used to provide information regarding the analytes in the sample;

(2) by varying the size, and/or shape and/or composition of a metal-like particle in various combinations, one or more of the light scattering properties can be adjusted to generate more easily detectable and measurable light scattering signals;

(3) illumination and detection of the metal-like particles of certain size, shape, and composition with RLS particle methods described herein provides a highly sensitive and easy to use method to detect and measure metal-like particles by their light scattering properties. The method provides for single particle detection with easy to use and inexpensive apparatus means;

(4) the RLS methods can be used with particle counting and/or integrated light intensity measurements to provide for detection and measurement of the particles across wide concentration ranges;

(5) the use of refractive index enhancement methods provides for enhancement of a particle's light scattering properties, and/or decreases in non-specific light background;

(6) the use of video contrast enhancement methods for RLS can provide for more sensitive detection in many different types of samples and diagnostic assay formats;

(7) for sensitive detection of analytes in a small solid-phase area such as commonly used in microarray and array chip formats, certain types of metal-like particles are more preferred to use than others. Metal-like particles in microarray and array chip formats can be most easily and inexpensively detected by using RLS methods. Such particles in these formats can also be detected by methods of laser scanning confocal microscopy, brightfield or epi-polarization microscopy, and reflection contrast and differential interference contrast microscopy. However these methods and apparatus are not as easy to use and inexpensive as detection by RLS methods and apparatus; and (8) useful apparatus and particle types for specific test kits can be constructed. These different test kits, and associated apparatus are useful for applications to consumer use, portable field use, point of care applications such as doctor's offices, clinics, emergency rooms and the like, research laboratories, and centralized high throughput testing. The above aspects of the present invention provide for detection of one or more analytes in many different types of samples and diagnostic assay formats.

The method of light illumination and detection is termed "DLASLPD" (direct light angled for scattered light only from particle detected).

As is discussed in more detail below, there are many variations of the type of particle, and of the light source and light detection mechanisms. In addition, many variations can be made on the types of particles used.

In preferred embodiments, the particle has a size, composition and shape suitable for producing specific light scattering signal(s) of specific wavelength(s), color(s), polarization, angular dependence, and RIFSLIW of the scattered light that is detectable by eye or photodetector means; the detection includes the methods of counting the particles, and/or measurement of the intensity of scattered light as a measurement of the concentration of the particles; the particle is formed from metal-like materials or is formed from a mixed composition including non-metal-like materials, the particles are spherical, oval, or asymmetrical (by asymmetrical is meant not roughly spherical in shape); the particles are coated with binding agents, polymers, reactive chemical groups, base material molecules, inorganic and organic compounds; secondary binding pairs are used to associate one or more light scattering particles to the analyte; the change in scattered light properties when two or more particles are brought into close contact with each other in assay formats is used; particle reagents comprised of metal-like material and coated with base material molecules adapted to bind to a binding agent are used; assay formats wherein two or more particles are brought sufficiently close together so that the light scattering property of the two or more particles can be resolved from single particles is used; assay formats wherein two or more particles that are held in close proximity to one another are caused to be separated so that the light scattering property of any one particle is altered is used; assay formats wherein two or more particles are linked together by one or more molecular interactions such that when the molecular interaction holding the particles together is disrupted, one or more particles are released from the molecular interaction is used; assay formats wherein the amplified detection of analytes is accomplished by cross-linking two or more particles together using chemical or biological cross-linking agents is used; assay formats wherein drug target substances including, cell surface receptors, intra-cellular receptors, intra-cellular signaling proteins, G-protein coupled receptors, ion channels, enzymes including proteases and protein kinases, DNA binding proteins, nucleic acids, and hormones are used to screen, identify and characterize new pharmaceutical agents; assay formats wherein a magnetic bead or other bead is used as the solid-phase and the light scattering particles are detected bound to the bead or are released into solution prior to detection; the particles are composed of additional materials to allow them to be oriented in an electric, magnetic or related electromagnetic field (EMF); the particles are attached to other particles of magnetic or ferro-electric properties; assay formats wherein the light scattering particles used have magnetic or electrophoretic properties such that a magnetic field or electric field respectively can be applied to the sample to concentrate the light scattering particles in one or more regions of the sample; and the illuminating light beam has a wavelength selected to reduce background as compared to other wavelengths.

In particular embodiments, the illumination light is steady-state or pulsed; the illumination light is coherent or not coherent; the illumination light is polarized or unpolarized; two or more different wavelengths either from the same light source or from two or more different light sources are used to illuminate the sample, and the scattered light signals are detected.

In particular embodiments, the method involves using a plurality of different particles, each having one or more scattered light properties which can be detected by eye or photodetector means; and/or a plurality of different wavelengths of light are used in the illumination or detection step; refractive index enhancement methods are used to reduce non-specific light background; the detector is placed at angles outside of the envelope of the forward direction of sample and light beam scattered light; spatial filtering methods are used, optical filters such as cutoff and/or narrow band pass filters are used in the detecting step to reduce non-specific background light.

Also in particular embodiments, the particle is increased in size by autometallography prior to detection; the illuminating light beam lacks infra-red radiation; the analyte is present in serum; the particles are released into solution prior to detection; the particles are concentrated into a small volume or solid-phase area prior to detection; the particles are detected by time-dependent binding to a surface or flowing the particles pass a detector or set of detectors; multiple analytes are detected on a solid-phase in an array or microarray composed of nucleic acids, proteins, peptides, antibodies, antigenic substances, pharmaceutical agents or targets or other binding agents; the pattern and amount of light scattering particles bound to different regions of an array or microarray is used to determine the level of gene expression, protein expression, identity of a nucleic acid sequence, identity of an organism or cell or specific strain thereof, and the pharmacological properties of a pharmaceutical agent; the microarray is covered with liquid or is dry; single or multiple analytes are detected on a cell surface, cell lysate, or chromosome preparation; the illuminating light beam is polychromatic white light or monochromatic light; the analyte is present in solution or solid-phase, or is present on a microscope slide, or a microtiter plate, test tube, capillary tube, flow cell, microchannel device, cuvette, dipstick, or another plastic container; the particle is a gold or silver particle, having a size between 1 and 500 nm, preferably between 10 and 200 nm; the detecting step does not include amplification of the light scattered by electronic means; and the illuminating light beam is directed toward the particle by a prism or other light guiding systems.

In addition, the detection may include observing the particle through at least a ×10 objective; the method of video contrast enhancement is used; fiber optic illumination and detection is used; bright-field, laser confocal scanning, reflection contrast or differential interference contrast microscopy detection methods are used; an apparatus which scans the sample and detects the scattered light intensity at one or more locations within the sample is used; a two-dimensional image of one or more regions of the sample is reconstructed from the detected light scattering signals at each of the detection points measured; an apparatus which collects images of one or more regions of the sample is used; the particles are detected with an imaging photodetector and digital images of one or more regions of the sample are obtained by image processing means; direct observation or image analysis methods are used to detect and measure one or more properties of the particles in the sample; edge detection methods are used to identify particles within a sample; imaged particles are identified and classified based on one or more of the detected and measured properties including grayscale or color based intensity values, size, shape, or some combination of these properties; the amount of light scattering particles in a sample is determined by counting the identified particles, summing the individual pixel intensity values in all areas of the image identified as particles, the sum of the mean or average intensity value for each image area identified as a particle, or some combination thereof; the detection and purification of combinatorial synthesized molecules is performed; particles and/or specialized coatings are used as solid-phase synthetic supports for combinatorial or other synthesized molecules; specially designed sample chambers are used; antireflective coatings on optical components and sample chambers are used; apparatus for field use, doctor's office, clinics and hospital care units are used; and specific particle types are provided in appropriate test kits.

The high sensitivity and ease of use of the signal generation and detection system of the present invention means that one skilled in the art can by inexpensive means, detect and measure one or more analytes in a sample to extremely low concentrations without need of signal (label) or target analyte molecule amplification methods.

The wide range of specific light scattering signals from different particle types in the present invention means that one skilled in the art can detect and measure to a high degree of specificity one or more analytes in a sample.

The high optical resolvability of two or more different particles types in the present invention means that very simple multi-analyte detection (i.e. two or more different analytes) in a sample is possible without the need for complex apparatus.

Those in the art will recognize that the methods and apparatus described herein have broad utility. They can be applied in one form or another to most situations where it is desirable to use a signal generation and detection system as part of an assay system to quantitate and/or detect the presence or absence of an analyte. Such analytes include industrial and pharmaceutical compounds of all types, proteins, peptides, hormones, nucleic acids, lipids, and carbohydrates, as well as biological cells and organisms of all kinds. One or another mode of practice of this invention can be adapted to most assay formats which are commonly used in diagnostic assays of all kinds. For example, these include heterogeneous and homogeneous assay formats which are of the sandwich type, aggregation type, indirect or direct and the like. Sample types can be liquid-phase, solid-phase, or mixed phase.

Other features and advantages of the invention will be apparent from the following description of the preferred embodiments, and from the claims.

4. BRIEF DESCRIPTION OF THE DRAWINGS

FIG. 1 illustrates illumination of a sample from below. L is a lens; D is the diameter of the lens; 0 is the area on surface S being detected; C is the cone showing the angles at which L collects light; LB is the illuminating light beam.

FIG. 2 illustrates the collecting angle of a lens. D is the diameter of the lens; f is the focal length; O is the area detected; $\theta_H$ is the planar half angle of the collection cone.

FIG. 3 is a diagram which defines angles used to describe reflection and refraction at a surface. S is the surface; $n_1$ and $n_r$ are the refractive indices of incident medium and surface medium respectively; RFRB and RFLB are the refracted and reflected light beams respectively; IB is the incident light beam; θi, θr, and θt are the angles of incidence, reflection, and refraction of the light beam.

FIGS. 4A, 4B, and 4C are light reflection graphs for $n_1<n_r$ taken from various texts.

FIGS. 5A, 5B, and 5C are light reflection graphs for $n_1>n_r$ taken from various texts.

Figure 9:
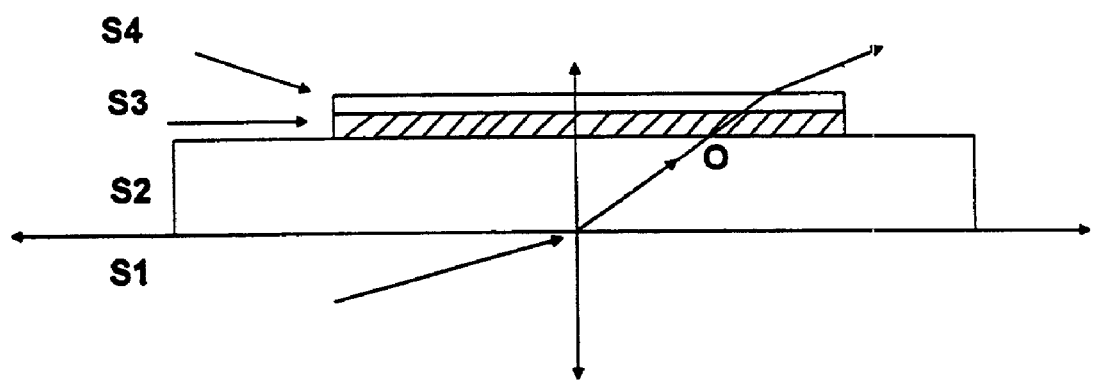

FIG. 9 shows a sample in a thin film of water that is on a microscope slide and covered with a cover glass. The illuminating beam encounters four media interfaces; S1 (air to glass); S2 (glass to water); S3 (water to glass); S4 (glass to air). The particles are at 0 on surface S2 or freely moving above surface S2. Incident light strikes surface S1.

Figure 10:
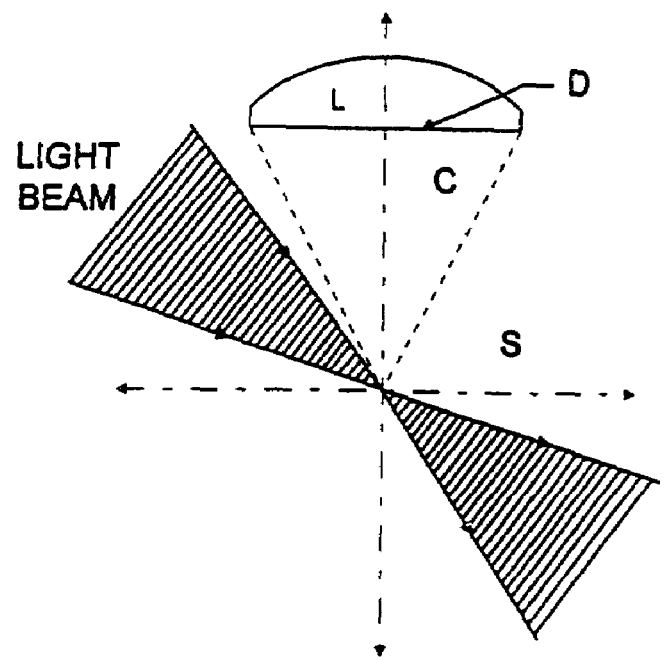

FIG. 10 shows illumination of a sample from above. L is the lens; C is the collection cone.

Figure 11:
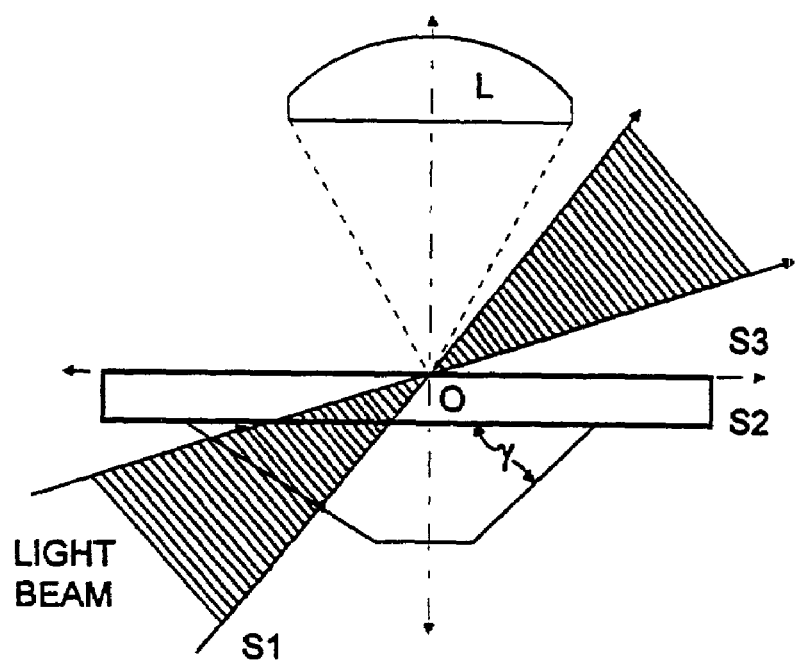

FIG. 11 shows illumination using a prism arrangement (illumination from below). S1 is surface of prism where light is incident; S2 and S3 are the bottom and top surface of a plastic piece substrate respectively.

FIGS. 12A, 12B, 12C, 12D, and 12E represent a pore prism (12A), an equilateral prism (12B), a home made prism (12C and 12D), and a plane convex lens, respectively.

Figure 13:
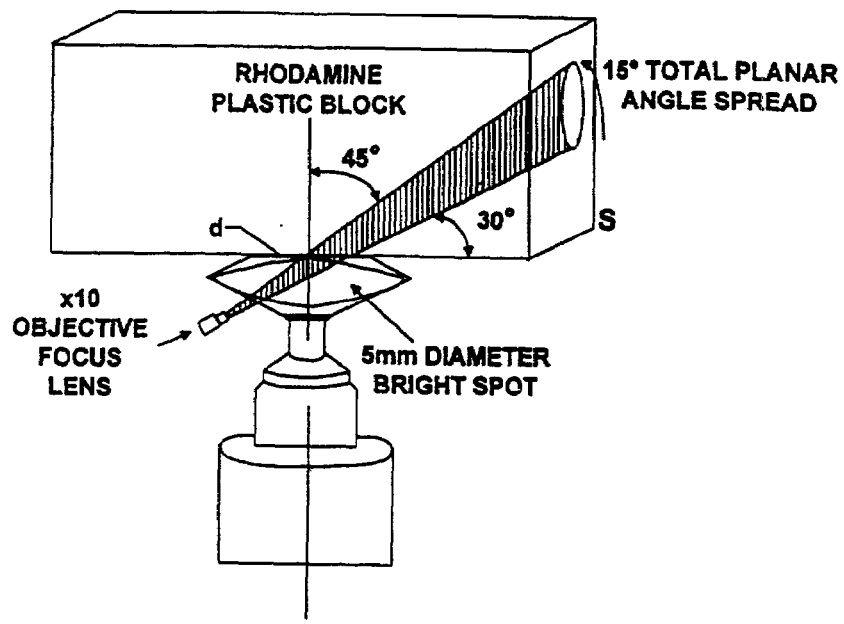

FIG. 13 shows an illuminating light beam as viewed with a rhodamine plastic block.

Figure 14:
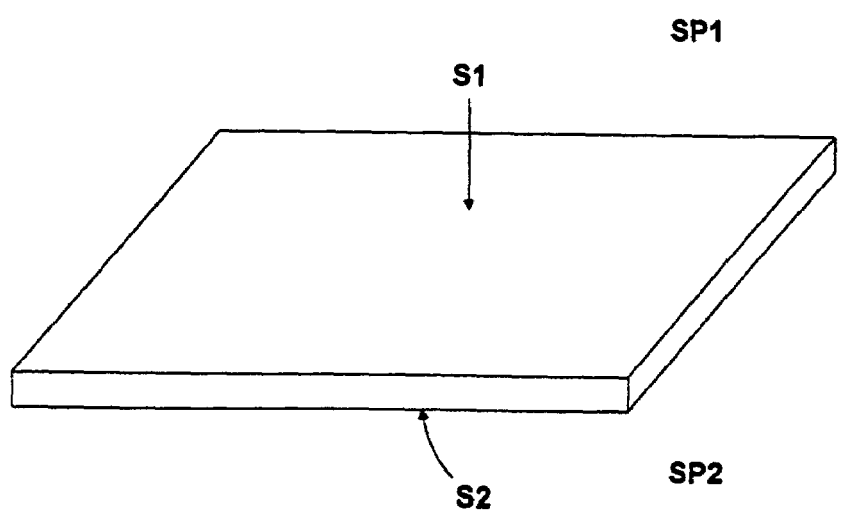
Figure 15A:
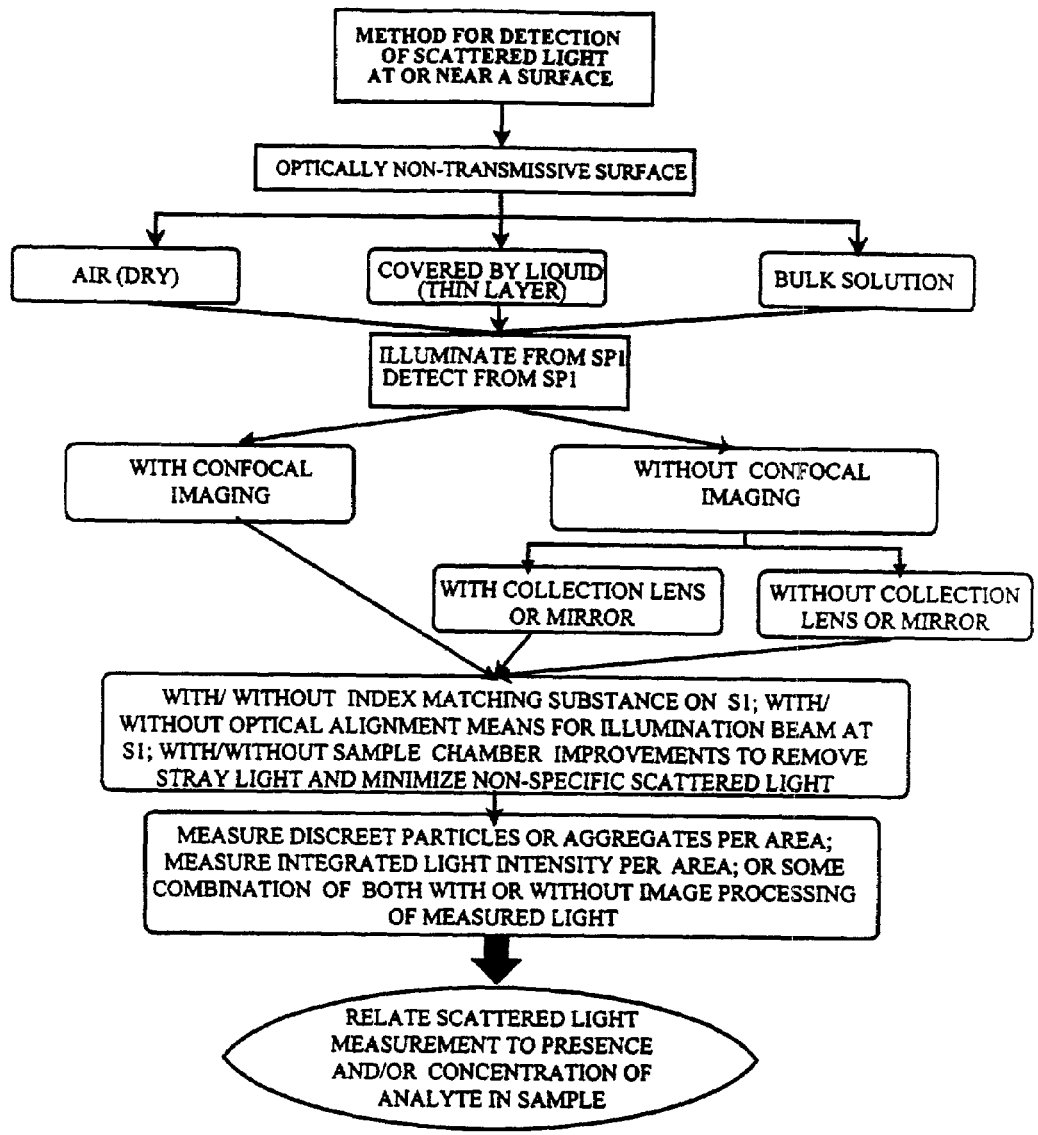
Figure 15B:
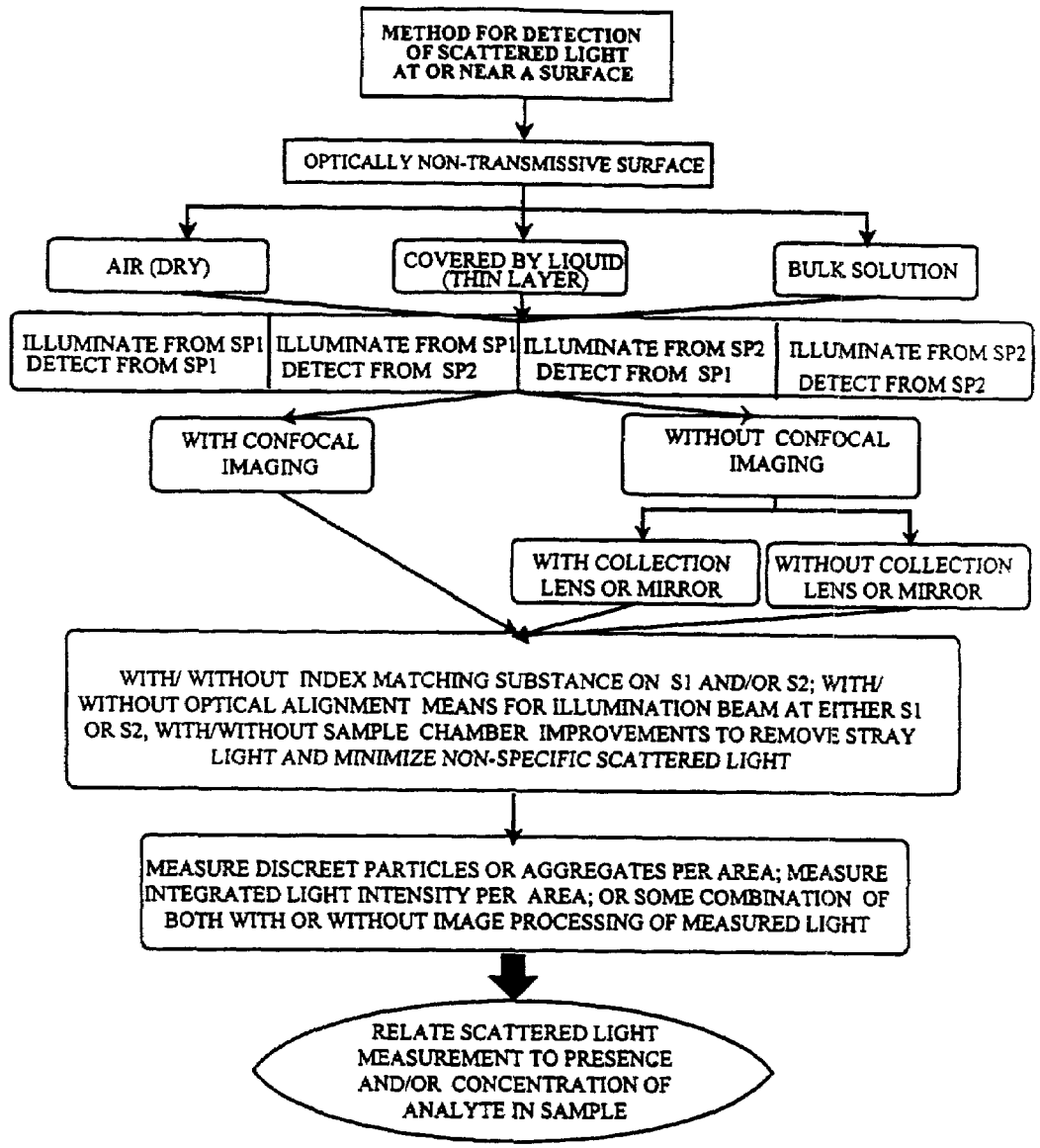

FIG. 14 shows a surface and associated planes for descriptive purposes for FIG. 15; S1 is solid substrate optically or not optically transmissive; SP1 is the 3-dimensional space above the plane of surface S1; SP2 is the 3-dimensional space below plane of surface S1. Light Scattering particles or material is in the SP1 plane at or near the surface S1.

FIG. 15 summarizes the different methods of DLASLPD illumination and detection.

Figure 16:
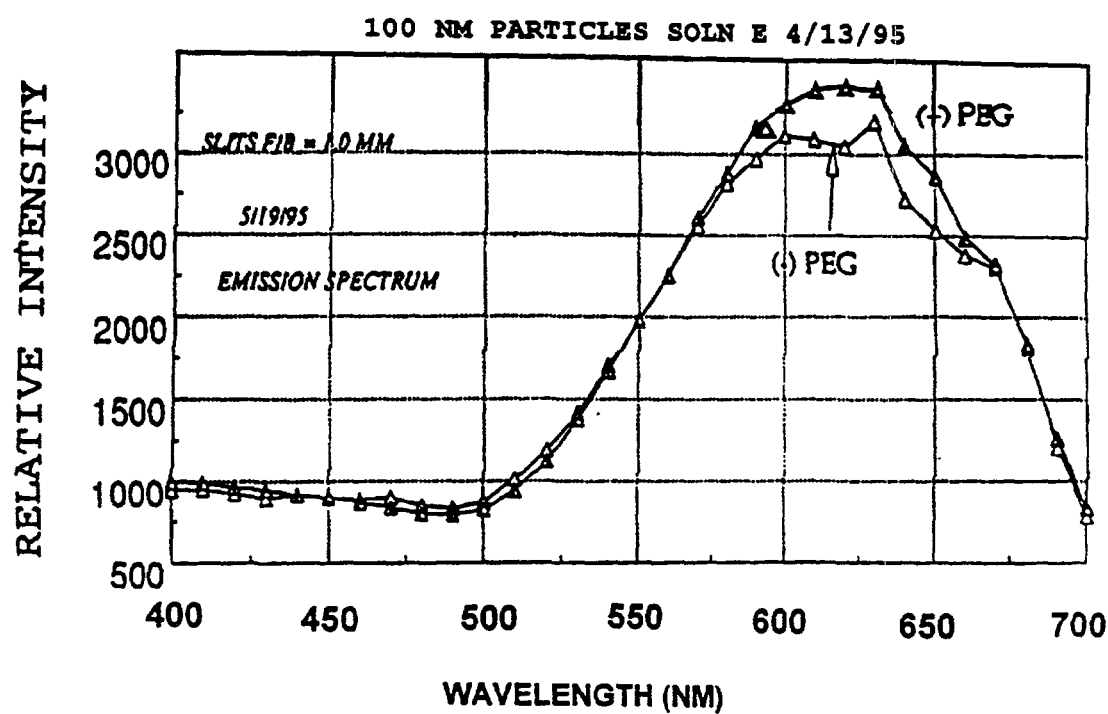

FIG. 16 shows the experimentally measured scattered light intensity versus incident wavelength spectrum for coated and uncoated 100 nm diameter gold particles.

Figure 17:
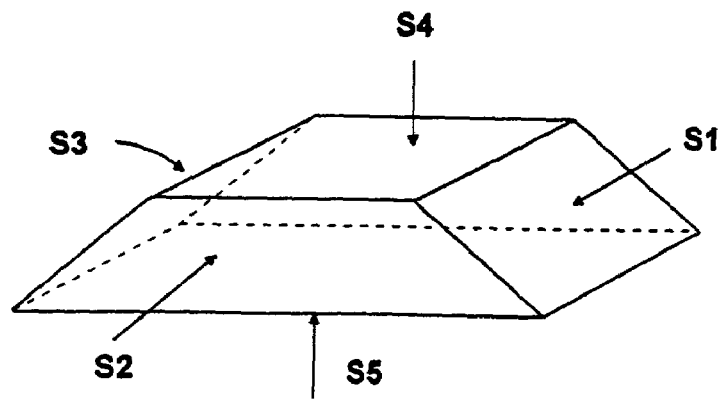
Figure 18:
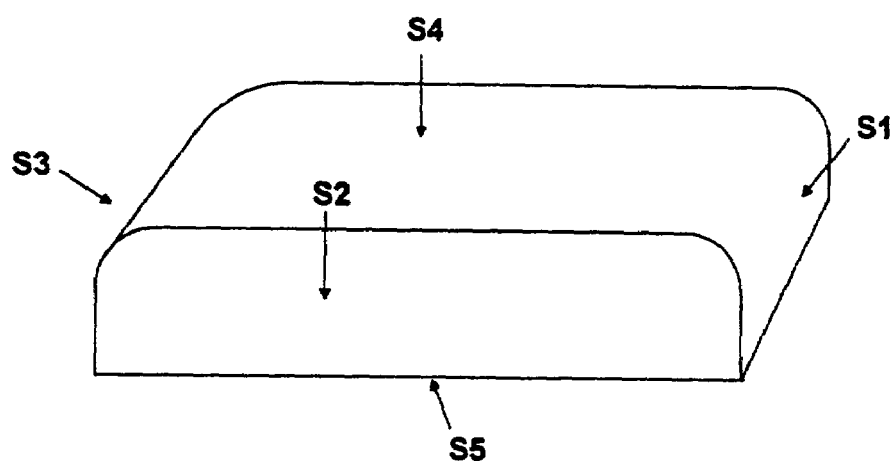
Figure 19:
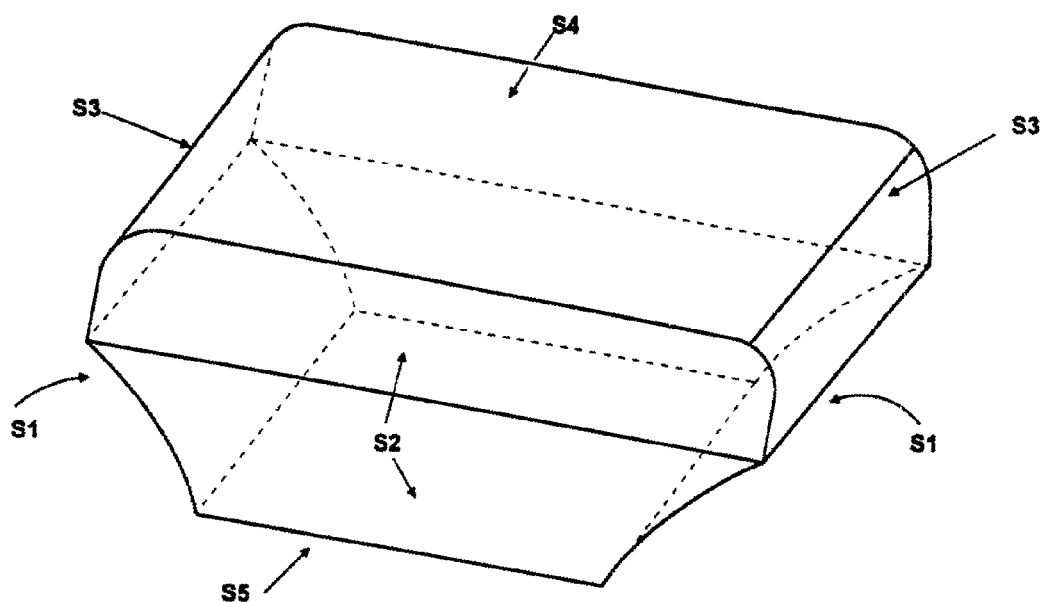

FIGS. 17, 18, and 19 show various sample chamber designs to reduce the level of non-specific light background. These sample chambers can test both liquid and immobilized samples. For FIG. 17, S1 is the surface where the light beam impinges on the sample chamber; S2 is the surface that contains the light scattering material (for immobilized samples). S3 is another beveled surface; the surfaces S1 and S3 are beveled at angles of from about 20 degrees to 70 degrees depending on the angle of illumination, the face of surface S1 should be angled so that the light beam strikes S1 at 0 degrees with respect to the perpendicular; S4 is a optically transmissive surface with or without an opening; S5 is the opposite side of the surface S2. If the chamber is enclosed(i.e. S4 is solid with no opening), a small opening is placed at one of the surfaces for the introduction of sample and washing if required.

FIG. 18 is similarly designed as FIG. 17 except the beveled sides are replaced with curved sides. Everything else is the same as the design of FIG. 17.

FIG. 19, S1 is a flat beveled optically transmissive surface where the light beam impinges on the sample chamber. The face of surface S1 should be angled so that the light beam strikes S1 at 0 degrees; S2 is the surface that contains the light scattering material if the material is immobilized; S3 is another curved or beveled surface. S4 is an optically transmissive surface for a sample chamber that is enclosed; Alternatively, S4 has an opening of various size and shape for introduction and washing of sample and detection; S5 is the opposite side of the surface S2. If the chamber is enclosed, then a small opening is required at one of the surfaces for the introduction and/or washing of sample.

Figure 20:
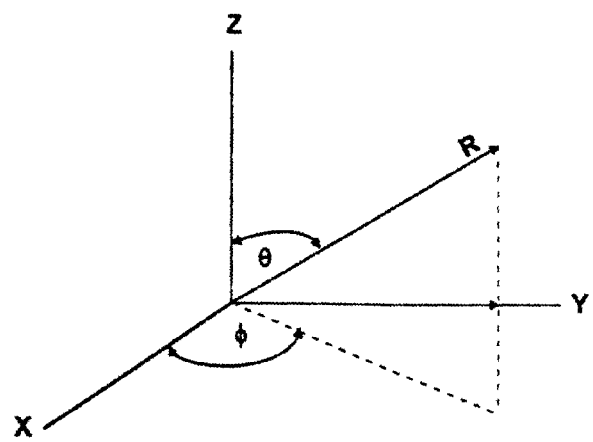

FIG. 20 shows a coordinate system that is used to describe the interaction of particles with polarized light. Light travels along y and is polarized in the z direction. D is the detector of scattered light intensity. γ is the direction of observation. θ and φ are the core angle and polar angle respectively.

Figure 21:
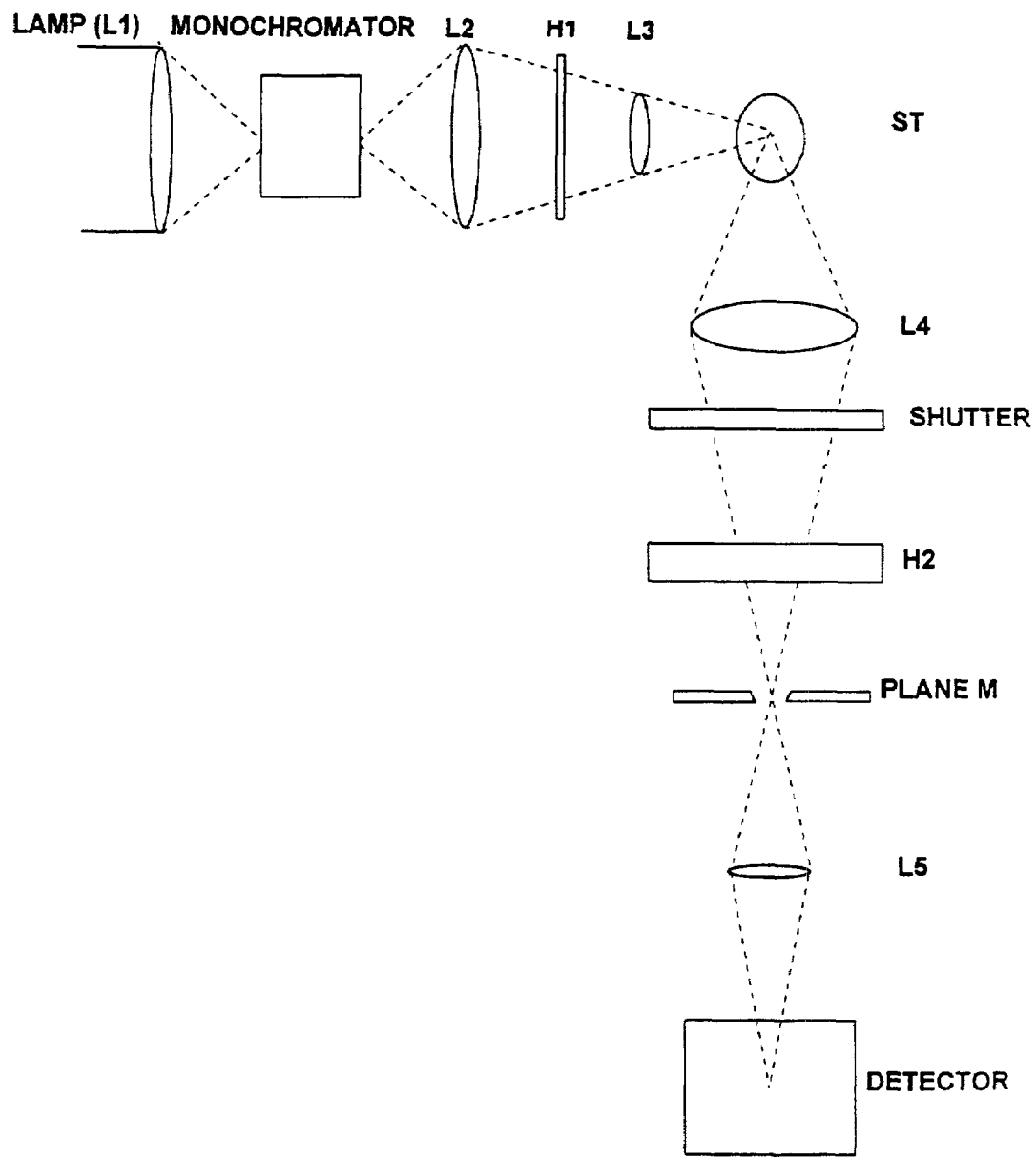

FIG. 21 shows a schematic of an instrument for analysis of liquid samples. Light from a filament or discharge lamp is focused by a lens system, represented by lens L1, onto the entrance slit of a monochromator; monochromatic light which exits the monochromator is collected by lens L2 and focused by lens L3 onto the center of the transparent sample cuvette (ST); the sample cuvette contains a liquid solution of fluorescent molecules or suspension of light scattering particles; the sample cuvette is angled or inclined so that light reflected from its walls is deflected downward and away from the photodetector; light scattered or emitted by the sample is collected by the lens L4 which forms at the plane M a magnified image of the sample cuvette and liquid contents; in the plane M is positioned a small aperture which selectively allows light emitted or scattered by the liquid at the center of the cuvette to reach the photodetector but blocks the photodetector from light reflected or scattered from the side walls of the sample cuvette; the magnified image at M of the center of the liquid contents is displaced from the optic axis of lens L4 by refractive index effects of the wall of the inclined sample cuvette through which the emitted or scattered light is detected; the photodetector and aperture are positioned to one side of the optic axis of lens L4 so that the displaced image of the liquid center falls on the aperture and photodetector; holders for introducing optical filters and/or polarizers into the illuminating light and scattered light paths are provided (H1 and H2); a light shutter is positioned in front of the photodetector. If the photodetector has a small light sensitive area, a lens L5 is used to focus the light crossing the aperture at M unto the light sensitive area. If monochromatic light is not required, the monochromator can be easily removed and light from the filament or discharge lamp can be delivered directly by lenses L1, L2 and L3 to the center of the sample container.

Figure 22:
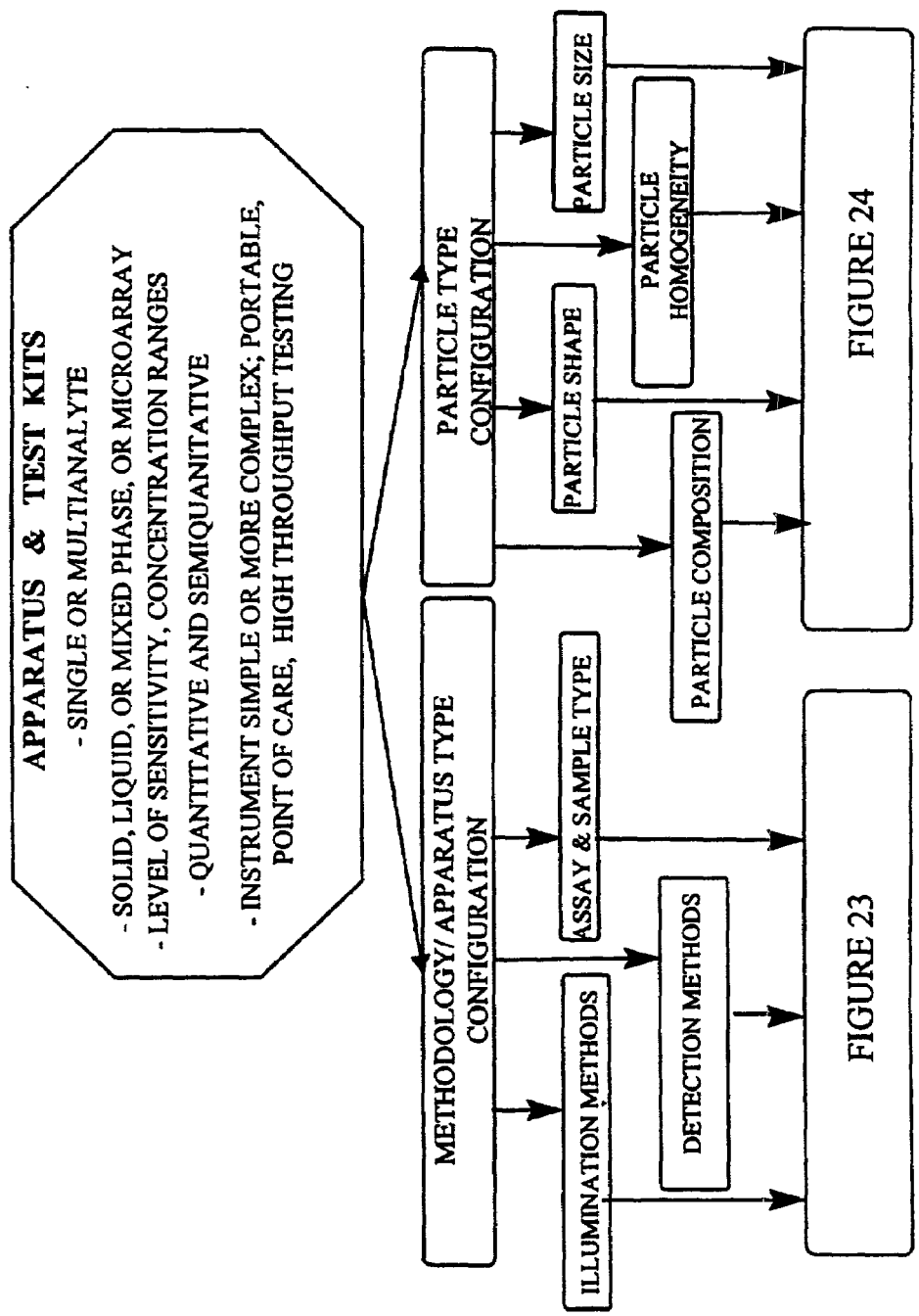
Figure 23:
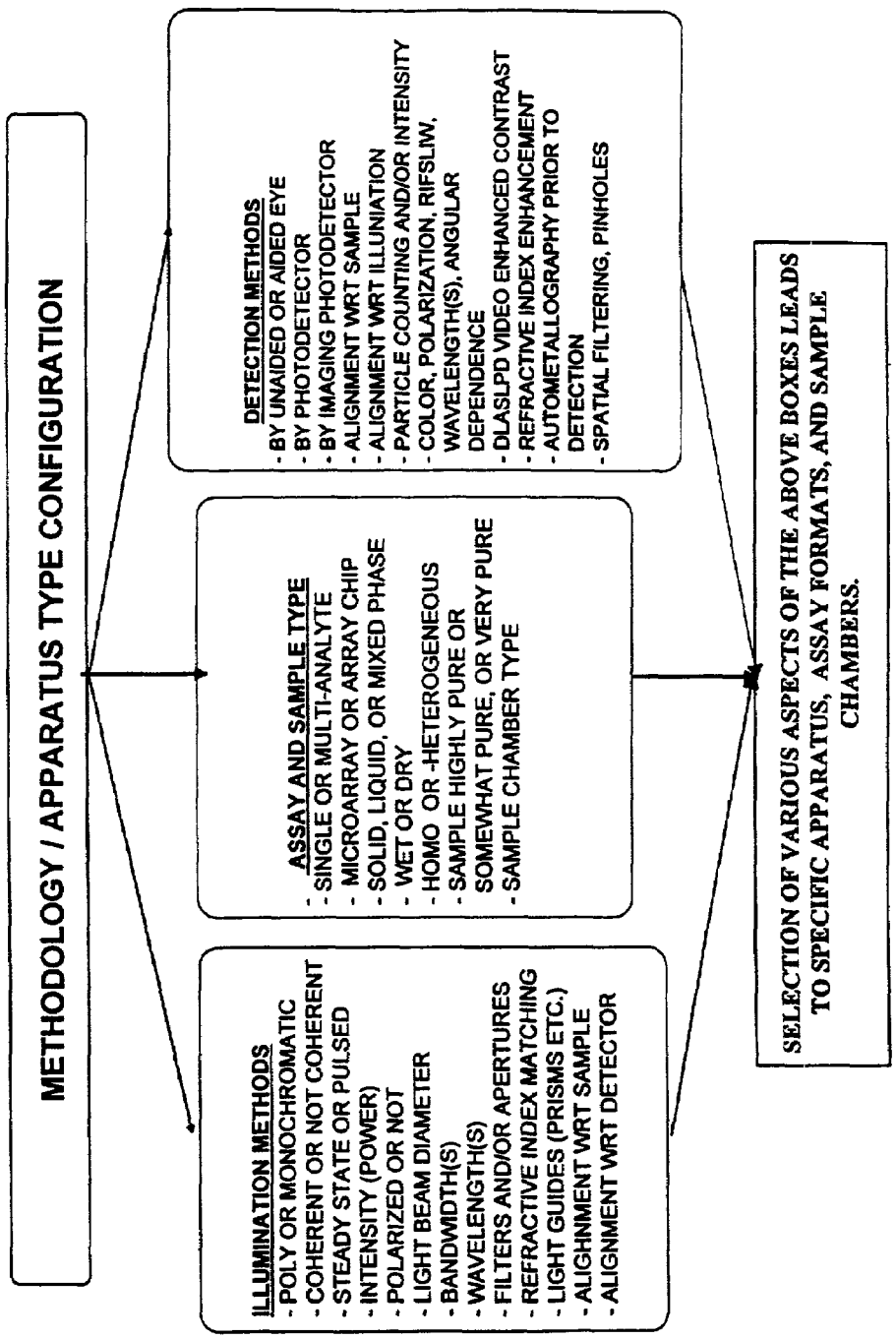
Figure 24:
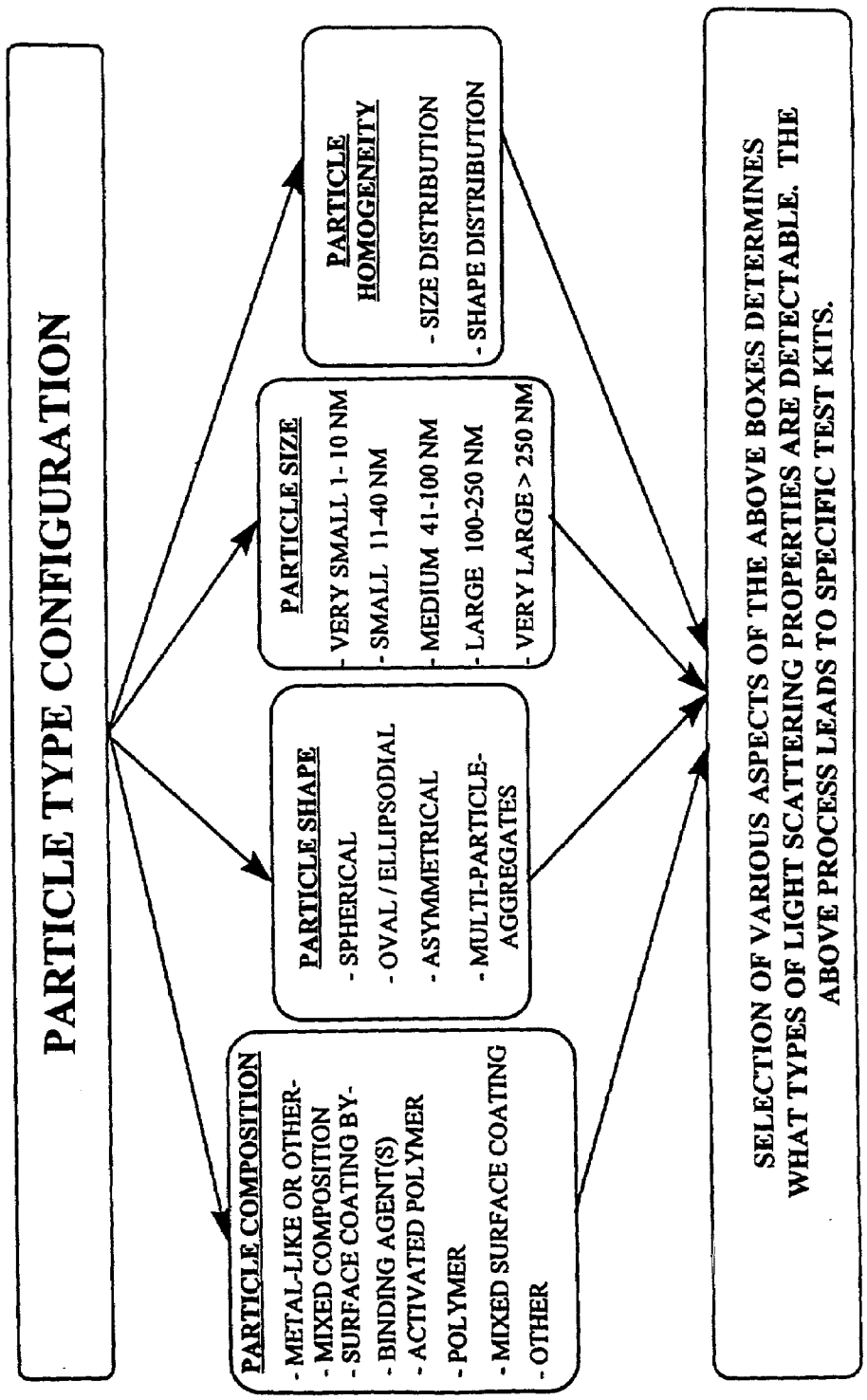

FIGS. 22, 23, and 24 outline methods for using light scattering particles and specific DLASLPD methods, which leads to specific test kits and apparatus.

Figure 25:
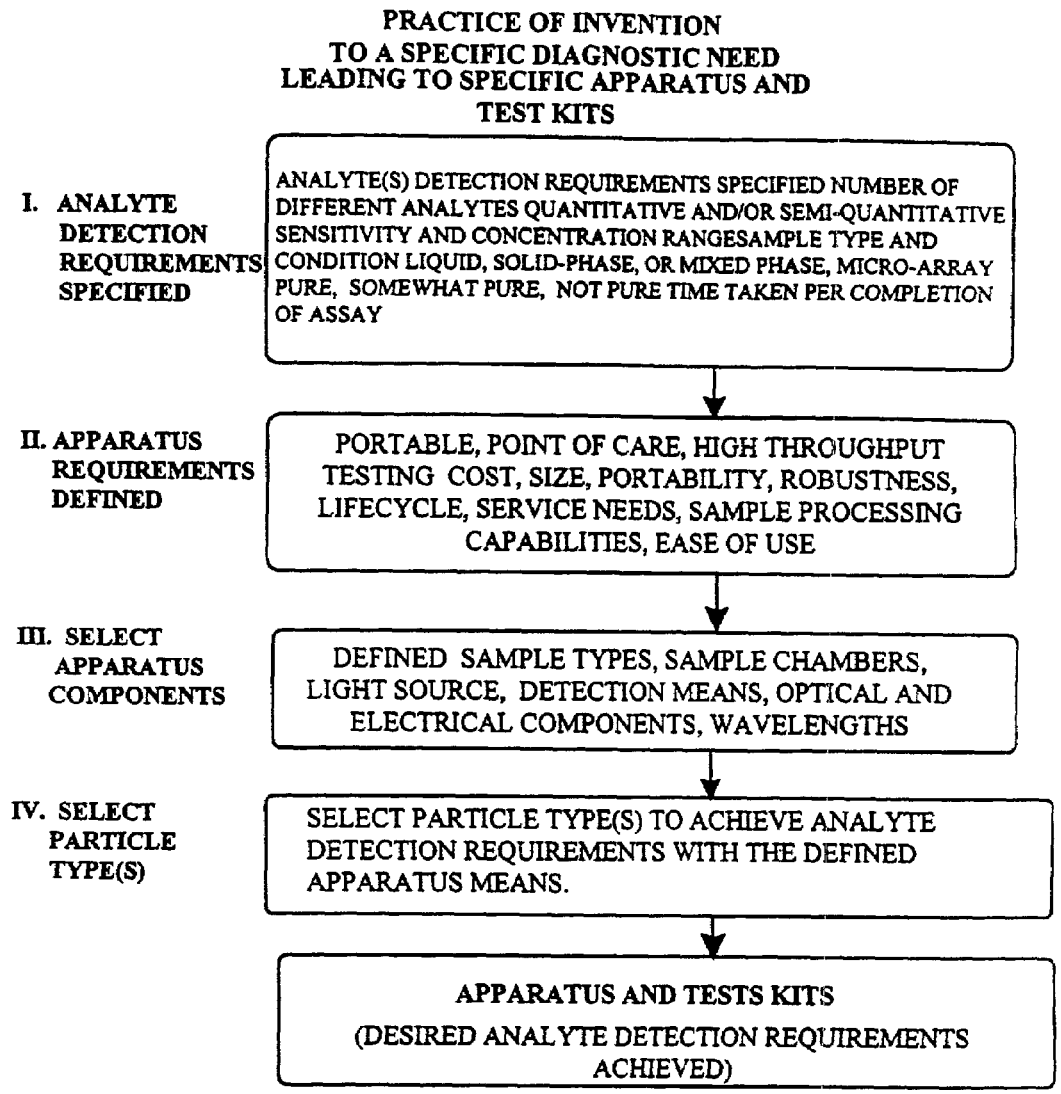
Figure 26A:
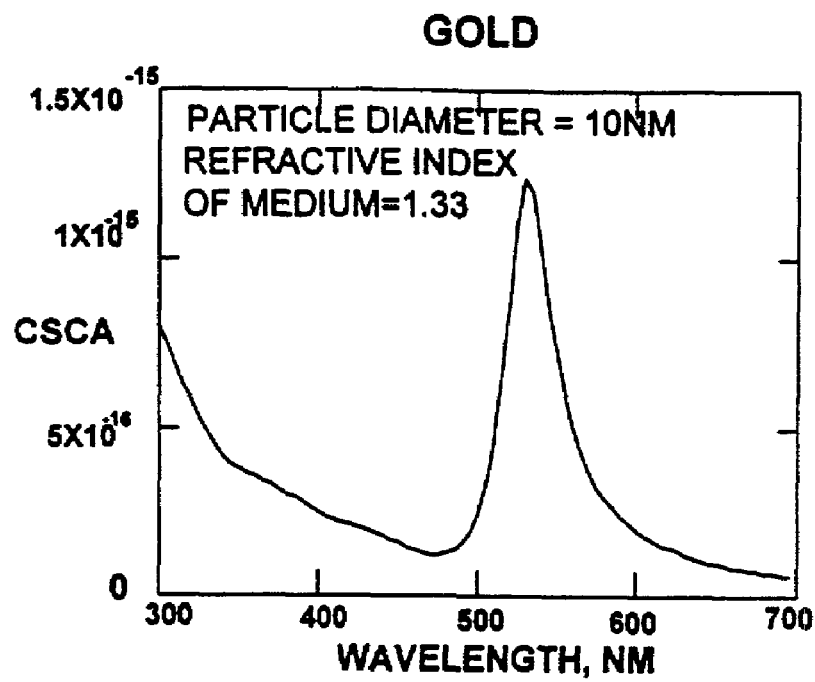
Figure 26B:
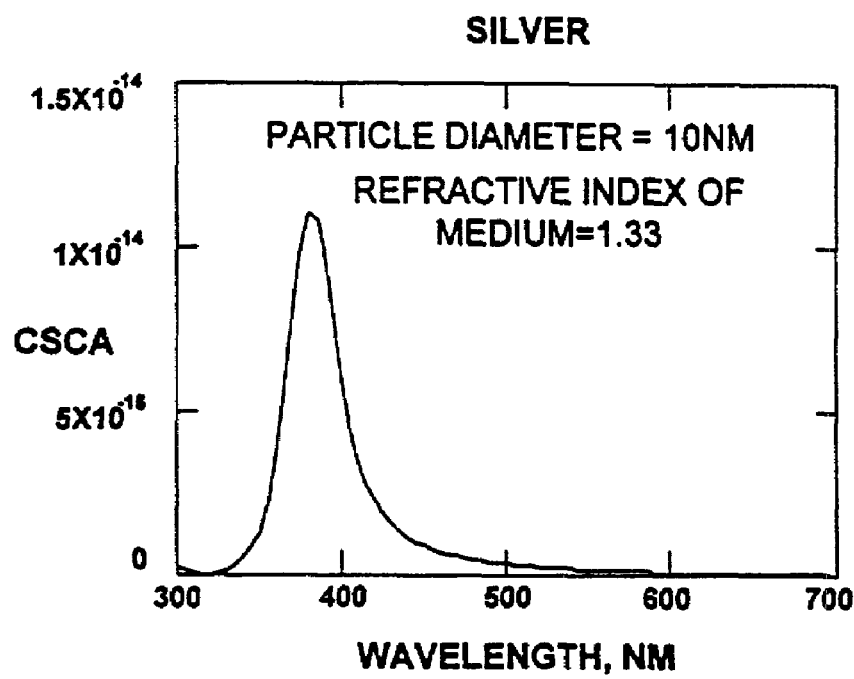
Figure 26C:
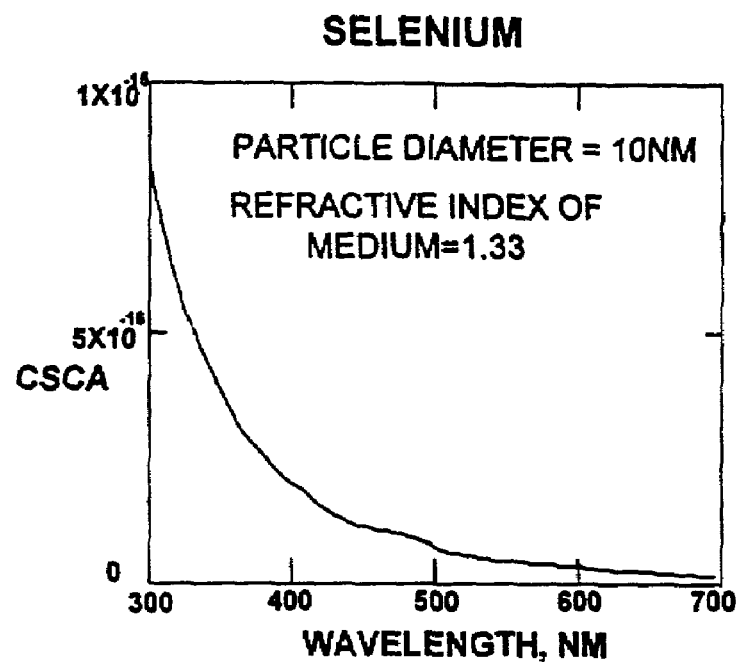
Figure 26D:
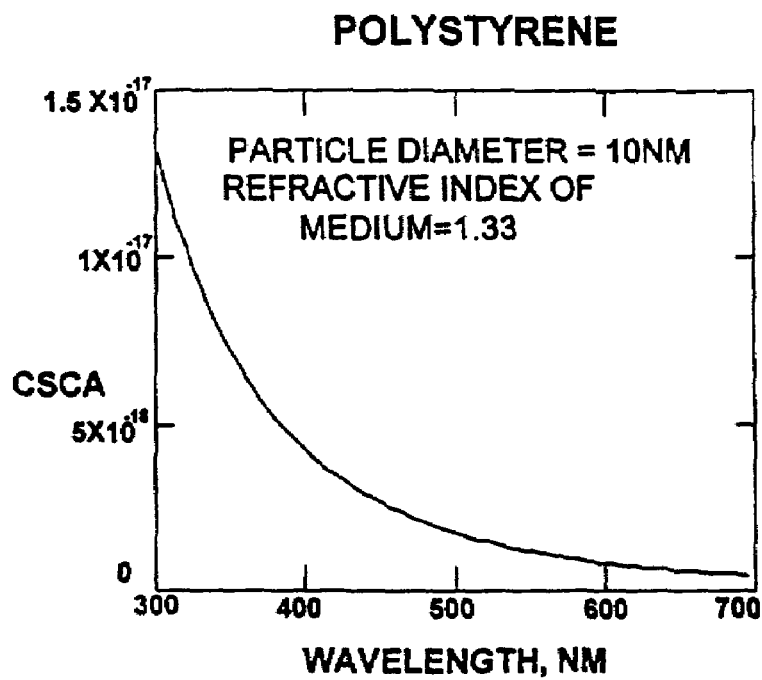
Figure 26E:
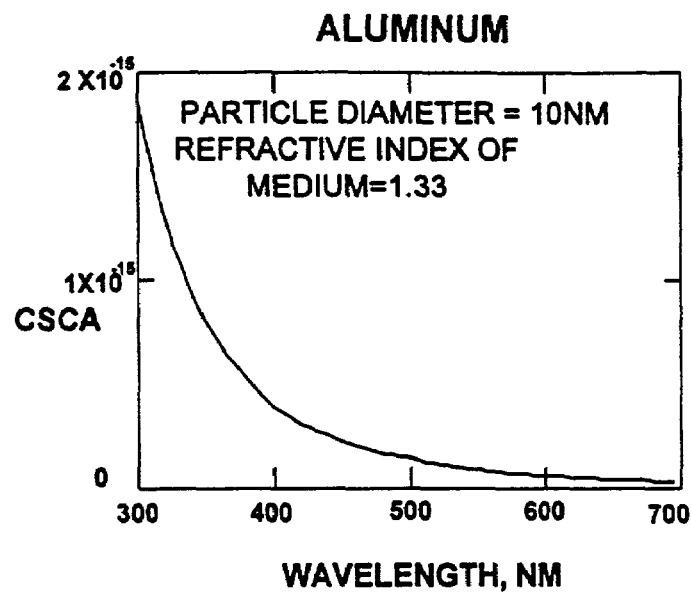
Figure 26F:
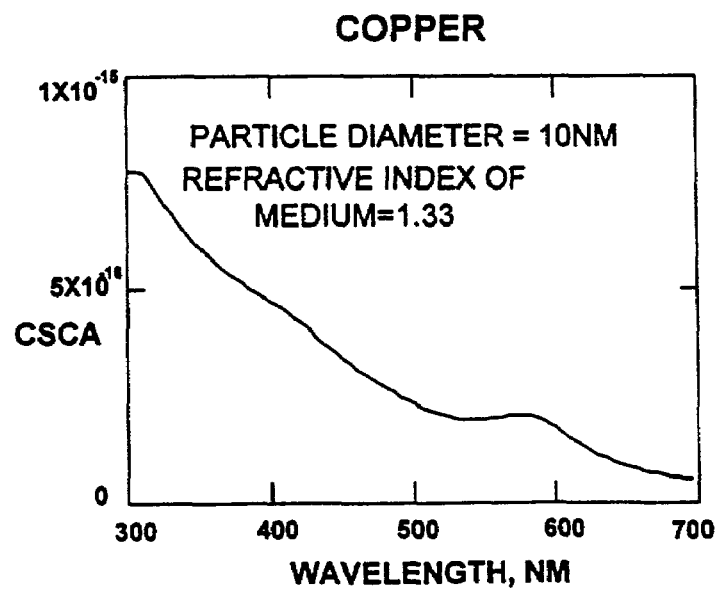

FIGS. 25 outlines an apparatus and assay development process.

FIGS. 26 A, B, C, D, E, and F show the calculated scattered light intensity versus incident wavelength profiles for spherical 10 nm diameter gold, silver, aluminum, copper, selenium, and polystyrene particles respectively. $L_k$ is the wavelength; $C_{sca}$ is the light scattering cross section.

Figure 27:
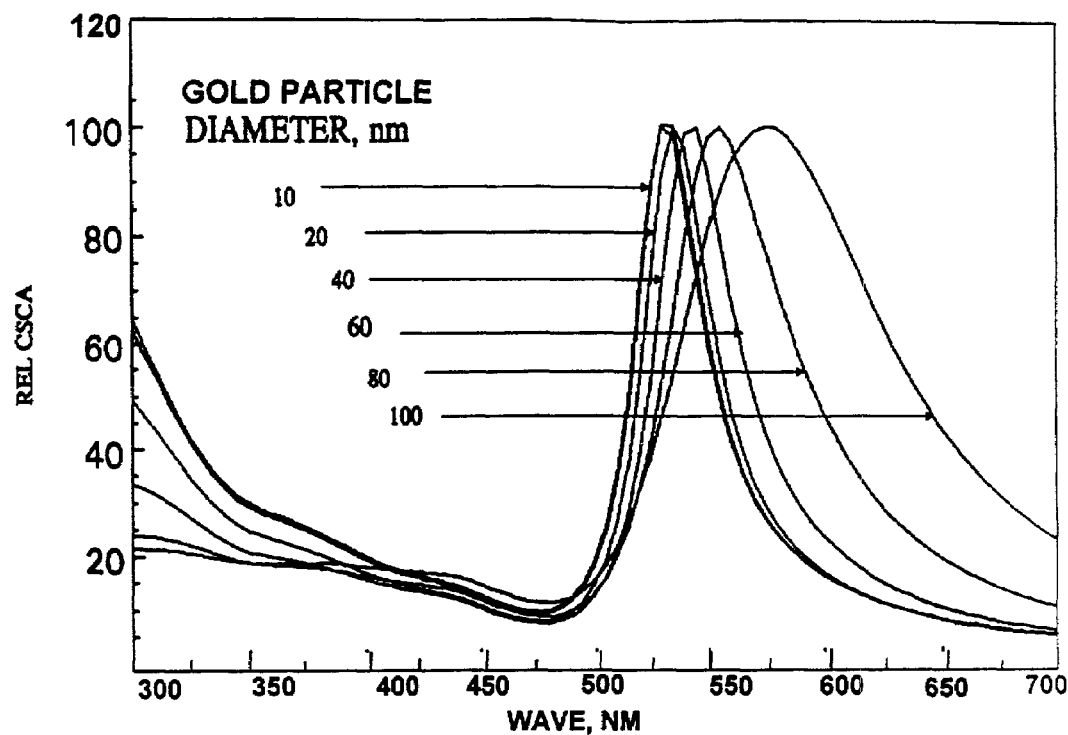

FIG. 27 shows the calculated scattered light intensity versus wavelength of incident light for spherical gold particles of 10, 20, 40, 60, 80, and 100 nm in diameter REL CSCA is the relative light scattering cross section; WAVE, NM is the wavelength.

Figure 28:
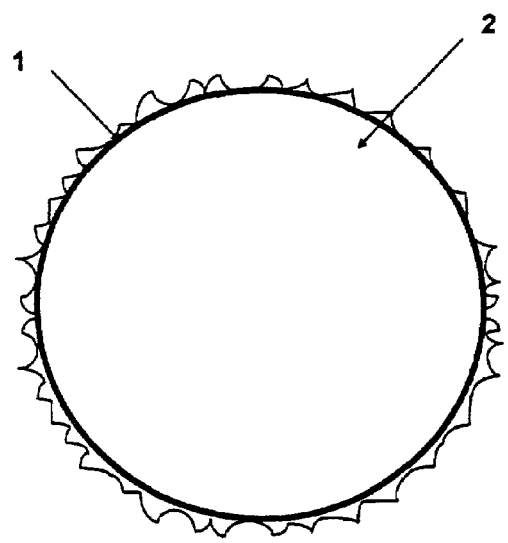

FIG. 28 is a diagram of a spherical coated particle (1) is a coat of polymer, binding agent, or other substance on the surface of the particle; (2) is the core particle.

Figure 29A:
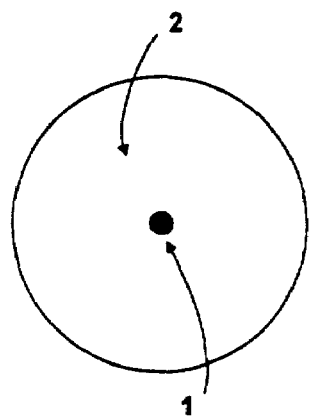
Figure 29B:
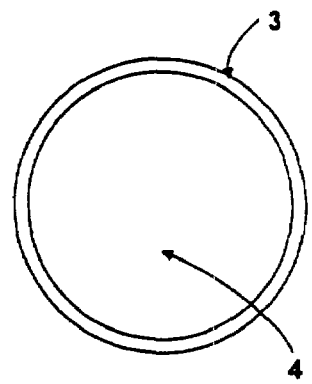
Figure 29C:
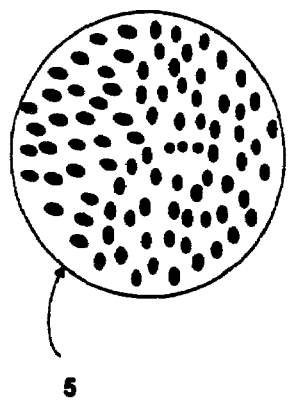

FIGS. 29 A, B. and C show diagrams of MLSP (Manipulatable Light Scattering Particle) mixed composition particles. A(1) is a core magnetic or ferroelectric material coated with (2)the desired light scattering material; B shows (4) a light scattering material core coated with (3) magnetic or ferroelectric material; C shows a mixture of (5) light scattering material with (6) magnetic or ferroelectric material.

Figure 30A:
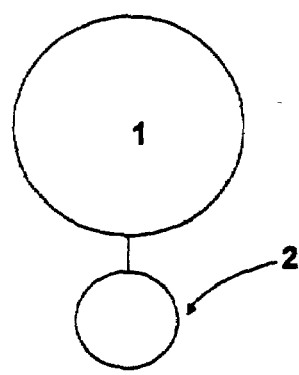
Figure 30B:
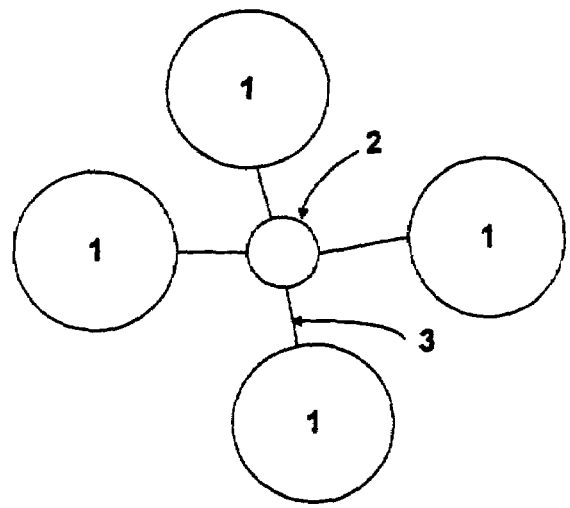
Figure 30C:
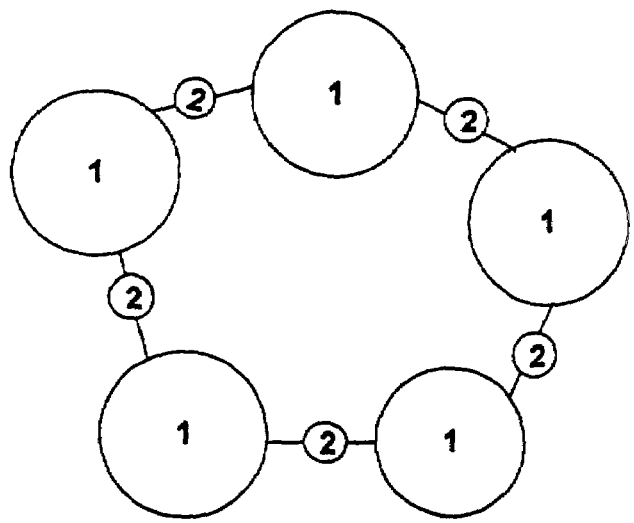

FIGS. 30 A, B, and C show dimer, tetramer, and higher order particle constructs respectively for orientable MLSP particles. (1) are light scattering detectable particles and (2) are magnetic or ferroelectric particles. The line (3) is the linkage chemical, ionic, or other that binds the particles together in the multi-particle construct.

Figure 31:
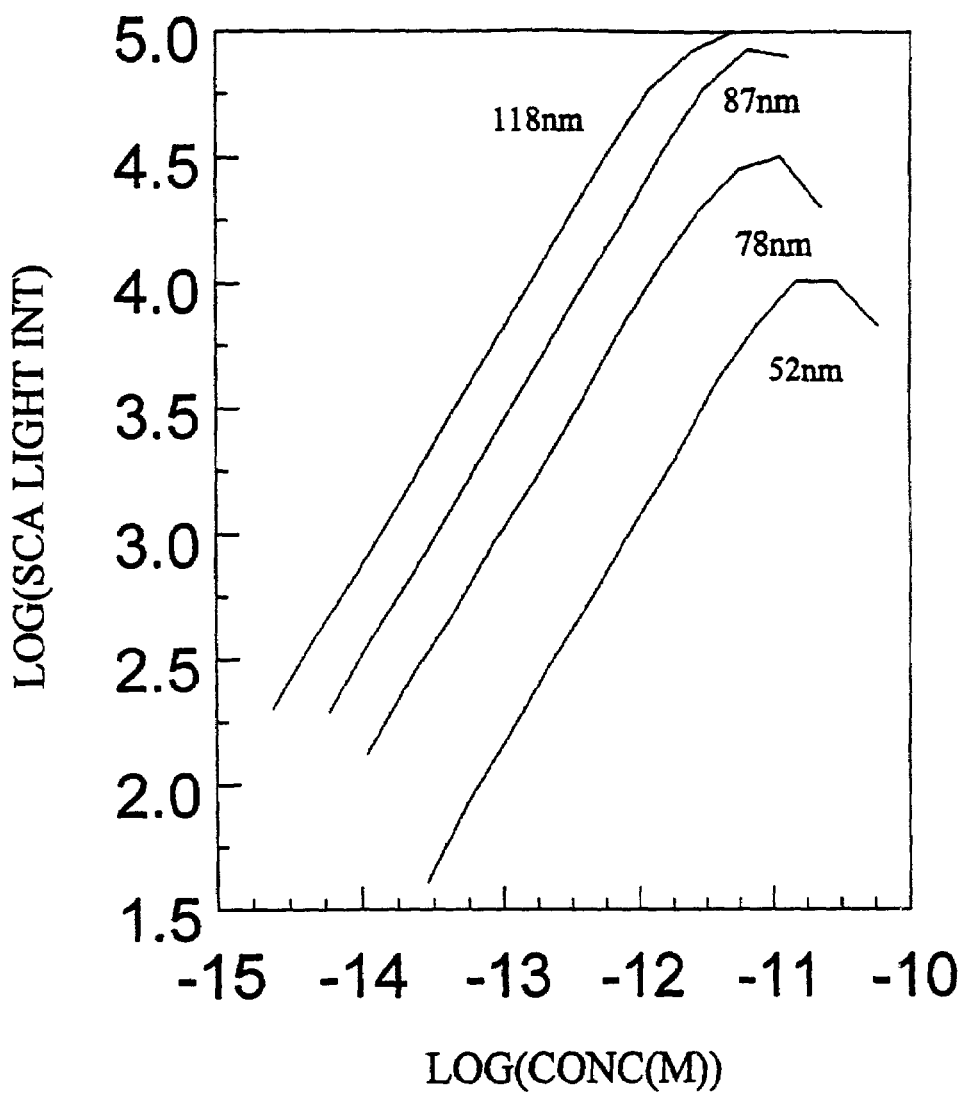

FIG. 31 shows the relationship of detected scattered light intensity versus particle concentration for a series of roughly spherical gold particles of different diameter.

Figure 32:
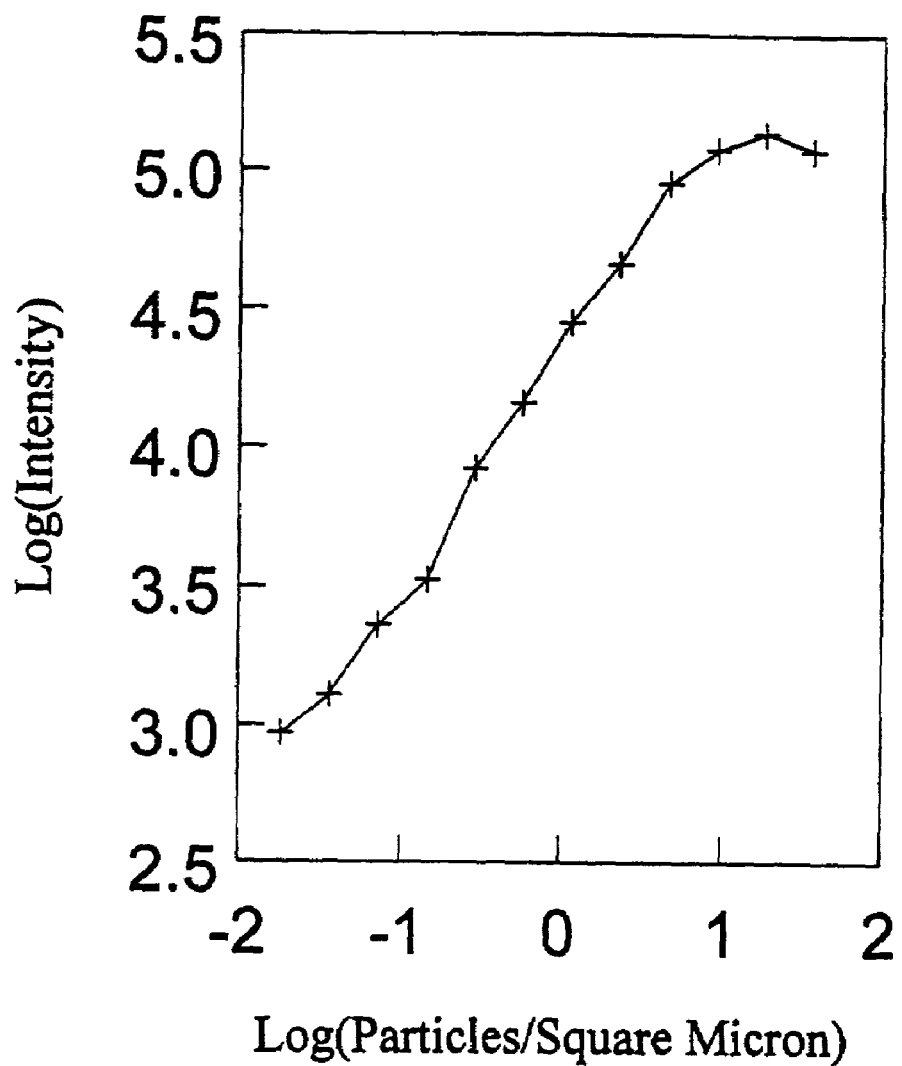

FIG. 32 shows the relationship of detected scattered light intensity versus particle density for roughly spherical gold particles of about 60 nm in diameter which are associated with a solid-phase.

Figure 33:
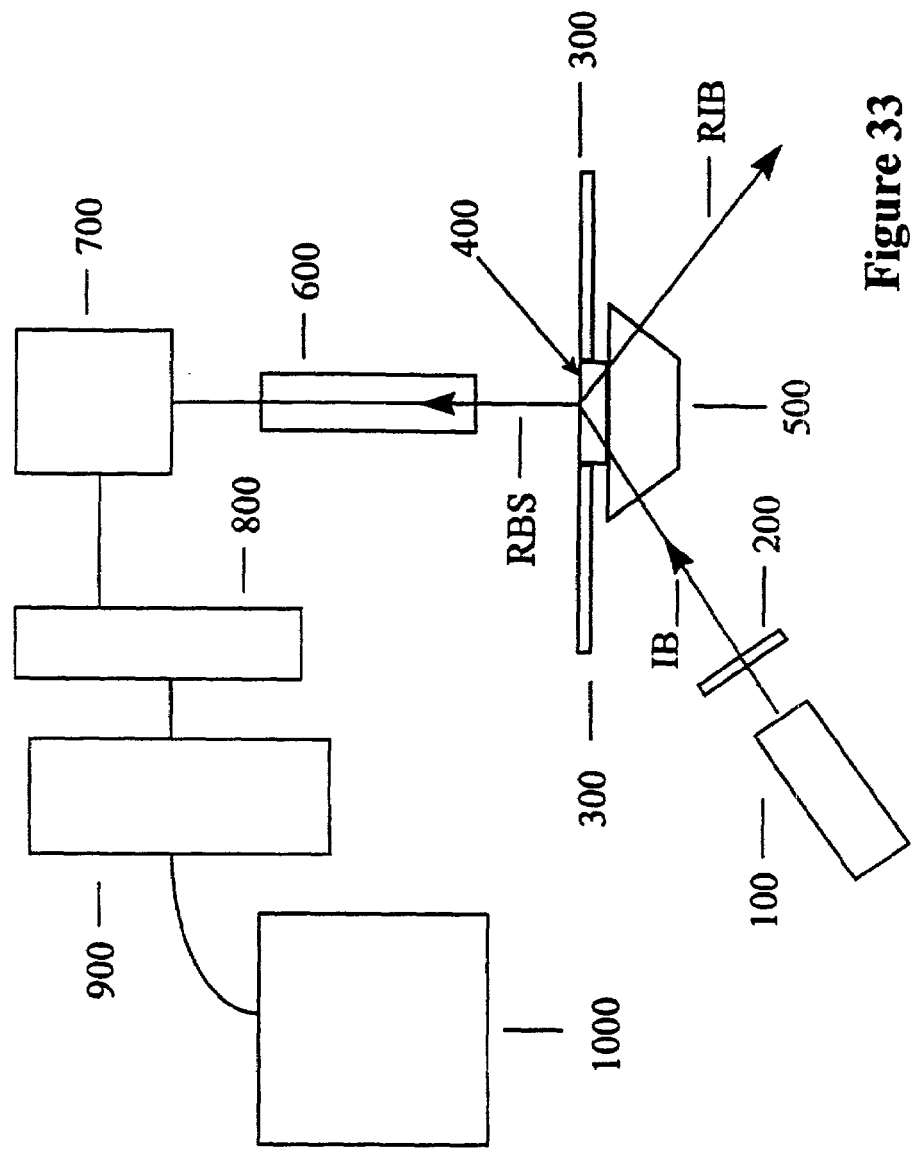

FIG. 33 shows a diagram of an apparatus for the detection of light scattering from light scattering particles. An illumination source (100) provides an illumination beam (IB) to the sample (400) through a focusing lens (200) and a light guide (500). Adjustment of the angle of illumination, the focusing of the beam and alignment with the light guide determine the location and size of the area within the sample being illuminated. A sample holder (300) is used to hold the sample in place and adjust the samples position with respect to the illumination and detection optics in three-dimensions. The illumination beam enters the sample (400) and is oriented such that little or no stray or reflected light (RIB) enters into the collection optics (600). The collection optics are adjusted by varying different combinations of lenses such that a desired field of view of the sample is obtained. The radiated beam of the sample (RBS) is focused through the collection optics onto an imaging photodetector (700). The output of the imaging photodetector is attached to an optical digitizer (800) and image processor (900) which in turn are part of or attached to a microprocessor controller or computer (1000) which controls the transfer of the digitized images to the computer screen and/or to storage media.

Figure 34:
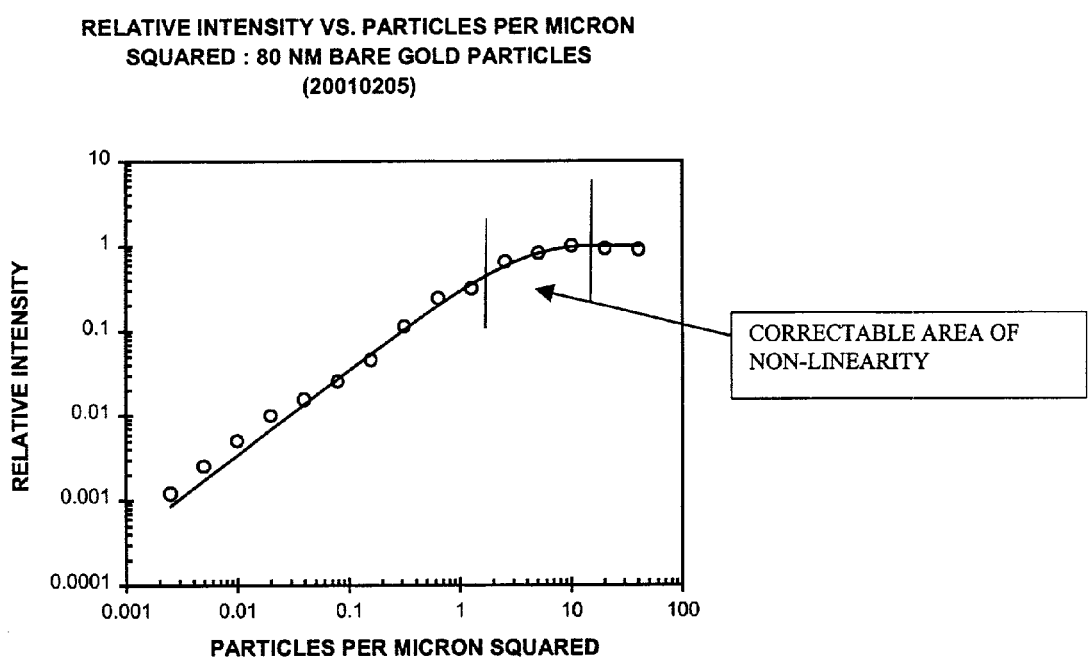

FIG. 34 illustrates a signal versus particle density curve, specifically showing an exemplary portion of the curve correctable by de-convolution.

5. DESCRIPTION OF THE PREFERRED EMBODIMENTS

5.1 Abbreviations

The following abbreviations are used herein.
E-EMR—Emitted Electromagnetic Radiation
I-EMR—Incident Electromagnetic Radiation
EMF—Electromagnetic Field
SC—Semiconductor
Sec—Second
$Q_f$—Fluorescence Quantum Yield
$I_{abs}$—Incident Light Absorption (Photons absorbed per sec)
$I_O$—Incident Light Intensity (Photons per sec)
M—Molarity (Moles per liter)
ml—Milliliter
mM—Millimolar
g—gram
mg—milligram
mm—millimeter
µl—microliter
pI—Isoelectric point
E or e—Molar Decadic Extinction Coefficient ($M^{-1}$ $cm^{-1}$)
C—Molar Concentration (M)
X—Optical Path Length (cm)
$I_f$—Fluorescence Intensity (Photons per sec)
$S_{eff}$—Scattering efficiency of a particle
$C_{abs}$—Absorption Cross Section ($cm^2$)
$A_{CSR}$—Ratio of Particle Absorbance Cross Section Over the Particle Physical Cross Section Area
$C_{sca}$—Scattering Cross Section ($cm^2$)
$S_{CSR}$—Ratio of Particle Scattering Cross Section Over the Particle Physical Cross Section Area
a—Radius of a Particle
$C_{ext}$—Scattering Extinction Cross Section of Particle ($cm^2$)
I—Photons per sec which exit a solution after passing through a solution thickness X
N—Particle Concentration (particles/$cm^3$)
t—Turbidity of Suspension
$I_S$—Scattering Intensity (Photons/sec)
$n_2$—Refractive Index of Material
$n_2$Rel—Real Component of $n_2$
$n_2$Im—Imaginary Component of $n_2$
$n_1$—Refractive Index of Medium
m—The ratio of Refractive Index of Particle Material to Refractive Index of Medium
$l_O$—Incident Light Wavelength (nm)
RI—Refractive Index Factor
Refmed—Refractive Index of Medium ($n_1$)
$e_m$—Dielectric constant of medium
$n_m$—Refractive index of medium
a—Determines the polarizability of the coated particle
nm—nanometer
cm—centimeter
µ—micron

5. DETAILED DESCRIPTION OF THE PREFERRED EMBODIMENTS

The methods of the present invention are advantageously applied to methods for the detection and measurement of one or more analytes in a sample, especially to analyte detection and/or quantitation methods based on the use of specific types of particles of certain composition, size, and shape (RLS particles) and the detection and/or measurement of one or more of the particle's light scattering properties.

The method described herein utilizing RLS particles is easier to use, has greater sensitivity and specificity, and is capable of detection and measurement across a wider concentration range of analyte(s) than was previously possible. The RLS particle methods described thus have many advantages over the use of the methods of signal and target analyte amplification (e.g. chemiluminescence and PCR), fluorescence labels and fluorescence methods, and previous particle-based assays and light scattering methods. The method is versatile and has broad application to the field of diagnostics as well as other fields. The method can be used in most, if not all, standard binding-pair type assays such as immunoassay and nucleic acid assays and the like for samples in the liquid-phase, mixed-phase, solid-phase, and solid-phase microarray assay formats.

Rather than illustrate the broad utility of the RLS particle method by explicit illustrations of each specific practice of a particular form of the invention, the key elements and considerations for one of average skill in the art to practice this invention to fit most, if not all, analyte detection needs. Such practice provides specific method embodiments, and specific apparatus and test kits.

The disclosure presented herein enables one of ordinary skill in the art to practice the RLS particle method in many different forms to achieve a desired analyte or particle detection capability to suit most if not all sample types, analyte types, diagnostic assay format types, and apparatus types. The method is so versatile that it can be practiced to detect one or more analytes in the field (away from a lab), or in a small medical or analytical lab, at the bedside, emergency rooms, specialized hospital care units (such as cardiac care, intensive care, trauma unit and the like), a research lab, or the capability to process many samples a day. Different types of inexpensive apparatus and test kits can be made by practice of the invention in one form or another to suit a specific analytic diagnostic need.

There are several features of the RLS particle method which, when practiced in various combinations with each other, define the analyte detection capabilities for a specific practice. Two of these features are (1) the use of specific particle types that possess highly measurable and detectable light scattering properties in a defined assay format and sample type, and (2) use of specific particle types with a preferred method of illumination and detection. In certain applications, refractive index enhancement methods and video contrast enhancement methods are also used.

Determination of Useful Light Scattering Properties of Metal-like Particles

The following provides information helpful to fully understand the RLS particle method. The formulae presented are useful in practice and optimization of the invention, but are not admitted to be prior art to the claims.

In the development of the signal generation and detection system for the detection of analytes of the RLS particle method, it was useful to develop new formulae which allowed us to evaluate various light scattering attributes of different particle types in terms of fluorescence parameters. This allowed us to study $\epsilon$, $Q_f$, fluorescence and excitation spectra, dependence of the emitted light intensity on the angle of observation, and state of polarization of the emitted light (these are defined below). These formulae allows one of ordinary skill in the art to select the specific particle parameters such as composition, size, and shape to embody desirable light scattering property(s) that can be detected and measured when used in diagnostic assays or any other application. Equations 1 through 7 are presented as background information so the reader will understand the new formulations of Equations 8 through 15. It should not be taken as an admission that any of the formulae or light scattering parameters described is prior art to the claims.

The analytical method developed is based on certain modifications of the art known light scattering theories of Rayleigh and Mie to evaluate many different types of particles with different parameters of size, shape, composition, and homogeneity to determine what specific configurations of particle parameters result in desirable light scattering signals that are easily detected and measured in analytical and diagnostic assays.

Definitions of Fluorescence Parameters

For fluorescent materials, the fluorescence intensity is determined by the product of the number of photons which are absorbed per second and the fraction of absorbed photons that are re-emitted as light (the $Q_f$) as shown by equation 1.

$$I_{abs}(\lambda)=2.303I_O(\lambda)e(\lambda)Cx \qquad (1)$$

where $I_O(\lambda)$ is the incident light intensity (photons/sec) wavelength $\lambda$, $I(\lambda)$ is the molar decadic extinction coefficient in units of $M^{-1}$ $cm^{-1}$ at wavelength $\lambda$ and C is the molar concentration (in units of M) of the fluorophore and x is the optical path length in cm.

The integrated fluorescence intensity $I(\lambda_f)$ (sum of photons emitted in all direction per sec) at the emission wavelength $\lambda_f$ and excitation wavelength $\lambda_e$ is given by (for low fluorophore concentrations)

$$I(\lambda_f)=2.303I_O(\lambda_e)Q_f(\lambda_f)e(\lambda_f)Cx \qquad (2)$$

The assessment of the usefulness of a flourescent compound in an assay application in terms of the listed parameters is a well known procedure. Use of fluorescent molecules and fluorescent techniques is limited by the photostability of the fluorescent molecule, and the ability to detect the specific fluorescence emission signal in samples with high levels of non-specific fluorescence, phosphorescence, and scattered light. For sensitive detection of fluorescent molecules or other fluorescent substances such as particles composed of fluorescent dye molecules, more sophisticated instrumentation is required.

Definitions of Light Scattering Parameters

Absorption Cross Section ($C_{abs}$) of a Particle

Consider a particle that is illuminated by a monochromatic beam of light of wavelength $\lambda$. The absorption cross section $C_{abs}$ of the particle is defined as an area (usually expressed in units of $cm^2$ or $\mu^2$) surrounding the particle, such that any photon falling on this area will be irreversibly absorbed by the particle. The value of $C_{abs}$ depends on the particle size, composition, shape and homogeneity. It also depends on the wavelength of light and a plot of Cabs vs. wavelength gives the pure absorption profile of the particle. The Cabs vs. wavelength profile for any spherical particle with a homogeneous composition can be calculated with Rayleigh or Mie theory. In our terminology, $C_{abs}$ is related to irreversible light absorption. The nature of $C_{abs}$ can be better understood by reference to the section below where we define the extinction cross section $C_{ext}$.

Relative Absorption Cross Section $A_{csr}$

The relative absorption cross section $A_{csr}$ is defined as the ratio of the particle's $C_{abs}$ divided by the physical cross sectional area of the particle $\pi a^2$ where a is the radius of the particle, i.e., $A_{csr}=C_{abs}/\pi a^2$. $A_{csr}$ provides a measure of the particle's ability to irreversibly absorb photons falling on the area surrounding the particle. $A_{csr}$ can have values in the range of 0 to 6 depending on the composition, shape, and size of particle and the wavelength of light. A value greater than one means that a particle can reach beyond its physical dimensions to attract photons to it and absorb them. In the physical literature, $A_{csr}$ is called the absorption efficiency factor of the particle. This nomenclature is misleading since $A_{csr}$ can have values greater than 1, uncharacteristic of an efficiency.

Light Scattering Cross Section ($C_{sca}$) of a Particle

There is a finite probability that a photon of light absorbed (absorbed here includes reversible and irreversible absorption) by a scattering particle is re-emitted at the same wavelength as the absorbed photon (quantum mechanical point of view). The re-emitted photon can be emitted in directions different from the direction of the incident photon. That is, the incident photons are scattered by absorption and re-emission. The scattering cross section of a particle ($C_{sca}$) at the incident wavelength is defined as an area surrounding the particle such that every photon which falls on that area is scattered (that is absorbed and then re-emitted in the quantum mechanical view). $C_{sca}$ is usually expressed in units of $cm^2$ or $\mu^2$ and depends on the composition, shape, size and homogeneity of the particle and the wavelength. The light scattering profile $C_{sca}$ versus wavelength can be calculated for any spherical particle of homogeneous composition using Rayleigh or Mie theory.

Ratio of $C_{sca}$ to Physical or Geometric Cross Sectional Area of a Particle ($S_{csr}$)

The ratio of the particle's $C_{sca}$ divided by the physical or geometrical cross sectional area of the particle $\pi a^2$, (where a is the spherical radius of the particle) provides a measure of the particle's ability to attract, absorb, and reemit photons from the area surrounding the particle). That is $S_{csr}=C_{sca}/\pi a^2$. In the physical literature, $S_{csr}$ is called the scattering efficiency factor.

Experimental and theoretical results show that the value of $S_{csr}$ can be in the range of 1 to 5 or greater depending on particle composition, shape, homogeneity and size and wavelength of light. A $S_{csr}$ value greater than one means that a particle can reach beyond its physical dimensions to attract photons to it and absorb and then re-emit them. This is possible because an electrical interaction of the particle with the electromagnetic wave of the photon can occur at distances larger than the radius of the particle. In general, $S_{csr}$ increases with particle size. For small particles (less than ~40 nm) the $S_{csr}$ is less than one while for larger particles $S_{csr}$ equals greater than one and can reach a value of five for the larger particles.

Extinction Cross Section ($C_{ext}$) of a Particle

The extinction cross section $C_{ext}$ of a light scattering particle is defined as the sum of the scattering cross section ($C_{sca}$) and absorption cross section ($C_{abs}$) of the particle.

$$C_{ext}=C_{sca}+C_{abs} \quad (3)$$

$C_{ext}$ is usually expressed in terms of $cm^2$ or $\mu^2$.

The extinction cross section $C_{ext}$ of any particle can be readily measured at any given wavelength in a regular absorption spectrometer. Let $I_o$ (photons/sec) be the intensity of a light beam falling on suspension of particles which are at a concentration of N particles/$cm^3$. X(cm) is the thickness of the solution and I (photons/sec) is the amount of light which exits the solution after traversing the distance x. The intensities are related to $C_{ext}$ by the expression:

$$I_{(\lambda)}=I_{o(\lambda)}e^{-NC_{ext(\lambda)}x} \quad (4)$$

This expression shows explicitly the parameters depend on $\lambda$. It is assumed that the photodetector is positioned such that it does not detect scattered light.

When the particles are pure scatterers, that is, do not irreversibly absorb any light, then $c_{ext}=C_{sca}$ and the above equation is written as $$I=I_o e^{-NC_{sca}x} \quad (5)$$

$$=I_o e^{-\tau x} \quad (6)$$

where $t=NC_{sca}$ is the turbidity of the suspension.

Molar Decadic Extinction Coefficient

In the field of chemistry, the strength with which a substance in solution absorbs light at a given wavelength is expressed in terms of the molar decadic extinction e which has units of $M^{-1}$ $cm^{-1}$ (M stands for moles/liter). This coefficient is related to the experimentally determined absorbance by the expression $$A_{(\lambda)}=e_{(\lambda)}Cx \quad (7)$$

Applicant Developed Formulae for Studying Particle Light Scattering Parameters

Theoretical methods used for the RLS particle method described herein are now described. One skilled in the art can use the following methods to evaluate, modify, and adjust specific particle parameters of composition, size, shape, and homogeneity to derive one or more desirable light scattering properties that are easily detected and measured. Considerations should be made with regard to sample types, diagnostic formats, and limitations of apparatus means. For example, in one application, multi-analyte detection may be performed on a solid-phase sample that contains a high non-specific light background on a high throughput testing apparatus, while in another application, single analyte detection in solution is performed in the doctors office.

A major interest was in optimizing particle types for use in analytical and diagnostic assays. In most of these applications, the particles are coated with a macromolecular substance such as polymer, protein, or the like to confer suitable chemical stability in various mediums. Some such coatings have been described in the art. Binding agents such as antibodies, receptors, peptides, and the like are placed on the surface of the particle so that the coated particle can be used in an analytic or diagnostic format. In some applications, the binding agent serves a dual function in that it stabilizes the particle in solution and provides the specific recognition binding component to bind the analyte. The coating of particles with proteins such as antibodies is known in the art. However, for the present RLS methods, for measuring one or more specific parameters of the light scattering signals of different types of particles which in some cases are of similar size and/or shape and/or composition, it was not known if such optical resolvability of one or more of the specific light scattering properties of coated particles was possible.

It was determined by physical experimentation and theoretical modeling that the presence of thin coats of binding agents, non-optically absorbing polymers (in the visible region of the spectrum), or other materials on the particle surface does not noticeably alter the light scattering properties specific for that type of particle which is not coated with these types of materials.

By "thin coat" is meant monolayer(s) of different amounts and compositions of the above materials coated on the surface of the particle.

It was determined that a molar decadic extinction coefficient can be determined at any wavelength for a coated or uncoated particle suspension by measuring its absorbance at that wavelength. The molar decadic extinction coefficient at that wavelength can then be calculated with Eq. (7) and the following expression to convert particle concentration from N(particles/cm³) to C(M). M is moles/liter.

$$C(M)=1000\ N(\text{particles/cm}^3)/6.03 \times 10^{23} \qquad (8)$$

The molar decadic extinction coefficient can be related to the extinction cross section Cext (or vice versa) by the expression $$\varepsilon(M^{-1}cm^{-1}) = \left[C_{ext}(cm^2/\text{particle})(6.03 \times 10^{23})\right]/2.303 \times 1000 \qquad (9)$$

$$= 2.63 \times 10^{20} C_{ext}(cm^2/\text{particle}) \qquad (10)$$

or $$C_{ext}(cm^2/\text{particle}) = 2.303(M^{-1}cm^{-1}) \times 1{,}000/6.03 \times 10^{23} \qquad (11)$$

$$= 3.82 \times 10^{-21}\ \varepsilon(M^{-1}cm^{-1}) \qquad (12)$$

With Eq. (9) or (10) we can calculate $\varepsilon$ from $C_{ext}$.

As described previously, it is well known in the art that for particles, the extinction cross section ($C_{ext}$) is equal to the sum of the scattering cross section ($C_{sca}$) and the absorption cross section ($C_{abs}$). The extinction coefficient $\varepsilon$ reflects the loss of photons from the incident beam by irreversible absorption as well as by scattering (absorption and re-emission). It was determined that the molar decadic extinction coefficient of a particle, evaluated experimentally or by calculation from the extinction cross section, can be used to compare the absorption power of a particle with, for example, that of a fluorophore as shown later.

Light Scattering Efficiency ($S_{eff}$)

It was determined that a light scattering efficiency $S_{eff}$ can be defined for a coated or uncoated particle, by analogy to fluorescence efficiency $Q_f$, as the fraction of photons absorbed (reversible plus irreversible absorption) by a particle that are re-emitted as scattered light. Mathematically, applicant defines the scattering efficiency by the expression $$S_{eff} = C_{sca}/C_{ext} \qquad (13)$$

$$= C_{sca}/(C_{sca}+C_{abs})$$

For particles which are pure scatters, that is, particles composed of a material which does not irreversibly absorb photons but only absorbs and re-emits photons, $C_{abs}$ is equal to zero and $S_{eff}$ is equal to one. Small polystyrene particles behave as pure light scatters in the visible region of the spectrum and $S_{eff}$ is 1 for these particles. For particles composed of materials which reversibly and irreversibly absorb photons, $S_{eff}$ is less than one. Gold particles display the latter type of behavior in the visible region of the spectrum.

Intensity of Light Scattered by a Particle

It was determined that the intensity of light scattered by a coated or uncoated particle is determinable by the product of the number of photons which are absorbed (reversibly and irreversibly) per second and the fraction of the absorbed photons that are re-emitted (quantum mechanical point of view). Light scattering intensity measurements are usually done in dilute solutions where the amount of light absorbed, $I_{abs}$ (photons absorbed per second) is given by $$I_{abs}=I_o 2.303 \varepsilon C x \qquad (14)$$

$I_o$ is the incident light intensity (photons/sec), $\varepsilon$ is the molar decadic extinction coefficient of the particles in terms of $M^{-1}$ $cm^{-1}$, C is the molar concentration of the particles and x is the optical path length in cm.

Applicant further realizes that the total scattered light intensity $I_S$, intensity integrated over all light scattering angles, is then given by the relation:

$$I_{S(\lambda)}=2.303 I_{o(\lambda)} S_{eff(\lambda)} \varepsilon_{(\lambda)}(C)(x) \qquad (15)$$

where $I_{o(\lambda)}$ is the intensity of the incident light. This equation is comparable to Eq. (2) for a fluorophore.

Note that when the expressions for $\varepsilon$ and $S_{eff}$ in terms of $C_{sca}$ and $C_{ext}$ are inserted in the above equation, the result shows that the scattered light intensity is directly proportional to and completely determined by the magnitude of the scattering cross section ($C_{sca}$). This means that the relative scattering intensities of different particles can be predicted from their scattering cross sections.

Specific Light Scattering Properties of Particles

Some of the most important light scattering properties that can be used to detect analytes in various sample types using a variety of different assay formats are now described. The measured light scattering properties that are detected are one or more of the following: the intensity, the wavelength, the color, the polarization, the angular dependence, and the RIFSLIW (rotational individual fluctuations in the scattered light intensity and/or wavelengths) of the scattered light.

Coated and uncoated metal-like particles have similar light scattering properties and both have superior light scattering properties as compared to non-metal-like particles. In addition, applicant has determined that it is relatively easy to adjust the types of light scattering properties in metal-like particles by varying in one form or another, the size, shape, composition, and homogeneity such that the specific light scattering attributes can be measured from the metal-like particle in various sample types.

Metal-like particles can be detected to extreme sensitivity. The individual particles are easily detected to the single particle limit using illumination and detection methods described herein with inexpensive and easy to use apparatus.

One or more types of metal-like particles are detected in a sample by measuring their color under white light or similar broad band illumination with illumination and detection methods as described. For example, roughly spherical particles of gold (for example, coated with binding agent, bound to analyte, released into solution or bound to a solid-phase) of 40, 60, and 80 nm diameters and a particle of silver of about 30 nm diameter can easily be detected and quantitated in a sample by identifying each particle type by their respective unique scattered light color and/or measuring the intensity. This can be done on a solid phase such as a microtiter well or microarray chip, or in solution. The measurement in solution is more involved, because the particles are not spatially resolved as in the solid-phase format. For example, one can detect the different types of particles in solution by flowing the solution past a series of detectors each set to measure a different wavelength or color region of the spectrum and the intensity at these different wavelengths is measured. Alternatively, a series of different wavelengths of illumination and/or detection can be used with or without the flow system to detect the different particle types.

For solid-phase analytical applications, a very wide range of concentrations of metal-like particles is detectable by switching from particle counting to integrated light intensity measurements depending on the concentration of particles. The particles can be detected from very low to very high particle densities per unit area.

In other assay applications, the particles which are bound to a solid substrate such as a bead, surface such as the bottom of a well, or the like can be released into solution by adjusting the pH, ionic strength, or other liquid property. Higher refractive index liquids can be added, and the particle light scattering properties are measured in solution. Similarly, particles in solution can be concentrated by various means into a small volume or area prior to measuring the light scattering properties. Again, higher refractive index liquids can be added prior to the measurement.

Figure 8:
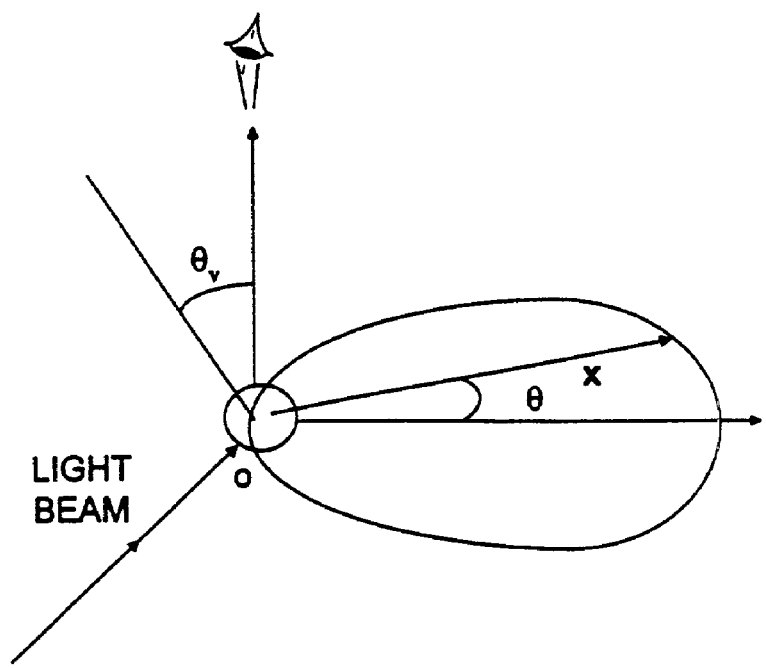
FIG. 8 illustrates an angular distribution of light scattered by surface artifacts and particles; the dashed lines represent light scattered by the particle; the solid line with an arrow is incident white light beam, and one beam of scattered light by surface artifacts, and the circle is an intensity envelope for the light scattered in the forward direction.

Both theoretical evaluation and physical experimentation indicate that for spherical particles of any composition up to about 120 nm in diameter and somewhat greater, a large proportion of the light scattered by the particle is radiated outside the envelope of the forward direction of the scattered light (see FIG. 8). Applicant determined that detection and measurement of the scattered light at angles outside of the envelope of the forward direction of scattered light provides for a significant decrease in non-specific scattered light from the light beam and other light scattering constituents and objects being detected. This significantly increases the specific light scattering signal/non-specific light scattering ratio for many samples.

The intensity of light scattered by a particle in different directions and the state of polarization of the scattered light depends on the wavelength and state of polarization of the incident light and on the particle size, shape and homogeneity. Below we summarize some of the most important facts concerning the intensity and state of polarization of light emitted in different directions by certain types of particles.

Smaller particles of spherical shape (smaller being about $\frac{1}{20}$ or smaller as compared to the wavelength of light) behave as isotropic dipole scatterers or emitters, that is, the light is highly polarized. This is very different to fluorescent molecules which usually behave as linear dipole emitters. For example, such particles when illuminated with unpolarized light, the light scattered in the direction $\phi=0$, $\theta=90$ (see FIG. 20) is one hundred percent linearly polarized (P=1). This property allows for the more specific and more sensitive detection of analytes by measurement of the light scattering properties as compared to fluorescent molecules in many different types of samples.

For even larger particles (>$\frac{1}{20}$ wavelength of light) there are certain ranges of particle sizes where the degree of polarization of light P decreases and becomes dependent on the wavelength as the size increases. As the particles become very large the degree of polarization approaches 0 for the direction $\theta=0$, $\phi=90°$. There appears to be certain size ranges where the change in polarization changes the most, that is, the slope of degree of polarization versus size is at a maximum. Those regions where the slope is changing are used in certain analytic applications as for example, agglutination or aggregation types of assays to detect and measure one or more analytes in a sample.

For larger spherical particles in certain size ranges, for example from about 200 nm to about 1.2 microns in diameter, the intensity of light oscillates (for monochromatic incident light) between relative values of 1 to 0 as the angle $\phi$ is changed from 90° to −90° for $\theta=0$ with reference to FIG. 20. That is, if one views the scattered light in the horizontal plane ($\theta=0$), the light intensity oscillates from bright to dark as the eye is moved from $\theta=90°$ to $\theta=−90°$. For illumination with white light, the light changes color as the eye is moved from $\theta=90°$ to $\theta=−90°$. That is, the particles behave as diffraction gratings. Such light scattering properties are very useful to detect more specifically and to greater sensitivity one or more analytes in many different types of samples.

Small nonspherical particles behave somewhat as linear dipole scatters with the absorption and emission moments along the long axis of the particle. Applicant has observed the following under suitably selected illumination and detection conditions in an ordinary light microscope. When the illuminating light is linearly polarized, the non-spherical particles flicker as they rotate. The particles are most intense when their orientation is such that their long axis is oriented in the direction of polarization and is at a minimum when the moment is perpendicular to this direction. In contrast, small spherical particles do not flicker when illuminated by polarized light.

For nonspherical particles of certain compositions, the color of the scattered light (with white light illumination) changes with the degree of asymmetry. As the asymmetry is increased, the color shifts towards longer wavelengths. For example, asymmetric particles of silver were observed by applicant to change colors as the particles were rotating in solution when viewed with an ordinary light microscope under DLASLPD like conditions. This property termed "RIFSLIW" by applicant (rotational individual fluctuations in the scattered light intensity and or wavelengths) is used in many different aspects of the current invention to more specifically and more sensitively detect and or measure one or more analytes or particles in a sample.

It was also determined that certain mixed compositions of particles made from metal-like materials, and non-metal-like and metal-like materials provides for additional light scattering properties and/or additional physical properties. These properties include the ability to manipulate the particles by applying an EMF field. This property of the particles can be used in many different ways with the practice of one or more aspects of this invention. Applicant now provides further illustrative discussions of particle-dependent light scattering properties and the use of these properties to detect one or more analytes in a sample.

It will be useful to first describe the present invention in terms of the light scattering properties of homogeneous, spherical particles of different sizes and compositions. However, the basic aspects of the invention apply as well to non-spherical particles as one in the art can determine. In addition, it will be useful to describe the present invention in terms of the incident light wavelengths in the range 300 nm to 700 nm. However, the basic aspects of the invention apply as well to electromagnetic radiation of essentially all wavelengths.

By "light" is meant ultraviolet, visible, near infrared, infrared, and microwave frequencies of electromagnetic radiation.

It will be further useful for the description of the RLS particle method to use polystyrene particles to represent non-metal-like particles of various types. Other non-metal-like particle types include those composed of glass and many other polymeric compounds. Such particles have roughly similar light scattering characteristics as compared to polystyrene particles.

The relative intensities of scattered light obtained from different particles irradiated with the same intensity and wavelengths of incident light can be directly compared by comparing their $C_{sca}$'s. The higher the $C_{sca}$, the greater the scattering power (light scattering intensity) of the particle. In the following sections we use the words "scattering power" to mean $C_{sca}$ or scattered light intensity.

We have calculated the light scattering powers, in water, of small spherical particles identical in size, and different in composition, for incident wavelengths over the wavelength ranges of 300 to 700 nanometers (nm). In these calculations, we have used values of refractive index vs. wavelength tabulated in standard handbooks for different bulk materials in vacuum.

For some particle compositions, the light scattering power decreases continuously from 300 to 700 nm while for other compositions the scattering power vs. wavelength profile shows peaks or bands. When these peaks or bands are in the visible region of the spectrum the light scattered by the particles is colored when the incident light is white.

For illustrative purposes we show in some of the following tables various comparisons of light scattering properties for different types of 10 nm diameter particles. The general trends with regard to the relative magnitudes and wavelengths of scattered light that is demonstrated for these 10 nm diameter particles is generally the same for larger particles up to about 100 nm. For example, the calculations of Table 1 were done with particles of ten nanometer diameter. However, for small particles (less than about 1/20 wavelength of the light) the light scattering intensity vs. wavelength profiles do not change in shape as the particle size is increased as long as one remains in the small particle limit. The apparent effect of increase in particle size is to increase the amplitude of the profile graph. It is well known in the art of theoretical physics and light scattering that the scattering power of small particles increases with the sixth power of the radius. One skilled in the art can calculate the relative scattering power of any small particle of diameter d from the value obtained for the 10 nm diameter particle by multiplying the light scattering power of the 10 nm particle by $(d/10)^6$ where d is in nm. This method can be used by one skilled in the art to determine the usefulness of certain particle sizes in various diagnostic assay applications where the intensity of the scattered light of a particle is used to detect the presence of an analyte.

From our theoretical and physical experimentation we were surprised to find that this general relationship does also apply to larger particles outside of the Rayleigh limit, that is, for particles with diameters larger than about 30 nm.

Table 1 presents the calculated $C_{sca}$ values(light scattering power) and their respective approximate wavelengths in the visible range where the particles scatter light most intensely. The data of Table 1 suggest that metal-like particles are much more powerful light scatterers than, for example, polystyrene particles.

FIG. 26 shows selected calculated light scattering intensity vs. wavelength profiles for certain types of 10 nm spherical particles. Small particles composed of gold or silver exhibit very prominent scattering and absorption peaks in the visible wavelength region, while copper particles exhibit a small scattering and absorption peak in this region. The gold and silver scattered light maxima occur at about 530 nm and 380 nm respectively. Even at incident wavelengths far removed from the light scattering maxima, the light scattering power of the gold, silver, and other metal-like particles is much greater than that of non-metal-like polystyrene particles of similar size.

Table 2 presents the calculated light scattering power ($C_{sca}$) values for metal-like particles and polystyrene(non-metal-like) of 10 nm diameter when the incident (illumination) wavelength has been shifted to much longer wavelengths. In many different analytic and diagnostic assays, it is preferable to work at longer wavelengths. Table 2 indicates that one skilled in the art may use illumination wavelengths at much longer wavelengths and that the metal-like particles are far superior to non-metal-like particles as for example, polystyrene for applications to analytical or diagnostic methods. For example, at an incident light wavelength of 700 nm, a wavelength far from the light scattering maximum at 530 nm for gold particles, the data suggest that a gold particle's scattered light intensity is about 220 times more than a polystyrene particle of similar size and shape. We have experimentally observed that indeed the light scattering power(intensity) of the metal-like particles is much greater than non-metal-like particles across the visible wavelengths of the spectrum.

These results indicate that metal-like particles have much greater light scattering power than non-metal-like particles of comparable size and shape and are broadly applicable as analytical and diagnostic tracers for use in most areas where it is desirable to use a signal generation and detection system. For example, in any assay designed to detect the presence or absence of an analyte substance by detecting the scattered light from the particles.

TABLE 1

CALCULATED ($C_{sca}$) VALUES FOR TEN NANOMETER SPHERICAL PARTICLES OF DIFFERENT COMPOSITION IN WATER

| Particle Composition | Wavelength (nm)[a] | Maximum $C_{sca}$ (cm$^2$) | Relative $C_{sca}$ |
|---|---|---|---|
| Polystyrene | 300 | 1.32 × 10$^{-17}$ | 1 |
| Selenium | 300 | 8.6 × 10$^{-16}$ | ~65 |
| Aluminum | 300 | 1.95 × 10$^{-15}$ | ~148 |
| Copper | 300 | 7.8 × 10$^{-16}$ | ~59 |
| Gold | 530[b] | 1.24 × 10$^{-15}$ | ~94 |
| Silver | 380[b] | 1.1 × 10$^{-14}$ | ~833 |

[a] Incident wavelength used and at which maximum value occurs in the visible range of the EM spectrum (300-700 nm).
[b] Some particles display peaks in certain regions. See FIG. 27.

TABLE 2

CALCULATED VALUES OF ($C_{sca}$) AT 700 NM ILLUMINATION FOR 10 NANOMETER SPHERICAL PARTICLES OF DIFFERENT COMPOSITIONS IN WATER

| Particle Composition | Incident Wavelength (nm) | Maximum $C_{sca}$ (cm$^2$) | Relative $C_{sca}$ |
|---|---|---|---|
| Polystyrene | 700 | ~3.1 × 10$^{-19}$ | 1 |
| Selenium | 700 | ~1.4 × 10$^{-17}$ | ~45 |
| Aluminum | 700 | 1.4 × 10$^{-17}$ | ~45 |
| Copper | 700 | 4.7 × 10$^{-17}$ | ~152 |
| Gold | 700 | 7 × 10$^{-17}$ | ~225 |

Table 3 shows a comparison of the molar decadic extinction coefficients ($\epsilon$) calculated and experimentally measured for spherical gold particles of different diameter.

We calculated the $\epsilon$ values at the wavelength of maximum value using the expressions previously described. Measured $\epsilon$ values were obtained by measuring the optical absorption in a standard spectrophotometer at the calculated wavelength of maximum absorption. The agreement between calculated and experimentally measured ε values while not perfect, is quite good. The approximately two-fold differences observed between the observed and calculated results may reflect inaccuracies in the stated diameters of the gold particles. Details of the experimental methods are given in the Example Section.

Thus, metal-like particles coated with various types of binding agents can be used in numerous ways in analytic type assays. The color properties of the scattered light of different types of metal-like particles allows for multi-analyte visual detection. For example, spherical gold particles of 40, 60, 80, and 100 nm diameter and 20 nm

TABLE 3

CALCULATED AND MEASURED MOLAR DECADIC EXTINCTION COEFFICIENT(S) AND WAVELENGTHS OF MAXIMUM ABSORPTION FOR GOLD PARTICLES OF DIFFERENT SIZE IN WATER

| | CALCULATED[b] | | MEASURED[b] | |
|---|---|---|---|---|
| PARTICLE DIAMETER[a],[b] | ($M^{-1}$ $cm^{-1}$) | WAVELENGTH AT MAXIMUM ABSORPTION | ($M^{-1}$ $cm^{-1}$) | WAVELENGTH AT MAXIMUM ABSORPTION |
| 10 nm | $1.8 \times 10^8$ | ~530 nm | $2.3 \times 10^8$ | ~525 nm |
| 16 nm | $9 \times 10^8$ | ~530 nm | $5.2 \times 10^8$ | ~522 nm |
| 20 nm | $1.8 \times 10^9$ | ~528 nm | $1.2 \times 10^9$ | ~525 nm |
| 40 nm | $1.6 \times 10^{10}$ | ~532 nm | $8.5 \times 10^9$ | ~528 nm |
| 60 nm | $5.6 \times 10^{10}$ | ~542 nm | $2.6 \times 10^{10}$ | ~547 nm |
| 80 nm | $1.1 \times 10^{11}$ | ~550 nm | $5.8 \times 10^{10}$ | ~555 nm |
| 100 nm | $1.6 \times 10^{11}$ | ~574 nm | $9.2 \times 10^{10}$ | ~575 nm |

[a]Denotes exact diameter of particle for calculating values.
[b]Denotes approximate diameter of gold particles used for measurements. Actual diameters were slightly higher or slightly lower than the diameters noted.

At visible wavelengths of incident light, the light scattering power (i.e., $C_{sca}$) of metal-like particles is much greater than for a comparable non-metal-like particle such as polystyrene. Another important distinction between the light scattering properties of metal-like and non-metal-like particles is that for metal-like particles, the profile of scattered light intensity versus incident light wavelength for metal-like particles of same composition but varying size can be very different. This is in contrast to non-metal-like particles where in the size ranges of about 10 nm diameter to a few hundred nm diameter the profile is essentially the same. These differences are extremely useful to more specifically and more sensitively detect metal-like particles in various samples. The incident wavelength at which maximum light scattering ($C_{sca}$) occurs for various diameter particles of silver, gold, copper, and aluminum are presented in Table 4.

FIG. 16 shows the experimentally measured scattered light intensity vs. incident light wavelength profile for roughly spherical 100 nm diameter gold particles coated with polyethylene compound (MW=20,000) and without the polyethylene compound. The data show that the wavelength dependent light scattering intensity properties of the coated and uncoated 100 nm diameter gold particle are very similar.

FIG. 27 snows the calculated scattered light intensity versus incident light wavelength spectra profiles for spherical gold particles of varying diameter. The scattered light intensity peak wavelengths shift to longer wavelengths as the size of the gold particles is increased. We have directly observed these light scattering properties for coated or uncoated gold particles of 40, 60, 80, 100 nm diameters and they appear as green, yellow-green, orange, and orange-red particles when illuminated with a white light source in solution or in a light microscope using DLASLPD illumination methods. Small spherical silver particles appear blue.

diameter silver particles, each coated with a different type of binding agent, can be used in the same sample to detect five different analytes in the sample. In one format, five different types of cell surface receptors, or other surface constituents present on the cell surface can be detected and visualized. Detection of the scattered light color of the differently coated particles that are bound to the surface of the cell under DLASLPD conditions with a light microscope with white light illumination makes this possible. The number and types of analytes are identified by the number of green, yellow, orange, red, and blue particles detected. Similarly, chromosome and genetic analysis such as in situ hybridization and the like can also be done using the method as described above where the different types of metal-like particles are used as "chromosome paints" to identify different types of nucleic acid sequences, nucleic acid binding proteins, and other similar analytes in the sample by the color of the scattered light of the different types of metal-like particles. These examples are provided as illustrative examples, and one skilled in the art will recognize that the color of the scattered light of different types of metal-like particles can be used in many different assay formats for single or multi-analyte detection Thus, adjusting the size of certain types of spherical metal-like particles is a useful method to increase their detectability in various samples by using the color and/or other properties of their scattered light. By using a white light source, two or more different types of particles are easily detectable to very low concentrations.

Table 5 shows that modest increases in gold particle size results in a large increase in the light scattering power of the particle (the $C_{sca}$). The incident wavelength for the maximum $C_{sca}$ is increased significantly with particle size and the magnitude of scattered light intensity is significantly increased. For example, the incident wavelength for maximum $C_{sca}$ is around 535 nm, 575 nm and 635 nm for gold particles 40 nm, 100 nm, and 140 nm in diameter, respectively. When illuminated with white light, the 40 nm gold particles strongly and preferentially scatter the wavelengths around 535 nm and the particles appear green, while the 100 nm particles appear orange-red and the 140 nm particles appear red in color. This further shows that when illuminated with white light, certain metal-like particles of identical composition but different size can be distinguished from one another in the same sample by the color of the scattered light. The relative magnitude of the scattered light intensity can be measured and used together with the color or wavelength dependence of the scattered light to detect different particles in the same sample more specifically and sensitively, even in samples with high non-specific light backgrounds.

In contrast, for non-metal-like particles, these particles do not possess these specific types of light scattering properties and thus, it is more difficult to detect the non-metal-particles in most types of sample medium as compared to the metal-like particles.

TABLE 4

CALCULATED INCIDENT VISIBLE WAVELENGTH AT WHICH MAXIMUM $C_{sca}$ IS OBSERVED IN WATER

| PARTICLE MATERIAL | PARTICLE DIAMETER | WAVELENGTH OF INCIDENT LIGHT AT WHICH MAXIMUM $C_{sca}$ OCCURS |
|---|---|---|
| Silver | 10 nm | ~380 nm |
|  | 40 nm | ~400 nm |
|  | 100 nm | ~475 nm |
| Gold | 10 nm | ~528 nm |
|  | 40 nm | ~535 nm |
|  | 100 nm | ~575 nm |
|  | 140 nm | ~635 nm |
| Copper | 100 nm | ~610 nm |
|  | 150 nm | ~644 nm |
| Aluminum | 100 nm | ~377 nm |
| Selenium | 130 nm | ~660 nm |
|  | 200 nm | ~702 nm |

TABLE 5

CALCULATED VALUES FOR LIGHT SCATTERING CHARACTERISTICS OF SPHERICAL GOLD PARTICLES OF DIFFERENT SIZES

| PARTICLE DIAMETER (nm) | WAVELENGTH AT MAXIMUM $C_{csa}$ (nm) | MAXIMUM $C_{sca}$ (cm$^2$) | CALCULATED RELATIVE SCATTERING POWER |
|---|---|---|---|
| 10 | ~528 | $1.26 \times 10^{-15}$ | 1 |
| 20 | ~525 | $8.4 \times 10^{-14}$ | 67.5 |
| 30 | ~530 | $1.03 \times 10^{12}$ | 817 |
| 40 | ~535 | $6 \times 10^{-12}$ | $4.8 \times 10^3$ |
| 60 | ~545 | $6.3 \times 10^{-11}$ | $5 \times 10^4$ |
| 80 | ~555 | $2.3 \times 10^{-10}$ | $1.8 \times 10^5$ |
| 100 | ~575 | $4.6 \times 10^{-10}$ | $3.6 \times 10^5$ |
| 120 | ~605 | $6.9 \times 10^{-10}$ | $5.5 \times 10^5$ |
| 140 | ~635 | $8.8 \times 10^{-10}$ | $7 \times 10^5$ |
| 160 | ~665 | $1 \times 10^{-9}$ | $7.9 \times 10^5$ |
| 200 | ~567 | $1.4 \times 10^{-9}$ | $1.1 \times 10^6$ |
| 300 | ~670 | $2.9 \times 10^{-9}$ | $2.3 \times 10^6$ |
| 600 | ~600 | $1.01 \times 10^{-8}$ | $8 \times 10^6$ |
| 1,000 | ~620 | $2.5 \times 10^{-8}$ | $1.8 \times 10^7$ |
| 1,000 | ~670 | $2.5 \times 10^{-8}$ | $1.8 \times 10^7$ |

The relative light scattering powers of particles of the same shape and size, but of different composition, can be directly compared experimentally by comparing the light scattering intensities at right angles to the path of the incident light. We experimentally compared the relative light scattering powers of gold and polystyrene particles of similar size and shape, using a tight scattering instrument we built designed to measure scattered light at right angles to the path of the incident light and which is described elsewhere. Table 6 shows that the experimentally measured scattering power of a particle composed of gold is much greater than the scattering power of a particle composed of polystyrene when both particle types are compared at the same incident visible wavelength. The experimentally measured values of Table 6 are a factor of two to three lower than the calculated values. A large part of this difference can be attributed to the approximately two-fold lower values obtained for the experimentally measured molar decadic extinction coefficients of gold particles relative to the calculated values (see Table 3). In addition, there is a certain level of uncertainty in particle sizes (e.g. for a polystyrene particle preparation 21 nm±1.5 nm the actual size could be about 1.5 nm larger or smaller). This uncertainty makes the quantitative values less certain for both the polystyrene and gold particles but does not change the basic conclusion concerning the relative scattering powers. Even at the greatest level of uncertainty, Table 6 indicates that at a minimum, the scattering power of a gold particle is 100 to 200 times greater than that of a polystyrene particle of comparable size and shape.

Table 7 compares the relative light scattering power of spherical gold and polystyrene particles of similar size and shape, at different wavelengths of visible light. Table 7 indicates that even at illumination wavelengths far away from the wavelength of maximum light scattering intensity, the light scattering power of a gold particle is much greater than that of a polystyrene particle of comparable size and shape. These experimental results agree with our calculated results(see Table 2).

Table 8 shows that the experimentally determined light scattering power of spherical gold particles is much greater than comparable polystyrene particles using white incandescent light illumination conditions.

Overall, the agreement between our calculated and experimentally determined results presented herein is quite good. This validates the calculated results as well as the use of the calculation process for identifying potentially useful particle materials and compositions and for evaluating the utility of the light scattering properties of such particles. Most types of light sources which produce polychromatic and/or monochromatic light, steady-state and/or pulsed light, and coherent or not coherent light can be used for illumination Our results indicate that more specific and more intense light scattering signals can be can be obtained from metal-like particles as compared to non-metal-like particles of comparable size and shape. Our results indicate that the present invention provides a means to detect lesser amounts of particles, and to more specifically detect lesser and greater amounts of particles than was previously possible.

TABLE 6

CALCULATED AND MEASURED RELATIVE SCATTERING POWER IN WATER OF POLYSTYRENE AND GOLD PARTICLES OF SIMILAR SIZE AND SHAPE AT THE INCIDENT WAVELENGTH AT WHICH MAXIMUM SCATTERING OCCURS FOR THE GOLD PARTICLES

| PARTICLE COMPOSITION | PARTICLE SIZE[b] | INCIDENT WAVELENGTH | RELATIVE SCATTERING POWER | |
|---|---|---|---|---|
| | | | [a]CALCULATED | MEASURED |
| PST[c] | 21 ± 1.5 nm | ~525 nm | 1 | 1 |
| Gold | 19.8 ± <1.9 nm | ~525 nm | ~664 | ~220 |
| PST | 32 ± 1.3 nm | ~527 nm | 1 | 1 |
| Gold | 29.5 ± <3.5 nm | ~527 nm | ~663 | ~318 |
| PST | 41 ± 1.8 nm | ~530 nm | 1 | 1 |
| Gold | 39.5 ± <6 nm | ~530 nm | ~985 | ~461 |
| PST | 83 ± 2.7 nm | ~560 nm | 1 | 1 |
| Gold | 76.4 ± 15 nm | ~560 nm | ~708 | ~211 |

[a]Calculated for perfectly spherical particles
[b]Manufacturer's measured particle sizes. The manufactured particles are spherical in shape but not perfectly spherical. This will have little effect on the quantitative aspects of this comparison.
[c]PST—polystyrene

TABLE 7

MEASURED RELATIVE SCATTERING POWER IN WATER OF POLYSTYRENE AND GOLD PARTICLES OF SIMILAR SIZE AND SHAPE AT INCIDENT WAVELENGTHS AWAY FROM THE GOLD PARTICLE ABSORPTION BAND

| PARTICLE COMPOSITION | PARTICLE SIZE[a] | INCIDENT WAVE-LENGTH | VISIBLE WAVELENGTH OF MAXIMUM SCATTERING | RELATIVE SCATTERING POWER | |
|---|---|---|---|---|---|
| | | | | DIRECT COMPARISON | [c]CORRECTED FOR PARTICLE SIZE |
| PST[b] | 41.1 ± 1.8 nm | ~530 nm | ~300 nm | 1 | 1 |
| | | ~460 nm | | 1 | 1 |
| | | ~400 nm | | 1 | 1 |
| Gold | 39.9 ± <6 nm | ~530 nm | ~530 nm | ~377 | ~443 |
| | | ~460 nm | | ~96 | ~113 |
| | | ~400 nm | | ~80 | ~94 |
| PST | 83 ± 2.7 nm | ~560 nm | ~300 nm | 1 | 1 |
| | | ~430 nm | | 1 | 1 |
| | | ~380 nm | | 1 | 1 |
| Gold | 76.4 ± <15 nm | ~560 nm | ~560 nm | ~251 | ~412 |
| | | ~430 nm | | ~36 | ~55 |
| | | ~380 nm | | ~27 | ~41 |

[a]Manufacturer's measured particle size
[b]PST—Polystyrene
[c]Adjust the relative light scattering values for the gold particles for any difference in size between the PST and gold particles by using the relationship that scattering power increases as the sixth power of the radius. Although in these size ranges, this is not quite accurate, the corrected figures are a good approximation.

TABLE 8

MEASURED RELATIVE SCATTERING POWER IN WATER OF WHITE LIGHT ILLUMINATED POLYSTYRENE (PST) AND GOLD PARTICLES OF A SIMILAR SIZE AND COMPOSITION

| [a]PARTICLE COMPOSITION | [b]PARTICLE SIZE | RELATIVE SCATTERING POWER AT SAME CONCENTRATION | [c]RELATIVE SCATTERING POWER ADJUSTED FOR PARTICLE SIZE |
|---|---|---|---|
| PST | 21 nm | 1 | 1 |
| GOLD | 19.8 nm | ~40 | ~58 |
| PST | 38 nm | 1 | 1 |
| GOLD | 39.9 nm | ~212 | ~158 |
| PST | 37.9 nm | 1 | 1 |
| GOLD | 39.9 nm | ~105 | ~77 |
| PST | 59 nm | 1 | 1 |
| GOLD | 59.6 nm | ~100 | ~94 |

TABLE 8-continued

MEASURED RELATIVE SCATTERING POWER IN
WATER OF WHITE LIGHT ILLUMINATED POLYSTYRENE
(PST) AND GOLD PARTICLES OF A SIMILAR
SIZE AND COMPOSITION

| [a]PARTICLE COMPOSITION | [b]PARTICLE SIZE | RELATIVE SCATTERING POWER AT SAME CONCENTRATION | [c]RELATIVE SCATTERING POWER ADJUSTED FOR PARTICLE SIZE |
|---|---|---|---|
| PST | 79 nm | 1 | 1 |
| GOLD | 76.4 nm | ~108 | ~132 |

[a]Polystyrene particles obtained from interfacial Dynamics, Inc., Portland, Oregon or Duke Scientific, Inc., Palo Alto, CA. While the gold particles were obtained from Goldmark Biologicals, Phillipsburg, N.J. a distributor for British Biocell LTD., Cardiff, UK.
[b]Manufacturers represented particle diameter.
[c]Done using the relationship that scattering power increases approximately as the sixth power of the particle radius.

Particle Light Generation Power Compared to Fluorescence

Fluorescence is currently being used in many assays designed to detect the presence or absence of an analyte substance.

Fluorescein is one of the best understood and most widely used fluorescent compounds. Many studies have been conducted with the purpose of detecting as few fluorescein molecules as possible. Fluorescein has a high molar decadic extinction coefficient (about $6 \times 10^4 M^{-1} cm^{-1}$) and has a very high fluorescent quantum yield of about 0.8.

Table 9 compares the calculated signal generating power of certain particles to fluorescein. Clearly, a single gold or silver particle is a much more intense light source than a single fluorescence molecule. Under ideal conditions and using appropriate optical filters, a good fluorimeter can detect fluorescein at a lower concentration of about $10^{-10}M$ to $10^{-11}M$. The comparison presented in Table 9 indicates that this same fluorimeter should be able to detect a lower concentration of a 60 nm gold particle of around $10^{-15}M$–$10^{-16}M$. We have verified these observations experimentally.

Table 9 indicates that the total scattered light output from a single 60 nm gold particle is equivalent to the output of about 350,000 fluorescein molecules. While one fluorescein molecule cannot be directly visualized in the light microscope, we are able to directly visualize individual metal-like particles in many different types of samples and assay formats. The light is directed at the sample with such an angle so that the light scattered from the particle is maximally visualized or measured by the eye or photodetector. This broadly applicable method of illumination and detection as we have developed in one form or another for use in analytic and diagnostic applications is called DLASLPD (direct light angled for scattered light of particle only to be detected). These methods are described in greater detail elsewhere. This allows the detection of single particles and the quantitation of such particles by particle counting methods including image analysis, photon correlation spectroscopy, light microscopy and other methods. In contrast, only very large particles of polystyrene can be seen in the light microscope using DLASLPD techniques.

Table 10 presents results comparing the experimentally measured relative signal generating power of fluorescein and gold particles of various sizes using white light illumination. These results are similar to those presented in Table 8 and show that the light generation power of a gold particle is much greater than a fluorescein molecule. For example, gold particles of a diameter of 39.9 nm and 59.6 nm emit a light intensity equivalent to that given off by about $2 \times 10^4$ and $2.3 \times 10^5$ fluorescein molecules respectively, when illuminated with white light.

The scattered light emitted by gold particles illuminated with white light is composed of all of the wavelengths present in the incident white light, but the efficiency of light scattering at any particular wavelength varies such that one or more bands of scattered light wavelengths are scattered more intensely. The actual wavelength composition and the scattered light wavelength versus scattered light intensity profile obtained when white incident light is used, depends on a number of variables which include the type of light source used and the method of light detection. The results of Table 10 were obtained with an incandescent light source or color temperature of 2,800° Kelvin and the light was passed through a simple filter to reduce the infrared component before passing through the sample. The scattered light intensity was measured with a standard photomultiplier tube. The results of Table 10 have not been corrected for phototube or light source properties. Any such corrections would not affect the conclusions discussed herein.

TABLE 9

CALCULATED RELATIVE SIGNAL GENERATING POWER
OF FLUORESCEIN AND SPHERICAL PARTICLES
OF VARIOUS COMPOSITIONS AND SIZES

| Particle Composition | Particle Diameter | Particle Volume (Micron)$^3$ | Number Of Fluorescein Molecules Necessary To Match The Total Light Intensity From One Particle[A] |
|---|---|---|---|
| Polystyrene | 10 nm | $5.23 \times 10^{-7}$ | ~0.07 |
| | 20 nm | $4.2 \times 10^{-6}$ | ~5 |
| | 40 nm | $3.35 \times 10^{-5}$ | ~280 |
| | 60 nm | $1.13 \times 10^{-4}$ | ~2800 |
| | 100 nm | $5.23 \times 10^{-4}$ | ~42,000 |
| Silver | 10 nm | $5.23 \times 10^{-7}$ | ~46 |
| | 20 nm | $4.2 \times 10^{-6}$ | ~3,500 |
| | 40 nm | $3.35 \times 10^{-5}$ | ~150,000 |
| | 60 nm | $1.13 \times 10^{-4}$ | ~770,000 |
| | 100 nm | $5.23 \times 10^{-4}$ | ~2,300,000 |
| Gold | 10 nm | $5.23 \times 10^{-7}$ | ~7 |
| | 20 nm | $4.2 \times 10^{-6}$ | ~455 |
| | 40 nm | $3.35 \times 10^{-5}$ | ~35,000 |
| | 60 nm | $1.13 \times 10^{-4}$ | ~350,000 |
| | 100 nm | $5.23 \times 10^{-4}$ | ~3,100,000 |

[A]Fluorescein and the particle are illuminated with the same light intensity at wavelengths which generate the maximum fluorescent or light scattering signal. For polystyrene the incident light wavelength used was 300 nm, while the incident light wavelength used for each gold or silver particle was the wavelength at maximum $C_{sca}$ for the various sizes.

Results from measurement of the relative signal generating powers of fluorescein and roughly spherical gold particles of different size when illuminated with incident monochromatic light are presented in Table 11. The fluorescein sample was illuminated with monochromatic light of an incident wavelength (490 nm) and the resulting emitted light was not monochromatic or polarized and was composed of the wavelengths characteristic of fluorescein emission. Different sized spherical gold particles were illuminated with monochromatic light of an incident wavelength at which maximum scattering of incident light occurs and the resulting scattered light was either completely or partially polarized, depending on the size of the particle.

TABLE 10

MEASURED RELATIVE SIGNAL GENERATING POWER OF FLUORESCEIN VERSUS GOLD PARTICLES WHEN ILLUMINATED WITH WHITE LIGHT[a]

| Signal Source | Particle Diameter (Nm) | [c]Measured Number Of Fluorescein Molecules Necessary To Match The Light Intensity From One Gold Particle |
|---|---|---|
| GOLD | 10.1 ± <1.2 | ~9 |
| GOLD | 19.8 ± <2 | ~2.3 × $10^2$ |
| GOLD | 29.5 ± <3.5 | ~4.1 × $10^3$ |
| GOLD | 39.9 ± <6 | ~2 × $10^4$ |
| GOLD | 49.2 ± <9.8 | ~7.3 × $10^4$ |
| GOLD | 59.6 ± <11.9 | ~2.3 × $10^5$ |
| GOLD | 76.4 ± <15.3 | ~9 × $10^5$ |
| PST[b] | 80 ± <6.6 | ~8.3 × $10^3$ |

[a]Incident light from an incandescent Leica microscope light source with a color temperature of 2,800° K, and the emitted light was passed through a glass lens to decrease the infrared component
[b]PST—polystyrene
[c]Results not corrected.

TABLE 11

MEASUREMENT OF RELATIVE SIGNAL GENERATING POWER OF FLUORESCEIN VERSUS GOLD PARTICLES WHEN ILLUMINTED WITH MONOCHROMATIC LIGHT

| PARTICLE TYPE | [a]PARTICLE DIAMETER | [b]INCIDENT WAVELENGTH | [c]MEASURED NUMBER OF FLUORESCEIN MOLECULES NECESSARY TO MATCH THE LIGHT SIGNAL FROM ONE GOLD PARTICLE |
|---|---|---|---|
| GOLD | 10.1 nm | ~525 nm | ~4 |
| GOLD | 19.8 nm | ~530 nm | ~120 |
| GOLD | 29.5 nm | ~532 nm | ~1,400 |
| GOLD | 39.9 nm | ~535 nm | ~7,800 |
| GOLD | 49.2 nm | ~550 nm | ~25,000 |
| GOLD | 59.6 nm | ~542 nm | ~78,000 |
| GOLD | 76.4 nm | ~565 nm | ~190,000 |
| GOLD | ~100 nm | ~560 nm | ~550,000 |

[a]Measurements represented size
[b]Incident monochromatic light composed of a significant fraction of horizontally polarized light arising from the monochrometer. Vertically polarized incident light would yield a significantly larger particle signal intensity but would not affect the signal intensity from fluorescein.
[c]Results not corrected.

Table 11 illustrates that the scattered light signal intensity generated from various sized individual gold particles illuminated with incident monochromatic light is much more intense relative to the light signal intensity from a single fluorescein molecule. These results further illustrate that individual metal-like particles, as for example, gold particles when illuminated with incident monochromatic light can be detected to very low concentrations. Such detectabilty is extremely useful for using such particles with appropriate detection methods as extremely sensitive light scattering labels in diagnostic assays and analytical applications.

Non-metal-like particles as for example, polystyrene which have 100's-1000's of highly fluorescent molecules incorporated into the body of the particle are well known in the art. An example of such a particle is a 110 nm diameter particle into which has been incorporated a fluorescent compound which has excitation and emission wavelength maxima, 490 nm and 515 nm respectively, which are similar to fluorescein. Each particle contains an average of 4,400 highly fluorescent molecules and the volume of such a particle is about 7×$10^{-16}$ $cm^3$ and the fluorescent molecule concentration in the particle is about $10^{-5}$M. Table 12 presents the experimentally measured results for the light generation power of 110 nm diameter polystyrene, polystyrene particles loaded with many molecules of highly fluorescent compound, and 100 nm diameter gold particles. The light generating power of these are directly compared against a solution of fluorescein which gives the same light generation power. It is interesting to note that the total scattered light signal from the 110 nm polystyrene particle alone is equivalent to the tight signal from about 12,000 fluorescein molecules. The presence of the fluorescent molecules in the polystyrene particle only increases the total light signal by about 1.5 fold of the particle. The fluorescence signal from this particle can be separated from the light scattering signal by using the proper filter between the sample and the detector which excludes incident light wavelengths and passes the wavelengths characteristic of the fluorescence emission. Such a filter results in this particle generating a fluorescent signal Intensity equivalent to about 3,000 fluorescein molecules. The 100 nm diameter gold particle was clearly far superior in emitted light generation power as compared to these particles.

TABLE 12

MEASURED RELATIVE SIGNAL GENERATING POWER OF FLUORESCEIN, POLYSTYRENE PARTICLES, POLYSTYRENE PARTICLES CONTAINING FLUORESCENT MOLECULES AND GOLD PARTICLES

| PARTICLE TYPE | [a]PARTICLE DIAMETER | FLUORESCENT MOLECULES PER PARTICLE | INCIDENT WAVELENGTH | [c]MEASURED NUMBER OF FLUORESCEIN MOLECULES NECESSARY TO MATCH THE LIGHT SIGNAL FROM ONE PARTICLE |
|---|---|---|---|---|
| [d]PST | 110 nm | 0 | 490 nm | ~12,000 |
| PST | 110 nm | ~4400 | 490 nm | ~19,000 |
| [e]Gold | 100 nm | 0 | 555 nm[b] | [e]~1.3 × $10^6$ |

[a]Measurements represented size
[b]See Table 11(b)
[c]Results not corrected.
[d]Polystyrene
[e]The 100 nm diameter particle used herein was from a different production batch than that used in Table 11.

Mixed Composition Particles

Spherical particles of mixed compositions were evaluated by theoretical and physical experimentation to assess their possible utility in various diagnostic and analytic applications. For theoretical evaluations, a gold "core" particle coated with different thickness of silver and a silver core particle coated with different thickness of either gold or polystyrene were studied. By "core" is meant a spherical particle upon which an additional layer or thickness of different light scattering material is placed, resulting in a mixed composition of certain proportions. Direct physical experimentation was done for particles composed of a mixed composition where an additional thickness of silver was added to a core gold particle of 16 nm diameter. In these illustrative examples, gold and silver are representative of metal-like materials and polystyrene is representative of non-metal-like materials. These examples are only a few of a larger number of different possible combinations which involve particles composed of mixtures of one or more different metal-like and/or non-metal-like materials.

Results from calculations for the light scattering properties of the above illustrative examples are presented in Tables 13 and 14. Table 13 section A shows that for a series of spherical 10 nm diameter particles which are composed of increasing proportions of a silver coat on a gold core, the light scattering properties are changing to those more like a pure silver particle. Most importantly, we observed in these calculations and by physical experimentation, that certain proportions of a silver coated gold particle can exhibit two intense light scattering maxima at incident wavelengths close to those characteristic of pure gold and pure silver particles of this rough size.

Direct experimental observation of 16 nm diameter gold particles coated with silver using white light illumination under DLASLPD conditions with a simple light microscope showed that there were new colors of scattered light from these particles which had not been previously seen in pure gold or pure silver particle preparations. Many of the particles had a brilliant purple to magenta color of scattered light.

Table 13 section B presents a comparison of the calculated results for mixed composition particles composed of a 10 nm diameter gold sphere coated with different thickness of silver. The results show similar trends as seen in Table 13 Section A for the light scattering properties of these mixed compositions as the proportion of silver to gold is varied. In additional calculations (Table 14), where a silver core particle is coated with varying gold thickness, the light scattering properties show similar trends in their changes as the proportion of gold and silver is changed as seen in Table 13.

and resolvable wavelengths of high scattering intensities can be made by varying the composition of the metal-like-materials.

In contrast, particles composed of mixed compositions of non-metal-like and metal-like materials generally exhibit light scattering properties similar to the metal-like materials at equal proportions or less of non-metal-like materials to metal-like materials. Only at very high proportions of non-metal-like to metal-like materials do the light scattering properties of the mixed composition particle resemble that of the non-metal-like material as the results of Table 14 section B indicate.

Both the mixed silver-gold compositions and the silver-polystyrene compositions exhibit the high light scattering power and visible wavelength scattering bands which are characteristic of particles composed of pure metal-like materials. Particles of certain mixed compositions are detectable by specifically detecting the scattered light from one or both of the scattering intensity peaks and or by the color or colors of these mixed composition type particles. Such mixed composition type particles enhances the capability for detecting lesser amounts of particles and more specifically, detecting lesser and greater amounts of particles than was previously possible.

Asymmetric Particles

The physical orientation of asymmetric particles with regard to a light beam allows for additional scattered light properties to be used in the detection of these particles. The property of RIFSLIW can be used in many different aspects of the current invention to more specifically and more sensitively detect and or measure one or more analytes or particles in a sample. For example, the flickering of the scattered light intensity and/or change in color provides

TABLE 13

CALCULATED SCATTERING PROPERTIES OF SPHERICAL PARTICLES
COMPOSED OF MIXED COMPOSITION - A GOLD CORE COATED WITH SILVER

| | PARTICLE DIAMETER | GOLD CORE DIAMETER | SILVER COAT THICKNESS | VOL GOLD TOTAL VOL | $C_{scr}$ AT WAVELENGTH MAXIMUM ($cm^2$) | INCIDENT WAVELENGTH AT SCATTERING MAXIMUM(S) |
|---|---|---|---|---|---|---|
| A | 10 nm | 10 nm | 0 | 1 | $1.26 \times 10^{-15}$ | ~530 nm |
|   | 10 nm | 9 nm | 0.5 | 0.73 | $7.3 \times 10^{-16}$ | ~340 nm |
|   |       |      |     |      | $8 \times 10^{-16}$ | ~516 nm |
|   | 10 nm | 8.4 nm | 0.8 nm | 0.59 | $9 \times 10^{-16}$ | ~340 nm |
|   |       |      |     |      | $6.8 \times 10^{-16}$ | ~510 nm |
|   | 10 nm | 4 nm | 3 nm | 0.064 | $5.7 \times 10^{-15}$ | ~380 nm |
| B | 10 nm | 10 nm | 0 | 1 | $1.26 \times 10^{-15}$ | ~530 nm |
|   | 11 nm | 10 nm | 0.5 nm | 0.75 | $1.25 \times 10^{-15}$ | ~340 nm |
|   |       |      |     |      | $1.45 \times 10^{-15}$ | ~518 nm |
|   | 12 nm | 10 nm | 1 nm | 0.58 | $2.8 \times 10^{-15}$ | ~340 nm |
|   |       |      |     |      | $2 \times 10^{-15}$ | ~505 nm |
|   | 20 nm | 10 nm | 5 nm Polystyrene Particle | 0.125 | $2.4 \times 10^{-13}$ | ~375 nm |
| C | 10 nm | 0 | 0 | — | $1.3 \times 10^{-17}$ | ~300 nm |
|   | 20 nm | 0 | 0 | — | $8.3 \times 10^{-16}$ | ~300 nm |

We have determined from our combined theoretical and physical experimentation the following. For particles composed of certain mixed compositions of metal-like materials, as for example, mixed compositions of gold and silver, new light scattering properties appear which are useful in many different sample types and specific diagnostic and analytic applications. Particles with two or more optically distinct additional detection means to determine which particles are bound to a surface and which particles are not. This allows for non-separation type of assays (homogeneous) to be developed. All that is required is to detect by particle counting, intensity measurements or the like the particles that do not flicker and/or change color. Unbound particles in solution will flicker and/or change color while those bound to the surface will not. Additional image processing means such as video recorders and the like allow for additional methods of detection to be used with both asymmetric and spherical (symmetric particles). For example, In either a separation or non-separation format, the bound particles are detected by focusing the collecting lens at the surface and only recording those scattered light signals per unit area which are constant over some period of time. Particles free in solution undergoing brownian motion or other types of motion results in variable scattered light intensity per unit area per unit time for these particles. Bound light scattering particles are fixed in space and are not moving. By using image-processing methods to separate the "moving" light-scattering particles from the "bound" light scattering particles, the amount of bound particles is determined and correlated to the amount of analyte in the sample. One of skill in the art will recognize there are many other image processing methods that can be used to discriminate between bound particles to a surface and unbound spherical or asymmetric particles in solution.

Addition of Other Materials to the Surface or Core of the Particle to Provide Additional Physical Attributes not Related to the Light Scattering Properties In certain applications and with the use of certain types of compositions, it may be useful to "coat" the surface of a particle to further chemically stabilize the particle, or to add additional surface binding attributes which can be very important in specific applications to analytical diagnostic assays. For example, it is well known that silver rapidly oxidizes. For use of silver particles or particles of mixed composition which contain silver, one can chemically stabilize the silver-containing particle by applying a thin coat of gold or other substance on the surface such that the silver is no longer susceptible to environmental effects on it's chemical stability.

In another example, one may want to coat the surface with another material such as a polymer containing specifically bound binding agents, or other materials useful for attaching binding agents, or the binding agents themselves to the particles. In each of these examples, these "thin" coats do not significantly alter the light scattering properties of the core material. By "thin" coats is meant a monolayer or similar type of coating on the surface of the particle.

Manipulatable Light Scattering Particles (MLSP's) are particles which in addition to having one or more desirable light scattering properties, these particles can also be manipulated in one-, two- or three-dimensional space by application of an EMF. A MLSP particle can be made in many different ways. For example, a MLSP particle is made by coating a small diameter "core" ferroelectric, magnetic or similar material with a much greater proportion of a material that has the desirable light scattering properties, for example a 10 nm diameter core of magnetic or ferroelectric material is coated with enough gold to make a 50, 70, or 100 nm diameter particle. This is shown in FIG. 29 A.

Another method of making such a particle is to coat the material that has the desirable light scattering properties with a thin coat of the magnetic or ferroelectric material. For example, a gold or silver particle of about 50 nm is coated with a 1-2 nm thick coat of the magnetic or ferroelectric material. This is shown in FIG. 29 B.

Alternatively, the MLSP particles are made by mixing in the appropriate proportions the light scattering desirable materials and the ferroelectric or magnetic materials such that as the particle is formed, the appropriate proportions of light scattering desirable material to magnetic or ferroelectric material per particle ratio is attained. This is shown in FIG. 29 C.

An alternative to the above MLSP particles is to link or assemble one or more types of particles with desirable light scattering properties to one or more particles that can be moved by a EMF. Such multi-particle structures can then have similar properties to the MLSP's. For example, small particles of magnetic or ferroelectric material are linked to one or more particles who's light scattering properties are detected. The linking is by ionic, chemical or any other means that results in a stable multi-particle structure. For example, the different particles are coated with appropriate polymers so that when mixed in the proper portion, a defined distribution of discreet multi-particle structures are achieved by crosslinking the different types of individual particles together. There many different ways to link the particles together to achieve the desired multi-particle structure(s). For illustrative purposes, a few of the possible multi-particle structures are shown in FIG. 30. FIGS. 30 A, B, and C show dimer, tetramer, and higher order particle constructs respectively for orientable MLSP particles. One skilled in the art will recognize that these are just a few of the many different types of multi-particle structures possible and there are numerous methods to make such structures.

These examples of particles composed of mixtures of one or more material are but a few of a very large number of different compositions of different materials which are possible, and which would be apparent to one of skill in the art.

Particle Size and Shape Homogeneity

Depending on how the light scattering properties of particles are detected, the approximate size and distribution of particle sizes in the particle population can be extremely important. As an example, many of the commercially available gold particle preparations quote the particle size distributions anywhere from about <10 to about <20 percent coefficient of variation. Percent coefficient of variation is defined as the standard deviation of the particle size distribution divided by the mean of the particle preparation. Thus, for a 60 nm particle preparation with a coefficient of variation of 20%, one standard deviation unit is about ±12 nm. This means that about 10% of the particles are smaller than 48 nm or greater than 72 nm. Such variation in size has significant effects on the intensity of scattered light and the color of scattered light depending on the approximate "mean" size of the particles in the preparation.

We have developed a particle growing procedure which seems to give narrower size distributions than those available commercially. The procedure involves first making a preparation of "seed" gold particles which is then followed by taking the "seed" particle preparation and "growing" different size gold (see examples 11 and 15) or silver particles (see Example 13) by chemical methods. For example, 16 nm diameter gold particles are used as the "seed" particle and larger diameter gold particles are made by adding the appropriate reagents (see Example 15). This method is also very useful for making mixed composition particles.

Particle Homogeneity—Detection of Analytes by Scattered Light Color of Individual Particles In certain applications, the color of the individual particles are used to identify and quantitate specific types of analytes. For example, in image cytometry applications, it may be of interest to identify and count different types of cell surface antigens or the like by detecting the number and color of different types of particles attached to the surface.

For this or any other related type of multi-analyte detection, the size distributions of the different particles need to be kept as tight as possible. The average particle diameter of the particle preparation should be chosen to provide the desired color of scattered light under white light illumination, using an average or "mean" particle size that is as close to the size midpoint between the mean particle sizes of smaller and larger particles which will be used in the same application to produce different colors of scattered light. In this fashion, the resolvability of the different types of particles by their color of scattered light is maximized.

Particle Homogeneity—Integrated Light Intensity Measurement

In other sections we have described how the intensity of scattered light can vary greatly as particle size is increased or decreased. This variation in the intensity must be taken into consideration especially when integrated light intensity measurements are being performed. Using the 60 nm particle preparation described above with a 20% coefficient of variation, this means that 10% of the particles have intensities about 3 times greater or less than a 60 nm particle. In addition, the particles within the remaining 90% of the population have quite varying intensities. In applications where there are many particles being measured, the "average" integrated light intensity should approximate a 60 nm particle. However, at lower concentrations of particles, the statistics of such a variation may affect the accuracy of the reading from sample to sample, and correction algorithms may be needed. By using the narrowest distribution of particles possible, the accuracy and ease of measurement is enhanced.

Useful Metal—like Particles for Detection of Analytes by their Light Absorption Color For some types of analyte assays, analytes are at concentrations where detection of the analytes by the light absorption properties can be accomplished. For example, a current problem in the art of immunochromatographic assays and the like is that the use of gold particles of the sizes typically used (4 to 50 nm diameter) only provides for particles that can not be optically resolved by their light absorption color. These particles have a pink to red color when observed on filter paper or similar diagnostic assay solid-phase media. By varying the size and/or shape of silver particles and other metal-like particles many different colors of light absorption can be achieved. These different colors of the particles by light absorption can be used to detect different analytes by the light absorption color of a particle. These colors which can be detected by the eye are very useful in many types of solid-phase assays such as immunochromatographic flow assays, panel type, and microarray or larger solid-phase single or multi-analyte assays. Spherical and asymmetrical particles of silver and certain mixed compositions of other metal-like particles allow for a wide range of colors by light absorption.

Autometallographic Enhancement of Light Scattering Properties of Particles

It is well known in the art that autometallography and related techniques can be used to enlarge the size of existing metal-like particles by small or large factors. The light absorbing power of particles composed of metal and/or semiconductor material, and in particular, gold and silver particles has often been used to quantitate and or detect the presence of these particles, by using either the eye or an instrument designed to measure light absorbance. Such a method is inferior to the light scattering detection methods of the present invention in its ability to detect small numbers of particles enlarged by metallography.

As an example, it has been reported (see Immunogold-Silver Staining, Principles, Methods and Applications, CRC Press, 1995 M. A. Hayat Ed.) that one nanometer diameter gold particles were enlarged by metallographic methods, coating the 1 nm diameter gold particles with silver to an average diameter of about 110 nm in about twenty minutes. The particles in this preparation ranged in size from about 40 nm to 200 nm diameter and were roughly spherical in shape. Surprisingly, our calculations show that enlarging the diameter of the 1 nm core tracer particle to 110 nm results in an increase in scattering power of roughly $10^{10}$ while the light absorption power is only increased by roughly $10^5$.

By increasing the diameter of a small particle, the incident wavelength at which maximum light scattering occurs shifts to much longer wavelengths, as compared to a small core particle of the same material. Thus, enlarged particles are easily detected in the presence or absence of small 1 nm particles by measuring the light scattering signal from the enlarged particles. The utilization for detection of the enlarged particles of incident light of the wavelength at which maximum scattering occurs for the enlarged particles allows the more specific detection of the enlarged particles relative to the smaller particles which constitute the major source of non-specific light scattering background.

TABLE 14

CALCULATED SCATTERING PROPERTIES OF SPHERICAL MIXED COMPOSITION PARTICLES - SILVER CORE PARTICLE COATED WITH GOLD OR POLYSTYRENE (PST)

| | Particle Diameter | Silver Core Diameter | Coat Composition | Coat Thickness | Vol Silver Total Vol | $C_{sca}$ At Wavelength Maxima (CM$^2$) | Incident Wavelength At Scattering Maxima |
|---|---|---|---|---|---|---|---|
| A | 10 nm | 10 nm | — | 0 | — | $1.1 \times 10^{-14}$ | ~384 nm |
|   | 14 nm | 10 nm | Gold | 2 nm | 0.36 | $4.5 \times 10^{-15}$ | ~372 nm |
|   |       |       |      |      |      | $5 \times 10^{-15}$ | ~518 nm |
|   | 20 nm | 10 nm | Gold | 5 nm | 0.125 | $6.5 \times 10^{-15}$ | ~525 nm |
| B | 10 nm | 10 nm | — | 0 | 1 | $1.1 \times 10^{-14}$ | ~384 nm |
|   | 10 nm | 9 nm | Gold | 0.5 nm | 0.73 | $1.9 \times 10^{-15}$ | ~384 nm |
|   | 10 nm | 7 nm | Gold | 1.5 nm | 0.34 | $5.6 \times 10^{-16}$ | ~300 nm |
|   |       |       |      |      |      | $6.8 \times 10^{-16}$ | ~520 nm |

TABLE 14-continued

CALCULATED SCATTERING PROPERTIES
OF SPHERICAL MIXED
COMPOSITION PARTICLES - SILVER
CORE PARTICLE COATED WITH
GOLD OR POLYSTYRENE (PST)

| | Particle Diameter | Silver Core Diameter | Coat Composition | Coat Thickness | Vol Silver Total Vol | $C_{sca}$ At Wavelength Maxima (CM$^2$) | Incident Wavelength At Scattering Maxima |
|---|---|---|---|---|---|---|---|
| C | (a)10 nm PST | 0 | — | 0 | — | $1.3 \times 10^{-17}$ | ~300 nm |
| | 10 nm | 10 nm | — | 0 | 0 | $1.1 \times 10^{-14}$ | ~384 nm |
| | (a)20 nm PST | 0 | — | 0 | — | $8.3 \times 10^{-16}$ | ~300 nm |
| | 20 nm | 20 nm | — | 0 | 1 | $7 \times 10^{-13}$ | ~382 nm |
| | 40 nm | 20 nm | PST | 10 nm | 0.125 | $9.3 \times 10^{-13}$ | ~412 nm |
| | 60 nm | 20 nm | PST | 20 nm | 0.037 | $1.25 \times 10^{-12}$ | ~418 nm |
| | 20 nm | 12 nm | PST | 4 nm | 0.216 | $4 \times 10^{-14}$ | ~408 nm |
| | 20 nm | 10 nm | PST | 5 nm | 0.125 | $1.4 \times 10^{-14}$ | ~410 nm |
| | 20 nm | 8 nm | PST | 6 nm | 0.064 | $4.3 \times 10^{-13}$ | ~414 nm |

(a)Particle composed of polystyrene only

Table 15 provides additional data with regard to the light scattering properties of small particles that are increased in size by metallographic or related methods. Our calculated data show that enlarging the size of a particle results in a greater increase in the particle's light scattering power as compared to it's light absorption power. For example, a twenty percent increase in particle diameter increases the small particle light scattering power by $(1.2)^6$ or about three-fold. An increase of two and ten-fold in small particle diameter will result in a scattering power increase of about sixty-four and one million-fold respectively, while the light absorbing power is increased by only eight-fold and one thousand-fold respectively.

Thus, when the method of the present invention is used to quantitate and or detect the presence of particles which have been enlarged by metallography (that is, the deposition of a coat of a metal-like material onto a small diameter composed of either metal-like or non-metal-like materials), it is possible to detect lesser amounts of such particles, and to more specifically detect lesser amounts of such particles, than was previously possible.

The above is an illustration of the combination of metallographic enlargement of a metal-like particle core by the deposition of a metal-like coat on the core, followed by the detection of the enlarged particles by the method of the present invention. Such methods can be used for enlarging particles free in solution and or particles attached to a surface. The preceding example is only one of the many different permutations of this combination method which include the use of the many different strategies and methods discussed herein for detecting particles by light scattering as well as different combinations of core and coat compositions and different degrees of enlargement. These alternate combinations will be readily apparent to one of skill in the art. Such a combination approach can be applied to almost any situation where it is desirable to use a signal generation and detection system to detect an analyte.

TABLE 15

2 nm DIAMETER GOLD TRACER CORE PARTICLE - DIFFERENT THICKNESS
OF A SILVER COAT OF UNIFORM THICKNESS - CALCULATED LIGHT
SCATTERING PROPERTIES

| DIAMETER OF PARTICLE | THICKNESS OF SILVER COAT | PARTICLE LIGHT SCATTERING POWER ($C_{sca}$) (cm$^2$) | WAVELENGTH AT WHICH SCATTERING MAXIMUM OCCURS | PARTICLES RELATIVE SCATTERED LIGHT INTENSITY | RELATIVE DECADIC MOLAR EXTINCTION COEFFICIENT OF PARTICLE |
|---|---|---|---|---|---|
| 2 nm | 0 nm | $~8 \times 10^{-20}$ | ~520 nm | 1 | 1 |
| 10 nm | 4 nm | $~10^{-14}$ | ~382 nm | $~1.25 \times 10^5$ | $~3 \times 10^{2(a)}$ |
| 20 nm | 9 nm | $~6.5 \times 10^{-13}$ | ~384 nm | $~8.1 \times 10^6$ | $~2.3 \times 10^3$ |
| 40 nm | 19 nm | $~2.8 \times 10^{-11}$ | ~400 nm | $~3.5 \times 10^8$ | $~1.6 \times 10^4$ |
| 80 nm | 39 nm | $~2.9 \times 10^{-10}$ | ~447 nm | $~3.6 \times 10^9$ | $~5.8 \times 10^4$ |
| 100 nm | 49 nm | $~4.3 \times 10^{-10}$ | ~481 nm | $~5.4 \times 10^9$ | $~7.6 \times 10^4$ |
| 150 nm | 74 nm | $~7.9 \times 10^{-10}$ | ~432 nm | $~9.9 \times 10^9$ | $~1.5 \times 10^5$ |
| 150 nm | 74 nm | $~7.6 \times 10^{-10}$ | ~600 nm | $~9.5 \times 10^9$ | $~1.2 \times 10^5$ |

(a)The molar decadic extinction coefficient, the $C_{sca}$ and the incident wavelength at which maximum light scattering occurs are essentially identical to those for a pure 10 nm diameter silver particle.

Method of Refractive Index Enhancement

The use of refractive index matching techniques in light microscopy, telecommunications, and other related fields is well known in the art. This technique is generally used to decrease the nonspecific light scattering and reflections that occur as a light beam passes from one medium or device to the other as for example, from the surface of one material to the surface of another different material.

We have determined that the light scattering power ($C_{sca}$) of a specific type of particle is affected by the medium in which the particle resides. Altering the refractive index of the medium results in a change in a particle's light scattering properties.

Table 16 provides an illustrative example of medium refractive index effects on selected particles. Calculated refractive index medium effects for gold, silver, and polystyrene spherical particles of 10 nm diameter are presented.

The effects of the refractive index of the medium are quite different for metal-like particles as compared to non-metal-like particles as Table 16 shows. Increasing the refractive index of the medium for metal-like particles as for example gold, results in increasing the intensity and wavelength maximum of the light scattered from the particle while for a non-metal-like particle, as for example polystyrene, the light scattering power is decreased.

The unique light scattering properties of metal-like particles as compared to non-metal-like particles as an effect of the refractive index of the sample medium can be used to more specifically and with greater sensitivity detect metal-like particles in samples including those which have high non-specific light scattering backgrounds. This is important for many different types of diagnostic analytical assays.

TABLE 16

CALCULATED MEDIUM REFRACTIVE INDEX EFFECTS FOR TEN NANOMETER DIAMETER PARTICLES OF DIFFERENT COMPOSITION. WAVELENGTH AND INTENSITY EFFECTS

| | GOLD | | SILVER | | POLYSTYRENE | |
|---|---|---|---|---|---|---|
| $N_1$ | (A) | (B) | (A) | (B) | (A) | (B) |
| 1 | 1 | 520 nm | 1 | 355 nm | 1 | 400 nm |
| 1.1 | 1.9 | 525 nm | 1.6 | 360 nm | 0.9 | 400 nm |
| 1.2 | 3.9 | 525 nm | 2.3 | 370 nm | 0.75 | 400 nm |
| 1.3 | 7.7 | 530 nm | 2.9 | 380 nm | 0.52 | 400 nm |
| 1.4 | 15.1 | 535 nm | 3.9 | 390 nm | 0.27 | 400 nm |
| 1.5 | 27.7 | 540 nm | 5.3 | 400 nm | 0.084 | 400 nm |
| 1.6 | 45.4 | 550 nm | 7.3 | 415 nm | ~0 | — |
| 1.7 | 71.5 | 555 nm | 9.7 | 425 nm | 0.1 | 400 nm |

(A) = Relative scattering power at different medium refractive indices
(B) = Wavelength at which scattering maximum occurs
$N_1$ = refractive index of medium In many types of samples and diagnostic assay formats, the problem of non-specific scattered, reflected, and other background light from sample containers and non-analyte sample constituents are well known. These non-specific light backgrounds make it difficult, if not impossible to perform sensitive to ultrasensitive detection of analytes by detection and/or measurement of the scattered light properties of a particle.

We have determined that metal-like particles can be detected to much greater specificity and sensitivity as compared to non-metal-like particles when the method of refractive index enhancement is used. The method is now described. The effect of the refractive index of the particle and medium on the scattered light intensity can be evaluated by using the following expression (RI is refractive index factor)

$$RI = refmed^4 \left| \frac{m^2 - 1}{m^2 + 2} \right|^2 \quad (16)$$

where refmed is the refractive index of the medium, and m is equal to the refractive index of the particle/refmed. m depends implicitly on wavelength but the exact dependence varies with particle composition and medium. The refractive index of most solvents which have no color is usually independent of wavelength, at least in the visible region of the spectrum.

It is of interest for the use of light scattering particles in sensitive assays to determine which values of refractive index leads to higher light scattering intensities. This is determined from the refractive index factor (RI) of Eq. (16). This factor has it's highest value when the denominator of Eq. (16) is zero. For this condition, the refractive index factor has an infinite value. Thus, the condition for high light scattering is $$m^2+2=0 \quad (17)$$

Solving above equation for m, we get $$m=\sqrt{-2} \quad (18)$$

$$=1.41i \quad (19)$$

where $i=\sqrt{-1}$. The above equation indicates that the refractive index factor has its highest value and light scattering from the particle is at a maximum when the refractive index is a pure imaginary number with a value of 1.41. The calculated data presented in Table 16 do follow the expected trends. In addition, the method of refractive index enhancement works very well at incident wavelengths far removed from the incident wavelength at which maximum light scattering occurs for the metal-like particles.

An illustrative example of the use of the refractive index enhancement method is now provided. In highly scattering samples, such as samples where there is a high level of non-specific light scattering background, metal-like particles and the method of refractive index enhancement are used as follows.

One skilled in the art increases the refractive index of the sample medium as for example, placing a film of water or other liquid on top of a dry or wet sample. This increases the refractive index of the medium. In another example, a serum or other type of highly scattering sample is diluted with a high refractive index liquid which substantially increases the refractive index of the medium.

For the above mentioned examples, the following processes occur. The specific light scattering signal of the metal-like particles increases and the non-specific light scattering background decreases as the refractive index of the sample is increased. The largest increases in particle light scattering/non-specific scatter background ratio is achieved when the refractive index of the sample medium approaches the refractive index of the metal-like particle as demonstrated in Table 16. This means that at the proper medium refractive index values, the non-specific light scatter from serum proteins or similar constituents can be significantly reduced or eliminated while the specific light scattering intensity of the particles is increased. This results in superior analyte detection signal/background ratios when the light scattering properties of metal-like particles are used as the analytical tracer. These methods can be applied to samples such as dry surfaces, surfaces covered by solutions, or solutions.

These index matching methods can also be used with longer wavelengths for the metal-like particles to increase the specific light scatter signal/non-specific scatter background ratio even further. While Table 16 only shows the effects for gold and silver particles, particles composed of other metal-like materials can also be used to detect lesser amounts of particles using the methods we have described. The description of the method of refractive index enhancement described herein presents only a few of many possible variations of this practice of the invention. Many other variations of the method are possible and will be apparent to one of skill in the art. One or another of these variations can be effectively utilized in most diagnostic formats to determine the presence or absence of an analyte. This aspect of the present invention provides a means for the detection of lesser amounts of particles, and for the more specific detection of lesser amounts of particles, and for the more specific detection of lesser and greater amounts of particles than was previously possible.

A method which combines refractive index enhancement with the narrow band pass filter approach described earlier has great utility for detection of lesser and greater amounts of particles than was previously possible. These approaches are complimentary. The refractive index enhancement method is used to decrease non-specific light scattering background while the narrow filter is used to reduce and minimize other sources of non-specific light background such as fluorescence and the like. A combination of these methods results in highly optimized particle specific scattering signal/non-specific light background ratios and allows for the more specific and more sensitive detection of particles.

The above example is only one of many possible variations of this combined method. Other variations will be apparent to one of skill in the art.

Detection of Light Scattering Particles in Highly Scattering and Fluorescent Samples—Serum Mammalian serum contains many medically important substances whose quantitation and or presence is determined in the clinical laboratory as well as elsewhere. Many different signal generation and detection systems are used to determine the presence of these analytes in serum and these include light signal generation methods such as fluorescence, light scattering, and chemiluminescence, as well as calorimetric methods which are used in formats involving both direct labeling and signal amplification methods. Natural serum contains a variety of substances which are capable of producing a non-specific light signal by either fluorescent, chemiluminescent or light scattering mechanisms. In addition, the serum often contains substances which interfere with the generation and or detection of the specific light signal from the tracer entity. These difficulties make it difficult if not impossible to conduct analyte detection in pure or nearly pure serum samples.

In order to be able to effectively employ most, if not all, of the existing test systems for detection of serum analytes, it is almost always necessary to pre-process the serum in some way to make it suitable for testing. Many such serum processing methods exist and perhaps the simplest is dilution of the serum into some appropriate solution which is usually aqueous in nature. Another commonly used approach is to conduct the actual test in such a manner that the undesirable serum components are removed before the presence of the specific light producing tracer is determined. From a cost and labor point of view, the less effort and reagents needed to conduct the test, the better. It is highly desirable not to pre-process the sample at all. Such capability could also be beneficial to the performance of the test. The method of the present invention provides a means to conduct such analyte tests in almost pure serum and further provides a means, to detect lesser or greater amounts of particles more specifically in high concentrations of serum than was previously possible.

For example, it is common to dilute serum samples to a final concentration of about 5 percent serum before analyzing it with a fluorescent tracer such as fluorescein. The serum sample is illuminated with monochromatic light at 490 nm, and optical filters are used to minimize non-specific scattered light background. The non-specific light signal is equivalent to a highly pure liquid sample of fluorescein which contains $10^{-8}$M to $10^{-9}$M fluorescein. Thus, in the 5% serum sample, one can detect $10^{-8}$M to $10^{-9}$M fluorescein at a signal to noise ratio of 2. In a 95 percent serum sample, the lower limit of detection of fluorescein would be about 19 times higher, or about $1.9 \times 10^{-7}$M to $1.9 \times 10^{-8}$M. Thus, in 95 percent serum with optical filters, the lower limit of detection of fluorescein is about $1.9 \times 10^{-7}$M to $1.9 \times 10^{-8}$M and this amount of fluorescein light signal results in a (total light signal) to (non-specific light signal) ratio of about 2 to 1.

Table 17 presents the experimentally measurable detection limits, at a (total light signal) to (non-specific light signal) ratio of 2 to 1, of fluorescein at very high serum concentration. At this high serum concentration, and in the absence of optical filtration to remove non-specific light signal due to scattered incident light, the lower limit of detection of fluorescein is about $6 \times 10^{-7}$M.

Table 18 presents the lower limit of detection of fluorescein at very high serum concentration when an optical filter which eliminates the non-specific light signal due to scattering of incident light is placed between the sample and the photomultiplier tube. In this situation, the lower limit of detection of fluorescein in high serum concentration is about $2 \times 10^{-8}$M.

In contrast to fluorescein, the results presented in Table 17 Section B and Table 18 demonstrate that in the absence of optical filtration the presence of 59.6 nm diameter gold particles in 95 percent serum can be detected with a (total light signal) to (non-specific light signal) ratio of 2 to 1 at a concentration of about $1.8 \times 10^{-12}$ M. The non-specific light signal observed from the serum was equivalent to that from about $5 \times 10^{-7}$ M fluorescein. Under these same conditions 60 nm diameter polystyrene particles in high serum concentration can only be detected at a lower limit of about $6 \times 10^{-9}$M (see Table 18).

TABLE 17

DETECTION OF 59.6 nm DIAMETER
GOLD PARTICLES AT HIGH SERUM
CONCENTRATION

|   | Percent Serum | Gold Particle Concentration | Incident Wavelength | Fluorescein Concentration | Relative Light Intensity |
|---|---|---|---|---|---|
| A | 97.8% | 0 | 490 nm | 0 | 1.02 |
|   | 95.7% | 0 | 490 nm | $8.7 \times 10^{-6}$ M | 15.8 |
|   | 97.8% | 0 | 545 nm | 0 | 0.52 |
|   | 95.7% | 0 | 545 nm | $8.7 \times 10^{-6}$ M | 0.56 |

TABLE 17-continued

DETECTION OF 59.6 nm DIAMETER
GOLD PARTICLES AT HIGH SERUM
CONCENTRATION

| | Percent Serum | Gold Particle Concentration | Incident Wavelength | Fluorescein Concentration | Relative Light Intensity |
|---|---|---|---|---|---|
| B | 97.8% | 0 | 490 nm | 0 | 0[c] |
| | 95.8% | $1.77 \times 10^{-12}$ M | 490 nm | 0 | 1.1 |
| | 97.8% | 0 | 543 nm | 0 | 0.55 |
| | 95.8% | $1.77 \times 10^{-12}$ M | 543 nm | 0 | 1.05 |

Fetal bovine serum purchased from Biowhitaker, Walkerville, MD catalog number 14-501F. Serum was passed through a one micron filter before sale and was clear but straw colored. Serum pH was adjusted to about pH 9 to 9.5.
No wavelength filtration of the emitted light was done
[a]The light signal obtained here represents a value of 1. This signal was equivalent to $3.7 \times 10^{-7}$ M fluorescein.

TABLE 18

LOWER LIMIT OF DETECTION OF
FLUORESCEIN, GOLD AND POLYSTYRENE
PARTICLES AT 92.8% SERUM CONCENTRATION

| PERCENT SERUM | FLUORESCEIN CONCEN-TRATION | TYPES AND CONCEN-TRATION OF PARTICLES | INCIDENT WAVE-LENGTH | FILTER FOR EMISSION | RELATIVE[c] SIGNAL INTENSITY |
|---|---|---|---|---|---|
| 92.8% | 0 | 0 | 554 nm | NO | 1 (~520 m)[b] |
| 92.8% | 0 | Gold $1.8 \times 10^{-12}$ M | 554 nm | NO | 2.1 (~1100 m) |
| 92.8% | 0 | 0 | 496 nm | YES[a] | 1 (~39 m) |
| 92.8% | $2.3 \times 10^{-8}$ M | 0 | 496 nm | YES | ~2 (~79 m) |
| 92.8% | 0 | 0 | 554 nm | NO | 1 (~468 m) |
| 92.8% | 0 | PST $6 \times 10^{-9}$ M | 554 nm | NO | ~2 (~960 m) |

Polystyrene (PST) and gold particles had a measured diameter of 60 nm and 59.6 nm respectively. The pH of the solutions containing fluorescein was adjusted to pH 9–10 before measurement The maximum light intensity in serum was observed at an incident wavelength of about 496 nm for fluorescein and about 554 nm for the 59.6 nm gold particle.
[a]The light signal emitted from the sample was passed through a No. 16 Wratten filter before encountering the photomultiplier tube.
[b]The instrument measurements were all obtained at identical instrument settings and are directly comparable to one another (mv = millivolts).
[c]The light detection instrument detects fluorescein emissions slightly more efficiently than the particle emitted light. In addition the incident monochromatic light is enriched for horizontally polarized light and this reduces the particle results due to a lower level of light scattering from the particles but does not affect the fluorescein light intensity. The total instrument bias towards the fluorescein signal is roughly 1.5–2 fold.

Results presented in Table 19 present a comparison of the relative detection limits (at total light signal to non-specific light signal ratio of about 2 to 1) of 100 nm diameter gold particles, 110 nm diameter polystyrene particles, and 110 nm diameter polystyrene particles containing 4,400 molecules of highly fluorescent compound per particle, in 95.7 percent serum. These results further demonstrate that the 100 nm diameter gold particles can be detected at a much lower concentration than 110 nm diameter particles composed of polystyrene or polystyrene containing many molecules of highly fluorescent compound. The gold particles can be detected in serum at about 230 times lower concentration than the other non-metal-like particles.

Table 20 compares the amount of scattered light measured from identical concentrations of 59.6 nm gold particles in a solution containing a high concentration of serum and a solution containing only water under the same illumination conditions. Under these conditions, a gold particle concentration of $1.8 \times 10^{-12}$ M was detectable at a signal/background ratio of about 3. These results indicate that the presence of serum or any of the common constituents does not appear to have any direct effect on the light scattering power of the gold particles. Such stability and inertness of the light scattering properties of metal-like particles make them extremely useful in samples such as serum and other related samples which contain many other constituents.

The detection of 100 nm diameter spherical polystyrene or gold particles in serum provides a further illustrative example.

Mammalian serum contains around 3.7 gram percent of protein, of which about two-thirds is serum albumin. The detection of polystyrene particles in serum is hampered by the non-specific light scattering which originates from protein and other substances in serum, as well as many other sources. The similarity of the light scattering intensity versus the incident visible wavelength profiles for polystyrene particles and the proteins and other substances in serum severely limits the ability to detect the polystyrene particles in serum or any other highly scattering medium.

TABLE 19

DETECTION OF PARTICLES COMPOSED
OF GOLD, POLYSTYRENE (PST),
AND POLYSTYRENE CONTAINING A
FLOURESCENT COMPOUND AT HIGH
SERUM CONCENTRATION

| Percent Serum | Particle Diameter And Composition | Particle Molarity | Incident Wavelength | Relative Light Intensity[D] |
|---|---|---|---|---|
| 100% | 0 | 0 | 490 nm | 1[e] |
| | | | 580 nm | 0.27 |
| 95.7% | 110 nm PST[b] | $1.9 \times 10^{-11}$ M | 490 nm | 1.9 |
| | | | 580 nm | 0.54 |

TABLE 19-continued

DETECTION OF PARTICLES COMPOSED
OF GOLD, POLYSTYRENE (PST),
AND POLYSTYRENE CONTAINING A
FLOURESCENT COMPOUND AT HIGH
SERUM CONCENTRATION

| Percent Serum | Particle Diameter And Composition | Particle Molarity | Incident Wavelength | Relative Light Intensity[D] |
|---|---|---|---|---|
| 95.7% | 110 nm PST[a] + fluor | $1.9 \times 10^{-11}$ M | 490 nm 580 nm | 2.2 0.54 |
| 95.7% | 100 nm gold[c] | $8.2 \times 10^{-14}$ M | 496 nm 580 nm | 1.1 0.59 |

[a]Obtained from Interfacial Dynamics Corp., Portland, Oregon. Each particle contains an average about 4400 fluorescent molecules. The excitation and emission maxima are 490 nm and 515 Nnm respectively for the fluorescent molecules. The fluorescent compound concentration in the particle is about $3 \times 10^{-2}$ M.
[b]Obtained from Interfacial Dynamics Corp.
[c]Produced by art known methods.
[d]No wavelength filtration of emitted light was done.
[e]The light signal observed here represent a value of one. All other values are relative to this value. This signal is equivalent to that from about $2 \times 10^{-7}$ M fluorescein.

TABLE 20

SIGNAL GENERATION FROM 59.6 nm
DIAMETER GOLD PARTICLES AT
HIGH SERUM CONCENTRATION AND
AT ZERO SERUM CONCENTRATION

| PERCENT SERUM | GOLD PARTICLE CONCEN- TRATION | INCIDENT WAVELENGTH | RELATIVE TOTAL SIGNAL SIZE |
|---|---|---|---|
| 0 | $1.8 \times 10^{-12}$ M | 543 nm | 1 |
| 95.7% | 0 | 543 nm | 0.58 |
| 95.7% | $1.8 \times 10^{-12}$ M | 543 nm | 1.38 |

Gold particles had a measured diameter of 59.6 nm respectively. 95.7% serum is straw colored and has an optical density at 1 cm pathlength and wavelength of 543 nm of about 0.14, The limit scattering measurements were made in a 6 mm by 50 mm glass tube with an inner diameter of about 5 mm. It is estimated that absorbance of light by the serum reduces the scattered light signal by about 15 percent.

The use of an incident wavelength of 575 nm instead of 300 nm to illuminate the serum results in an about 13 fold reduction in the non-specific light scattering signal, but also results in about the same extent of reduction for the specific scattering signal from the polystyrene particles. Increasing the wavelength of illumination for polystyrene or other non-metal-like particles does not appear to significantly increase the specific signal to background ratio, that is, the detectability of the polystyrene particles in the sample.

In contrast, metal-like particles are detected to greater signal to background ratios as compared to non-metal-like particles by increasing the visible wavelength of illumination and/or detection. A 100 nm diameter gold particle maximally scatters light around wavelengths of about 575 nm in aqueous media similar to water. Illumination of the sample with monochromatic light of wavelengths around 575 nm results in the generation of the maximum light scattering signal from the gold particles and significantly reduces the non-specific light scattering signal. For example, under these conditions, the total non-specific light scattering is reduced by about thirteen-fold as compared to an illumination wavelength of 300 nm relative to an incident wavelength of 300 nm.

The illumination of the serum sample with incident white light and appropriate optical filters which minimize the amount of light outside of the wavelengths of interest (less than and or greater than a specified band centered at about 575 nm) provides another means to detect lesser amounts of metal-like particles in serum. Under these conditions the incident visible wavelength which produces the maximum light scattering intensity from the gold particle is utilized, and the non-specific light scattering signal originating from serum protein and other substances as well as other sources is greatly reduced. Multiple types of different metal-like particles are detectable in serum samples when illuminated by white light (or several different wavelengths) and using an appropriate array of optical filters. This method makes use of each type of particle having a different incident wavelength at which maximum light scattering occurs.

Another approach involves filtering the total light signal from the sample through a proper polarization filter and/or a bandpass filter. Use of the proper polarization filter will result in the effective removal of unpolarized fluorescence background but will have little effect on the non-specific light-scattering background since it is mostly polarized. When using broad band illumination, as for example, white light illumination, using optical band pass filters of higher wavelength allows for significant reduction of the non-specific light scattering and fluorescence background. Many of the metal-like particles have high light scattering intensities at longer wavelengths and this property can be utilized in combination with the bandpass filter and/or polarization filter approach. For example, a spherical gold particle of 300 nm diameter has near maximum scattering efficiency at a wavelength of about 700 nm and its scattered light intensity is about six times than a 100 nm diameter gold particle. Using the 300 nm particle and a bandpass filter centered at 700 nm decreases the non-specific light by half and increases the gold particle scattering power by a factor of 6 (as compared to the 100 nm particle). Thus, the signal to background ratio in this system has been increased by a factor of 12. Use of this approach with non-metal particles, for example, polystyrene of comparable size, does not significantly increase the signal to background ratio but may actually lower it. The use of anti-reflective coating on the optical components of the apparatus, and/or sample chamber may also improve the signal to background ratio. Many other schemes and approaches are also possible and these would be apparent to one of skill in the art.

This aspect of the invention results in improved discrimination between the specific light scattering signal and the non-specific light scattering background signal of a diagnostic assay system over that attainable by other methods which use the detection of scattered light as part of a test system format. In addition, the availability of different types of metal-like particles which exhibit different colors when illuminated by white light makes it possible to detect the presence of multiple types of particles in one sample, which has utility for detecting multiple analyte types in one sample.

A further advantage of particles of metal-like particles is the chemical inertness of these particles, relative to fluorescent compounds. Such particles do not photobleach and their signal generation capacity is not affected by such mechanisms.

The above approaches are just a few examples of the many possible approaches for using particles composed of metal-like materials to improve discrimination between the specific light scattering signal due to the particle, and the non-specific light scattering signal which can originate from a variety of sources. For example, a large number of schemes are possible in which such particles are specifically detected at a wavelength different from the wavelength at which maximum light scattering occurs for the particle being used. Many other schemes or approaches are also possible and these would be apparent to one of skill in the art.

The detection of one or more analytes in a solid-phase or related sample by detection of one or more of a light scattering particle's properties is now discussed.

Solid-Phase Detection Methods

In the previous sections we have described various aspects of the invention as they relate to certain light scattering properties of metal-like particles, and the detection of these particles in a solution. We now describe our methods for detection of particles that are on a surface or very close to a surface.

We have determined that by using gold, silver, and other metal-like particles with our methods of DLASLPD illumination and detection, we are able to detect very low quantities of particles and particle-labeled binding agents (coated particles) per unit area, being able to detect single particles and particles coated with binding agents on or near a surface using simple illumination and detection means. These methods can be used on either optically transmissive or non-optically transmissive surfaces.

We have determined that with the use of certain combinations of particles and methods of illumination and detection, we can detect a wide range of particle densities from about 0.001 to $10^3$ particles per square micron ($\mu^2$) in a sample. By using the proper type(s) of particles, different types of analytes can be detected to very low levels and across very wide concentration ranges in the same sample, as for example, in microarrays. This is accomplished on one apparatus by utilizing both particle counting (at low particle densities) and integrated light intensity measurements (at high densities) on the same sample. For example, if a sample is to be analyzed for two or more different analytes by using solid-phase related means such as array chips or other solid-phase methods, different types of analytes exist at different concentrations in the samples. That is, some analytes may be at higher or lower concentrations from a couple to a few orders of magnitude as compared to other analytes in the sample. The selection of the proper types of particles is extremely important in achieving the desired analyte detection sensitivity and range of concentrations the method will work for. Our methods as we describe herein provide for detection of analytes in such samples. Even wider detection ranges and greater sensitivities are possible if more powerful light sources such as lasers are used, and more sophisticated detection methods such as confocal imaging are added to our basic illumination and detection methods.

We have determined that we can detect high densities of particles more specifically and easily, that is, with very good signal to background ratios using simple methods. In some aspects of the present invention, a collection lens(imaging lens, mirror or similar device) is used and in other aspects, a collection lens is not used.

The scattered light from the particles is detected by a photodetector as for example, a photodiode or photodiode array, photomultiplier tube, camera, video camera or other CCD device, or the human eye. The amount of particles is determined by counting the number of particles per unit area and/or measuring the total integrated light intensity per unit area. The specific scattered light properties detected and measured are one or more of the following: the scattered light intensity at one or more wavelengths, the color, the polarization, the RIFSLIW, and/or the angular dependence of the particle scattered light per unit area. This is then correlated to the presence, absence, and/or amount of the analyte(s) in the sample.

In some assays where one or more analytes is to be determined, one or both of the particle counting or integrated light intensity measurements can be used. It should be noted that with proper selection of particles and the use of DLASLPD illumination and detection methods, there is usually so much optically resolvable and detectable scattered light intensity available that more sophisticated light sources, and spatial and optical filtering techniques are not necessary. However, in some samples where there may be significant amounts of non-specific light background, the ultimate signal to background is improved by using optical filters, confocal imaging, or other aperture type spatial filtering techniques to increase the particle scattered light signal(s) to total non-specific light background ratio.

In some analytical and diagnostic applications, the scattered light intensity can be detected and measured using our basic methods without the use of a collection lens or mirror. In these samples, one or more properties of the scattered light is detected and measured in the same manner as described above without the use of a collection lens. The methods are now discussed in more detail.

Detection of Scattered Light from Light Scattering Particles using a Collection Lens or Mirror We have found that we can use various types of light collection optical devices to collect the scattered light of the particles. We have used both particle counting and intensity measurements (integrated intensity per unit surface area) to detect one or more of the specific light scattering properties of the particles in a given area with our methods of DLASLPD illumination and detection. We have found that in most of the experiments we have done, that it is generally useful to use the counting measurement method when the particle densities are about 0.1 particles per $\mu^2$ or less. When the particle densities are greater than about 0.1 particles per $\mu^2$, we find that measuring the total integrated light intensity is a useful measurement method. It should be noted however, that one can use the counting measurement or integrated light intensity measurement methods at particle densities greater than or less than about 0.1 particles per $\mu^2$.

The use of a specific type or types of lens to collect and/or image the scattered light from the sample we have found useful relates to the field or area of the surface we are interested in measuring, the type of sample container that is being measured, and the upper limit of particle densities that are to be measured by particle counting. For example, if we are interested in measuring larger areas to detect the scattered light, a ×10 or even smaller microscope objective or lens or mirror can be used to collect the scattered light from the sample. Similarly, if smaller areas of the sample is to be measured, a ×20, ×40, ×100, or greater microscope objective lens or similar lens or mirror can be used to collect the light. If the method of particle counting is to be used at higher particle densities, greater power objective lenses allow for better resolution of the particles at high densities. It should be noted that when larger objectives are used, additional requirements and limitations come into play. For example, the working distance becomes very small and immersion oil may be needed to be added to the sample. When a camera, video camera, or similar CCD type photodetector is used, the total scattered light from the sample area is detected. This information can then be processed by simple hardware and/or software means to analyze the scattered light measurements. This is a powerful capability, because many different analytes in a sample can be detected and quantitated by use of a solid-phase microarray, array chip, or similar format. In the microarray format, small areas of the surface are each covered by a different type of binding agent in a spatially distinct region that specifically binds a particular analyte. We describe later specific applications of the present invention to solid-phase multi-analyte microarrays and the like.

The method of particle counting is usually more instrumentally demanding than the method of integrated light intensity measurement. However, for very sensitive detection of one or more of the light scattering properties of a particle, there are many advantages to using the counting technique. For example, fluctuations and inhomogeneities in the light source or sample chamber do not affect the particle counting measurement whereas these problems can cause severe problems when the method of integrated light intensity measurement is used. In addition, there are many software and hardware options to enhance the quality and signal/background ratios of the measured particles by counting techniques.

Detection of Light Scattering Particles without the use of a Collection Lens or Mirror We have also developed methods where the use of a collection lens is not necessary to detect the scattered light of the particles at or near a surface. In this arrangement we usually detect the scattered light coming from the area of interest by the integrated light intensity. This can be done by the aided or unaided eye, or a photodetector as previously described. We have found that when we use metal-like particles that are about 120 nm in diameter or less, we can significantly increase the particle light scattering signal to total non-specific light background ratio by placing our detector (either eye or photodetector) at angles outside of the envelope of the forward direction of the scattered light.

Key Concepts for Increasing Signal/Background Ratios

Before we describe the DLASLPD methods of illumination and detection in detail, it is useful to summarize the key concepts that when used in one form or another determine the signal and signal to background ratio limits for the detection of the light scattering particles. These methods are in addition to adjusting or changing various apparatus components such as using a more powerful light source, a more highly collimated light source, a smaller wavelength band light source, a different wavelength light source, a more sensitive photodetector, optical and/or spatial filters between the illumination source and the sample and/or between the sample and the detector, and/or confocal or similar imaging techniques. These strategies and methods are outlined below.

(1) by the use of larger diameter metal-like particles, the light scattering power of the particle can be significantly increased. The increase in size may also change the scattered light intensity versus incident wavelength profile. These properties can be adjusted to suit the need of any particular assay such that one or more of the scattered light properties are easily detectable. For example, for the measurement of analytes in samples with high non-specific light backgrounds, a larger gold particle, about 80-120 nm or greater in diameter is useful. The maximum wavelength at which maximum light scattering occurs shifts to higher wavelengths and the intensity of the scattered light also increases as compared to a 40 nm diameter gold particle. The combination of these two effects significantly increases the signal/background ratio as compared to the 40 nm diameter gold particle.

(2) by measuring the scattered light of the sample at angles outside the envelope of the forward direction of the scattered light, the signal/background ratio in either the intensity or counting mode is substantially increased. We have observed that the detector can be placed either above or below the surface plane of the sample as well as on the same side or opposite side of the sample plane where the illumination beam is located. In these various orientations, the specific light scattering signals from the particles are detected outside the envelope of the forward direction of the scattered light, while most of the non-specific scattered light from optical aberrations in the sample chamber and other constituents in the sample are within this envelope of the forward direction of scattered light. This allows for more sensitive and specific detection of the particle scattered light.

(3) the amount of non-specific reflected light also affects the sensitivity of detection as we have previously described. We have found that the amount of reflected light can be substantially reduced by moving the incident light surface as far as possible away from the collection area that is being detected. This can be accomplished in many different ways, including the proper design of the sample chamber (discussed later). For example, we noticed that if we put a thin layer of immersion oil on the bottom of a glass slide, through which the light beam illuminates the particles on the opposite surface, we saw highly improved results. In another experiment, when we glued a small plastic light guide to the bottom of a plastic sample chamber with a microarray of bound articles on the opposite side of the surface, we saw very improved results. We have also used much larger optical alignment means such as an equilateral prism and/or other types of prisms or optical light guides and placed immersion oil at the surface where the sample container interfaces with the prism. We have concluded that these superior results are a result of (i) having the light incident surface removed a greater distance away from the area of detection that contains the light scattering particles; (ii) having an angle of incidence of 0 degrees on the surface of the light guide such as a prism face and the like (with respect to the perpendicular) and (iii) that much of the reflected light which occurs in the system is guided out of the system and away from the collection point. All of these methods are useful in increasing the signal/background ratios for the detection of light scattering particles in various samples. There are several light guiding strategies that can be used to effectively remove the reflected light out of the system to improve signal to background.

(4) refractive index enhancement methods are also extremely useful in increasing the signal to background ratios in many different types of samples. We have found several methods to increase the signal to background, a few of which are now discussed. The use of liquid to cover the surface containing the particles, where the closer the liquid's refractive index is to the refractive index of the surface that contains the particles, the better the signal/background ratio. We have found that for detecting analytes on a dry solid-phase, the signal/background ratio is improved by placing a liquid layer on top of the surface. For example, when an aqueous buffer solution of refractive index of about 1.33 is used to cover the sample surface we get much improved results as compared to measuring the particles on the same surface in air. Even better signal/background ratios are obtained by using liquids that more closely match the refractive index of the solid-phase. For example, an assay can be performed by first binding the analytes with light scattering particles coated with binding agent to the solid-phase in the sample medium or other appropriate reaction mixture or buffer. The solution in the sample is then diluted or replaced with a solution of chosen refractive index that covers the solid-phase prior to detection of the particles. In this fashion, highly sensitive results can be achieved.

In addition to the above methods, the further use of narrow band pass optical filters, cutoff optical filters, spatial filtering such as apertures either between the illumination beam and the sample and/or between the sample and the photodetector or eye will also increase the signal/background ratio. Use of confocal imaging techniques may also be useful in certain analytical assay applications where the cost and sophistication of such techniques and apparatus are not an issue. The use of longer wavelength sources either optically filtered or not are also ways to increase the signal/background ratio. Guiding the excess non-specific light out of the system by using specifically designed sample chambers to remove the excess light is another useful method. General sample chamber designs that are useful are described later. All of these variations on one or more aspects of the current invention provide for increased signal/background ratios and thus provides for the more specific and sensitive detection of one or more analytes in a sample.

There are many different ways the DLASLPD illumination and detection methods can be specifically applied to a sample and these are outlined in FIG. 15. FIG. 14 provides a diagram for orientation and description of the outline of the DLASLPD methods shown in FIG. 15. One skilled in the art will recognize the utility the method affords when used with certain metal-like particles to detect one or more analytes in a solid-phase or similar sample.

Extended Dynamic Range

The present invention provides methods for enhancing the performance of an analyte assay. A broad dynamic range is advantageous particularly in assays in which quantitation of analyte is desired. By having an extended dynamic range, it is possible to distinguishably detect and quantitate the amount of label present in a detection area or volume (as a representation of the amount of analyte present) over a wide range of label densities or concentrations in a single assay. The methods of the invention are useful with particulate labels that scatter light, especially in assays that produce extreme light intensities at multiple assay sites. Extreme light intensities include high light intensities, low light intensities, or both within an assay or an assay site, such as when more than one color of light is detected in a multiplex analyte assay.

Limitations to dynamic range generally fall into two categories. One category represents inherent limitations in the components of the assay and the assay format, and includes limitations on analyte density, label density, and label interactions. Typically, such limitations only become significant at high analyte and/or high label densities.

The second category of limitations originates from the sensor. These include sensitivity limitations, such as non-linear sensor response at low light levels or at different wavelengths (i.e., color of light), and background problems such as poor signal-to-noise ratio at low signal levels. The second category of limitations also appears at high light intensity levels. Many types of sensors collect light over a period of exposure time, thereby accumulating light energy for conversion into a signal. The signal generated by the sensor corresponds to the detected light integrated over the exposure time. If the intensity of the light is high and/or the exposure time is long, many types of sensors become saturated, leading to a non-linear response curve and/or blooming. Under these situations, the resolution of the assay is reduced as the output signal of the sensor is not proportional or linearly proportional to the light detected by the sensor. Therefore, the signals produced by the sensor in response may be distorted or inaccurate, and are invalid for analysis. The second category of limitations may also depend on the wavelengths of the light detected by the sensor, for example, the sensor may generate signals of different strength in response to light of same intensities but of different wavelengths.

An example of a sensor with limitations at both the low and high signal levels is photographic film. Typically such film has non-linear response at low light levels, an approximately linear response portion at intermediate light levels, and a non-linear response portion at high signal levels, resulting in a sigmoid response curve. At very high light intensity levels, the film will be saturated and will not provide any further increase in response to still higher light Such limitations may also occur with electronic sensors, e.g., CCD sensors. In addition, many such sensors experience blooming when total light exposure results in excessive accumulation, with the result that both signal strength and localization discrimination are lost or at least impaired.

In assays where there are multiple analyte detection sites, some sites may have strong signal and some sites may have weak signal. The wide differences in signal levels could be due to large variations in label concentration from site to site. It could also be due to large variations in signal intensity levels among combinations of light scattering labels present at the site, for example, in multiplex assays where sets of distinguishably different particles are used that have different peak scattering wavelengths. There are also embodiments where the wide differences in signal levels from site to site are due to a combination of both differences in particle concentrations and difference in signal levels from each distinguishably different particles labeling the sites. If a simple, single exposure time is used with a sensor that has a narrower useful response range than the difference between the weak signal and the strong signal, one or the other or both of the signals will fall in a non-optimal response range. Such difficulties can be addressed in various ways as described below. Usually these techniques for providing extended dynamic range would be used in assay formats where there are a plurality of separately addressable sites at which the signal may vary widely. Examples include many solid phase and multi-well formats, such as microtiter plates, and arrays on microarrays on slides, chips, membranes, gels, and filters.

The methods described herein utilizing particulate light scattering labels (RLS particles) generally include a range in which the light scattered from particles is linearly related to the number of particles present in the detected area or volume.

The present methods for providing extended dynamic range, when used in conjunction with the RLS particle assay methods described herein can generally provide at least 4 orders of magnitude of dynamic range, and often 5, 6, 7, or even more. The methods of the invention can also be applied to multiplex analyte assays which comprise different labels that may generate different color light of considerably different intensities, thus requiring an assay of broad dynamic range. Typically, multiplex assay comprises detecting light of distinguishably different colors (i.e, different wavelengths) from different labels within an assay site or an examination zone. In various embodiments of the invention, various different light intensity readings of an assay site from a sensor for one wavelength are combine to produce a signal or a reading for that same wavelength that is accurate and quantitative for the assay site. In preferred embodiments, the methods of the invention do not use the one or more light intensity readings at a first wavelength to estimate, extrapolate, or produce a signal or a reading for a second different wavelength.

The methods of the invention for extending dynamic range are described in details below:

1. Combination of Integrated Light Intensity and Particle Counting Detection

In one embodiment, the invention provides a method that combines integrated light measurements for moderately high light intensity, and particle counting for low light intensity. Such a method would typically be used to address limitations on the low signal end of the scale. The transition point for changing from integrated light measurement to particle counting can be established based on empirical testing. Thus, for example, integrated light measurement can be used with a selected exposure time. Preferably the exposure time is selected so that high label density sites provide an intensity that will not saturate the sensor or otherwise push the total signal received into a range in which the sensor cannot provide accurate, quantifiable detection. In this period of selected exposure time, integrated light measurement are made at a range of light intensities or particle densities that the sensor can provide accurate detection and/or measurement of the label present. At a lower limit, particle counting is carried out where the particle density in a site, or in at least a statistically acceptable portion of a site can be counted in a practical amount of time and with acceptable precision, e.g., so that adjacent particles are not so close together that single particles cannot be reliably distinguished. One of ordinary skill in the art will recognize that the transition density will depend on the sensor and detection device used, the specific particles utilized, and the assay format. As indicated the optimal or acceptable transition point can be made empirically. The selection can also be made in automated fashion. Thus, for example, the exposure time can be set by a computer camera controller to provide appropriate signal accumulation for quantitation. Those sites that do not provide a sufficiently strong signal at that exposure time can then be read by particle counting, including increasing magnification. As indicated herein, particle counting can be performed in various ways, but is preferably performed electronically. In some cases, the lower limit of integrated signal measurement may overlap with the practical upper limit for particle counting. In such cases, the overlap region may be read by both methods, and serve as a calibration control.

Such a combination of detection modes can be implemented in many different ways. One preferred implementation for array embodiments would involve initial imaging of the sample using integrated signal mode. Array features (or at least portions of features) that are below a signal threshold (generally a pre-set threshold) are scanned and the particles counted. Preferably the scanning is controlled by a computer, and an image or images are created that are then processed with image processing software known in the art to identify and count the particles. The signals for array features above the threshold are used directly for integrated light quantitation, and the particle counted array features are scaled to provide quantitation for an equivalent array feature area.

Such a dual mode approach can usually extend the dynamic range for RLS particles 1-2 orders of magnitude toward the lower end of the density scale, e.g., for 80 nm gold particles from about 0.003 particles/$\mu m^2$ down to about 0.00003 particles/$\mu m^2$. Two orders of magnitude are achievable when the background and/or electronic noise is low. Under ideal conditions, particle counting extends down to 1 particle present in an array feature or per field of view. Under practical conditions with statistical requirements for reliable data analysis, particle counting can, for example, reliably count particle surface densities of $10^{-4}$, $10^{-5}$, or $10^{-6}$ particles per $\mu m^2$.

An exemplary system for carrying out such dual mode analysis utilizes motor driven XY stage control (preferably computer controlled) for scanning a spot at higher magnification, as well as highly preferably motor driven zoom control (preferably computer controlled). Thus, the instrument sample holder is fitted with a precision, motor-driven XY stage allowing a slide or other format sample medium to be positioned under the camera lens via computer. A digital camera used to capture images is connected to a powered zoom lens with both zoom and focus controlled through computer. During a measurement, an initial image is captured with the zoom set for a wide field of view, preferably at the maximum field of view. The XY stage is positioned so that the camera is centered on the array (or the portion of the array covered by the field of view. The initial image is captured and processed with a grid overlay program to subtract background and extract the data from each spot.

Spots that are determined to be at or below a predetermined threshold are marked for analysis by particle counting technique. Integrated signal quantification data for spots above the threshold are used for the final report, and no particle counting of these spots is required.

During the particle counting phase, the camera lens is zoomed in to a magnification allowing the visualization of particles within a spot. If the necessary zoom level were not achievable by a mechanical zoom lens, two such lenses can be utilized. Using the XY stage, the computer positions the camera lens over each spot determined to be below the threshold by the initial image. Several images are taken with small movements in XY around each of these spots. A computer program performing image analysis performs particle counting on each image, and averages the results to determine the particle density of each spot. Preferably, this image processing is performed in real-time using specially designed hardware.

The two different regimes can be combined using information on the characteristics of the spectrum that is produced by a single particle. In one embodiment of the invention, the signal of an assay site with low particle number can be generated by multiplying the known signal of a single particle by the number of particles counted at a site or a field. In alternative embodiments, with this information on the characteristics of the spectrum of a single particle, the integrated light intensity signals could also be converted to equivalents in particle numbers. In this way, the results from the two different measurement types can be combined and/or compared.

According to the invention, a method for providing an extended dynamic range in an analyte assay that uses light collected from light scattering particles at a plurality of sites as signals is provided. The method comprises detecting integrated light from the sites with a sensor, wherein, at one or more sites due to low integrated light intensities, signals generated by the sensor are not proportional to the integrated light detected. Either automatically as controlled by a computer or manually by an operator, the image of those sites with low integrated light intensities is analyzed by counting the number of particles per site. Detection at those sites may be repeated for particle counting. The signals obtained from sites with low integrated light intensities by particle counting are normalized with integrated light intensities, thereby providing the extended dynamic range for the assay. Preferably, the extended dynamic range is a linear dynamic range. Optionally, magnification of the field of view may be used to aid particle counting. The use of separately addressable sites is preferred when this method of extending dynamic range is used.

2. Multiple Exposure Times

In another embodiment, the invention provides a method for extending the dynamic range of an analyte assay by the use of multiple detections with different exposure times. This method involves image data processing to provide increased dynamic range especially when imaging arrays or microarrays with large differences between intensities from spot to spot (feature to feature). Sensors in cameras, e.g., CCD array sensors, have limited range from dark to light that they can quantifiably read with a single light collection (exposure) time in the absence of light-intensity reducing filters. Because it is necessary to view and quantitate areas of low signal, brighter spots can saturate the camera sensor at the long exposures needed to read the low signal spots. Saturation of areas or pixels on the sensor results in non-linear response, and, with many sensors, blooming. Such effects make suitable quantitation of the intense spots impossible. Since it is desirable to quantitate over large density or concentration ranges, such quantitation advantageously utilizes an image with extended linear response. Thus, this technique of image processing can extend the range of the image far beyond the actual limitations of the camera (when a single exposure time is used).

For example, for a single assay unit with a plurality of separately addressable sites (e.g., spots), at least two different exposure times are selected. It may also be beneficial to use more than two different exposure times, for example, 3, 4, 5, or even more. The number of different exposure times that are advantageous will depend, at least in part, on the dynamic range capabilities of the detector sensor and the signal range that may occur for the particular assay format and particle type selection. In general, a short exposure time is utilized to maintain the signal from very high density assay sites within an acceptable quantitation range for the detector sensor, and preferably within a linear response range for the sensor. With this short exposure time, sites with very low particle density will not produce sufficient signal for the detector to provide acceptable results, or in some cases, for the detector to provide any response. A long exposure time will be used that will allow the detector sensor to accumulate sufficient signal to allow quantitation of the weak signal sites and preferably to provide a response within the linear response for the sensor. As desired, intermediate exposure times can be utilized, e.g., to maintain responses for intermediate density sites in an advantageous range for the sensor. The methods of the invention that are based on making multiple exposures can also be applied to multiplex assays which comprises detecting light of distinguishably different colors (wavelengths) from different labels within an assay site or an examination zone.

In this process, it is advantageous to use non-blooming sensors. Blooming occurs with many sensors due to the overflow of electrons from saturated pixels to adjacent pixels for high density sites with longer exposures. Due to the contamination of adjacent pixels, the ability to read the low signal sites using longer times may be compromised by nearby saturated pixels. Thus, it is preferable to use non-blooming sensors, in which saturated pixels do not contaminate adjacent or nearby pixels. In such devices, the excess electrons are generally diverted to a "sink" or "channel".

Images from the camera are recorded with the exposure time set at two or more levels at long and short time intervals. The sample is kept static during the recording of all images. The data from each image can be scaled by a factor equal to the exposure difference, or the two images can be combined. The combination of the two images can be done as follows. Starting with a 12 bit image:

1. Convert both images to 16 bit without scaling. That is to say, if a pixel value is 200 in the 12 bit image it would 200 in the 16 bit file.
2. Multiply the image with the short exposure time by a factor determined by the ratio of the two exposure times, i.e., Long exposure time/Short exposure time=Conversion factor The conversion factor is used on images that have the instrument and camera background removed (i.e., the scaling is applied to the signal due to the label only). The image with the short exposure time with the background subtracted is multiplied by the conversion factor to normalize the two images.

Before overlaying the images, the saturated pixels for the long exposure are replaced with zero values (black). The two images are then merged by overlaying only the lighter pixels (i.e., the normalized pixels from the short exposure time image) over the dark pixels from the long exposure image. This replaces what were originally saturated pixels from each of the separately addressable sites with "amplified" (normalized) pixels from the short exposure image for the given site.

Thus the composite image derived from each of the separately addressable sites of the array is comprised of image data collected while the signal from the site is in the preferred range of the detector. This invention provides a method for extending the dynamic range of an assay based on a global scaling conversion factor. This eliminates the potential errors in analyte detection and quantification that could result from extrapolating data based on correlations from neighboring array sites.

The exposure time used to collect the image from an assay will vary according to several factors, including the sensitivity of the detector being used, the amount of light being given off by the particles used to label the assay, and the illumination and detection geometry of the optical setup. In preferred embodiments, the exposure time is on the order of 10 or more milliseconds or less, to 100 milliseconds or more, if for example some of the particles labeling the assay are good scatterers (such as the RLS particles) or fluoresce strongly. The exposure time can also be on the order of 1 or more seconds. In other embodiments, the exposure time can be considerably longer, ranging from ten to 100 or more seconds and even 1000 or more seconds, if for example some of the particles labeling the array sites are poor scatterers or fluorescence weakly.

This process can be extended to cover images created with more than two different exposure times. For example, the overlay process can be repeated with adjacent exposure time images until all images are merged. The overlay process can be arranged so that pixel values are used from an image in which the pixel value is in a desirable range. For example, in a 3 exposure time overlay, a pixel in the long exposure image may be saturated, in an intermediate exposure time image the corresponding pixel may be in a preferred range, and in a short exposure time image the corresponding pixel may be below the optimal range. In this case, the merged image would utilize the amplified or normalized pixel from the intermediate exposure time image, and not from the short exposure time image. Thus, one way of performing the overlay process is to overlay sequentially from longest to shortest exposure times, but, for each pixel, stopping the replacement process when a pixel had an original value within a preferred range, determined by the response characteristics of the camera.

The extended range technique using multiple exposures as mentioned above can also be normalized using integrated spot values. In this approach, the spot finding and quantification procedure are applied to each of the images taken at 2 or more exposures. The normalization is then performed as described above on the integrated signals, still factoring the exposure into the equation. Using this technique, no composite image need be created. The advantage is that a large image file, such as the 16-bit file described above, is not necessary to store the combined image at the necessary precision. Two 12-bit files require significantly less disk space than 2 or 3 16-bit images.

For embodiments using a sensor(s) with limited dynamic range, a desirable exposure time (i.e., light collection period) can be determined manually by inspecting the image or by reading the range of values for a particular exposure. However, preferably, the exposure time selection is performed in an automated fashion. Preferably the exposure time selection also includes selection of the number of different exposure times to utilize for a particular assay or set of assays (which is preferably also automated). Such automation can be implemented in many different ways, either in hardware, or more commonly in software.

Briefly, in an exemplary implementation, a computer reads the pixel values for a test exposure. The test exposure is preferably set to a time that will provide proper exposure for the weakest signals to be expected for the assay that will be analyzed using integrated signal measurement. Such level will typically be based on experience with the particular type of assay and particle size used. The exposure time can, if desired, be adjusted to a longer time if there are no pixels at or near the lower intensity limit. The range of intensities is determined by comparing values and marking or storing the highest values read (highest and lowest values, or other desired selections, can also be marked or stored). An exposure time suitable to read the highest value can be calculated that will place the signal accumulation for that most intense signal within the quantification range (or preferably the linear response range), and preferably the linear response range of the sensor/camera being used. If two exposures are insufficient to maintain the entire intensity range within the quantification range of the sensor/camera, one or more intermediate exposure times can also be calculated that will allow the entire intensity range to be read, with all sites within the quantification range (preferably linear response range) of the sensor for at least one of the different exposure times.

Depending on processing efficiency and/or data storage space, it may be preferable to perform a fixed number of exposures, which may be with pre-selected exposure times, without determining the optimum number or duration of exposures for a particular assay. For example, it may not be necessary for a particular type of assay to quantify the analytes at the highest densities, so pre-selection of exposure times that will allow quantification over a more limited range would be sufficient. One of ordinary skill will readily understand that the exposure time selection and/or adjustment can be conveniently adapted to cover the label density/concentration range of interest.

According to the invention, a method of extending the dynamic range in an analyte assay that uses light collected from light scattering particles at a plurality of sites as signals is provided. The method comprises detecting integrated light from the plurality of sites with a sensor, wherein signals generated by the sensor are not linearly proportional to the integrated light detected at one or more sites due to extreme integrated light intensities; and repeating detection of integrated light intensities using at least one different exposure time such that signals generated by the sensor are linearly proportional to the integrated light intensities detected at one or more of the sites with extreme integrated light intensities. The signals from at least two of the different exposure times are combined to quantify the light from one or more of the sites with extreme integrated light intensities, thereby providing an extended dynamic range. When the signals are combined, they are scaling by a conversion factor based on the exposure times. Preferably, the extended dynamic range is linear.

3. Light Filters

In yet another embodiment, the method provides an extended dynamic range in an assay by the use of filters. This technique provides extended dynamic range when imaging assays with large differences in intensities from spot to spot (i.e. feature to feature) by using optical filters to control the amount of light illuminating the array, or entering the CCD, Photomultiplier Tube, photodiode, or other photosensitive array sensors. The optical filters can be combined with the use of a single or multiple exposure times in imaging a wide range of particle densities or light intensities in a given analyte array that would otherwise exceed the range of the sensor and the electronics.

Optical filters provide extension of the dynamic range by reducing the intensity of the transmitted light at one or more wavelengths. The images formed (or taken) using one or more filters are combined to create a composite image of the assay sites after the images have been converted to the same scale using a conversion factor calculated from both the exposure time and the wavelength dependent light reducing capacity of the filter.

Various types of filters can be used in collecting the images. Longpass filters transmit light with wavelengths longer than a cut-off wavelength for the filter, while blocking the shorter wavelengths. Shortpass filters transmit light with wavelengths shorter than a cut-off wavelength for the filter, while blocking the longer wavelengths. An interference bandpass filter that transmit wavelengths of light that fall within an interval, while blocking wavelengths that are higher and lower than the interval can be used to single out a specific desired spectral feature in the image of the array if more than one type of distinguishable label (e.g., light scattering particle of different sizes and/or compositions) is used, as in the case for a multiplex assay. In an alternate embodiment, filters that exclude a specific spectral feature from the image, while allowing the collection of all of the other features by transmitting wavelengths lower and higher than a wavelength interval, allow you to focus on most of the spectrum. This would be desirable in an assay where one spectral feature is much more intense than the others, e.g. for different types of RLS particles in an assay. Such filters include notch filters, notch-plus filters, supernotch filters, and supernotch-plus filters. Other types of filters, including color filters, filter wheels, filter monochrometers and neutral density filters can also be used in different embodiments for collecting the images. The choice of filters is well within the skill of those in the art.

In exemplary embodiments, especially in situations where the spectral feature of the light from the assay sites is well characterized, light with high intensity at a particular wavelength (i.e, a peak in the spectrum) is collected separately from light at other wavelengths using one of the filters and using one set of exposure times. The light at the other wavelengths are collected, but using a different choice of filters and possibly different exposure times. Thus, when the two or more different readings at the various wavelengths are combined, the signals are the actual light readings from the particles at the assay sites.

If not provided by the manufacturer, the wavelength dependent transmission curve for the filters can be calculated from measurements using a commercially available white light source. The image of the white light source is first collected with a given exposure time to yield a spectrum for 100% transmission. Light is then collected using the same exposure time after the white light has passed through the filter. The wavelength dependent transmission curve for the filter can then be calculated from taking the ratio of the image taken with the filter in place to that taken in the absence of the filter. The wavelength dependent transmission curve for combinations of filters can also be taken in a similar manner by placing the two or more filters in the path of the white light source. The transmission curve of the filter can then be used in calculating a conversion factor for scaling images that are taken using a given filter or combination of filters.

In a preferred embodiment, neutral density (ND) optical filters, also sometimes called gray filters, are used to collect the images. Ideally, ND filters reduce the intensity of visible light at all wavelengths equally, and so the transmission curve calculated using the white light source would be wavelength independent. ND filters have no effect on color, and light reduction is uniform over the entire assay site image, therefore they would allow direct comparisons among array sites within a given image, even in the absence of a calculated transmission curve. ND filters are graded by a number that is indicative of the amount of light they transmit. The grade (or optical density) of the ND filter is defined as the logarithm to the base ten of the ratio of the power of the incident light to that of the transmitted light. For example, a filter with "ND 0.1" stamped on it transmits 80% of the incoming light, while the ND 1.0 filter transmits only 10%. The table below shows the gradation range, percentage of light transmitted and scale factor for various ND filters.

| Neutral density filter grade | Amount of light transmitted | Scale Factor (*) |
|---|---|---|
| ND 0.1 | 80% | 1.25 |
| ND 0.15 | 70% | 1.43 |
| ND 0.2 | 63% | 1.59 |
| ND 0.3 | 50% | 2.00 |
| ND 0.4 | 40% | 2.50 |
| ND 0.5 | 32% | 3.13 |
| ND 0.6 | 25% | 4.00 |
| ND 0.7 | 20% | 5.00 |
| ND 0.8 | 16% | 6.25 |
| ND 0.9 | 13% | 7.69 |
| ND 1.0 | 10% | 10.00 |
| ND 1.2 | 6.30% | 15.87 |

-continued

| Neutral density filter grade | Amount of light transmitted | Scale Factor (*) |
|---|---|---|
| ND 1.5 | 3.20% | 31.25 |
| ND 2.0 | 1.00% | 100.00 |

As an example of the use of optical filters for a single assay unit with a plurality of separately addressable sites (e.g., spots), at least two images are collected with high and low light levels as a result of the use of light-reducing filters in collecting one or both images. It may also be beneficial to collect images using three, four or more optical filters with different light reducing levels. The number of differently filtered images collected in an assay will depend, at least in part, on the dynamic range of the sensor and the range in intensities of the light use in the assay.

In a preferred embodiment of the invention, images from the sensor are all recorded with a single exposure time. The first image is captured with no filter in place, thus recording a high intensity image. In this first image, a number of sites in the image may exceed the preferred dynamic range of the sensor. A second image is captured using an optical filter which is placed in the path of the light illuminating the particles or between the sample and the detector. Additional images can be collected using optical filters with greater or lesser levels of light reduction capacity. The sample is kept static during the recording of all images. In this preferred embodiment the data from each image is combined and normalized using a conversion factor based solely on the wavelength dependent optical density of the optical filter(s). The combination of the two or more images into a single composite image includes the steps of.

1. Starting with an 8, 12, 14 or 16-bit image, convert all images to floating point to preserve precision during the mathematics operations.
2. Multiplying each image by a scale factor based on the value of the optical filter (preferably an ND filter) used for collecting the image. The scaling factor is applied to the images after the instrument and camera background have already been removed (i.e., the scaling is applied to the signal due to the particle labels only).
3. Before overlaying the images, the saturated pixels for all images are replaced with zeros (i.e. black). The two or more images are then merged by overlaying the pixels with the higher intensity values on the ones that were set to zero (i.e., the normalized pixels from the optically filtered image). This replaces what were originally saturated pixels with "amplified" (normalized) pixels from the images collected using the filter(s).
4. The floating-point image can then be converted to 16-bit image via a stretch process to use all of the precision available in the 16-bit file.

The procedure is repeated for each additional image until a composite floating-point image is created. For example, in an image set overlay involving three images, a pixel of the detector may be saturated in the non-filtered image, in the preferred range for an intermediate ND filter, and below the preferred range in a highly filtered image. In this case, the merged image would utilize the amplified or normalized pixel from the intermediate filtered image, and not from the highly filtered image. Thus, one way of performing the overlay process is sequentially from unfiltered to highly filtered image, however ending the replacement process for a pixel once its signal for an image falls within the preferred range of the sensor.

Thus the composite image derived from each of the separately addressable sites of the array in this embodiment is comprised of data collected within the preferred range of the detector for each site. The wavelength dependent light reducing capacity of the optical filters provides a global conversion factor in extending the dynamic range of the sensor, and thus eliminates potential errors in analyte detection and quantification that could result from extrapolating data based on correlations from neighboring array sites.

In an alternative embodiment of the present invention, linear normalization procedure could be used to recombine a number of different images to correct for any non-linearity of the system. This technique would use an image processing function to determine the median deviation between frames for all pixels within a valid range. Each image would then be normalized to the non-filtered image, then combined in the same manner described in the previous two paragraphs.

In another embodiment of the present invention, one or more optical filters are used in combination with varying the exposure time to extend the dynamic range of the sensors. This combination is particularly advantageous when the intensity of the signal from the most intense spot on the array exceeds the dynamic range of the detector even when the shortest exposure time attainable for the given detector is used (in the absence of optical filters). Two or more optical filters can be combined for collecting a single image. The optical filter(s) to use in combination are chosen such that signal intensities fall within the preferred range, i.e. linear response range, of the detector. Subsequent images can be taken with varying combinations of exposure times and optical filters. Calculation of the scaling conversion factor for each image includes a factor for the exposure time as well as a wavelength dependent factor for the light reducing capability of the one or more optical filters used.

According to the invention, a method is provided for extending the dynamic range of an analyte assay that uses light from light scattering particles as signals, which comprises detecting integrated light with a sensor, wherein the intensity of integrated light from one or more sites is reduced by one or more light filters to an extent that the signal generated by the sensor is linearly proportional to the integrated light detected; and scaling the signal by factors determined by the light transmitted by said one or more filters in order to quantify the integrated light from one or more of the sites. The extended dynamic range provided is preferably linear. The filters used in the method may transmitted 1%, 3.2%, 6.3%, 10%, 13%, 16%, 20%, 25%, 32%, 40%, 50%, 63%, 70%, 80%, 90%, and 95% of the light entering the filter.

4. Non-Destructive Sensor Reading

In yet another embodiment, the method of the invention uses specific types of sensors can be used that are capable of providing a range of exposure times within a single actual exposure. One type of sensors allow only a single reading of the signal after which the sensor must be reset, i.e., the process of reading is destructive to the signal. The methods of this particular embodiment uses sensors that allow non-destructive reading of signal, thus allowing multiple readings during a single period of exposure time. Such multiple readings can be carried out in various ways. One way is to take multiple readings over an entire imaging sensor during the entire exposure period. Some imaging sensors, however, allow random access to individual pixels or groups of pixels. Such sensors allow greater flexibility in handling signals from particular assay sites. For example, individual pixel readings can be monitored at time intervals, including regular time intervals, non-regular time intervals, and preferably registered time intervals. Any pixel that is approaching the maximum desirable accumulation can be reset. Such resetting avoids the problems with electron overflow in the pixel, causing blooming, which will ultimately contaminate nearby pixels. Such reset pixels can be used over a single such time interval, or the time intervals can be combined to provide an average response, or can be combined to provide a total accumulation period. At the same time, pixels corresponding to low density assay sites can continue to accumulate, thereby providing a response over a longer exposure time.

An example of such a device is a Charge Injection Device (CID) imaging sensor, which can be incorporated in a camera. Each pixel of a CID sensor array is individually addressed during readout, which is accomplished by transferring or "shifting" the collected "charge packet" within an individually addressed pixel, and sensing displacement values across the row and column electrodes at the sensor array site. This type of readout is non-destructive because the charge remains intact in the pixel after the signal level has been determined. To empty the pixel for new frame integration, row and column electrodes are biased to "inject" the charge packet into the substrate collector. Such CID sensors are available, for example, from Thermo Cidtech®, e.g., the RACID84, 85, and 86 imaging sensors. These sensors provide 1024×1024, 1024×256, and 512×512 pixel configurations respectively.

According to the invention, a method for providing an extended dynamic range in an analyte assay that uses light collected from light scattering particles is provided which detects integrated light with a sensor that provides non-destructive reading of signals from individual pixels or groups of pixels. The assay sites are exposed to the sensor for a single exposure period of time while the signals from the pixels are read at time intervals such that any pixel that approaches saturation is reset. Preferably, each pixel can be accessed randomly, and the time intervals are registered. The signals are combined for each reset pixel taking into account of the time intervals to quantify the detected integrated light, thereby providing the extended dynamic range. The processing of the signals may include summing the signals read at said time intervals and/or averaging the signals read at said time intervals.

5. Deconvolution at High Particle Densities

In yet another embodiment, the invention provides a method for extending the dynamic range of an assay which tackles a limitation which does not relate to the sensor. The method of the invention uses deconvolution to compensate for the deviations in response at high particulate label densities due to the inherent characteristics of the assay format and the label. The description below is directed specifically to RLS particle labels, but similar effects also occur with particulate fluorescent labels.

RLS particle labels produce a scattered light signal that is linearly related to the number of particles present within the detection field over a broad range of particle densities, up to a density where particles begin to interfere with each other. This density will depend, at least in part, on the particle size, with larger particles interfering with each other at lower densities than smaller particles. Several different types of interferences or interactions can occur that contribute to non-linear response at high densities.

One type of interference occurs when particles become sufficiently close-packed that the surface begins to act as a reflective surface, essentially as a mirror. This is particularly applicable to solid phase applications, such as arrays on chips or slides. When the particles on an array feature become close-packed, the particles essentially form a plating, that acts as a reflective surface, rather than as a population of discrete scatterers.

A second interference is a blocking effect. Even with arrays on solid phase media, there is a certain depth to the bound particles. Thus, when the array feature is illuminated at an angle, there is some probability that a particle can be in the "shadow" of another particle. The probability of such blocking is greater the larger the particles and the denser the packing. The light scattered from a particle can also be blocked, in part, by another particle or particles, and the magnitude or probability of this effect is also dependent on the density and size of the particles.

Without being limited by this explanation, the dominant interference phenomenon between "blocking" and "reflecting" may be different for trans verses epi-illumination. For trans illumination, when the particle density increases to the point at which one particle can "shadow" another from receiving the illumination from the source, the signal will actually decrease as particle density increases. In addition, particles located closer to the detection source are essentially blocking the scattered light from other particles located closer to the illumination source. In the case of epi-illumination, the increase of particles creates a layer which acts as a reflector, similar to a layer of gold foil. So, with epi-illumination, the intensity will remain constant after the density of particles increases to the point of complete coverage of the surface of the slide.

Yet another type of interaction is due to perturbations in light scattering that occur as particles are brought close together. These perturbations can also contribute to deviations in response.

Deconvolution can be performed using standard curves, using one or more analytical or semi-analytical type of equations, or a combination of the two types.

Deconvolution using standard curves can be performed as follows. Integrated RLS signals for spotted microarrays remain linear up to about 10 particle per $\mu m^2$, depending on particle size. Beyond about 10 particle per $\mu m^2$, wavelength shifts due to the close proximity of particles to one another, coupled with shadowing effects from overlapping particles, causes a reduction of signal at the peak detection wavelength of the particle. Between about 10 and 100 particles per $\mu m^2$, corrected integrated intensities can be calculated by generating an equation from a standard curve generated from data gathered for a standard dilution series of spots in the 10-100 particles per $\mu m^2$ range (the series can be on a single slide or chip). Beyond about 100 particles per $\mu m^2$, the slope of the curve of scattered light intensity versus particle density approaches the horizontal, making de-convolution impossible. The standard curve (data) can be used to determine an equation by curve fitting. A number of different curve fitting methods are available, for example, linear regression, non-linear regression, and the splines method, as well as others. The equation generated from the curve can then be applied to any data collected to de-convolute the intensities in the non-linear, but correctable, range. In applying this technique, the camera exposure time is also factored into the equation to properly scale the data. In addition, in establishing the standard curve, it is important for achieving good accuracy in experimental quantitations, that the density of particles in each spot be accurately determined.

Deconvolution equations can also be obtained semi-analytically. Equations can be obtained for quantitating analytes in solution and on solid surfaces. In doing so, it is beneficial to know the quantitative relations between light scattering intensity and particle (label) concentration or surface density as well as the relation of light scattering intensity and analyte concentration or surface density with RLS particles. The former relation is more fundamental because it sets the maximum ranges and sensitivities that can be achieved with a given RLS particle.

The relation between light scattering intensity and particle (label) concentration in solution and solid surfaces was examined, and mathematical expressions that can be used to describe these relations and serve to represent quantitative calibration data (i.e., deconvolution equations) were obtained.

According to the invention, a method is provided which extends the dynamic range in an analyte assay that uses light collected from light scattering particles at a site as signals, wherein light collected from said light scattering particles is not proportional to the number of particles at the site. The method comprises detecting integrated light with a sensor; generating a standard curve of integrated light intensities versus number of light scattering particles per site; and applying the standard curve to calculate the number of particles at the site based on the detected integrated light, thereby providing the extended dynamic range of the analyte assay. The standard curve can be generated from a dilution series comprising sites with different numbers of particles per unit area or volume. In a preferred embodiment, the sites comprising the dilution series are all associated with the same physical form of the analyte assay.

On the basis of conservation laws, we can state that the intensity of light scattered by particles in a volume V or on a surface S is proportional to the incident light intensity $l_0$ (photons/s-cm$^2$), the fraction $\phi_A$ of incident photons which are absorbed by the particles and the fraction $\phi_E$ of absorbed photons which are reemitted. All of these parameters depend on wavelength. Mathematically, we can write $$I_S = aI_0\phi_A\phi_E \quad (1)$$

where a is an instrumental constant. Equation (1) assumes that the incident light is monochromatic and has a specified wavelength $\lambda$.

In order to obtain an explicit relation between Is and particle concentration in a suspension, we consider the particle concentration dependence of the various parameters in Eq. (1). In general, $I_0$ is independent of particle concentration. a and $\phi_E$ are independent of concentration at low particle concentrations. Thus at low particle concentrations, only $\phi_A$ depends on concentration, and the dependence of Is on concentration is completely determined by $\phi_A$ At higher concentration $\phi_E$ becomes dependent on concentration due to particle-particle perturbations and a also becomes dependent on concentration due to geometrical and inner filter effects discussed in-a following section.

Assuming the validity of the Beer-Lambert Law, we can write for the dependence of $\phi_A$ on concentration.

$$\phi_A = (1 - 10^{-\epsilon Cx}) \quad (2)$$

where $\epsilon(M^{-1} cm^{-1})$ is the molar decadic extinction coefficient, C is the molar particle concentration and x(cm) is the optical path length. Thus for particle concentrations where the distance between particles is large and there are no geometrical and inner filter effects, we can write from Eqs. (1) and (2).

$$I_S = a(1 - 10^{-\epsilon Cx})\phi_E \quad (3)$$

For low particle concentrations where $\epsilon Cx$ is much less than 1, we can expand the exponential term in Eq. (3) in a power series expansion using the expression $$10^{-z} = 1 - 2.303z + \frac{(2.303z)^2}{2!} - \frac{(2.303z)^3}{3!} + \dots \quad (4)$$

Retaining only the first two terms (for z<<1) we can write from Eq. (2)

$$\phi_A = 2.303 \epsilon Cx \quad (5)$$

so that $$I_S = 2.303 a I_0 \epsilon Cx \phi_E \quad (6)$$

The above well known approximations essentially apply to particle suspensions where the amount of light absorbed in the pathlength x is very small. For this condition, the intensity of incident light is practically constant throughout the path x. However, if the suspension is strongly absorbing, the intensity of light is not the same at every point in the path x, but instead decrease from x=0 to x. In the latter case one uses Eq. (2) and (3). Equations (5) and (6) are correct within 5% for values of $\epsilon Cx < 0.05$.

From theory we expect $\phi_E$ to be particle independent when the average distance between the particles is greater than about 3× their diameter d. For distances smaller than about 3 d, the particles interact such that (1) their absorbance and light scattering spectra shift towards longer wavelengths and (2) the values of $\phi_A$ and $\phi_E$ change with increasing particle concentration. Thus, at high particle concentrations, we expect $\phi_E$ and $\epsilon$ to become concentration dependent. If the particles are randomly distributed in suspension, then the average distance D between particles, in cm, is given by $$D = \frac{0.554}{c^{1/3}} \quad (7)$$

at a concentration c(particles/cm$^3$) is approximately equal to $1/(c)^{1/3}$. However, if the particles have a tendency to associate, then $\phi_F$ can depend on particle concentration, even at low particle concentrations, depending on the values of the association constants. From this equation we can calculate the concentration at which D=3d using the following equation (where C is molar concentration, d in cm.)

$$C = \frac{1000}{Nav} \left( \frac{0.554}{3d} \right)^3 \quad (8)$$

For example, for d=60 nm, C=4.8×10$^{-8}$ M which corresponds to an absorbance of around 1200 for a 1 cm path length. Because of the very high extinction coefficients of our gold particle suspension we never work at concentrations around 10$^{-8}$. Therefore, interparticle perturbations do not seem to be important at the concentration ranges which we generally use.

The scattered light intensity from a suspension of particles can also be affected by inner filter effects and geometry of the light scattering volume. These effects depend on the relative orientations of the illuminating beam, the direction of detection and spatial filters that are used to reduce stray light. In the present work, the detection system is at right angles to the direction of the illuminating beam. To minimize non-specific scattered light, the detection optics are arranged such that only light scattered from a small volume in the center of the cuvette is detected. To reach this detected volume, the incident light must first cross through the intervening volume of suspension between the cuvette face on which the light is incident and the center of the cuvette. The amount of incident light which is absorbed in the intervening volume increases with increase in particle concentration and the intervening volume thus acts as a concentration dependent inner optical filter. At very high particle concentrations, most of the light is absorbed in the intervening volume and a very small amount of light reaches the center of the cuvette. Similarly, light which is scattered towards the detector must pass through an intervening volume of suspension between the light scattering volume and the wall of the cuvette facing the detector. These effects also act as a concentration dependent inner optical filter. Because of these geometrical and inner filter effects, the scattered light intensity decreases with particle concentration at high particle concentrations. Geometrical effects can be accounted in Eq. (1) by multiplying this equation by a factor which has the form $10^{-\alpha x}$.

For particles attached to a transparent surface (as in solid phase immuno- or DNA probe assays), Eq. (1) applies, and at low surface particle densities, the dependence of Is on particle density is completely determined by $\phi_A$. Writing an equation equivalent to Eq. (2) for particles on a surface depends on how the particles are distributed on the surface, that is, whether they are all confined to one plane or are distributed over a finite height from the surface (particles piled on top of each other). However, the expression for $\phi_A$ depends on whether the particles are all exactly in the same plane or distributed throughout a space of finite thickness. If the particles are all in the same plane then we can write $$\phi_A = \rho \sigma_{ext} \quad (9)$$

where $\rho$ is particle density (particles/cm$^2$) and $\tau_{ext}$(cm$^2$) is the particle extinction cross section in cm$^2$. The extinction cross-section represents a circular area around a particle such that every photon of light which falls on the area is absorbed and every photon outside the area is transmitted. The fraction of light that is absorbed is then simply the fraction of the total surface area occupied by the particle cross section times the particle density as shown in Eq. (9). Equation 9 can be written in terms of extinction coefficients using the relation $$\sigma_{ext} = \frac{2.303 \times 1000 \varepsilon}{Nav} \quad (10)$$

$$= 3.8 \times 10^{-21} \varepsilon \quad (11)$$

where Nav is Avogadros number. The scattered light intensity from a surface in which all of the particles are in the same plane is, from Eqs.(1) and (5) given by the expression $$I_S = a I_0 \rho \sigma_{ext} \phi_E \quad (12)$$

For solid surfaces in which the particles are not confined to a specific plane but are distributed over a finite thickness, $\phi_A$ is given by the expression $$\phi_A = (1 - 10^{-\rho \sigma_{ext}}) \quad (13)$$

and the scattered light intensity is $$I_S = aI_0(1-10^{-\rho\sigma_{ex}})\phi_E \quad (14)$$

For values of $\rho\sigma_{ext} < 0.05$, Eq. (14) reduces to the form of Eq. (12).

Geometrical and inner filter effects are also important for light scattering from particles on a surface. The effect s depend on whether trans or epi- illumination is used. The effects are usually smaller for epi-illumination. Finally, interparticle perturbations can also affect Is when the average interparticle distance is less than about 3d.

In the following sections, we present experimental tests for the validity of the above expressions.

The applicability of the Beer-Lambert law to RLS particles can be tested by measuring the absorbance vs. particle concentration of RLS particle in suspension. In terms of absorbance A (also called optical density) the Beer-Lambert law can be written as $$A = \epsilon C x \quad (15)$$

where $\epsilon$ C and x are as defined in Eq. (2). A vs C was plotted for gold particle of different diameters covering an absorbance range of 0.01 to 2. Absorbance was measured at the peak absorbance wavelength for each particle diameter as follows: 525 nm (40 nm), 535 nm (60 nm), 545 nm (80 nm) and 525 (100 nm). The plots showed that A increases linearly with particle concentration as expected from Eq. (15). The results indicate that the Beer Lambert law applies to RLS particles and that the particles do not associate or perturb each other, at least to A=2. Using small path length cuvettes we have found that the Beer-Lambert Law actually applies to values of A greater than 2. The results thus show that we can use the Beer-Lambert law in theoretical relations between scattered light intensity and particle concentration or surface density. From the slopes of the plots in FIG. 1, we obtain the following extinction coefficients: $8 \times 10^9$ M$^{-1}$ cm$^{-1}$ (40 nm, 525 nm), $2 \times 10^{10}$ M$^{-1}$ cm$^{-1}$ (60 nm, 535 nm), $6 \times 10^{10}$ M$^{-1}$ cm$^{-1}$ (80 nm, 545), $10^{11}$ (100 nm, 555 nm).

To determine the quantitative relation between scattered light intensity Is vs particle concentration in suspension, we performed the required measurements using 6×50 mm tubes as cuvettes. Detection was at right angle to the incident beam and was confined to a small volume in the center of the cuvette. The particles were illuminated at a wavelength equal to the wavelength of maximal absorption. Scattered light intensity vs particle concentration was measured for particles of 40 nm, 60 nm, 80 nm and 100 nm diameters.

Scattered light intensity vs particle concentration in the range $5 \times 10^{-14}$ M to $2 \times 10^{-10}$ M concentration was plotted in natural and semilog forms. If Eq. (3) were to apply at all concentrations, we would expect that the scattered light intensity would increase linearly with particle concentration at low particle concentrations, become nonlinear at higher concentrations and finally level off at a constant value. For the most part the experimental graph displays these relations but at high concentrations the intensity decreases with concentration instead of leveling off. This effect is attributed to inner filter and geometrical effects. Equation (3) therefore does not give an accurate description of the experimental data because it ignores inner filter and geometrical effects. To take account of these effects we rewrite Eq. (3) in the form $$I_S = B(1-10^{-\epsilon Cx})10^{-\epsilon CL} \quad (16)$$

In the above expression, we have $B = I_0 a\phi_E$ and the new exponential term outside the parenthesis accounts for the inner filter effects while the term in parenthesis accounts for the amount of light absorbed by the detected light scattering volume. To determine whether Eq. (16) gives a correct description of the graphs of scattered light intensity vs particle concentration, we have curve fitted this equation by nonlinear regression analysis. The fitting parameters are B, x and L and $\epsilon = 8 \times 10^9$ M$^{-1}$ cm$^{-1}$. The resulting values of the analysis are B=201.474, x=0.008484 cm and L=0.62754 cm. It was seen that Eq. (16) gives a very good fit to the data. At low particle concentrations we expect the exponential term outside the parenthesis to be equal to 1 and concentration independent and the term in parenthesis to reduce to $2.303\epsilon Cx$ as suggested by Eqs.(4) and (6). Thus for low concentrations, we can write from Eq. (16)

$$I_S = 2.303 B\epsilon Cx \quad (17)$$

To test the applicability of the above relation at low particle concentrations, we calculated Is vs C using the values of B and x quoted above and plotted them together with the experimental data at low concentrations. Eq. (17) agrees within 10% for values of C up to $5 \times 10^{-13}$ M.

We have found that Eq. (17) also gives a good description of the experimental Is vs concentration graphs for 60 nm, 80 nm and 100 nm diameter particles using the values of B, x, L and $\epsilon$.

Specific fitting parameters for different particle sizes are provided in the following table. The specific values given apply only to the specific instrumental arrangement used in the measurement. However, Eq. (17) is generally applicable and we have demonstrated how this relation can be used as a quantitative representation of experimental $I_s$ vs C. Thus, this relation can be used to represent calibration data.

| Diameter (nm) | B | X (cm) | L (cm) | $\epsilon$ (M$^{-1}$ cm$^{-1}$) |
| --- | --- | --- | --- | --- |
| 40 | 239.19 | 0.005688 | 0.5065 | $8 \times 10^9$ |
| 60 | 184.77 | 0.008827 | 0.58864 | $2 \times 10^{10}$ |
| 80 | 172.716 | 0.007287 | 0.4596 | $6 \times 10^{10}$ |
| 100 | 201.47 | 0.00848 | 0.6274 | $1 \times 10^{-11}$ |

To obtain experimental relations between scattered light intensity and particle surface density, we prepared spots of gold particles with different particle densities. The spots were deposited on clean microscope glass slides. To measure scattered light intensity, a spot was illuminated through the bottom of the slide and the scattered light intensity was measured through a green filter with a video camera that was positioned above the slide (trans illuminating detecting system). The measured intensities were corrected for the nonlinearity of the camera.

Plots of experimental scattered light intensity vs particle density for 80 nm gold on solid phase surface show that the experimental graphs resemble the graphs of calculated plots, that is, the intensity increase linearly with particle density at low particle concentrations, becomes nonlinear at higher concentrations and decreases with increase in surface density at still higher concentrations. The decrease at higher concentrations indicates that inner filter effects are important. In analogy with the results in the liquid (suspension) phase, we use Eq. (14) for the solid phase but modify it for inner filter effects. The modified equation can be written as $$I_S = B(1-10^{-\rho\sigma_{ext}})10^{-L\sigma} \quad (18)$$

where B, $\sigma_{ext}$ and L are the fitting parameters. The experimental data was well fitted with Eq. (18) using B=1.73, σext=0.01887 μ² and L=0.00407 μ² with ρ expressed in units of particles/μ². The latter values were obtained by nonlinear curve fit of Eq. (18) to the experimental data. Thus, Eq. (18) gives a very good representation of the experimental data. At low particle densities, we would expect scattered light intensity to vary linearly with surface density. At these low concentrations, Eq. (18) reduces to $$I_S = 2.303 B \sigma_{ext} \rho \qquad (19)$$

FIG. 6b shows a plot of experimental data at low particle densities. The solid line through the plot was calculated with Eq. (19) using the values for B, $\sigma_{ext}$ and L presented above. The figure shows that scattered light intensity varies linearly with particle density at low particle concentrations and that Eq. (19) give a very good fit to the data. We have similarly shown that the Eqs. (18) give a very good representation of experimental data for other particle diameters.

At a given illuminating wavelength, the useful range of scattered light intensity is usually about three orders of magnitude without the use of dynamic range extending techniques. However, this range can be increased by performing measurements at different illuminating wavelengths. In addition, at high surface densities, where the interparticle distance becomes comparable to a wavelength of light, the light scattered by each particle is in phase with the light scattered by neighboring particles. This gives rise to specular reflection. At low particle densities the particles do not interact with each other and each particle scatters independently of each other. If the particle density is sufficiently high, the spot displays a color in room lights, the spot looks like a diffuse dyed spot (diffuse reflection). However, at particle concentrations where the interparticle distance is comparable to the wavelength of illuminating light, light impinging on the spot is reflected as from polished gold surface, i.e, the spot behaves as a mirror.

Above we have presented methods for obtaining experimental relations between scattered light intensity and particle density. These are fundamental relations. In practice we are interested in the relation between scattered light intensity and amount of analyte detected in a given site. Amount can be expressed in terms of analyte surface density. If in an RLS labeling experiment, each analyte molecule on a site binds a gold particle than the amount of analyte in the site can be determined from the scattered light intensity and the calibrating graph or calibrating expression relating scattered light intensity to particle density. The particle density and analyte density are the same. However, it may be that not every analyte molecule on a surface binds a gold particle because of geometrically effects, affinity constants and other factors. In this case, scattered light intensity vs analyte concentration can be determined using a calibrating slide and representing the results by a mathematical expression. This can, for example, be done by the methods described above.

As indicated, the techniques described herein for extending dynamic range are particularly advantageous for use with assays utilizing RLS particles, whether the assay employs a single type of RLS particle, or as in multiplex assays, where sets of distinguishably different RLS particles that have different peak scattering wavelengths are used. However, the techniques can also be applied to other particulate labels. For example, they can be applied to fluorescent particles, e.g., polystyrene beads loaded with multiple fluorophores such as fluorescein or other fluorescent dyes. In general, single small molecule fluorophores are not amendable to individual visualization in assays, but loaded beads or microspheres can be. However, applying the present techniques to fluorescent labels also present difficulties associated with the nature of the label. For example, at high label densities, it may be necessary to deal with fluorescence quenching and bleaching, and for repeat or extended exposures it may be necessary to deal with bleaching. Furthermore, the time course of signal decay for fluorescent labels is dependent on label density.

Thus, for deconvolution methods, the mathematics to perform the deconvolution is more complicated for fluorescence than for RLS particles, due to factors such as label quenching and bleaching. The multiple exposure technique is more limited for many assay formats involving fluorescence than for RLS particles, because the multiple exposure technique is most useful where the detection method has a high signal/noise ratio. In many fluorescence applications, the signal/noise ratio limits that benefit, e.g., because increasing the exposure time to pull in weak signals also increases the inherent background noise. Nonetheless, the techniques described are also useful with detection of labels other than RLS particles, though RLS particles are the highly preferred label.

Many electronic sensors have a response that is approximately linear throughout a range of intensities for a particular exposure time, and thus can be directly used for quantitation. However, if a sensor does not provide such linear range, or if significant deviations occur at some point(s) in the range, the recorded values can be compensated by weighting the values for different detected signals to correct to accurate quantitation. The correction can also be wavelength dependent, as response of the sensor may differ at different wavelengths. In addition, for sensors that have different sensitivities to different wavelengths, the quantitation will also include the use of different weightings or of different standard curves depending on the wavelength of scattered light detected. This is particularly important in multiplex assays where sets of distinguishable particles are used that have different peak scattering wavelengths and so provide scattered light signals of different colors on illumination with polychromatic, preferably white, light. Compensating for differing sensitivities to different wavelengths of light allows proper quantification. Specifications on such sensitivities and response deviations may be available from the sensor or camera manufacturer or distributor, or can be determined for each sensor with the use of standard media, e.g., slides with spots of defined particle type (for defined scattered light characteristics) and defined densities.

In preferred embodiments of the invention, after the sensor has generated the signals, the signals corresponding to the background portion of the spectrum is removed before any conversion factors are applied, or before the signals are scaled, such that it is the signals from the labels that undergo processing or manipulation. The background spectrum can be identified and removed since the peaks of the light from the labels are known. For example, when longer exposure times are used, light of wavelengths other than those from the label will increase along with the light from the labels. The elimination of the background spectrum before data processing and manipulation is particularly beneficial when multiple readings are being combined to create a final spectrum, as it helps to eliminate erroneous or anomalous spectral features.

In other embodiments of the invention, where the signals are combined to form an image, standard software tools available in the art can be applied to identify the signals from the sites or objects (such as individual particles) of interest in the image. Other signals that correspond to the background portions of the image can be subtracted from the image to aid analysis and viewing of the image. The background portions of the image can appear as a result of many factors, including but not limited to labels in between assay sites, physical spaces between the labels within an assay site, and physical spaces between assay sites. The method comprises making a first round of detection resulting in an image that would allow the software to identify the background portion of the image, such as areas that are not assay sites, or anomalous labeling, etc. In one or more subsequent detections the signal or the signal from pixels that collect light from these background portions of the image (i.e., the off-site areas) would be disregarded, or subtracted from the image.

Systems (i.e., apparatus) suitable for carrying out the assay methods with extended dynamic range as described above are also useful. In general, the systems are configured as described in other parts of this description.

Illuminating and Light Collection Optics

1. General Concepts

The solid-phase methods we now describe can be applied to the detection of light scattering particles. The detection and measurement of one or more light scattering properties is then correlated to the presence, absence, or concentration of one or more analytes in a sample. These methods can be used with most, if not all known solid-phase analytic methods including microarray, array chip, or similar formats. The method is designed to have a wide range of sensitivities (from low sensitivity to the ultra sensitive range). This range of sensitivities is achieved with easy to use and inexpensive apparatus.

In the technology, the number or relative number of particles on a surface is determined through methods that depend on the light scattering properties of particles. The detection system consists fundamentally of (1) a magnifying lens (also called an imaging or collection lens) that forms a magnified image of the light scattering particle patch or a portion of the patch and (2) an illuminating system that makes the particles appear as bright objects on a dark background (the DLASLPD method). The method can be performed without the need for the collection lens also. The number of particles in the magnified image can be quantified by particle counting or by measuring the scattered light intensity (which is proportional to particle number or density). Particle counting can be done by (a) eye (unaided or with an ocular lens, depending on particle size), (b) an electronic imaging system (for example video camera, CCD camera, image intensifier) or (c) a photosensitive detector with a field limiting aperture and a scanning light beam arrangement. Scattered light intensity can be measured with an electronic imaging system or photosensitive detector. At low particle surface densities (less than about 0.1 particles per $\mu^2$), the particle counting method is preferred while at higher surface densities (especially, where the individual particles are closer than the spatial resolution capabilities of the magnifying lens) the steady light scattering intensity measurement is preferred. The technology is designed to easily shift between these two methods of detection, that is, between particle counting and intensity measurements and can be used with particle diameters down to about 20 nm depending on the light scattering power of the particles and specific hardware components of the detection apparatus.

Light Illumination Systems

The illuminating system is a key element in the technology. The illuminating systems are designed to illuminate a particle patch or group of particle dots with high light intensity in such a manner that the individual particles appear as bright objects on a dark background. This allows visualization of particles attached to a surface or free in a fluid film above the surface. Free particles are distinguished from attached particles by their Brownian motion which is absent in attached particles. In the following sections we describe the details and logic of the illuminating systems.

Applicant has experimented with many different illumination systems including an expensive commercial dark field illuminator called an ultracondenser (Zeiss). Two fundamental methods of illumination and several versions of these two methods can be used. These methods are simpler and seem to produce higher illuminating light intensities than, for example, the ultracondenser.

General Description of the Fundamental Illuminating Methods

The illuminating systems are designed to (1) deliver a beam of high light intensity to a patch (or group of dots) of light scattering particles and (2) minimize the amount of the illuminating light that enters the detecting system directly or through reflections. This is achieved by constraining the light beam and its reflections to angles that are outside the light collecting angles of the detecting system. In one illuminating method, the collecting lens and the light source are on opposite sides of the solid-phase surface (illumination from below) and in the other method, the illuminating light source and magnifying lens are on the same side of the surface.

Direct Illumination from below the Magnifying Lens

FIG. 1 presents a schematic diagram of one of the basic methods of illumination used. In this method, the light impinges on the solid-phase surface S from below the surface. It is assumed that S is transparent (although it could have some color). O is a region on the surface that contains light scattering particles. The magnifying or light collecting lens L is located above S. The angles at which L collects light are shown as a shaded cone C (light collecting cone of lens L) with an apex at the surface S (where the light scattering particles are located) and a base determined by the diameter D of the lens. The illuminating light beam (LB) is angled so that is does not enter the light collecting cone of L. The arrows show the direction of travel of LB.

The solid-phase can be, for example, a microscope slide, a microtiter plate or other types of transparent solid-phases used in clinical diagnostics. The light source can be any type of light source, such as filament lamps, discharge lamps, LEDs, lasers and the like. Light is collected from the illumination light beam using optical light fibers and/or light collecting lenses, and then focused onto the scattering light particles using a condenser lens. The mean angle θ which the light beam makes with the surface S is adjusted so that the beam of light does not enter the lens L as explained above. The adjustment of the angle θ can easily be done by visual observation of the light scattering particles through the magnifying lens and occular (compound microscope arrangement),adjusting the angle so that the particles appear as bright objects on a dark background. This angle also serves well for light scattering intensity measurements although at high particle densities, the focusing requirement is not as stringent.

The magnitude of the angle θ can be deduced from the numerical aperture of the magnifying lens. For ultrasensitive detection, a microscope objective is used as the magnifying or imaging lens. A microscope objective usually has its numerical aperture inscribed on its housing. Numerical aperture can be defined in terms of the diagram of FIG. 2. This figure shows a magnifying lens (with focal length f) that is focused on a patch of light scattering particles at O. The distance between the lens and O is equal to f. The lens (L) collects all light scattered from O into the solid cone whose base is the diameter D of the lens. The angle $\theta_H$ is defined as the planar half angle of this solid cone. The numerical aperture (N.A.) of the cone is related to $\theta_H$ by the expression $$N.A.=n\sin(\theta_H) \quad (36)$$

where n is the refractive index of the medium between the lens and the point O. The medium, for example, can be air (n=1), water (n=1.33) or immersion oil (n=1.5). For small values of $\theta_H$, N.A. is approximately equal to D/2f where D is the diameter of the lens and f is focal length.

The following table gives typical values for the numerical apertures and $\theta_H$ of objectives that can be commonly used (for n=1).

| Magnification | N.A. | $\theta_H$ in degrees |
|---|---|---|
| x10 | 0.25 | 14.47 |
| x20 | 0.5 | 30 |
| x40 | 0.65 | 40.54 |
| x63 | 0.85 | 58.2 |

As already mentioned, the exciting light beam must be angled so that it is outside of the light collecting solid cone of the magnifying lens. For high magnifications, the angle at which the exciting beam impinges on the solid-phase surface must be large. For example, for a ×40 objective, the incident angle must be larger than 40°. Since the fraction of light reflected at a surface increases with incident angle, we must consider whether the angles that have to be used in our illuminating system result in a large loss of light due to reflection. Furthermore, we must consider whether critical reflections (total internal reflections) are involved at high incidence angles. The following is a brief discussion of the fundamental laws of refraction and reflection needed in the subsequent discussion of the effects of reflections in this illuminating system.

Snells Law of Refraction

We describe Snells law of refraction in terms of the diagram of FIG. 3. This figure shows a light beam that travels along a medium of refractive index ni (i for incident medium) and impinges on the surface S of a medium of refractive index nt (t for transmission medium). Part of the incident light is transmitted into medium t (the refracted beam) and part is reflected (the reflected beam) back into medium i. If the angle of incidence is $\theta i$ then the angle of the refracted beam is given by Snells Law which can be written as $$ni\,\sin(\theta i)=nt\,\sin(\theta t) \quad (37)$$

If ni<nt then $\theta i$<$\theta t$. If ni>nt then $\theta i$>$\theta t$. Note that angles are measured with respect to a line that is perpendicular to the surface S. The reflected beam makes an angle $\theta r$=$\theta i$ (that is, the reflected and incident angles are equal).

Laws of Reflection. Fraction of Incident Light that is Reflected at a Surface

The fraction R of incident light intensity which is reflected for different incident angles $\theta i$ can be calculated using Fresnels equations of reflection. (It should be noted that intensity is here defined as energy per unit time per unit area. Intensity is also called irradiance). However for simplification, we present our discussion in terms of plots relating R to $\theta i$. The exact dependence of R on $\theta i$ is determined by the values of ni and nt and the state of polarization of the incident light. Important facts concerning reflectance are as follows.

i. Reflectance for the Case where the Light Beam Travels from a Medium of Low Refractive Index to one of High Refractive Index (ni<nt)

Figure 4A:
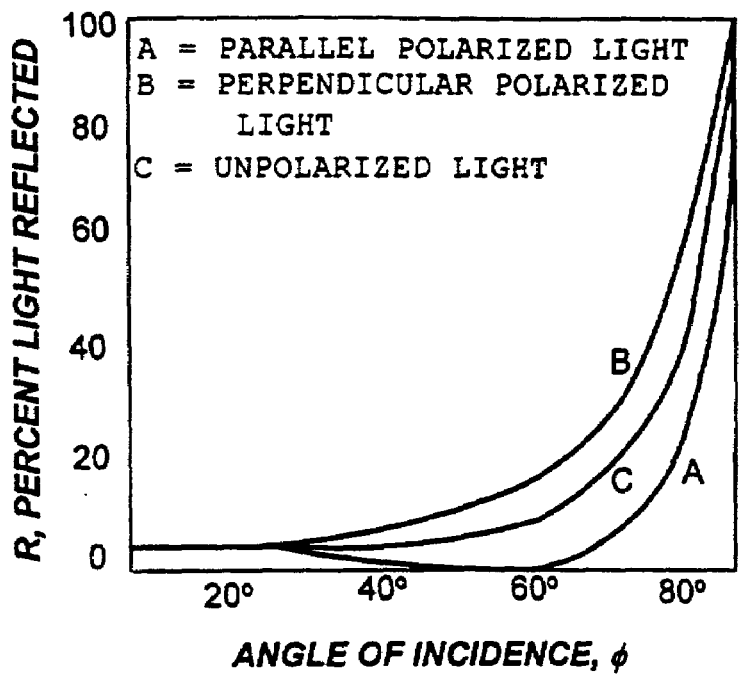
Figure 4B:
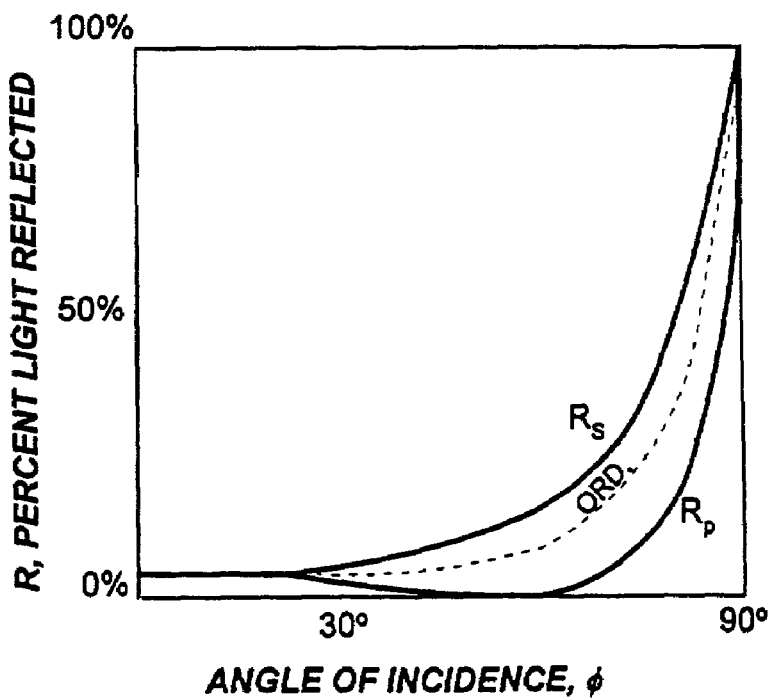
Figure 4C:
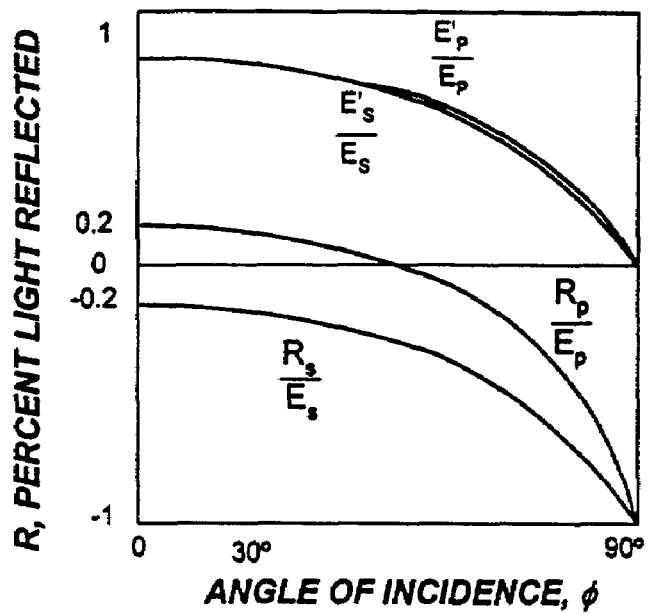

FIG. 4 shows plots of R vs. $\theta i$ ($\phi$=$\theta i$) for the case where ni=1 (air) and nt=1.5 (the latter is close to the refractive index of glass or plastic) and for light polarized parallel (rp) and perpendicular (rs) to the plane of incidence. The plane of incidence is defined as the plane which contains the incident light beam and the line perpendicular to the surface (see FIG. 3). The reflectance R of unpolarized light is given by the average of the graphs for light polarized parallel and perpendicular to the plane of incidence. In FIG. 4, the reflectance graph for unpolarized light is labeled Ord (for ordinary). The graphs of FIG. 4, show that a. rs increases continuously with increasing $\phi$ in FIG. 4 is the same as $\theta i$ as used herein). The increases in rs is small up to about 70° (where the reflectance is only about 15%) and then increases much more rapidly reaching 100% reflectance at 90°. Thus, the fraction of light that is reflected is less than 20% up to incidence angles of 60°.

b. rp decreases with increasing $\phi$ up to about 57° where rp is zero. The angle at which rp=0 is called the Brewster angle or polarizing angle. The Brewster angle $\theta b$ can be calculated with the expression $$\mathrm{Tan}(\theta b)=nt \quad (38)$$

assuming that ni=1 (air). For nt=1.5, above equation gives $\theta b$=56.3. It should be noted that at the Brewster angle, $\theta i$+$\theta t$=90°. Thus for nt=1.5, $\theta i$=$\theta b$=56.3° and $\theta t$=33.7°. For angles greater than the Brewster angle, rp increases rapidly with increase in $\phi$ and reaches a value of 100% at 90°.

c. For unpolarized (ordinary light), the reflectance increased gradually with increase in $\phi$ up to about 70° and then increases rapidly reaching 100% at 90°. Less than 20% of the incident light is reflected for $\theta i$<70°.

d. It should be noted that the intensities of the reflected and transmitted light do not add up to the intensity of the incident light. This seems to violate the law of conservation of energy. This apparent violation is actually due to the definition of intensity as energy per unit time per unit area. Because of refraction, the incident and transmitted light do not have the same cross sectional area. If the differences in cross sectional areas are taken into consideration, then it can be shown that the energy per unit time in the reflected and transmitted beams add up to the energy per unit time in the incident beam.

ii. Reflectance for the Case Where the Light Beam Travels From a Medium of High Refractive Index to One of Low Refractive Index (ni>nt)

Figure 5A:
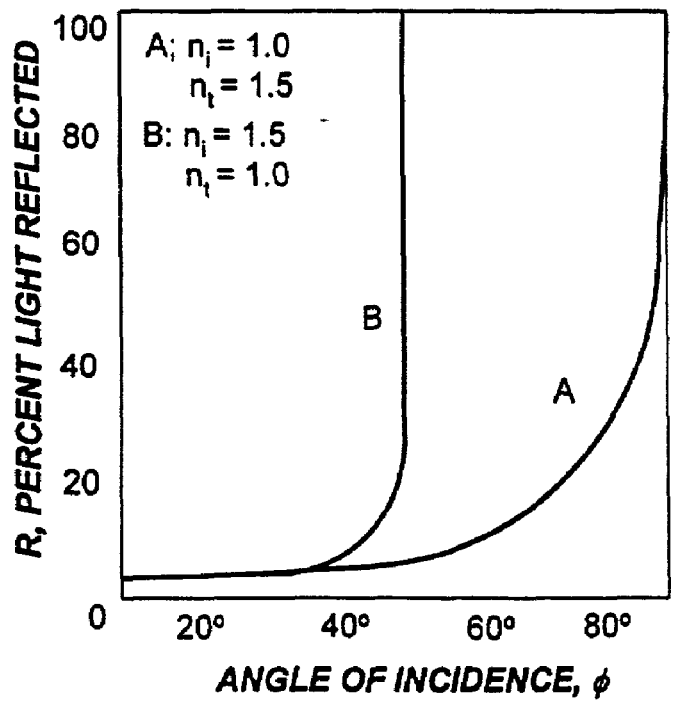
Figure 5B:
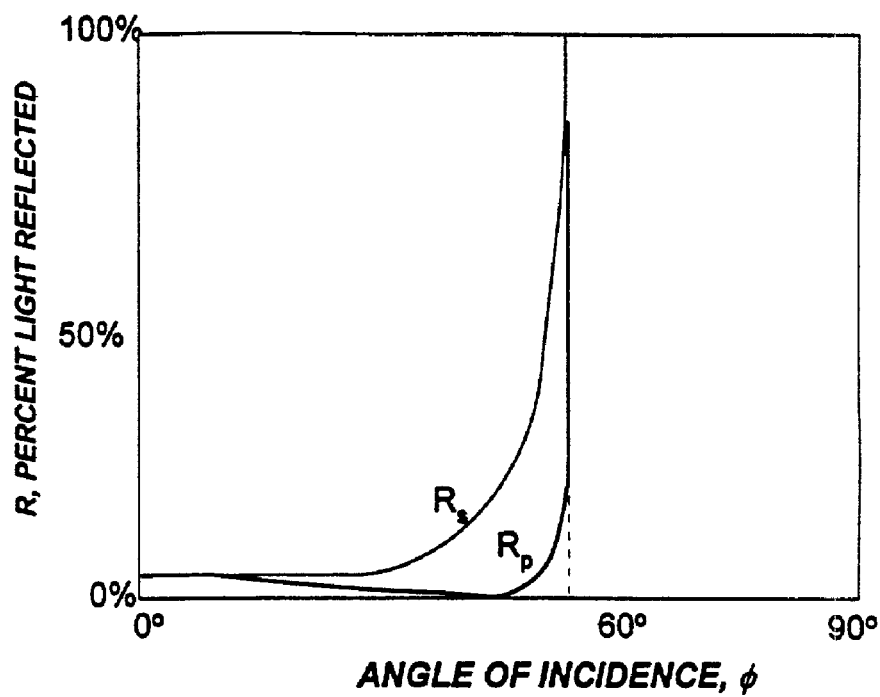
Figure 5C:
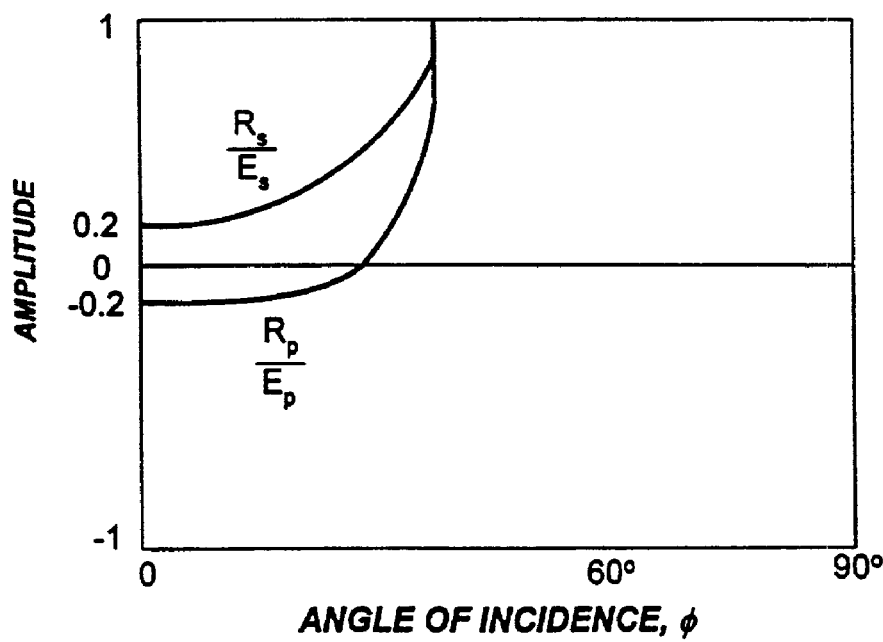

FIG. 5 shows plots of reflectance of polarized light vs. angle of incidence ($\phi$=$\theta i$) for ni=1.54 and nt=1. The plots are quite different than those of FIG. 4 for ni<nt. The most significant difference is that at an incident greater than about 41° all of the light is reflected (100% reflection, total reflection). The smallest incident angle at which total internal reflection occurs is called the critical reflection angle $\theta c$. The value of this angle depends on the values of ni and nt. An expression for calculating $\theta c$ from values of ni and nt can be derived by considering the angles of the incident and transmitted light beams at the critical angle. At the critical angle θc, the reflected beam contains most of the incident light and makes an angle θc with the respect to a line perpendicular to the surface as required by the laws for specular reflection. The transmitted light has low intensity and its angle θt with respect to perpendicular line is 90°. That is, the transmitted light beam travels parallel to the surface. We can therefore obtain the value of θc by inserting θt=90° in Snell's equation. This insertion gives $$nt\ \text{Sin}(90) = ni\ \text{Sin}(\theta c) \quad (39)$$

Since $$\text{Sin}(90) = 1,$$

we can write $$\text{Sin}(\theta c) = ni/nt \quad (40)$$

For nt=1.54 and ni=1 (air), the above equation gives θc=40.5°. It should be noted that the critical angle is the same for unpolarized light and light polarized perpendicular or parallel to the incident plane. That is, θc is independent of whether the light is unpolarized or plane polarized.

iii. Effects of Reflectance and Refraction on the Illumination of a Patch of Light Scattering Particles.

Figure 6:
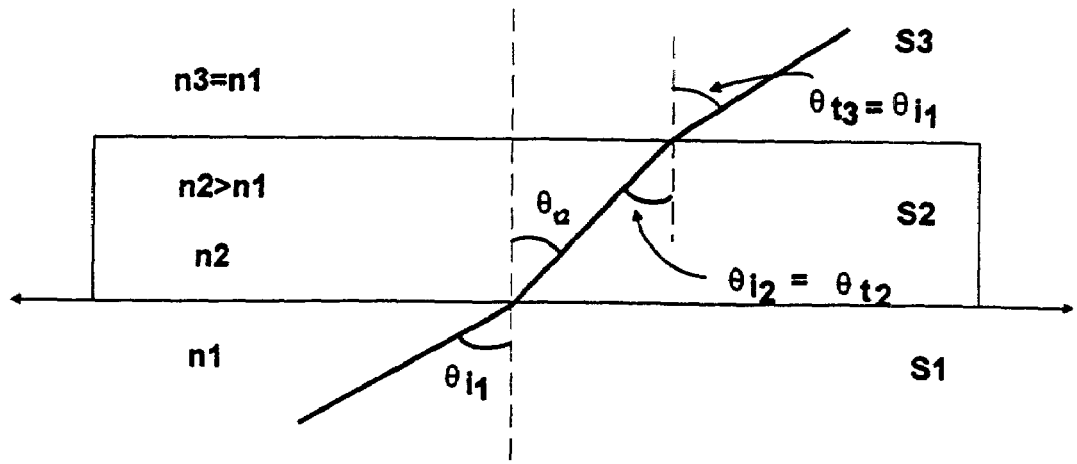
FIG. 6 illustrates the refraction and reflection involved in the illumination of particles on a dry surface in air.

We first consider the simple case where the particles are on the surface of a dry microscope slide in air. That is, the particles are dry and air is the medium on both sides of the microscope slide. FIG. 6 shows a schematic diagram of the reflections and refractions involved in this case. The first reflection occurs at the surface S1 (ni<nt, ni=1 and nt=1.5). FIG. 4 shows that the fraction of light reflected is below 20% for incident angles up to 70°. Therefore, reflections at S1 are not problematic in this method of illumination. Surface 2 could be problematic because the light beam passes from a low to a high refractive index and the possibility exists for total internal reflection at this surface. The critical angle for total internal reflection at a surface where ni=1.5 and nt=1 (air) is about 42° (calculated with Eq. (40)). The question now is whether this critical angle is attained when the incident light beam at surface 1 has a large angle.

Figure 7:
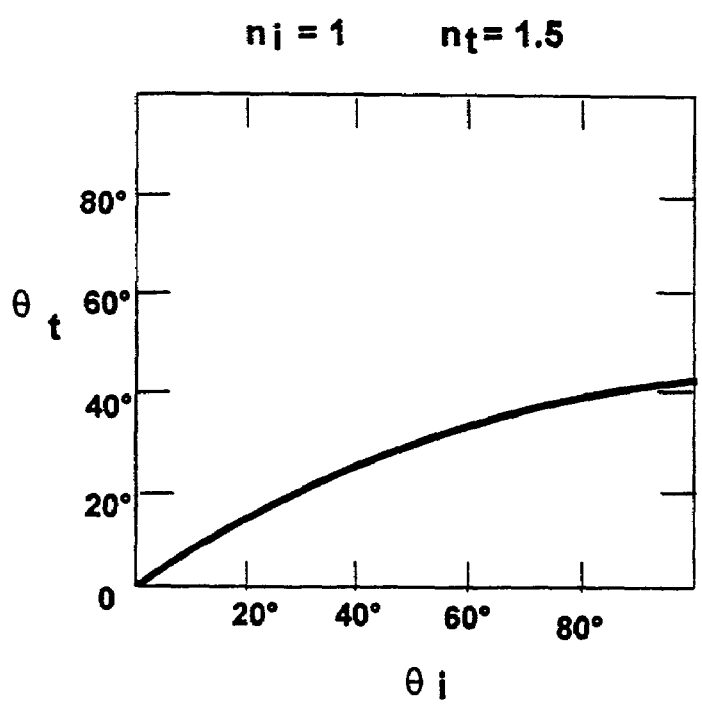
FIG. 7 is a graph of plot of $\theta_{12}$ VS. $\theta_{11}$ for $n_2=1.5+n_3=1$ (see FIG. 6).

FIG. 7 shows a plot of θi2 [θtj] vs. θi1 [θij] calculated with Snells Eq. ((37)) and using θt1=θi2. As can be seen from the plot, θi2 rapidly increases with increase in θi1 up to about 1i1=70°. The increase in θi2 then levels off and does not reach the critical angle until θi1=90°. However at θi1=90°, no light is transmitted across S1. We thus conclude that for the arrangement of FIG. 4, critical illumination is never achieved at any practical angle of θi1. Furthermore, reflections do not significantly diminish the amount of light delivered to the particles on S2 for θi1 values less than about 70°.

We have verified the above conclusions experimentally. In our experiments, however, we have found that light scattered by smudges, dirt, scratches and other irregularities or artifacts on surfaces S1 and S2 (non-specific light scattering) can become comparable to the light scattered by the particles on S2 and thus significantly increases the background light and diminishes the sensitivity of particle detection. However, the non-specific light scattered by artifacts on S1 and S2 is concentrated in the forward direction of the illuminating light beam whereas the light scattered by the particles (for small particles) is in all directions. These effects are demonstrated in FIG. 8.

In FIG. 8, the intensity of non-specific light scattered by surface artifacts in any direction θ is given by the length of the line (with angle θ) extending from the origin O to the intensity envelope. The light scattered by the particles is shown as dashed lines which go out in all directions from O. The effects of non-specific light scattering on the detection of specific light scattering can be demonstrated experimentally using a microscope slide containing 60 nm gold particles on the surface. In air, these particles scatter green light, and in the absence of non-specific light scattering, an illuminated patch of particles appears as a green patch on a dark background Surface artifacts scatter white light and when this type of non-specific light scattering is superimposed on the specific particle light scattering, the light scattered from a patch of particles has a greenish-white color instead of a pure green color. The effects of preferential forward scattering by surface artifacts can be seen by viewing the scattered light by eye positioned at different angles θv as shown in FIG. 8. When the eye is placed at θv=0, the scattered light has a greenish white color. As the angle of observation θv is increased, the white color decreases and, at θv greater than 30°, only the pure green color of gold particles is seen. Thus, in the present invention, it is useful to observe by eye or detect with photodetector means at an angle greater than θv of 30°. As we show later, non-specific light scattering due to surface artifacts can be further reduced by illuminating through light guides as for example, a prism type of arrangement.

We next consider the case where the light scattering particles are in a thin film of water that is on a microscope slide and covered with a cover glass as shown in FIG. 9. The illuminating beam encounters four surfaces where changes in refractive index occur, namely S1 (air to glass), S2 (glass to water), S3 (water to glass), S4 (glass to air). Consideration of the reflection and refraction at each surface as done in previous paragraphs leads to the conclusion that in the system of FIG. 9, reflections do not significantly reduce the amount of light energy delivered to the scattering light particles and that critical reflection does not occur at any surface. Non-specific light scattering due to surface artifacts on surfaces S1 and S4 are present as in the case of FIG. 8. However, the presence of water greatly reduces non-specific light scattering for surfaces S2 and S3.

Direct Illumination from the Same Side as the Magnifying Lens

This method of illumination is shown in FIG. 10. The meaning of S, L, C, and LB are the same as in FIG. 2. In this Figure, the exciting light beam impinges on the surface S from above the surface. The light collecting lens is also above S. The exciting light beam is angled so that neither the incident or reflected light enter the light collecting cone C of the lens L. In this method of illumination, it is necessary to keep the light reflected from the different surfaces in the path of the beam from being reflected into the light collecting cone C of the magnifying or imaging lines L. Since the angle of reflection is the same as the angle of incidence at each surface, collection of unwanted reflected light by L can be minimized by confining the illuminating light beam to those angles which are outside of the cone C. It can be shown, as in the previous section, that reflections do not significantly reduce the amount of energy delivered to the light scattering particles and that critical reflections do not occur in dry or water covered particles. Nonspecific light scattering due to surface artifacts are the same as discussed in the previous section.

Illumination Through a Prism Arrangement.

i. Illumination from below.

FIG. 11 presents a schematic diagram of a prism setup. In one of its simplest forms, it consists of a triangular prism on which can sit microtiter wells, glass slides, microarrays on plastic or glass substrates and the like which contain the light scattering particles to be detected. The sample chamber or slide that contains the light scattering particles is located on the upper surface S2 of the prism, the surface containing the particles is at the focal point of the lens L.

Immersion oil is placed between the sample chamber or slide and the prism to minimize non-specific light by refractive index matching. The particles are dry in air. If the index matching at S2 is exact or almost exact, then the light beam does not undergo significant refraction or reflection at S2. Thus, an illuminating light beam travels in an approximately straight line as it transverses the prism and surface containing the light scattering particles. However, there is refraction at the air-prism interface S1 and at S3.

Consider an illuminating light beam which enters the prism in a direction which is perpendicular to S1 (angle of incidence is 0°) and suppose that the prism is a 45° prism (angle $\gamma=45°$). Because the beam travels in a straight line from S1 to the point O on S3, it strikes the surface S1 at an angle of 45°. The beam will then undergo total internal reflection since the critical angle for glass to air is about 42°. Thus, in contrast to illumination from below without a prism (see FIG. 6), the prism arrangement allows critical reflection.

Recall, that in the absence of a prism (FIG. 6), critical reflection cannot be achieved because of the refraction of light at S1 as shown in FIG. 6 (also see FIG. 7). In order to deliver a high energy light beam when using a light guide such as a prism, the illuminating light beam must be directed so that it strikes S3 (FIG. 11) at an angle less than 42°. The question now is whether incident angles less than 42° at S3 allow one to satisfy the condition that the light which exits at S3 must be outside the collecting cone of the lens L. Suppose that the angle of incidence at S3 is 35°. From Snells law (with ni=1.5 and nt=1) we calculate that the exit angle is 62° which is outside the collecting cone of our most demanding objective, namely the x40 objective with $\theta H=41°$. We conclude that the prism arrangement of FIG. 11 permits delivery of high light energy to dry light scattering particles in air while maintaining a dark background.

We now consider the prism arrangement of FIG. 11 in which the light scattering particles are covered with water and a cover glass. As described before, an exciting light beam travels in a straight line from S1 to O where it encounters the glass-water interface. It then travels through the water and cover glass, finally encountering the glass-air interface at the upper surface of the cover glass. It is of interest to consider the reflections that occur at the glass-water and glass-air interfaces. The angle for critical reflection at the air water interface is equal to 62.5° (using ni=1.5 and nt=1.33 in Eq. (40)). The introduction of water at the surface S3 thus permits illumination at much higher angles, than in air, without encountering total internal reflection. Furthermore, at angles less than 62.5°, reflectance is low at the glass-water interface.

We now consider the reflection at the cover glass-air interface. Consider a beam of light which enters perpendicular to the surface at S1. If the prism is a 45° prism, then the beam strikes S3 at an angle of 45° where it undergoes total internal reflection. Refraction at S3 (glass to water) changes the angle of the beam to 55°. However, refraction at the water-cover glass interface bends the beam back to 45°. The beam thus strikes the cover glass-air interface at 45°. The prism arrangement with particles in water and a cover glass thus permits efficient delivery of light energy to the light scattering particles (attached to the surface S3 or free in water) but the incident light is totally reflected at the cover glass.

From the above discussion we conclude that there are no reflections that seriously affect the delivery of light energy to light scattering particles in a film of water. Total reflection does occur at the cover glass-air interface but these reflections do not affect the delivery of incident light energy to the scattering particles.

From the above discussions, it is evident that both prism and non-prism arrangements permit efficient delivery of energy by angled illumination of particles attached to a surface or free in solution. By efficient delivery we mean that the beam of light does not undergo total internal reflection at any pertinent surface and the collection of non-specific light is minimized. However, we have found experimentally that superior detection capabilities occur with the prism arrangement in certain applications because it eliminates or considerably reduces artifacts due to scattering from irregularities on glass or plastic surfaces close to the light scattering particles. The immersion oil used to couple the solid-phase to the prism, eliminates almost completely non-specific light scattering from irregularities at S2 (FIG. 11). These effects seem to be due to an index matching mechanism. The non specific light scattering at the point of entry of the light beam at S1 is far removed from the specific scattering particles at point O (if the prism is sufficiently large) and does not contribute to the scattered light collected by the magnifying lens.

Furthermore, if the specific scattering particles are in water, index matching by the water film considerably reduces non-specific scattering on the surface S3. Moreover, in the presence of water and a cover glass, the illuminating light beam undergoes total reflection at the cover glass-air interface. This reflection considerably diminishes non-specific scattering from irregularities at the cover glass-air interface because only a small amount of light energy reaches the irregularities on this surface. In addition, the total internal reflection diminishes or eliminates the probability that illuminating light can enter directly the light collecting cone of the magnifying lens. It should be noted that total internal reflection can also affect the collection angle of the lens L because particle scattered light which makes an angle greater than 42° at the cover glass-air interface is totally reflected. This effect however is not a serious one.

Microscopic Observations

In the previous section we discussed our illumination and detection (magnifying lens) systems with emphasis on the factors (reflections and refractions) that govern the efficient delivery of light energy to light scattering particles (which are attached to a surface or free just above the surface) while minimizing the non-specific light that is collected. In this section we present experimental details obtained by visual observation, through an ocular, of the magnified image produced by the magnifying lens L.

a. Details of Light Sources and Optical Fibers

We have used three different types of light sources as follows.

i. Leica Microscope Illuminator

This is a standard commercial microscope illuminator. It uses a tungsten filament light bulb and lenses that produce a 5×7 mm focused image of the filament at a distance of about 22 mm from the tip of the illuminator. To produce a more focused light beam, we attached a ×10 objective lens to the microscope. The lens is about 6.5 cm from the tip of the illuminator. The objective produces a focused spot of light of about 4 to 5 mm in diameter at a distance of about 7 mm from the objective lens.

ii. Bausch and Lomb Fiber Lite Illuminator

This is also a commercial illuminator. It uses a 150 watt tungsten filament lamp that is mounted on a parabolic reflector. The reflector produces a beam of almost parallel light with a diameter of about 25 mm. An 11 mm diameter optical light guide (consisting of many small optical fibers bundled together) is positioned close to the filament lamp. The optical light guide is then split into two equal light guides, each with a diameter of about 5.3 mm and a length of about 2 feet. We use one of the light guides. To produce a focused light spot, we collimate the light from the optical fiber using a 25 mm focal length lens (20 mm diameter) positioned about 25 mm from the end of the optical fiber. The collimated light is then focused, into a 5 mm diameter light spot, by a ×10 objective which is positioned about 50 mm from the collimating lens. The collimating and objective lenses are in a compact holder that is rigidly attached to the optical fiber. The flexibility of the optical fiber makes this type of light source system much easier to use than the rigid Leica Microscope Illuminator.

iii. Custom Illuminator

This is an illuminator which we constructed. It uses a 12 V, 28 Watt tungsten filament lamp that is mounted on a parabolic reflector. The reflector produces an almost parallel beam of light which is focused into an optical guide that has a diameter of 0.125 inches. The optical guide is 36 inches long. Light from the reflector is focused unto the optical fiber with a lens (23 mm focal length, 9 mm diameter) that is positioned close to the lamp. The light guide has a numerical aperture of 0.55 and accepts a cone of light with a planar half angle of 60°. Light which exits at the other end of the light guide is collimated by a 12 mm focal length lens (diameter 11 mm) positioned about 17 mm from the end of the fiber. The collimated light is finally focused into a bright spot of 5 mm diameter by a ×10 objective. The objective lens is positioned at a distance of about 26 mm from the collimating lens. The 5 mm bright spot is at a distance of about 12 mm from the end of the focusing lens.

b. Prisms (Light Guides)

FIG. 12 shows diagrams of some light guides such as prisms which we have found useful in our illuminating systems. Some of these are not actually prisms in the classical sense but may rather be called light guiders or light guides. The light guider allows light to be delivered efficiently at an angle while allowing the reflected light beam to exit at the face opposite to the incident light face. It must have some minimum dimensions for the following reasons. The spots where the light beam enters and reflected light exits can produce significant non-specific light scattering due to surface irregularities. These spots must be sufficiently removed from the patch of specific light scattering particles to minimize their non-specific light scattering contribution. The light guides can be molded into one piece with the sample chamber thus eliminating the need to use immersion oil between the light guider and analysis piece. We have proto-typed such a device by gluing a small light guide to the bottom of a plastic chamber which has a microarray of streptavidin spots coated on the inner surface of the sample chamber well. Our detection and measurement of bound light scattering particles to the individual microspots of the microarray using this device were essentially the same as our measurements by particle counting and intensity measurements with the sample chamber placed on a prism with immersion oil between the two surfaces.

c. Microscopic Observations

Using an ocular for visual microscopic observations, we have evaluated several illuminating arrangements with special emphasis on brightness of particles, darkness of background, and usefulness in different types of clinical assay formats. We have found several arrangements that give good results. Here we will limit our discussion to one of the easiest to use and least expensive arrangements which gives excellent results. By excellent results we mean bright particles on a dark background using ×10 and ×40 objectives as magnifying lenses.

Figure 12A:
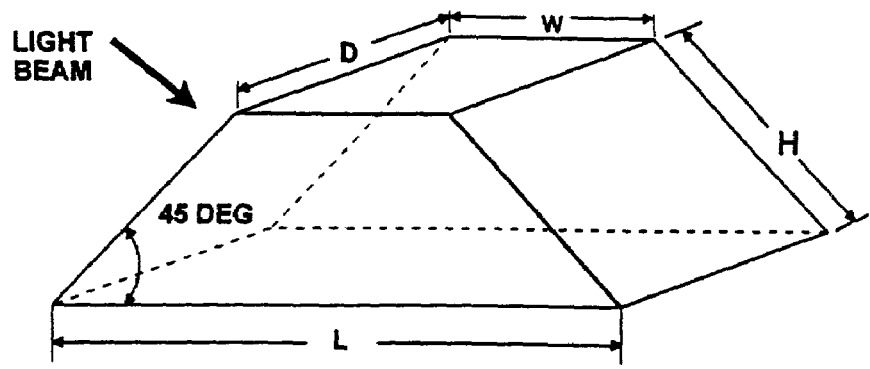
Figure 12B:
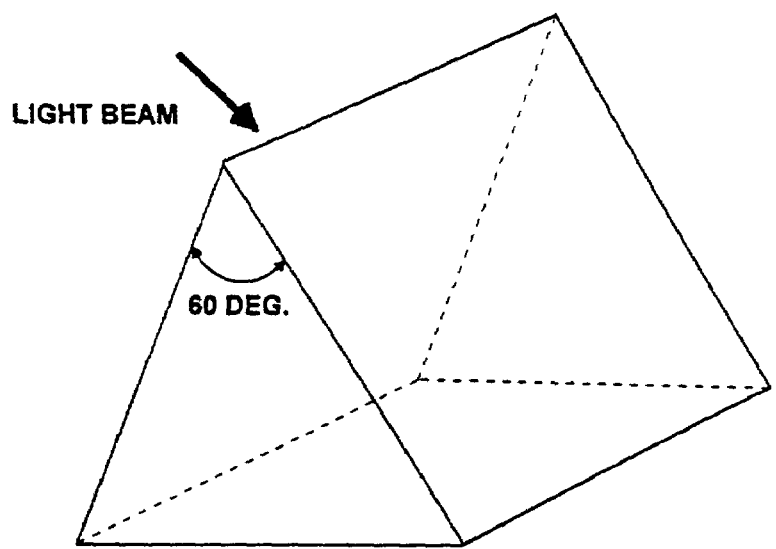
Figure 12C:
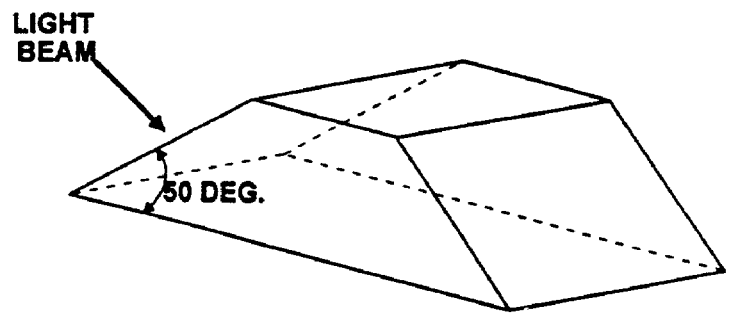
Figure 12D:
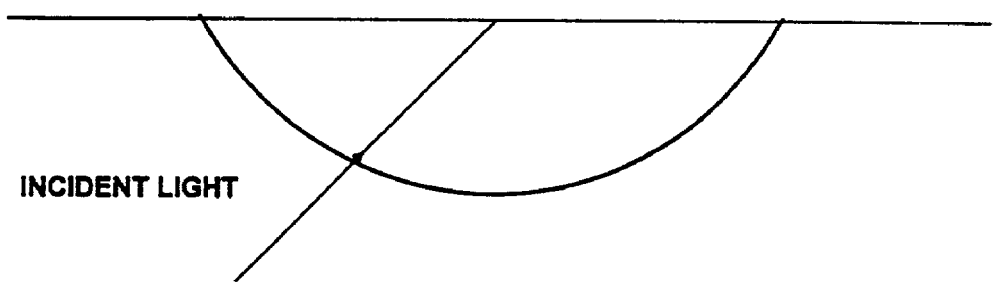
Figure 12E:
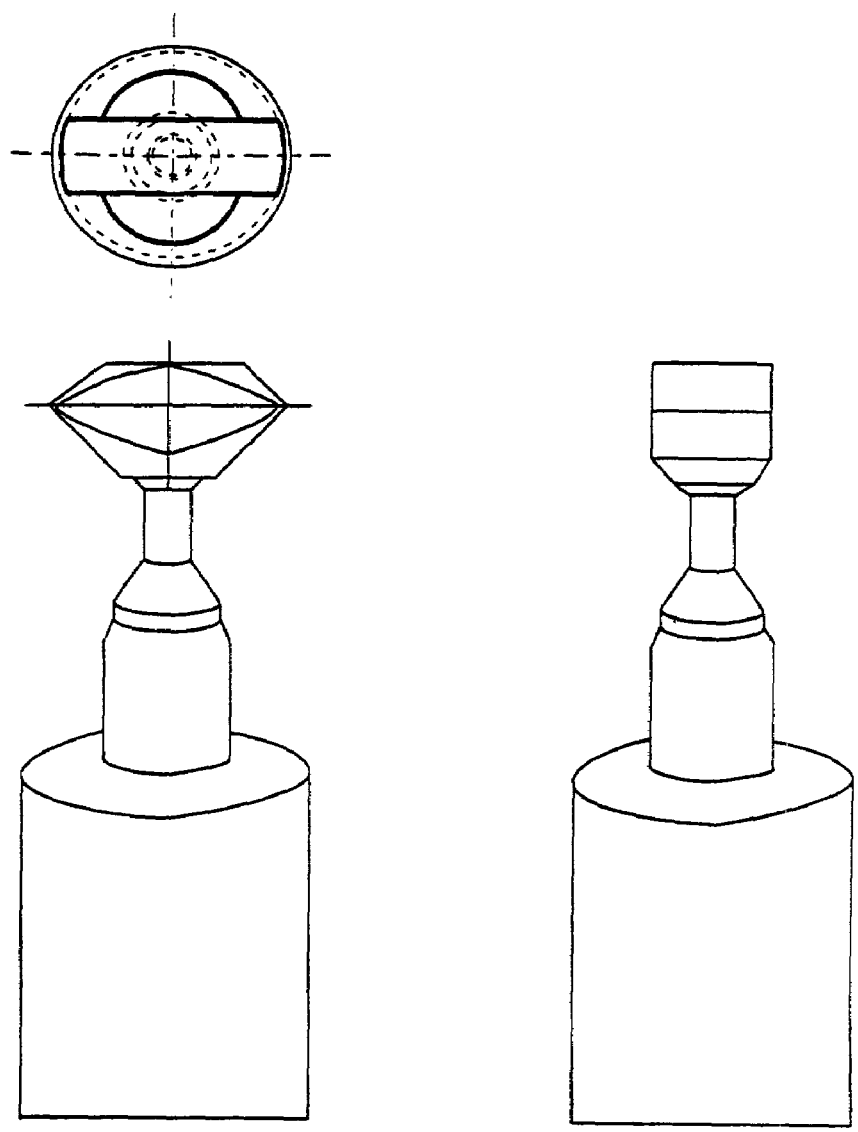

The imaging system is an inexpensive microscope from Edmund Scientific. The microscope consists of an objective (×10 or ×40) and an ocular in a standard 160 mm tube. The reason for using a microscope, instead of just simply an objective and an ocular, is the convenience provided by the fine/course focusing mechanism of the microscope. However, we have modified the stage of the microscope to adapt it to our method of illumination and have replaced the microscope condenser with a light guide (prism type) as shown in FIG. 12(d). The cylinder below the prism fits into the condenser holder. The modified stage and illuminator make it possible to work with microscope slides, microtiter plates and other plastic plates. However, the ×40 objective cannot be used with the thick plastic plates because of the small working distance (about 0.45 mm) of this objective. ×40 objectives with longer working distance are available. The custom Illuminator is used for illumination.

To setup the microscope system for the DLASLPD method, a microscope slide containing free or surface bound gold particles (60 nm gold particles in a thin water film covered with a cover glass) is placed on the microscope stage. The prism is positioned so that its surface is almost in contact with the microscope slide. The slide and prism surfaces are coupled with immersion oil. The ×10 focusing objective of the illuminating system is positioned so that it is almost in contact with the side of the prism that is illuminated (see FIG. 13). The objective is angled so that the light enters perpendicular to the illuminating surface and strikes the surface S (surface in contact with the microscope slide) at an angle of about 45°. If the gold particle film on the slide has a sufficiently high concentration of particles (about $6 \times 10^9$ particles/ml or higher) the spot where the light crosses the particle film displays a strong yellow-green color due to light scattering by the particles. The position of the ×10 focusing objective is adjusted so that the yellow-green spot is centered with respect to the microscope (magnifying) objective. The microscope is then focused on the spot so that the particles appear as sharp objects when viewed through the ocular. The position and angle of the ×10 illuminating objective is than repositioned to produce bright objects on a dark background. This adjustment is repeated with the ×40 objective of the microscope. There is a narrow range of positions which produce bright objects on a dark background for both ×10 and ×40 objectives.

It should be noted that none of the illuminating light is transmitted into the air space above the microscope slide when the illuminating light beam strikes the prism surface at greater than about 42° (critical angle for total internal reflection at the plastic or glass-air interface). In our arrangement, the angle of incidence is 45°. This can be verified by placing a piece of white paper above the microscope slide.

No illuminating light falls on the paper. However, it is of interest to visualize the illuminating beam to determine its shape or profile in space. This can be done by placing a rhodamine plastic block on top of the slide using immersion oil for coupling. The rhodamine block is a transparent plastic block that contains the fluorescent molecule rhodamine. A beam traveling through the block can be seen from the rhodamine fluorescence that it produces. The immersion oil eliminates the air space and allows the illuminating beam to enter the plastic block. The profile of the illuminating beam seen by fluorescence inside of the block is shown in FIG. 13.

Once the illuminating system has been properly positioned, gold particles greater than about 30 nm can easily be seen on microscope slides, plastic wells, and solid-phase microarrays or array chips. The ×10 objective permits detection of particles densities less that 0.005 particles per $\mu^2$ The ×10 objective has a working distance of about 8.5 mm so that it can be used with plastic pieces that are about 8 mm thick.

Method of DLASLPD Video Contrast Enhancement

We have determined that metal-like particles and non-metal-like particles can be detected to greater sensitivities in samples by using the method of DLASLPD Video Contrast Enhancement. This method involves adjusting the imaged non-specific light background electronically such that it is essentially removed from the imaged field while keeping individual particles visible. The method works extremely well with the other methods as described herein. We have observed improved specificity and sensitivity results using this method.

Sample Chamber Improvements

In the spirit of taking certain aspects of the present invention and now further improving it in terms of ease of use, adaptability to different testing environments and conditions, we have found that several aspects of the present invention can be embodied in the design of sample chambers that are used to conduct the assay and detect the analytes.

For example, based on our observations and conceptualizations we can apply our principles to the general design of the sample chamber, that is the container which contains the sample to be analyzed. These improvements can facilitate the ease of use and applicability to the types of tests and testing conditions briefly outlined above. It should be stated however, that the invention as described herein can be practiced equally well without use of the following sample chamber improvements. These improvements are for the means of increasing the practical applicability of the present invention to specific testing conditions and environments and described elsewhere herein.

We have found that by moving or displacing the surface S1 (incident light surface) as far as possible away from the area that contains the particles to be measured, the signal/background ratio is significantly increased. We have previously described the use of an optical alignment means such as a prism or similar optical light guide which is used to assist in orienting the delivery of the illumination beam to the surface S1. Usually one will use immersion oil between a surface of the light guide (prism etc.) and a surface of the sample chamber. There are numerous conditions in analyte testing where it may be preferable to not have immersion oil as a component in the analytical methodology. We have determined that by increasing the thickness of the surface upon which the particles are on or nearby significantly reduces the level of non-specific light as described earlier.

We have applied this and other aspects to the design of sample chambers for the detection of one or more analytes in a sample. These general sample chamber designs are diagrammed in FIGS. 17, 18, and 19. FIG. 17 shows a sample chamber that has beveled flat sides. The degree of angle of the beveled sides is matched to the angle of illumination such that the illumination beam strikes the face of the beveled side at an angle as close to 0 degrees as possible (with respect to the perpendicular). In this fashion non-specific reflected and scattered light is minimized. FIG. 18 shows a sample chamber that has curved sides instead of the flat beveled sides as described for FIG. 17. In this sample chamber, for the exit beam which is diverging, the curved surface allows for the more efficient removal of this non-specific light. FIG. 19 shows a sample chamber that utilizes both concepts of moving the incident surface where the light beam strikes the sample further away from the area to be measured and the curved sides to allow for more efficient removal of non-specific light. Thus, this sample chamber has an increased thickness of material below the bottom surface of the well, beveled flat surfaces below the plane of the surface for illumination, and curved sides above the surface plane of the bottom of the well to allow for the efficient removal of non-specific light. The sample chambers as shown in FIG. 17, 18, and 19 are useful for measuring immobilized samples as well as solution samples.

Selection, Detection, and Measurement of Light Scattering Particles

In most forms of the present invention, the light scattering signals from the light scattering particles are detected from particles that are suspended in solution or from particles that are associated with a solid-phase. We have described many variations of the method of DLASLPD illumination and detection for samples in the liquid-phase and solid-phase. These variations in the DLASLPD methods are primarily related to the nature of the sample and the sample container.

The present invention has great utility in that many different types of assay formats and hence assay containers or other devices can be used to detect and measure the presence and amount of one or more analytes in a sample. For example, microtiter wells and plates, test tubes, capillary tubes, flow cells, microchannel devices, cuvettes, dipsticks, microscope slides, optically transparent surfaces, beads, magnetic beads, dot blots, and high and low density arrays can be used.

Of great importance for application of the present invention to the detection of analytes is the proper selection of the best mode of the particle type for a given analyte detection application. This in part is dependent on the assay format and the level of detection sensitivity required. The light scattering signals of the particles are either determined on an individual particle basis, or, the light scattering properties of many particles are detected and measured.

There are many considerations that come into play in selecting the best light scattering particle for any given specific assay application. These considerations are generally related to (1) the attributes of the illumination and detection system being used; (2) the nature and properties of the container or device which is used for measurement; (3) the assay format being used; (4) if individual particles and/or many particles are being detected and measured and (5) the concentration and ranges of analyte(s) detection. We now describe how one of average skill in the art can optimize one or more forms of the present invention to the detection of analytes.

Of critical importance in either liquid phase or solid-phase based assays is the relationship of scattered light signal to the concentration of particles being detected. In order to measure the amount of light scattering particles present in the sample, an algorithm which relates one or more of the detected light scattering signals to the amount of particles must be developed and used. The light scattering signals from individual particles or many particles can be detected and measured in many different forms in the present invention.

For the case where the collective light scattering signal of many particles (i.e. individual particles are not detected) is detected on a solid-phase or in solution we have determined how the relative light scattering intensity, polarization, and color spectrum of the detected particles change as a function of concentration. As described herein, the intensity of scattered light and color spectrum is dependent on particle size, shape, and composition, the concentration of the particles, and the refractive index of the medium. In the method of detection and measurement of the collective light scattering signal of multiple particles, the detection and measurement of the integrated light scattering intensity is a very useful light scattering property for measurement. FIGS. 31 and 32 show the relationship of scattered light intensity to concentration of particles for particles suspended in solution or associated with a solid-phase respectively. In these illustrative examples, the refractive index of the medium is ~1.33. The suspended particles in solution were measured with the SpectraMetrix Liquid Phase detection apparatus and the solid-phase particles were detected with the microscope based detection apparatus described herein. In the examples given, the SpectraMetrix liquid phase detection apparatus and the microscope based detection system used a photomultiplier and a CCD single chip color video camera to detect the scattered light signals respectively.

As an illustrative example, FIG. 31 demonstrates the scattered light intensity versus particle concentration properties for a series of roughly spherical gold particles of different diameter. Similar graphs for silver, selenium, and other metal-like particles are also obtained by measuring the light scattering intensity of the particle scattered light as a function of particle concentration. The wavelength of illumination light was adjusted to maximum wavelength of scattering for the different particles. The collective data of FIG. 31 show that the sensitivity of detection and working concentration ranges for detection and measurement vary as a function of the gold particle diameter. Utilizing plots of scattered light intensity versus particle concentration obtained with any specific embodiment of the present inventions methods of illumination and detection allows one skilled in the art to determine which particle types are best suited for any given analytical application. For maximum analytical performance the best light scattering particle type is chosen based on (1) an acceptable dynamic range of detection; (2) adequate detection sensitivity at the low end of the expected analyte concentrations in the sample; (3) and adequate resolution of detection (e.g. number of discreet detectable intensity values over a certain range of particle concentrations). Using FIG. 31 as an example, the 52 nm diameter gold particles are best used for analyte detection applications where the minimum and maximum light scattering particle concentrations detected are about $5 \times 10^{-13}$ M and $1 \times 10^{-11}$ M respectively. The 87 nm particles are best used for the detection of analytes where the minimum and maximum detection concentrations are about $1 \times 10^{-15}$ M and $5 \times 10^{-11}$ M respectively. The absolute detection sensitivities for any particle are based on the inherent light scattering power of the particle and the method of illumination and detection. One of average skill in the art realizes that the upper and lower absolute detection limits can be expanded or reduced by variation of the illumination source and optics (e.g. wavelength, power, beam size, path length etc.) and the collection optics and photodetector used. As disclosed herein, silver particles have greater scattering power than gold particles of comparable diameters. Metal-like particles are preferred with silver and gold particles most preferred. Optimization of the generation of light scattering signals from any given particle type is achieved by illuminating the particle at wavelengths close to or near their wavelength maximum for scattering. However, the light scattering power of many of the particle types we have studied is so great that in many cases, adequate light scattering signals can be obtained by using illumination wavelengths which are not close to or approximate the wavelength of maximum scattering. For example, we have been able to detect the light scattering of roughly spherical 60 nm gold particles to very low concentrations ($10^{-14}$ M<) utilizing a 3 milliwatt laser light pen with an illumination wavelength of about 630 nm and using the unaided eye as a photodetector. In this system, clear microtiter wells were used as a sample container. The wells were illuminated with the laser pen at angles approximating the perpendicular of the surface of the side of the wells. By placing our angle of observation below or above the well, or, at angles approximately 90 degrees to the illumination beam the scattered light of the particles could be detected with the unaided eye.

For solid-phase based assays, the selection and optimization of the best particle type is determined as we have described for the liquid phase except that (1) the particles are associated with a solid-phase during detection and measurement and (2) additional factors come in to play. FIG. 32 shows an illustrative example of the relationship of scattered light intensity as a function of particle concentration for 60 nm diameter gold particles. For detection and measurement of light scattering particles associated with solid-phases, we describe the concentration of particles by particle density (number of particles/square micron surface area). An additional consideration in selecting the best particle type for applications to solid-phase assays and detection is the particle size. For example, array chips and the like may contain individual binding sites which could be as small as 10 square microns. Thus, the relative physical size of the light scattering particle limits how many particles can be bound to the surface at saturation of the available binding surface area. Careful studies as to the sensitivity of detection and dynamic range of detection of different particle types must be evaluated on the apparatus to determine the best mode of particle type with respect to the required sensitivity of detection and range of particle concentrations that will be detected. For example, selection of smaller particle types with lower scattering powers may lead to many more particles being bound per the binding surface. However, at low binding densities, the signal may be too weak for detection. On the other hand, particle types which are larger in size and with much greater light scattering power may allow for detection at low binding densities, but may have a limited dynamic range because the binding site saturates with particles at much lower number of particles and/or the overall intensity may be saturating to the detection apparatus. One of ordinary skill in the art can thus select the best light scattering particle type which allows for maximum analytical performance in a given analytical application.

The relationship of detected light scattering intensity as a function of particle concentration for any light scattering particle within the illumination and detection constraints of a detection system provides the basis for the development of algorithms from which the particle concentration of a sample can be determined from the measured light scattering intensity.

One of ordinary skill in the art determines the best particle type and develops particle type-system specific algorithms for relating the measured light scattering intensity or any other detectable and measurable light scattering signal to the concentration of particles in a sample as follows. An existing apparatus, breadboard or prototype optical train (e.g. illumination source, sample holder, photodetector and optics) and the sample container or device are used to determine the relationship of light scattering signal to concentration of particles. These standard curve plots for each of the different particle types evaluated are then used to determine which particle type has the best performance parameters (dynamic range, resolution, minimum detection sensitivity etc.) for the analyte(s) being detected. The mathematical relationship of the measured light scattering intensity or other light scattering signal to particle concentration of particles is then as the basis of algorithms from which the concentration or amount of particles in the sample can be determined from the measured light scattering signal. In associated algorithms, the amount of particles detected is related to the amount of analyte in the sample. One of ordinary skill in the art can thus select the best particle type and develop specific particle type/sample container/detection apparatus algorithms that relates the measured light scattering signal to the amount of particles detected for most any form of the present invention.

Detection and Measurement of Individual and Multiparticle Structures

For applications where the method of detection and measurement of individual particles or multiparticle-particle aggregates thereof is utilized, there are two general sample analysis approaches: (1) the particles are flowed by an illumination source and detector or (2) particles in a field of view (either associated with solid-phase or in liquid phase) are detected with an imaging photodetector.

Examples of flow-based methods include the use of capillaries, microchannels, or, devices consisting of such structures therein. Additional examples include flow cells for optical spectroscopic analysis such as used in commercial spectrophotometers and flow cytometry.

In contrast to the flowing of the sample pass the detection system, all or part of the sample can be detected and measured by the method of field analysis. In the method of field analysis, a solid-phase or thin film of liquid is detected and analyzed by imaging a certain surface area and/or depth of view of the field. Microscopy is an example of a general method of field analysis. Specific applications include the detection and measurement of dot blots, microarrays, biological cells, tissues and the like.

Flow-based Detection and Measurement of Light Scattering Particles

For applications to flow-based systems, the detection and measurement of light scattering signals from light scattering particles can be accomplished by various methods utilizing one or more aspects of the present invention. The methods can be broadly grouped into two classes: (1) applications where single particles and multiparticle-particle aggregates are detected; and (2) applications where one or more particles are attached to a mobile solid-phase as for example a bead, biological cell, or other particulate matter.

In the method of detection and measurement of individual particles and particle aggregates in a flow-based system, there are preferred arrangements of the illumination beam and detector. These preferred orientations are dependent in part on the nature of the sample being analyzed. One or more photodetectors can be used to detect and measure the light scattering signals of the light scattering particles. In some embodiments the detector(s) may be placed outside the envelope of the forward direction of the scattered light. In other embodiments, if the background light scattering signals from other material in the sample is relatively low, the detector(s) may be placed within the envelope of the forward direction of the scattered light. The illumination beam(s) should be highly collimated and can be polychromatic or monochromatic. One or more components of the light scattering signal from the light scattering particles can be detected by one or more photodetectors. The polarization of the detected scattered light, the intensity of the scattered light, and the color spectrum of the scattered light can be detected and measured.

As an illustrative example, an assay is performed on a sample to detect the presence of a target nucleic acid. A solution-based sandwich assay format is used in which two or more probe nucleic acid stands with unique sequences which bind to a different region of the target strand are used. The probes in one form or another each have a light scattering particle attached to them. The probes are mixed with the sample, allowed to incubate and then some or all of the sample is placed on the flow-system for analysis. The physical attributes of the flow cell and the flow cell dynamics are adjusted such that single and multiparticle-particle aggregates are passed through the detection zone one at a time. The detection system is calibrated and set such that the signal from one particle can be distinguished from the signal from two or more particles. If the target nucleic acid is present, there will be some fraction of particles in the sample which have two or more particles in multiparticle structures. The amount of target nucleic acid in the sample is determined by detecting and measuring the amount and/or type of multiparticle aggregates. Immunologically based agglutination assays are well known in the art and these too can be used in the present invention to detect an analyte. In this method, light scattering particles are attached to one or more types of antibodies or antigens that can bind to the analyte such that multiparticle structures form. The multiparticle aggregates formed are detected and measured.

In another variation of the present method using a flow-system approach, the light scattering particles are associated with biological cells, beads, or another substance in the sample. As an illustrative example, biological cell typing and the determination of the levels of surface receptors and other cellular constituents are of great interest in the art. In one method of the present invention, biological cell identification and counting, and/or the determination of the amounts of cellular constituents of a cell is accomplished by using light scattering particle reagents wherein the particle-binding agent reagents have specific binding activity for a component of the cell.

A requirement for adequate detection and measurement of the aforementioned cell properties is the ability to detect and resolve the light scattering signals of the light scattering particles attached to the cell from the light scattering signal of the cell. Light scattering particles with high light scattering power are most preferred. One or more detectors can be used. Detector(s) placement and light scattering particle type used must be optimized for best performance.

For example, in one embodiment of the method, a single beam illumination source with two photodetectors placed at different positions can be used to detect and measure the light scattering signals of the sample. One detector is used to detect the light scattering signal of the cell and is generally placed inside the envelope of the forward direction of scattered light. Another detector is used to detect the light scattering signal of the light scattering particles and is generally placed outside the envelope of the forward direction of scattered light. The basis for this method is our finding that for many of the metal-like particles at sizes less than about ~120 nm in diameter they essentially radiate scattered light in all directions in about the same proportions. Larger particulate matter, as for example biological cells and micron-sized and larger beads generally radiate a majority of their scattered light in the forward direction. The exact placement of the detectors can vary and depends on the type(s) of light scattering particles used, the illumination and detection optics, and the nature of the sample. To optimize the method for a specific application, one places a sample containing the beads or cells in the sample container and while illuminating the sample, moves the first detector to various positions recording the values of the light scattering signals detected. This procedure is then repeated with a flow cell with light scattering particles and a second photodetector.

An analysis of the cell specific and light scattering particle specific scattered light by the two detectors at the various positions is performed to determine the best placement positions for the photodetectors. The photodetector that is to be used for detection of the bead or cell specific scattered light is placed at a position where the scattered light from the light scattering particles is at a minimum and adequate detection of the light scattering signal from the beads or cells can be detected. The photodetector used for the detection of the scattered light of the particles is placed at a position where the specific scattered light of the particles can be adequately detected over the scattered light from the bead or cell. Two or more wavelengths of light and/or optical filters may be used to further resolve the two types of light scattering signals. More than one type of light scattering particle can be detected by using two different particle types such that the light scattering signals of the different particles can be resolved in one form or another.

An appropriate algorithm is used to measure the amount of beads or cells and particles per bead or cell based on the detected light scattering signals from the two detectors. For example, in one algorithm, for each object detected, the intensity of light detected by each of the detectors is measured. Depending on the intensities detected by each of the detectors, it is determined that either (1) no particles are associated with the bead or cell; (2) a relative level of light scattering particles are associated with the bead or cell; or (3) discreet numbers of particles are associated with the bead or cell. Each bead or cell then can be identified based on the presence, absence or amount of particles associated with the bead or cell. The detector that measures the cell specific scattered light is used to count the number of beads or cells. There are many other variations on the measurements and algorithms possible for the analysis of cells possible as is evident to one of average skill in the art.

Identification and Measurement of Individual Light Scattering Particles and Multiparticle Structures In many forms of the present invention individual particles and multiparticle structures can be observed and detected. We have determined that particle type and the nature of multiparticle structures can be identified by one or more of the observed and detected light scattering properties. These properties are then used to detect and measure the presence and amount of an analyte in a sample. This aspect of the invention is of great utility in that currently available label and detection technologies as applied to analyte detection do not have such capability. For example, fluorescence labels and methods of fluorescence detection are generally regarded as one of the most sensitive direct label and detection systems currently available in the art. However, the direct visualization of individual fluorescent molecules and individual molecular binding events in biological or other samples with inexpensive, robust, and easy to use microscope-based systems has not been achieved. Florescent particles or beads of several hundred nanometers in size which contain thousands of fluorescent molecules can be detected in such systems but the large size of these particles and tendency to aggregate in many applications has limited their utility. The present invention thus provides new means for the detection and measurement of single molecular binding events, individual analyte substances and the localization within the sample thereof. The ability to identify and locate the analyte is of great importance especially in the fields of cellular, molecular, developmental, and neuro biology and the related use in the identification and development of new drug targets and pharmaceutical agents.

The identification and quantification of light scattering particles and multiparticle structures thereof can be accomplished generally by (1) direct visualization by viewing through suitable collection optics or (2) use of imaging photodetectors and image analysis hardware and software to collect images, digitize the information, and analyze the optical information collected. The requirement of the photodetector be only that it has the ability to spatially resolve objects in the Field of view based on their respective optical properties. For direct visualization, the human eye is an example of a photodetector which possesses great spatial resolution capabilities. Examples of imaging photodetectors include charge-coupled devices (CCD) and charge-injection devices (CID). Monochrome or color images of various resolutions can be obtained depending on capabilities of the photodetector used.

The detection, measurement, and identification of light scattering particles in a sample are defined by (1) the specific light scattering properties of the particle; (2) the method of illumination and detection; (3) the capabilities of the photodetector, digitizing and image processing hardware and software; and (4) the algorithms used to identify and measure the light scattering particles based on the detected optical signals.

One or more variations of the method of DLASLPD illumination and detection are used preferably such that by proper spatial filtering, stray illumination and reflected light is minimized. The collection optics and photodetector are generally placed perpendicular to the sample being detected. An imaging photodetector is used which provides adequate spatial and/or color resolution of the light scattering particles being detected if images are to be collected. The particles are identified, localized, classified, and quantified in one or more variations by direct visualization and/or utilizing appropriate digitizing and image processing hardware and software. For example, in some applications, a monochrome CCD chip with a 8-bit optical digitizer may be adequate while in other applications a 3-chip color CCD photodetection camera with 8-bit or higher optical digitizer may be required. A computer or other microprocessor based controller is used to operate the system. The software which is used to analyze the digitized data collected is based on algorithms which identify and quantify in one form or another the particle type(s) and amounts in the sample based on one or more measurable properties of the light scattering particles. A diagram of an apparatus containing the essential features required for image analysis of light scattering particles is given in FIG. 33.

The variation of the apparatus now described is an illustrative example and one of average skill in the art recognizes that there are many other configurations possible in the present invention. For any given application, the basic system described herein can be made into a commercial grade apparatus in many different forms depending on the nature of the application. In this illustrative example, the apparatus is designed for maximum operator flexibility as would be desirable in the fields of research. For example, a manual system for use by researchers can be made which accepts microscope slides or most any other sample device. Many of the system parameters such as the angle, wavelength, polarization, and beam diameter of illumination light, magnification and focusing of the collection optics, biasing of the photodetector, and movement of the sample with respect to the detector can be performed by the operator. A light source and light guide is used to direct the illumination light to the sample. The sample is placed on a stage or other mechanical component which allows movement of the sample in two or three dimensions by the operator. The light illumination position is adjusted with the desired collection optics in place such that the particles can be maximally detected and resolved within the sample. The radiated light from the sample is collected with a lens or series of collection lenses and imaged onto the face of an imaging photodetector. The photodetector may be monochrome or color. In the case of color, a three chip camera device can be used if desired to optimize the color resolution of the collected image. The photodetector is connected to a digitizer and image processor which in turn are attached to or part of a computer. Image processing software and algorithms for the identification, classification, and quantification of light scattering particles is used to collect, store, and analyze the optical information as detected by the imaging photodetector.

The analysis, measurement, and determination of the particle types and number thereof by image processing means rely on specific algorithms which identify the particles by one or more of their light scattering properties. In general, in the analysis of the image data three operations must be performed: (1) identification of particles; (2) measurement of one or more of each particles light scattering properties and (3) classification and quantification of the particles.

The light scattering particles radiate specific light scattering signals which can be used to identify them. For example, the intensity and color spectrum of the radiated light from individual particles and multiparticle structures can be easily detected and measured with an imaging photodetector. In addition, the imaged particles also posses properties of size and shape which can be used to identify and further characterize particle types. The identification and classification of particles by image analysis methods is dependent on the ability to resolve the particles from the background and other particle types by one or more of the detected particles properties. The background may consist of other light scattering particulate matter of varying size, intensity, and color as recorded by the photodetector. For the identification and spatial localization of light scattering particles by image analysis methods, one form or another of edge detection is generally used. The method of edge detection is used to display the boundaries of regions within the image with different intensities of detected optical signal. The photodetector is made of individual pixels, each of which can sense the amount of light radiating from the sample at a given position. The method of edge detection groups together associated pixels of specified intensities and marks them in one form or another as an identified object, in this case a light scattering particle or multiparticle structure. The criteria for the discrimination of intensities can be varied depending on the nature of the image being analyzed. We have determined that light scattering particle types can be identified and localized using many variations of the edge detection method for both monochrome and color images. All the art known methods of edge detection, image processing, and image analysis processing are incorporated herein by reference. The end result of performing the edge detection method is that specific areas of the image have been identified as light scattering particles.

The accuracy and discreet resolvability of light scattering particles in a sample by image analysis methods is dependent on the selection criteria used and the resolution capabilities of the photodetector. For example in an image collected with a monochrome photodetector and a 8-bit digitizer, there are 256 gray levels that can be associated with the detected intensity signal at each pixel location of the photodetector. Using a single or multiple chip color photodetector the Red, Green, and Blue wavelengths (i.e RGB components) of the radiated light detected can be measured. One of skill in the art can use higher resolution photodetectors and greater resolution optical digitizers to improve the resolution of the collected image. Most of the preferred light scattering particles we have studied and used in various analytical and analyte detection applications appear as bright point light sources of a given color spectrum of roughly spherical shape. The eye and brain can easily detect and identify the various particles by measuring one or more properties of the imaged light scattering particles. The accuracy and precision of these direct measurements by eye may vary according to the abilities of the observer. In order for such an analysis to be performed on a photodetected image by image processing means, software algorithms which in one form or another perform the method of edge detection are used to evaluate the image. For any given combination of light scattering particles, illumination source, photodetection and sample optical background conditions, there is a preferred selection of the type(s) of discrimination used in the edge detection routine and optimum minimum and/or maximum threshold value settings thereof. For example, in some applications a monochrome photodetector is used to collect the image data. It is determined that by setting the gray scale minimum threshold value at 50 and the maximum gray scale threshold value at 220 for the discrimination, the light scattering particles can be accurately identified and quantified in the sample. The threshold values and type of discrimination may vary from sample to sample.

In a manual mode of operation, the operator can directly visualize the sample and the collected image. The operator varies the method of discrimination and limiting threshold values to determine which give the most accurate results with respect to his visual interpretation of the collected image with regard to identification and quantification of light scattering particles. For semi-automated or fully automated optimization of the type(s) of discrimination and limiting threshold values used to analyze the image, these can be (1) preset for any sample type or (2) calibration particles and or other materials to reflect background conditions are used to calibrate the discrimination type(s) and threshold settings prior to, during, or following photodetection of the sample. Based on the type(s) of discrimination and settings of the threshold(s) values, objects (in this case light scattering particles) are identified as groups of pixels grouped together and identified in one form or another as a light scattering particle. Any measurable property of the light scattering particle which can be used to identify different light scattering particle types and optimize the accurate identification of the particles in the sample can be used.

Once the light scattering particles have been identified, the particles can be further resolved, classified, and quantitated by various means. We have determined that the light scattering particles can be accurately classified based on many detectable properties. These properties include (1) the sum of all pixel intensity values in the identified particle area (either gray scale, red, green, or blue wavelengths or some combination thereof); (2) the mean or average value of the pixel intensities in the identified particle area (either gray scale, red, green, or blue wavelengths or some combination thereof); (3) the dimensions of the area of the particle identified; (4) the shape of the particle identified; or (5) a combination of two or more of these detectable and measurable properties is used.

The quantification of each type of light scattering particle in the sample is an important result and can be accomplished by various means. For example, the number of identified particles in any given area of the sample are counted. In another variation, for the particles identified as a given particle type, the sum or ratios of any of the sums of any of the measurable light scattering particle properties described above can be used to quantify each particle type in the sample.

In some applications, the detection and measurement of only one particle type is required while in other applications, the detection and measurement of two or more particle types including multiparticle structures is required. For example, in microarray based methods of analysis, the same particle type may be used to determine the amount of binding in each separate binding zone of the array. In other applications such as biological cell based analysis, two or more types of light scattering particles may be used to identify and quantify different cellular constituents. In other applications of the present invention, the presence and amount of multiparticle structures are detected and measured. In yet other applications, the distribution of particle sizes and multiparticle structures is determined.

As an illustrative example, in applications to cell biology, the cell is a highly scattering object and contains intracellular components that can appear as particles of various shape, size, and color. One of skill in the art uses light scattering particle type(s) which have one or more detectable and measurable properties which can be resolved from the cell. For example, particles whose radiated light color(s) are different from the scattered light radiating from the cell can be used with a color photodetector and appropriate discrimination methods and limiting threshold values to specifically detect, measure, and quantify the light scattering particles.

In summary, for each application of the present invention where light scattering particles are detected, measured, and quantified by image analysis means, the particle detection and measurement algorithms are optimized. One of skill in the art determines which of the detected properties of the light scattering particle(s) can best be used to resolve the particles in the sample. Particle identification is based on any of the measurable properties of the identified particles which provide the ability to specifically identify the particle. Minimum and maximum threshold values for the different particle type detection criteria are set in the algorithm to further resolve and properly identify and measure the particles. Minimum threshold values are used to set the cutoff for what is considered to be a specific light scattering particle and maximum threshold values are used to provide a high end cutoff value to separate other particulate matter such as dust, dirt, or other particulate matter and the like from being identified and counted as a specific light scattering particles.

Exemplary Application to Analytical Diagnostic Assays-Apparatus Types and Test Kits It is well known in the art that there is a wide range of analyte types. These analytes exist in different sample environments such as water, urine, blood, sputum, tissue, soil, air, and the like. Depending on the requirements of a particular type of analytic assay, one may want to get semi-quantitative or quantitative information, or both with regard to the analytes of interest. There are conditions where it is desirable to perform the analysis with a small, inexpensive, and highly portable instrument. For example, consumer use, use in the field (away from a lab), or at bedside in the hospital. One wants to be able to quickly get either semi-quantitative and/or quantitative measurements on the analytes in question. In other applications, it is desirable to have a small and inexpensive instrument for analyte detection in a small lab where from a few to several samples are tested a day, capable of quantitative results. For example, doctor's office, clinic, satellite testing lab, research labs and the like. There are also conditions where one wants to test several hundred to thousand samples per day, such as high throughput testing. Each of the above testing conditions and environments thus require different types of apparatus means. The advantages and disadvantages in terms of ease of use and cost of such apparatus can only be determined in detail when the exact requirements of testing for the analyte(s) in a sample is well defined.

We have determined that the use of certain metal-like particles with certain variations of the DLASLPD methods of detection allow for the development of specific test kits and apparatus for the above mentioned testing environments and applications. There are numerous different combinations of analytes, testing environments, sample types, assay formats, analyte detection requirements, and apparatus cost and size requirements. One of average skill in the art will recognize the tremendous utility of the present invention in that the practice of the current invention in one form or another leads to easy to use and inexpensive apparatus and test kits to solve most analytical or diagnostic testing needs.

There are many different configurations and combinations of the DLASLPD methods, particle types, and sample types that are used together to achieve a specific analyte detection capability. In any specific diagnostic assay application, the sample type(s), and method(s) of illumination and detection are usually fixed, as for example, assay format, sample chamber type, and detection apparatus. The metal-like particles have unique scattered light properties which vary by size, shape, composition, and homogeneity of the particles. The specific properties of light scattering that can be detected and/or measured from the particles is set by the previous mentioned particle properties, and the method and apparatus used to detect and measure the scattered light properties. Therefore, the ultimate utility and practice of the current invention in one form or another is achieved by combining various aspects of the illumination and detection means, and sample type, with the appropriate type(s) of light scattering particles. This results in specific apparatus and test kits.

One skilled in the art can practice many different aspects of this invention by using various particle types, assay formats, and apparatus in many different configurations to achieve many different resultant diagnostic analytic detection capabilities. FIG. 22 diagrams the various aspects of the invention which, when configured in a specific combination, yields apparatus and test kits to suit a specific diagnostic analytic testing need. The resulting apparatus and test kits are made by choosing the appropriate components of the Methodology/Apparatus Type Configuration (FIG. 23) and the Particle Type Configuration (FIG. 24). FIG. 23 shows that one skilled in the art chooses the illumination source, method and other apparatus components, the assay and sample type, and the detection method and apparatus components. FIG. 24 shows that one skilled in the art chooses the appropriate particle composition, shape, size and homogeneity to detect the desired light scattering properties of the particle. These processes as outlined in FIGS. 23 and 24, and summarized in the diagram of FIG. 22, lead to specific apparatus and test kits. The diagram in FIG. 25 shows one of the general methods we have used to develop specific apparatus and test kits for a particular diagnostic testing need. One skilled in the art does not need to practice the method in FIG. 25 to practice the present invention in one form or another.

The remarkable signal generation and detection capabilities of combining metal-like particles with the DLASLPD methods of illumination and detection as described herein allows for a wide range of analyte detection sensitivities. With regard to the general types of testing environments and the FIGS. 22-25 briefly described above, one skilled in the art can easily develop apparatus and test kits where in some diagnostic testing applications one only need to use the naked eye for detection and/or measurement, and in other cases a simple light source such as an LED (light emitting diode) or low power filament lamp are used and a photodiode or photodiode array can be used to detect and/or measure the signal. In other analytical testing applications, a laser, laser diode, filament lamp, or the like can be used with a camera, video camera or other CCD device (charge-coupled device), and with simple image processing means, the scattered light from the particles in a microarray format, or any other format can be detected and measured. These examples are not meant to be limiting but rather to generally show the versatility and broad utility of the present invention to detect one or more analytes of interest in a sample.

For example, a small hand-held apparatus for portable use that can measure one or more analytes in a sample can be built by using a low power filament bulb, LED, or laser-diode as a light source. A photodiode or photodiode array is used as a detector. Depending on the sensitivity of detection required, certain types of metal-like particles can be used with this apparatus to satisfy the analyte detection requirements. Test kits are constructed for multi-analyte or single analyte detection in liquid or solid-phase samples. For example, for liquid samples, different particle types, each having different easily detectable scattered light properties are used. In solid-phase samples and formats, such as a microarray, one particle type can be used for all the different analytes or various combinations of particle types could be used (depending on the concentrations of the different analytes in the sample).

In another example, an inexpensive apparatus and test kits capable of measuring to low analyte concentrations can be constructed as follows. A low or high power light source is used with a photomultiplier tube, photodiode array, or video camera. A lens is used to collect the scattered light from the surface(s) containing the particles. A microprocessor or external desktop computer is used to collect and analyze the scattered light data. Test kits for multi-analyte solid-phase analysis are made by using the proper particle type(s) with appropriate microarray sample chambers to achieve the concentration ranges and detection limits as required. This type of apparatus and test kits may be useful in research labs, doctor's offices, satellite clinics, environmental testing labs, and high throughput testing labs.

The above examples of apparatus and test kits are given as illustrative examples and should not be interpreted as the only practices of the present invention. One skilled in the art will recognize the broad utility of the present invention. By practicing one or more aspects of the present invention to suit a specific analyte(s) detection need, one skilled in the art will recognize the wide range of apparatus and test kits that can be made.

Use of Magnetic or Electrophoretically Active Light Scattering Particles in the Detection of Analytes An ongoing problem in the field of analytical assays and analyte detection is the problem of reaction kinetics. In certain embodiments of the present invention, light scattering particles which possess magnetic or electrophoretic properties can be used to increase the rate of the binding reaction of a particle-binding agent reagent to target analyte. By magnetic is meant that the light scattering particle can be moved and concentrated in a region of the sample container by the application of a magnetic field. By electrophoretic is meant that the light scattering particle can be moved and concentrated in a region of the sample container by the application of an electric field.

In one embodiment of the present invention, light scattering particles which have magnetic properties are used to make a light scattering particle-binding agent reagent which can bind to a target analyte. The magnetic particle reagent is applied to the sample. A magnetic field is applied to the sample so as to direct the magnetic particle reagent to one or more sites within the sample container. One or more regions of the sample container contain binding agents associated thereto which can bind the analyte and further allow the binding of the particle-binding agent to the analyte immobilized by the solid-phase binding agent. For example, one or more areas of a solid-phase can be subjected to a high density of the magnetic particle-binding agent reagent by orienting the magnetic field such that the magnetic particle-binding agent reagent is highly localized in the binding site area of the sample device or container. Following sufficient reaction time, the magnetic field can be changed to remove any unbound magnetic particle reagent. The amount of analyte present is determined by the amount of light scattering detected from the magnetic particles which have become associated with the binding site on the solid phase. In a similar fashion an electrophoretic light scattering particle-binding agent reagent and application of an appropriate electric field can be used to concentrate the electrophoretic particle-binding agent reagent to the area of interest. The amount of analyte present is determined after removing any unbound electrophoretic particle-binding agent from the binding site and detecting the scattered light from the bound electrophoretic particle-binding agent to the site. In another variation, the light scattering signals can be measured at the binding site or released from the binding site and measured on a solid-phase or liquid suspension of various area or volume respectively as is useful in the detection. One of average skill in the art recognizes that this method of the present invention provides for a substantial improvement in the time required to perform an assay.

Assays Involving the Association or Aggregation of Two or More Particles by Interaction of Analyte and Specific Analyte Recognition Reagents.

It is known in the art that by using the appropriate binding agent(s) and concentration of binding agents and analyte, agglutination, aggregation, cross-linking, networking and similar binding events can occur and that these events can be used to detect one or more analytes in a sample. In some immunoassays, visible precipitates are formed if the antigen is soluble and multivalent. In some nucleic acid assays, one specific single-stranded probe can "crosslink" two or more single-stranded targets and propagate networks. Alternatively, two or more different unique single-stranded nucleic acid probes can be used to bind to different sites on the same target single-stranded nucleic acid. In this approach, cross-linking of two or more targets can be accomplished, or, by just having the two unique probe sequences bound to the same target allows for detection.

The present invention allows for easier to use, more sensitive, and more versatile detection of analytes than was previously possible. In specific assay formats, the submicroscopic particles of this invention can form different types of aggregates that can be detected visually or instrumentally in a microscope or through macroscopic observation or measurements without having to separate free from analyte bound particles. The type of aggregates formed depends on the size of the cross-linking agent or agents and their valency and on the type of binding agent attached to the particle. Aggregates can range from two particles to many.

The particles used in a homogeneous, liquid phase, aggregation detection assay can be labeled directly or indirectly. In a direct labeling assay, an agent that can bind directly to the analyte is attached to the signal generating particle. For example, in a direct labeling nucleic acid analyte assay, the DNA probe is attached to the light scattering particle. In an indirect assay, the analyte detecting agent is labeled with a chemical group A and the particle is labeled or coated with an agent that can recognize the group A. Using direct or indirect labeling, an assay can be formatted so that interaction of the analyte recognition binding agents with the analyte (and with group A in the case of indirect labeling) lead to aggregation of the particles. The aggregates can be composed of two or more particles.

We have found that if the aggregating or cross-linking agent(s) in an assay are small in size so that the particles in the aggregate are in very close proximity, then aggregates containing two or at most a few particles appear as a single particle (submicroscopic aggregate) in the microscope. However, this submicroscopic aggregate displays different light scattering properties than unaggregated particles due to particle-particle perturbations. Depending on particle composition, size and shape, we have observed changes in the color, intensity RIFSLIW, and polarization of the scattered light. These changes can be used to measure the amount of analyte without having to separate free from analyte bound particles. In a microscope the changes can be used to distinguish submicroscopic aggregates from nonaggregated particles even though both may appear as single particles. If the aggregating or cross-linking agents are large in size, such as a long DNA chain where the distance between the particles in the aggregate is larger than the resolution of the microscope, then the particles in the aggregate can be seen individually and distinguished from unaggregated particles by the fact that they stay or move together. These microscopic aggregates can readily be seen in the microscope when as few as two particles are in the aggregate. If the distance is sufficiently large so that particle-particle perturbations are small, than, the particles in the aggregate retain their original light scattering properties. There are also particle-particle separation distances which are between the two general cases discussed above. We have observed in some specific cases that the particles in a submicroscopic aggregate do not perturb their light scattering properties presumably because they are not close enough for particle-particle-perturbation to occur. The aggregate can nevertheless be distinguished from nonaggregated particles because their intensity is n times that of the unaggregated particle where n is the number of particles in an aggregate and/or the particles are "fixed" into position relative to one another.

From the above discussion, it can be seen that liquid, phase homogeneous assays based on macroscopic measurements or visual observations can readily be achieved if aggregates produced by the presence of analyte have different light scattering properties than free unaggregated particles. If particle-particle perturbations in the aggregates are small so that the light scattering properties of aggregated and free particles are similar, homogeneous assays are still possible using methods of detection which allow visualization or measurement of the light scattering intensities of the individual particles and aggregates. In the situation where the individual particles in an aggregate can be seen, then the aggregates can be easily distinguished from free particles and quantified as described above by visual observations or computerized image analysis. Aggregates can also be distinguished from free particles and quantified in a flow cytometer or similar apparatus or device since aggregates would have a higher light intensity than individual particles. In situations where the individual particles in an aggregate cannot be seen in the microscope and particle-particle-perturbations are absent, the free particles and aggregates can be distinguished by their differences in intensities and the number of particles in an aggregate established from the scattered light intensity of the aggregate (assuming that the intensities are additional). This can be done by image analysis or flow cytometry and includes the development of an image by laser scanning or other methods which can spatially analyze an area or volume of the sample.

As the number of particles in a submicroscopic aggregate increases, the aggregate can be seen as an enlarged particle or large particle even though the individual submicroscopic particles in the aggregate may not visible through the microscope. In the case of microscopic aggregates, increase in the number of particles in the aggregate produces visible networks and the particles in the network can be counted. Large networks and particle aggregates produce macroscopic entities that can be observed with the unaided eye and can form precipitates or agglutinates.

One of average skill in the art will recognize that the different aggregation phenomena described in the preceding paragraph can be exploited to develop many different types of homogeneous assays, some of which employ a microscope or other image analysis techniques and others which involve macroscopic observations or measurements.

The following are selected illustrative examples of how a homogeneous type or other types of assays can be performed.

Examples of Assay Formats Using Light Scattering Particles

Below are given a few illustrative examples which demonstrate the broad versatility and great utility of the present invention in different assay formats. One of average skill in the art will recognize that there are many variations of the present invention which allows for the more specific, easier to use, and more sensitive detection of one or more analytes in a sample than was previously possible.

i. Assay Formats Involving the Association of two or More Particles by Molecular Recognition Based Binding Events. General Principles In one set of experiments, we biotinylated the surface of a preparation of 40 nm diameter gold particles using the method of base material molecule attachment. After purification by centrifugation and washing, we placed a drop of this material on a glass slide and covered it with a coverslip, and observed with the light microscope using the DLASLPD method of light illumination and detection. The material appeared homogeneous, the particles moving very fast in Brownian motion with a green color. We then removed the coverslip, and placed a drop of a solution of streptavidin onto the slide and recovered it with the coverslip. After a period of time, new yellow-orange and orange, and orange-white colored particle structures appeared in solution which had much greater intensity and moved much slower than the green particles. Some of these new particle structures also appeared to be asymmetrical, as they flickered as they rotated in solution. After some time, many of the green particles had disappeared and there were many of these yellow-orange and orange particle aggregates. When the edge of the coverslip was examined under the microscope, it was coated with a layer of orange, yellow-orange, and white-orange particle aggregates which were very bright in color. We have observed similar phenomena in a homopolymer nucleic acid system. These observations show that in various forms of the present invention, changes in the particle scattered light properties can be used to detect molecular binding events either by visualization of the aggregates, decrease in the number of "free" single particles, or in bulk solution by using other methods. For example, for detection in bulk solution or a flow system, the increase in number of new particle forms with unique scattered light properties and/or the decrease in the amount of particles with the original light scattering properties can be detected by illuminating a part of the solution under appropriate conditions and looking for changes in the scattered light emanating from the solution. Alternatively, by using a flow-based system, the material in the sample can be more specifically analyzed. For example, a microchannel, capillary, or flow cytometry apparatus or device is used such that a portion or the entire sample solution can be analyzed on a particle by particle basis. The solution flows by an illumination source(s) and detector(s) or alternatively, the solution is captured in a microchannel or capillary tube and then all or part of the microchannel or tube is analyzed by moving either the sample container, light source or detector (or some combination of these) along the length of the sample.

For example, a certain nucleic acid analyte is composed of about 100 nucleic acid bases and is present in a sample. The sample is prepared so that this nucleic acid is in single-strand form. Then two or more unique single-stranded "probe" nucleic acid sequences are added to the sample where these different probe nucleic acids bind to different regions of the target strand. Each of these probe nucleic acids also has attached to it by indirect or direct labeling means one or more particles. Following incubation, the sample is placed in a flow cytometer apparatus or similar flow device where the solution containing the sample can be analyzed. If the target sequence is present, there will be two or more particles which are "bound" together in close proximity. Depending on the separation distance of the particles, particle-particle perturbations may or may not be occur. These molecular structures which contain two or more particles as a result of the hybridization of the probe strands to the target strand are detected using appropriate means as described earlier.

ii. Assays Involving the Release of Molecular Entities

There are assay format applications where the present invention can be used to detect the presence of an analyte as the result of a molecular, chemical, or other event. For example, intra or inter molecular bonds, linkages, or other molecular structures can be altered such that the overall molecular geometry changes, or, a molecular piece(s) is dissociated as a result of the process. For example, peptides, proteins, nucleic acids, or pharmaceutical agents and the like can be attached to the surface of a sample container by various means that are known in the art. In some of these substances, there is one or more intramolecular linkage or bonding sites which can be cleaved or otherwise altered by chemical, biological, or other processes. For example, the presence of a specific enzyme or ribozyme can be detected by monitoring the amount of cleavage products that are released as a result of it's activity. A light scattering particle(s) is attached directly or indirectly to areas of the molecular substrate such that the cleavage process is minimally affected. The presence and amount of free particles in solution or alternatively, the decrease of bound particles attached to the sample container, or to other particles, can be related to the presence, amount, and activity of the enzyme. In another example, light scattering particles have been coated with an antigenic substance and mixed with an antibody such that all of the particles are bound together by the antibody-antigen bond in a multivalent fashion. This network or agglutinated material is placed in or if desired attached to a sample container. A sample is placed into the container which may contain the analyte (which could be either the same antibody or antigen or a competing antibody or antigen of somewhat similar structure). Depending on the presence and amount of antigen or antibody specific analyte present in the sample, some fraction of the antibodies and particle coated antigens will become dissociated from the network structure by competition. The amount of analyte present can be detected by measuring the amount of particles in solution and/or the amount of particles that remain in the agglutinated network. This variation on the method can also be used by coating the antibodies on the particles, or using other binding agents as for example, nucleic acids, peptides, receptors, pharmaceutical agents, hormones and the like.

iii. Detection and Characterization of Molecular Binding Events

In another illustrative example, the Brownian motion of a particle that is coated with a binding agent can be used in an image analysis format to detect the presence and amount of an analyte present. This method can also be used to study the molecular binding event and properties in a binding pair where one partner is attached to the particle and the other is free in solution. Such capabilities are extremely important in characterizing the binding properties of antibodies, antigens, pharmaceutical agents, receptors and any substance where it's molecular binding properties are important. For example, a 40 nm gold particle preparation is made to contain either antigen, pharmaceutical agent, or antibody on the surface. These particle-binding agents are then placed on a microscope slide and viewed on a microscope using the methods of DLASLPD illumination and detection. The particles Brownian motion properties are determined and quantified. Then a sample solution which may contain an analyte that may bind to the attached binding agent on the particle is added. If the added solution contains the binding agent partner it will bind to the bound binding agent on the particle and a change in the Brownian motion can be observed. Alternatively, for characterization applications, known concentrations of the substance whose molecular properties are being characterized are titrated in at known concentrations to determine it's binding properties. In this fashion the molecular binding events of most any molecular recognition binding pair can be studied.

iv. Amplified Detection of Analytes

In certain analytical and diagnostic assays, it may be preferable to increase the detectability of the scattered light properties of the particles so that very simplified or no detection instrumentation is required. By use of the appropriate molecular recognition binding-pairs and particles it is possible to significantly increase the level of detection sensitivity. Single-stranded nucleic acid homopolymer or repeating sequences (e.g ATATAT etc.) sequences, avidin-biotin, streptavidin-biotin, and other binding-pair systems can be used to "chain-together" and "build-up" many particles. As an example, a solid-phase assay is designed where a sandwich antibody-antigen-antibody structure is formed. One antibody is attached to a solid-phase so that the antigen analyte is captured. Additional antibody is then added which contains a biotin group. Then particles that are coated with streptavidin and free biotin are added to the solution. From the (solid-phase-antibody)-antigen-(antibody-biotin) complex grows a . . . (streptavidin-particle)-biotin-(steptavidin-particle)- . . . structure which contains many particles bound together. Such a particle aggregate or network structure produces a high level of intensity which is much easier to detect than one particle. As another example, polydeoxyadenylic acid (Poly dA) and polythymidylic acid (Poly dT) or other homopolymer single-stranded nucleic acids can be used where Poly dA homopolymer sequence is incorporated into a region of the single-stranded "probe" molecule. Particles are coated with the complementary dT sequence to this homopolymer and are added to the sample with additional "free" dA single-strands to produce the structure containing many particles.

In another example, one or more streptavidin molecules is attached to an antibody specific for a given analyte. The antibody binds to the analyte which is detected by adding light scattering particles labeled with biotin groups. Many light scattering particles become attached to the analyte depending on the number of streptavidin molecules attached to the antibody and the number of biotinylated light scattering particles that become attached to the analyte-antibody-streptavidin complex.

The above examples are for illustrative purposes and one of ordinary skill in the art will recognize that there are many variations of this aspect of the invention possible depending on the analytical and diagnostic conditions and requirements.

Improved Particle-binding Agent Reagents

The attachment of binding agents that are proteinacious such as antibodies to metal-like and non-metal like particles and other surfaces by the method of adsorption are well known in the art (see M. Horisberger, Scanning Electron Microscopy (1981),2, p9-31). The method of adsorption can be used as for example, with antibody molecules to attach substances which have a binding property to the particle. In the case of antibodies, the attachment of the antibody molecules to the particle also confers partial chemical stability to the particle. If the adsorption conditions are carefully controlled, some of the antibody molecules will still possess binding activity towards it's respective antigen. The use of certain synthetic and biological polymers as chemical stabilizers for metal particles is also known in the art (see Heller et al.(1960), Journal of Polymer Science, 47, p203-217). The methods of adsorption of substances to particles and other surfaces are hereby incorporated by reference herein.

The exact mechanism(s) and nature of the adsorption of substances to particles and other surfaces is not well understood. When antibody molecules are adsorbed to a particle or other surface, the density and orientation of the adsorbed antibodies seem to be related to the level of binding activity. Due to the lack of control of the adsorption process, it is likely that many of the bound antibody molecules have become attached in such a manner that the molecular recognition region of the molecular structure has been altered such that the binding activity may become significantly reduced or possess no activity at all.

While the method of adsorption provides for the attachment of proteinacious binding agents and other substances which may or may not be useful in analyte assays to particles, it is difficult to attach some types of substances which may be of interest in analyte testing and other fields. For example, nucleic acids, smaller protein and protein-like substances such as peptides, and other non-proteinacious substances such as low molecular weight antigenic substances, hormones, pharmaceutical agents and the like can not effectively be attached to particles by the adsorption process. Further limitations of the adsorption technique are that there are unique adsorption conditions for each type of substance which must be carefully controlled. Even when such procedures are followed rigorously, there can be significant variation in the amount of protein and the integrity and binding properties of the substance that has been adsorbed to the surface. In many cases the binding activity (affinity and specificity) of the adsorbed binding agent is significantly reduced as compared to the unadsorbed form.

Our experience with attaching various proteinacious binding agents such as antibodies to the surface of the particle by using the method of adsorption have shown us that there is great variability in the binding properties and stability of the resulting particle-binding agent materials. The binding affinities of the absorbed antibodies or other binding agents are highly sensitive to the labeling conditions and can also vary significantly from batch to batch. A significant decrease in the binding activity of antibodies, avidin, streptavidin and other binding agents that have been adsorbed to the particle is common. In some of the preparations, it appears that some fraction of the adsorbed binding agent is prone to dissociating from the particle. This can pose serious problems as this dissociated material will compete against the particle-binding agent for analyte in an analytical or diagnostic assay.

Such lack of control of the attachment process, variability in binding activity, and limitations as to what types of substances that can be attached to particles by adsorption methods poses many problems for the production and use of such materials for analytic diagnostic purposes. Perhaps most importantly, particle-binding agent conjugates prepared by the adsorption technique may not be of sufficient quality for many analytical applications where very or ultra low concentrations of analytes are being detected.

It would be of great use in the art to have a method where any type of substance including binding agents of varying size and composition could be attached specifically to a particle or surface whereby the binding activity of the attached substance is minimally affected. It would also be of great use in the art to have a method for achieving a desired density of agent per particle (or, in general any surface). In addition, it would be desirable for these methods to allow binding of more than one type of agent. From a manufacturing and cost standpoint, it would be of great utility if the synthetic procedures are easy and inexpensive to perform such that a wide variety of different types of substances can be attached to particles using the same basic procedures.

We have developed new methods that allow for the specific attachment of binding agents and most other substances to metal-like particles and other surfaces. The particle reagents produced by these new methods are highly stable and possess high binding affinities with low non-specific binding properties. These new methods overcome many of the limitations of the prior art adsorption procedures with the additional benefit that the procedures are easy to perform at low cost. In some embodiments, these new procedures allow for a universal linker chemistry platform where almost any type of substance can be quickly and simply attached to a particle or surface using many of the same materials and procedures. This is extremely important in the day to day manufacture of such particle-binding agent reagents for use in analyte testing.

The following procedures apply to any substance which includes binding agents or other substances as for example, antigens, antibodies, lectins, carbohydrates, biotin, avidin, streptavidin, nucleic acids, peptides and proteins, receptors, pharmaceutical agents and the like. The methods can be used to attach most substances to metal, metal-like, and some non-metal like particles and macroscopic surfaces. For example, non-metal-like surfaces and particles include materials that may be composed of organic or inorganic material such as glass, plastics, and the like.

Methods of Attachment of Substances to Particles and Other Surfaces i. Base Material Molecule Method In this method of attaching substances to particles or other surfaces, a two step approach which involves the use of base material molecules is used. Suitable base material molecules are any substance which can approach and interact with the surface by adsorption or other chemical process, and have accessible functional groups to which additional substances, as for example, binding agents can be attached. The base material molecule may also have the additional property of conferring chemical stability to the particle. Generally the base material molecule is of a macromolecular form (size>1000 MW) but it can be smaller or much larger. Preferred base material molecules are those which attach to the particle with high affinity, confer some level of physical stability to the particle, and possess accessible chemical groups which are easy to conjugate most any substance thereto. The chemical groups allow for binding agents or other substances to be linked either through chemical, covalent, or non-covalent attachment. For example, covalent attachment could involve photochemical or chemical attachment. Non-covalent attachment could involve cross-linking with molecules such as streptavidin, or by adsorption through hydrophobic, hydrogen bonding, or electrostatic interactions. The base material molecule may also contain one or more chemical groups which can be used to cross-link several base unit molecules together across the surface of the particle utilizing the appropriate chemical or cross-linking agents.

The following are selected examples of how the method of base material molecule attachment can be used to create particle-binding agent reagents which are highly stable, possess high binding affinities for the entity(ies) they bind to, and provide for a highly flexible, easy to use and low cost method of attaching most any substance to particles or other surfaces. One of ordinary skill in the art will recognize that there are many variations of the general technique to synthesize particle-binding agent reagents for most any purpose. Using this new method, antibodies, peptides, proteins, nucleic acids, pharmaceutical agents and most any other substance can be attached to the particle in a highly controlled and predictable fashion.

As an example, we have used a derivative of a polyethylene glycol compound of approximately MW 20,000. The properties of this molecule (bis(Polyoxyethylene bis[3-Amino-2-hydroxypropyl])) allow for it's use as a base material molecule. Each molecule of this polymer has four amine groups which can serve as linkage sites for the conjugation of additional substances. The hydrophobic backbone of the polyethylene derivative interacts with the particle and is attached to the particle surface by adsorption or some other process. This interaction is very strong, as we have not detected any of this material dissociating from the particle surface following labeling and use in analytical and diagnostic assays. The amine groups do not appear to interact with the particle surface and are accessible as conjugation sites for the attachment of additional substances as for example, binding agents. Using this polymer as the base molecule we have prepared two different types of particle-binding agent reagents. One reagent contains biotin groups as binding agents and the other particle-binding agent reagent was made to contain single-stranded nucleic acids as binding agents. The biotin used for attachment was a chemically modified form where it will covalently link to amine groups. For the nucleic acids, the 5' ends were chemically modified so that they would chemically react with the amine groups. In our use of these reagents in various assay formats we have observed that both of these particle-binding agent reagents demonstrated a high degree of stability in low and high salt aqueous solutions with exceptional binding activities. In experiments where the particle-biotin reagent was used no effect upon the binding affinities was detected. This was determined by placing the concentration of the particle-biotin reagent at concentrations of $6 \times 10^{-14}$M in suspension and submerging a plastic solid-phase that was coated with avidin into this solution. After a couple of hours of incubation the solid-phase was removed and washed. When examined under the light microscope using DLASLPD methods of illumination and detection, particles were detected specifically bound to the avidin coated solid-phase while the control solid-phase (which contains no avidin) showed no particle binding. At these working concentrations of particle-biotin reagent, if the binding properties of the biotin attached to the particles was substantially decreased, no binding would have been visible.

In another example, gelatin is used as a base material and the gelatin can be cross-linked on the particle surface by use of chromate ion or other cross-linking agents to minimize the chance of desorption. Binding agents or other substances are then linked to the particle by using the appropriate conjugation chemistries for attachment of these substances to accessible amine, carboxylic or other chemical groups to which attachment can be accomplished.

In another example, streptavidin or avidin can be used as a base material. Substances such as binding agents and the like are attached to the particle by using a chemically modified version of the molecule which contains at least one biotin group.

In a further example, polymer-like materials and other materials which possess polymer-like properties, as for example, carbohydrates, polyamino acids, proteins, and the like can also be polymerized from co-polymer units in solution right onto the surface of the particle under appropriate conditions.

For all of the above examples, one can also first conjugate the binding agents or other substances to the base material and then apply this material to the particle surface with or without chemically cross-linking the base materials together. In addition, two or more different types of base material molecules, or one or more base material molecules can be used with other chemical stabilizer molecules such that the amount of chemically reactive groups available for conjugation and the chemical stability of the particle-binding agent conjugate can be adjusted to suit most any analytical need.

In the examples above, available materials were used and selected for use as base material molecules. One skilled in the art can synthesize new types of base material molecules to further optimize their use for attachment of substances to particles and other surfaces. The following improvements allow for particle-binding agent reagents which are more chemically stable, and optimization of the conjugation process with enhanced performance with regard to binding affinities of the attached binding agents or other substances. For example, additional chemical groups can be added to the backbone structure of the polymer which increases the stability of the binding of the base material molecule to the surface of the particle. Linker arms of various lengths with appropriate reactive chemical groups at the end or close thereto can be added to increase the distance from the particle at which the binding agent or other substance is attached and ultimately resides. Different types of reactive chemical groups can be added to the base material to further improve the ability to cross-link or otherwise attach the individual base material molecules together across the surface of the particle.

ii. Direct Attachment of Substances to Particles or Other Surfaces By Means of Chemical Groups Which Adsorb to Metal Surfaces.

We have developed additional methods which allow for direct attachment of many different types of substances, including binding agents, to be attached to metal and metal-like particles and surfaces. In the art of material science and related fields, it is known that certain types of small molecules (<1000 MW) can be attached to metal surfaces and the like. For most of these small molecules there are certain types of chemical groups at specific locations within the molecule which allow for one part of the small molecule to become bound to the metal surface while other parts are not bound to the surface. For example, the adsorption of thiol and disulfide containing substances, and amphiphilic substances, such as n-alkonic acids and certain detergent molecules onto metal surfaces is known in the art of material science (see Nuzzo et al. (1983), *Journal of the American Chemical Society*, 105, p4481-4483; Allara et al. (1984), *Langmuir*, 1:45-52; and Bain et al. (1989), *Journal of the American Chemical Society*, 111:321-335). The methods of adsorption of substances to metal surfaces are hereby incorporated by reference herein. Therefore, the properties which allow for attachment of the above substances can be conferred onto binding agents and other substances by incorporating the appropriate chemical group(s) into specific location(s) within the molecular structure of the substance that is to be attached. Certain types of substances will be easier to attach with this method than others. For example, substances whose molecular structure is charged or ionic, or is polarized such that at one end of the molecular structure it is hydrophobic while at the other end it is hydrophilic will generally be useful in this particular variation of the method.

For example, nucleic acids contain a phosphate backbone which contains a high negative charge. A single-stranded nucleic acid is end labeled with a thiol or disulfide at the 3' or 5' end with or without additional hydrophobic groups incorporated into the same region of the molecule. This modified nucleic acid will bind to the metal surface or particle at the end labeled with these groups. The ionic part of the nucleic acid keeps the main chain of the nucleic acid's molecular structure away from the surface such that it is accessible for molecular interactions with most any substance that can specifically bind to it.

Other substances such as biotin, peptides, pharmaceutical agents, polymers, and the like can be attached to the particle using this method. The method is generally useful for most substances which do not interact significantly with the particle or surface in their native form. For substances that may interact with the particle or surface additional methods are required. For example, certain small molecules, proteins and the like may interact with the particle or surface such that their binding activity is diminished. In one variation of the method, the particle is first labeled with, for example, a polymer stabilizing agent. Following this labeling, there are usually open areas on the surface of the particle to which small molecule entities can bind. The appropriately modified substance is then added to the chemically stabilized particle to confer a desired binding activity or other property. Alternatively, the chemical stabilizer and chemically modified binding agents can be mixed together in a desired ratio prior to mixing with the particle or surface. By using these methods, the amounts and types of substances that are attached to the particle or surface can be controlled to yield a coated surface or particle with the desired chemical stability and binding activity properties.

Linker arms of various lengths and composition can also be incorporated into the molecular structure. For example, a small molecular weight base material molecule can be used where it's molecular structure is optimized for attachment to the particle or surface, attachment of most any substance to it with any desired orientation, and with a high level of binding activity. As an example, a linear polypeptide twenty amino acids in length is chemically modified at one terminus by the addition of disulfide or thiol chemical groups. The native polypeptide is composed of amino acids such that the polypeptide chain will not interact with the surface except through the chemically modified end. At the other terminus a free amino group exists, or alternatively, has been chemically modified for a desired conjugation process such that most any substance can be attached at this position. This low molecular weight base material molecule then is used in one or more variations of the methods as described herein.

The method of base material molecule conjugation and the method of direct attachment as described herein allows for the more specific control of the amounts, types, and orientations of substances that can be attached to particles and other surfaces. A further advantage is that these methods provide for the synthesis of particle-binding agent reagents where the binding affinity of the attached binding agent remains at high levels.

An important feature of the base material molecule method utilizing either small molecular weight or larger molecular weight base material molecules is that with the proper selection and utilization of base material molecules, the base material molecule can serve as a universal linker platform to which most any substance can be attached to a particle or surface. This capability becomes extremely important in the day to day manufacturing of particle based reagents for testing of analytes. One of ordinary skill in the art will recognize the many different variations of these new attachment methods that can made by varying the chemical groups, molecular weights, molecular structure, labeling reaction conditions, and the type of conjugation chemistry (i.e. cross-linking, covalent attachment, etc.) that is used.

Another important aspect of the present invention is the ability to define the surface charge, hydrophilicity and hydrophobicity of the surface of the particle-binding agent reagent. For example, in the use of light scattering particle-nucleic acid reagents in a nucleic acid assay, the surface charge and related physical characteristics need to be carefully controlled in order for the reagent to bind to the target nucleic acid. If many nucleic acid molecules are attached to the surface of the particle, the particle will have a large negative surface charge in typical solutions used for hybridization reactions. This high charge may impede the binding reaction of the particle-nucleic acid reagent to the target strand because of charge repulsion effects. The composition of the groups attached to the surface and their relative amounts can be used to tailor the surface charge of the particle-binding agent reagent to fit most any application. For example, in the case of nucleic acid assays, a fixed amount of nucleic acid molecules are attached to the particle using the method of base material molecule attachment wherein other base material molecules which do not have any nucleic acid molecules attached to them are mixed in a specified ratio with nucleic-acid containing base material molecules yielding a particle-nucleic acid reagent with specific properties of surface charge, hydrophilicity and hydrophobicity. One of skill in the art recognizes that there are many variations on the methods of attaching binding agents to the surface of particles and tailoring the surface charge in addition to the examples given.

Microarray or Micropattern Assays with Light Scattering Particles

The microarray or micropattern method of analysis uses discreet spatially addressable areas of a solid-phase to detect different types of analytes. For example, each spatially addressable area or microspot may contain a different type of antibody, receptor, nucleic acid or the like. The arrangement of the spatially addressable areas on the solid-phase is dictated by the size of the solid-phase, the number of analytes or different areas that will be used, and the method of detection. Each of the spatially addressable microspots which contain a particular type of binding agent may be shaped as a square, circle, or any pattern depending on the methods used to make the microarray. The dimensions may be from a few square microns to square millimeters or even larger. The microarray method can be implemented using any one of the many solid-phase formats that are used for single analyte detection and in which the final quantification is done by measuring a solid-phase signal that is related to the amount of analyte bound to the solid-phase. In practice, the general analytical steps for the microarray method are as follows. The microarray is exposed to an analyte sample, e.g. serum, and after a suitable incubation period the array is washed and exposed to a second analyte binding entity. In one format, the second analyte binding entity is bound to the light scattering particles whose light scattering properties are detected. The number of light scattering particles attached to each microspot is then a measure of the amount of analyte present in each microspot and can be correlated with the concentration of the analyte in the sample. In another format, the second specific analyte binding entity is not bound to the light scattering particles. In this latter format, a third entity, that binds specifically to the second specific binding entity, is bound to the light scattering particles. This third entity, for example, can be streptavidin which binds specifically to biotin covalently attached to the second entity. There are many other assay methods which can be used for detecting the second entity with the third entity bound to the light scattering particles. In any of these formats, the amount of analyte bound to each microspot is established by measuring a light scattering signal that is related to the number of light scattering particles bound to each microspot.

Different methods can be used to detect the number of light scattering particles on each microspot in a microarray. The amount of analyte bound to each spot is established from the number of light scattering particles attached to each spot in the final assay step. In general, some type of imaging system is needed to separate the light scattering signals from the different areas in the array. This may involve the use of imaging photodetectors which image one or more regions of the sample or, a scanning approach where one or more regions of the sample are illuminated and detected, recording the detected light scattering signals at each scanned location. Many different types of formats can be used for imaging and particle quantification. The method of choice depends on the precision that is required and the number of samples to be analyzed per day. The needed precision can range from low as in the cases where only a positive or negative type of answer is needed to very high precision in cases where the amount of analyte has to be determined with a precision of a few percent. Examples of different imaging and particle quantification formats are now described.

Special features can be introduced into the microarray for any imaging method for example, the chemistry of some of the microspots in the array can be formulated to yield a background signal of known magnitude for calibration, or the chemistry of some of the microspots in the array can be formulated to serve as calibrating spots containing known amounts of analytes and/or particles. The signals from these spots can be used to correct for variations in incident light intensity, light transmission between multi-microspot array carriers, light collection efficiency and photodetector sensitivity from one sample to the next.

Some specific imaging and light-scattering particle quantification methods for applications to microarray and array chips are now described.

a. The DLASLPD Method with Simple Light Microscope i. Low Particle Surface Density (less than 0.1 Particles per $\mu^2$) on a Spot.

If the number of samples to be examined is not high, the number of particles in each spot can be determined by visual or other counting methods of the number of particles on each spot. A background count is also made. The counting can be done on liquid covered or dry microarrays. The number of particles per microspot which is considered to be positive is defined by previous test experiments. If many samples are to be examined, the counting can be done automatically using a simple video detector and object counting software.

ii. High Particle Surface Density (greater than 0.1 Particles per $\mu^2$) on a Spot.

For positive or negative types of analysis, the intensity from each spot can be detected by visual observation or photodetection. A Result is positive if the intensity is higher than that of the background. If a quantitative result is needed and there are not too many samples to be examined (for example, bedside, field, small clinic, or research lab testing), a manual technique with a two observation port microscope can be used as follows. A single microspot is illuminated with a narrow beam of light. The beam is positioned on the spot by visual observation through one observation port and the intensity is measured quantitatively through a photosensitive device with or without spatial filtering aperture depending on the level of stray light signal. The scattered light intensity from each spot is measured by manually scanning each spot through the beam. Alternatively, the beam could be scanned manually and the light detected from each spot detected by a large area photodetector or a small area detector in which the detector area is kept confocal with the illuminating spot. This could also be automated. If many samples are to be analyzed, the microarray can be illuminated with a broad beam of light and an image of the microspot array digitized through a video camera and frame grabber. The intensity of each microspot is then determined by software image analysis. We have determined that these methods allow for very sensitive and wide concentrations of one or more analytes in a sample to be detected. One skilled in the art will appreciate that many other variations of the method are possible.

Use of Certain Types of Metal-like Particles in Microarray and Array Chip Detection of Analytes In our work with microarrays, we have found that metal-like particles are preferred light scattering particles. The size, shape, composition, and homogeneity of the particle type(s) used in a specific microarray application depend mainly on the following; the amount of non-specific light background in the sample; if the microarray is dry or covered with liquid; the dimensions of the discreet solid-phase binding areas; amount and concentration ranges of the analyte(s) that are detected; detection by eye or by photodetector, and measurement by particle counting and/or intensity measurements.

As an example, we were easily able to detect the binding of individual 60 nm diameter gold particles coated with BSA-biotin to 80 micron diameter spots containing streptavidin on a plastic solid-phase in a microarray format covered with buffer solution. We used our custom illuminator under DLASLPD conditions and the inexpensive microscope system we developed. In microarray streptavidin microspots with lower densities of bound 60 nm diameter gold particles coated with BSA-biotin, we counted the number of particles bound. At higher densities, we measured the intensity of the scattered light arising from the particles bound to the individual streptavidin microspots. We detected particle densities down to about 0.06 particles per $\mu^2$ at a signal to background ratio of 13. This implies that for this type of assay, densities down to about 0.015 particles per $\mu^2$ can be detected at a signal to background ratio of about 3. Very high densities of bound particles were also detected (saturation of available binding sites per individual microspot of 80 micron diameter). To perform the same type of microarray assay in a dry form (not covered with liquid), the use of larger diameter gold particles or other metal-like particles with greater light scattering powers may be required to achieve the same sensitivity. Also, using a longer wavelength light source such as a HeNe laser with illumination above 600 nm and spatial filtering may also be useful.

For detection of samples by use of a small handheld or other type of portable device, even larger particles may be needed to be used depending on the level of sensitivity required as typically one skilled in the art must use low power light sources in such a device.

For multi-analyte detection in the microarray format, the concentrations of different analytes may exist at very different levels with differences of 1,000 to 1,000,000 or even greater in concentration. In such situations, the light scattering power and the relative size of the particles become very important. For example, if one is analyzing multi-analytes on an array chip or microarray where the individual discreet binding areas are about 100 square microns, the number of particles that can be bound to this 100 micron square area is highly dependent on the size of the particle used. For example, if a 40 nm particle is used, at binding saturation, about 79,600 particles can be bound to this area. However, if a particle of 120 nm is used, only about 8,800 particles can be bound to the area. Depending on the amount of non-specific light background and non-specific binding of the particles, the minimum number of particles that must be bound to the area for a reliable measurement can be quite variable. For example, in certain situations a few thousand or more particles may be needed to be bound to the binding site area on the microarray in order to get a positive detection result. Using larger particles thus limits the detectability of the analyte. In binding site areas of small dimensions, the smallest particle that can be used which gives adequate signal/background should be used. In addition, optical and spatial filtering, confocal imaging, more powerful light sources and other instrumental components can be optimized to increase the detection limit. Similarly, if two or more of the analytes exist at very different concentrations, then different types of particles with the appropriate size and light scattering power may be needed to be used.

These examples are not meant to be limiting but to show how in various applications, the selection of certain types of metal-like particles leads to specific test kits for microarray analysis and detection of multi-analytes. One skilled in the art will recognize that there are many other variations of the method of the present invention to detect multi-analytes on array chips and microarrays.

Use of Certain Aspects of the Present Invention with Other Illumination and Detection Methods This discovery means that you can use various aspects of the present invention in the art existing diagnostic detection methods and apparatus even without using the optimal light and detection methods and systems as the present invention has disclosed. For example, laser confocal microscopy methods, brightfield and epi-illumination microscopy methods, and the methods of reflection contrast and differential interference contrast microscopy can be used with certain types of metal-like particles for measurement of multiple analytes on microarray chips and the like.

For example, a confocal microscope as described by Ekins in U.S. Pat. No. 5,432,099 (hereby incorporated by reference) can be used. Generally, such confocal microscopy relies on point illumination rather than field illumination and usually works in a fluorescence mode with epi-illumination. Usually the detector is a photomultiplier because the signal to be detected is very low. The light source is frequently a laser. In the present invention even though the signal is extremely high (compared to normal confocal microscopy) and the light source need not be a laser, an apparatus as complex as the confocal microscope can still be used. Clearly, the use of such an apparatus provides even more sensitive detection of particles as described in this invention as we have found, and minimizes stray light problems.

Thus, in another example, the methodology of Fodor et al., *Nature* 364: 555, 1993 for detection of target molecules using biological chips can also be used.

These methods when combined with the use of one or more aspects of the present invention are useful in certain microarray analysis applications where the cost and ease of use of the method and apparatus are not of concern. We are not aware of anyone using these above mentioned art existing techniques with metal-like particles and/or the method of refractive index enhancement and/or autometallography and/or any other aspects of the current invention. We thus claim use of these previously described art existing detection methods and apparatus with one or more aspects of the present invention.

Other Adaptations of the Invention for Applications to Microarrays

The methods of the present invention provide an excellent means for detection of one or more analytes using a microarray format. The following methods provide additional variations which are useful in certain analytical applications.

We can miniaturize our illumination and detection methods such that a single or multi-optical fiber based apparatus is constructed. This provides an alternative to using the imaging methods for detection.

One problem in using a two-dimensional array, or other type of solid-phase spatially addressable system is the problem of signal crosstalk between different areas of the microarray. Crosstalk, glare or other similar problems can arise from several sources, for example, (1) the individual areas containing the light scattering or fluorescent material(s) are so close together that they appear as one area, or (2) one area contains a high amount of light scattering particles or fluorescence while other adjacent areas contain very low amounts of light scattering particles or fluorescent materials. Depending on how close the areas are to each other, some portion of light coming from the highly intense areas will be picked up by the detector in the areas from which lower light intensities are coming from.

One potential solution in the art is to illuminate each spatially addressable solid-phase site separately by using a scanning process and recording the light signals coming from each spatially addressable site separately when it is illuminated. This can be accomplished by scanning the different areas one at a time by moving the illumination beam, or the sample. However, these scanning mechanisms are usually complicated and add a tremendous amount of cost and complicated procedures to the analytical method, and may be too costly and not robust enough for the everyday rigors of a clinical testing laboratory or highly active research laboratory.

An example of a further variation of the present invention is now described. An optical fiber at one end is beveled to a suitable angle and is used as a discreet illumination source such that when brought close to an area to be measured, the emitted fluorescent or scattered light from the area is detected from the other side of the sample surface. This configuration allows for the specific illumination of an area and eliminates the above mentioned problems of crosstalk. It also removes the requirement for an imaging-type of detector such as a video camera, and any type of photodetector can he used. As an example, for an array of 24 microspots or distinct areas to be measured, 24 individual illumination fibers are used, one for each spot. All that is required is that the individual spots are illuminated at different times with respect to one another. Several small spatially addressable areas, down to about ½ the diameter of the optical fiber can be measured in this fashion.

In another embodiment of the method, where the use of epi-illumination or similar methods are desired, as for example, confocal imaging, one could miniaturize the system by placing at the end on an optical fiber a very small imaging lens and then achieve confocal conditions where the scattered or fluorescence light can be measured from the desired region of the microarray. For any area to be measured on the microarray surface, a single optical fiber is used with a microlens to deliver the incident light and collect the emitted fluorescent or scattered light that is to be detected. Multiple optical fibers could be used as described above if desired to detect more than one area of the surface at a time.

One of skill in the art will recognize that the preceding illustrative examples are only a few of the many variations of the present invention that are possible.

Applications of the Present Invention

The present invention can be used to detect and measure a wide range of target analytes. These analytes can be organic and inorganic compounds, viruses, bacteria, cells, proteins, peptides, hormones, protein-lipid complexes, nucleic acids, pharmaceutical agents, pharmaceutical drug targets, lipids, carbohydrates and carbohydrate-containing substances, antibodies, antigenic substances, and the like. Many different types of assays have been developed to detect and measure these types of target analytes. Immunoassays, nucleic acid assays, and many other ligand-receptor assays are well known in the art. These types of assays are also known as binding pair or molecular recognition type assays. One member of a binding pair is used as a probe to detect and measure the presence of it's partner. Many variations of assay formats and detection labels are known in the art. In many binding-pair based assays, a detectable label is attached to the target analyte as a direct result (e.g. detection label directly attached to the probe) or indirect results (e.g. use of secondary binding pairs to the probe or probe-target complex) of binding pair formation of the probe to the target.

To use the present invention in one form or another, the attachment of a detectable light scattering particle to the target analyte is generally accomplished by one of three methods: (1) The probe molecule (e.g. antibody molecule, complementary nucleic acid sequence, etc.) of the binding pair contains one or more detectable light scattering labels; (2) the probe member is labeled with one or more members of a secondary binding pair; (3) one or more light scattering detection labels are contained on an antibody, nucleic acid intercalating substance, nucleic acid binding proteins, or other agents that have specific binding properties for the probe-target analyte complex. Examples of secondary binding pairs include biotin and avidin/streptavidin/antibiotin antibodies; digoxinin and antidigoxinin antibodies; fluorescein and antifluorescein antibodies.

We now disclose several applications of the present invention for the detection and measurement of a wide variety of analytes. The examples and discussion below are not meant to be limiting, but rather to show the broad utility of one or more forms of the present invention. Those with average skill in the art will realize that there are many variations of the present invention.

Applications to Nucleic Acid Detection and Analysis

The detection and analysis of nucleic acids continues to be problematic despite the intense activity in the field over the last several years. In many situations the amount of nucleic acid sequence that is present is very low with perhaps just a few or even one copy of the sequence per cell or organism. In order to be able to detect the presence of the nucleic acid sequence, sophisticated methods of "target amplification" for example PCR, NASBA, TMA and other nucleic acid sequence amplification technologies must be used. These methods add significant complexity to the assay and must be carefully controlled and monitored. Signal amplification technologies have also developed. Chemiluminescence, electrochemiluminescence and enzyme based calorimetric or fluorescent signal amplification systems are examples. As is the case with target amplification technologies, signal amplification technologies must be carefully applied and used and are susceptible to interference and high variability in their activity.

We have found that by using hybridization techniques in combination with one or more variations of the present invention, specific target nucleic acid sequences can be detected and measured more easily and with greater detection sensitivity than was previously possible. The enablement of greater detection sensitivity with less time consuming and complicated methods allows for the more widespread detection and analysis of nucleic acids in many different fields including Medical, Biological, and Biochemical Research, Pharmaceutical Drug Discovery and Development, Veterinary and Clinical Diagnostics, Agriculture, Food, Water, Industrial and Environmental Science.

The combination of hybridization techniques with one form or another of the present invention allows for the identification and measurement of specific nucleic acid sequences of RNA, DNA, and other nucleic acid sequences. For example, HnRNA (heterogeneous RNA), tRNA (transfer RNA), mRNA(messenger RNA), ribosomal RNAs (rRNA), and DNAs can be detected, measured and analyzed. In applications to DNA, genes, polymorphisms, linkage patterns, gene mutations, abnormal genes, other associated sequences, and the expression levels of one or more genes can be detected, measured and analyzed. The present invention in combination with hybridization methods can also be used to detect, measure, and analyze nucleic acid sequences which are synthesized by chemical or biochemical methods as for example, oligonucleotides, cDNAs and the like.

Nucleic acid hybridization methods are of great utility in the detection and identification of nucleic acid sequences. The method of hybridization and hybridization assays make use of the unique physico-chemical properties of nucleic acids which allows for double stranded and even triple stranded structures to form between two or more nucleic acid strands which are complementary to one another. Many different variations of the hybridization method exist and many different assay formats have been developed to perform a hybridization assay. These art known methods are incorporated by reference herein.

In a hybridization assay, a nucleic acid sequence with a known sequence is used as a "probe" to detect a "target" sequence in a sample which has a sequence complementary to one or more regions of the probe nucleic acid sequence. The probe nucleic acid sequence is added to the sample and the probe nucleic acid sequence binds to a complementary target sequence if it exists in the sample. Following the hybridization reaction, the probe-target complex can be detected and measured by using a detection label and identifying the probe-target complexes. Usually, this involves the direct or indirect labeling of the probe nucleic acid or the probe-target complex with a reporter group which can be detected. Well known reporter groups in the art of nucleic acid detection include radioisotopes, fluorescent molecules, chemiluminescent and electroluminescent molecules, and enzymes which produce a calorimetric, fluorescent, or luminescent signal.

Several different methods for the direct attachment of light scattering particles to nucleic acid molecules have been disclosed herein. Additional direct methods include the chemical or photochemical modification of one or more chemical groups of the nucleic acid for new chemical groups that are used to form a chemical bond or other linkage to the surface of a light scattering particle. For example, the method of transamination as described by Jackson in Ph.D. Dissertation, Department of Chemistry, University of California, San Diego (1991) can be used to develop reactive amino groups on cytosine residues. This method is incorporated by reference herein. Those of ordinary skill in the art will recognize that there are many different methods for the attachment of a light scattering particle to a nucleic acid sequence.

Alternatively, a secondary binding pair as described above is used. For example, One or more molecules of biotin, fluorescein or digoxinin is incorporated into the target nucleic acid sequence by any of the art known techniques including: (1) the use of individual nucleotides containing these in the synthesis of the target nucleic acid sequence; (2) chemical or photo chemical reaction of the groups into the target nucleic acid sequence or the 3' or 5' ends;(3) use of biochemical methods to incorporate the groups. These methods are incorporated by reference herein.

Nucleic Acid Sequence Detection and Identification

The use of light scattering labels as a reporter group in applications to the detection of nucleic acids is known. For example, in U.S. Pat. No. 5,599,668 and Stimpson et. al., *Proc. Natl. Acad. Sci., USA*, pp. 6379-6383 (1995) the use of light scattering labels with an evanescent waveguide device to detect nucleic acid hybridization is described.

The publications claim to achieve nM detection sensitivities with evanescent illumination which are comparable to fluorescence based detection sensitivities. The many problems associated with evanescent techniques are well known in the art and the lack of commercial diagnostic or research products attests to the complexity, difficulty of use and other problems with such a system.

The present invention has overcome many of the limitations of the evanescent method. In certain forms, the present invention is capable of detecting individual light scattering particles and discreet, individual molecular binding events. Advantages of the present invention as compared to the art known evanescent and fluorescence techniques include broad utility to many different analyte types, assay formats and devices, and the substantial decrease in complexity, increase in ease of use, increase in detection sensitivity, and decrease in cost.

For example, utilizing the present invention and hybridization methods, we have been able to detect very low quantities of target nucleic acid and even single molecular binding events between two complementary nucleic acid sequences in solution (see Example 32).

In a solid phase variation of a nucleic acid assay utilizing the present invention, we have attached either Polyinosinic (Poly(I)) or Polycytidylic (Poly (C)) nucleic acid sequences to small areas on a glass microscope slide. 2-4 mm diameter spots of "capture" nucleic acid sequence were made by coating the slide with a solution of polylysine, air drying the slide, then placing small 1-2 microliter spots of nucleic acid solution on the slide. Following incubation of the drops, the slides were washed and then the surface of the slide was blocked against non-specific binding using a blocking solution. In one embodiment, a target nucleic acid is labeled with a light scattering particle. A sample containing target nucleic acid-light scattering particle conjugates is applied to the glass slide containing the complementary immobilized probe. Following incubation the presence and amount of the target nucleic acid is determined by detection and measurement of the light scattering signals from the light scattering particles in the capture nucleic acid areas of the slide. For example, we placed spots of Poly(I) nucleic acid sequence of 2-4 mm in diameter on a glass slide as the immobilized capture probe. Poly(C) nucleic acid sequences which had been attached to 80 nm diameter gold particles were used as the target. An aliquot of a sample containing the Poly(C) targets labeled with the gold particles was applied to the surface of the slide. The slide was covered with a coverslip and placed on a light microscope specially modified for our methods of illumination and detection (DLASLPD). After a few minutes, the individual Poly(I) capture spots on the slide became visible as the Poly(C)-80 nm conjugate became bound to the Poly(I) capture probe areas on the slide. We were surprised that the capture spots could be seen without removing the sample solution by direct visualization of the slide on the microscope stage (with the unaided eye. The Poly(I) capture zones became very bright as time progressed. Viewing the slide through the microscope, we could see the individual particles attached to the slide, and many of the particles which were attached could be seen to be moving slightly, as would be expected for a particle tethered to a surface. We washed the slide, covered it with a buffer solution and coverslip and placed it back on the microscope. We were able to detect and measure the amount of target Poly(C)-gold particle conjugate hybridized to the Poly(I) capture spots by several methods. In one method, we could detect and measure the relative light scattering signal from the spots with the unaided eye by viewing the slide as it sat on the illumination stage of the microscope. In another method, we detected the spots by eye through the microscope and the relative scattered light intensities from each spot could be determined. In another method, we increased the magnification of the microscope so that the particles could be visualized. We then counted the total number of particles in each spot manually by eye. In another method, we used a photodetector in the form of a video (CCD) camera to collect images of the slide. We used a frame grabber and image processing software to create digital representations of the slide surface. The digitized data files are stored within the computer or on other storage media and devices. The images are viewed on a computer screen and can be analyzed by visual inspection and/or use of image processing means. The images can also be printed out using various printer devices and printing media. From the digitized data, we were able to determine the amount of light scattering signal from each capture spot or any other area on the slide by using various methods. For example, in one method we viewed the digitized image of the slide on a computer screen using commercially available image analysis and image processing software. By the unaided eye, we could determine the relative light intensities in the different spots on a slide or on different digitized images of different slides by comparing the relative brightness of the spots. In another analysis method, we used commercially available software and selected various user functions to which we supplied different parameters and combinations of parameter constants, variables, and algorithms to analyze the light scattering signals of the different spots. For example, we measured the integrated light intensity of the digitized image of a spot as follows. Using a drawing tool, we drew a circle around the perimeter of the imaged spot containing the light scattering particles and identified the spot as one object to be analyzed. The detection threshold of the software with regard to the brightness or light intensity per pixel was adjusted to reflect a similar size object spot where no light scattering particles were attached. This served as the background signal of the slide system. Then using various measurement functions, we integrated the total light intensity of the spot. Alternatively, the integrated light intensity of the spot is measured without the background threshold detection level set to the background of the slide and then the signal from the background is subtracted from the total integrated light intensity measured per spot.

In many of the images, individual particles could be seen. To measure the relative amount of light scattering particles in the spot and/or the relative amount of scattered light intensity per spot the following methods were used. Using the drawing tool of the software to identify objects, we drew circles around individual particles and then analyzed them for various measurable parameters such as the size(area) of the imaged particle, the density of the light scattering signal (amount of detected intensity per unit area), and the color spectrum of the detected scattered light in terms of it's Red, Green, and Blue components. Using one or more of these measured parameters for a small population of the particles identified, we developed calibration parameters for these types of measurements. We then inputted one or more of these calibration parameters into the software to serve as a limiting threshold value as to what objects are identified as light scattering particles. Using this approach we selected a capture spot with the drawing tool for analysis. Using our defined calibration parameters, we used the software to identify the light scattering particles in the capture spot. Following this approach we were able to count the number of particles per capture spot and also sum the detected light scattering signals of the identified light scattering particles in the capture spot. We were surprised to find that by using either the direct counting of the particles method or the method of first identifying the particles followed by summing of the individual particle intensities, very high signal to background ratios were obtained as compared to the integrated light intensity measurement approach of the entire spot. For quantitative measurements that are comparable within a slide or between many different slides or samples an internal calibration zone can be added to the slide in a specific area. The calibration area can consist of light scattering particles, or any other material that is found to produce consistent calibration data from sample to sample on slides, array chips or any solid-phase surface being measured. The calibration area is used to (1) set calibration parameters for the detection of the light scattering intensities and identification of light scattering particles;(2) adjust the amount of illumination light being delivered to the sample; (3) adjust the gain of the photodetector; (4) normalize the determined light scattering intensities of the various sample zones for fluctuations in illumination light intensity and detection efficiency. For ultrasensitive detection of light scattering particles at densities where the individual particles can be identified, the method of counting and/or summing the individual particle light scattering intensities is preferred for superior signal to noise ratios.

Alternatively, the integrated light intensity of each spot can be detected with other photodetector means such as a photomultiplier tube or photodiode. To detect the signals from the light scattering particles in this method, the slide can be scanned as for example as described in Fodor et. al. *Nature* 364: 555 (1993), or alternatively, an array of photodiodes or other detectors can be made where each photodetector detects the signal coming from one spot as for example as described by Stimpson et. al. in U.S. Pat. No. 5,599,668. These methods are incorporated by reference herein.

In another variation of the method, we wanted to determine if a sandwich type assay format was feasible utilizing the present invention. In a sandwich type format, two or more probe nucleic acid sequences which are complementary to different regions of the target sequence are used. We conducted a sandwich type nucleic acid assay as follows. Poly(C) sequences were attached in small 2-4 mm spots on a glass slide. The function of the immobilized Poly(C) is to function as a probe to capture the target Poly(I) nucleic acid sequence that is in the sample. It should be noted that the Poly (C) and Poly(I) sequences used in these experiments were a heterogeneous population of lengths and that the mean average length of the Poly(I) was a few hundred bases longer than the mean length of the Poly(C). Thus, for many of the Poly(I) molecules it should be possible to attach two or more Poly(C) molecules to the same Poly(I)molecule As the detection probe nucleic acid sequence, we attached 80 nm gold particles to Poly(C) nucleic acid sequences. The presence and amount of target Poly(I) nucleic acid sequence in solution is detected and measured by detecting the amount of light scattering signal that is present in the Poly(I) capture spot. Alternatively, the amount of unbound Poly(C)-particle probe remaining in solution can be measured, or a combination of the amount bound to the amount remaining in solution can be used. We performed the sandwich assay in one of two ways. In the first method, the target Poly(I) and probe Poly(C)-particle were mixed together and then applied to the slide. In the second method, the Poly(I) target was first incubated with the slide, and then the probe Poly(C)-particle added. Utilizing either of these methods, we observed the binding of the Poly(C)-particle to the probe capture spots on the slide and were able to measure the amount bound using various methods as we have previously described.

In another embodiment of the present invention, we were able to detect, measure, and determine the sequence of a target nucleic acid sequence in a sample by using the method of sequence by hybridization ("SBH") and a specific oligonucleotide array chip made by the Affymetrix company. The method of sequencing by hybridization is disclosed by Dramac et.al in U.S. Pat. Nos. 5,202,231 and 5,525,464 and similar related methods are well known in the art and are incorporated by reference herein. We used an Affymetrix variable density 1164 Chip which consists of multiple repeating arrays of specific oligonucleotide sequences attached to small areas on the surface of the chip. By placing the appropriate sequences on the chip, virtually any nucleic acid sequence in a sample can be analyzed. The 1164 Chip contains thousands of discreet binding areas on the surface, each binding area containing many copies of a known sequence and length of oligonucleotide nucleic acid sequence immobilized to the surface. The binding areas range in size from about 100×100 microns to about 20×20 microns. As described in the publication of Chee et al., *Science:* 274, pp. 610-614 (1996), fluorescence techniques involving confocal imaging and scanning of the array are used to detect and measure the binding areas on the chip.

Current challenges to bringing the use of SBH oligonucleotide chips and other nucleic acid arrays into widespread use are related to simplifying the current instrumentation and procedures, reducing the overall cost, and increasing the sensitivity of detection. If these challenges can be overcome, the use of oligonucleotide array and related array technologies may play a very important role in disease diagnosis at the molecular level with applications including infectious disease detection, genotyping, gene mutational analysis, and polymorphism analysis.

We detected, measured, and determined the internal 10 base sequence of a 20 base long target nucleic acid sequence in a sample as follows. As a target sequence, a DNA oligonucleotide 20 bases long was used. In this variation of the method, an indirect method of detection was used with biotin and antibiotin antibodies as the secondary binding pair. A biotin molecule was attached to the target as one part of the binding pair and a antibiotin-gold particle conjugate preparation with a mean particle size of 70 nm was used as the detection probe. A biotin group was attached to one end of the target nucleic acid. The assay was conducted as follows. An Affymetrix 1164 chip was blocked with a blocking solution to minimize non-specific binding. A sample containing the target 20 base long nucleic acid sequence was incubated with the blocked Affymetrix 1164 oligonucleotide array chip. Following hybridization, the array chip was washed with a buffer solution. The gold particle-antibiotin conjugate was then applied to the chip, incubated for a short time, then removed and the chip washed with a buffer solution. We were able to detect and measure the amount of target nucleic acid sequence hybridized to each of the individual oligonucleotide binding sites on the chip by using many variations of the DLASLPD method. In one variation, we held the 1164 chip with our index finger and thumb and used a microscope illuminator with a ×10 objective as a light source. We angled the surface of the chip with respect to the light beam of the source such that most of the non-specific scattered light that was reaching our eye was minimized and enough illumination light was delivered to the chip to detect it. Using this method, we were able to detect the scattered light in the arrays, and with the unaided eye we were able to resolve many of the individual binding areas. In another variation of the DLASLPD method, we used a magnifying glass placed between our eye and the array such that it was focused on the surface of the chip. Our ability to resolve the individual binding sites in each array unit was improved. In another variation, we placed the array chip on top of a prism similar to that depicted in FIG. 12A and placed a drop of immersion oil between the top surface of the prism and the bottom surface of the chip. We observed the surface of the chip in a semidry state and also covered with a thin film of buffer solution covered with a coverslip. Utilizing this method, we were able to detect and measure the relative levels of light scattering intensities by the unaided and aided eye (e.g. magnifying glass). We then used a color CCD video camera on a tripod stand and oriented the camera such that an image of the entire chip surface that was being illuminated could be detected. In another variation of the method, we used a similar prism as just described which had been modified for mounting to a light microscope, and viewed the chip through the microscope optics. At low magnifications, we were able to see in greater detail the amount of light scattering signal coming from each binding site. We saw very discreet binding with many variations in intensity among the individual binding sites in each array unit. Each array unit on the chip contains the same composition and two-dimensional pattern of oligonucleotide binding sites. The relative amount of light scattering intensity from each of the binding sites on an array appeared very similar in each of the arrays on the chip. Using different magnifications we captured images of various regions of the chip by manually moving the chip and capturing images with the CCD camera mounted to the microscope. We used different objective settings depending on what level of detail and how much of the chip surface we wanted to view, detect, and measure. From the digitized data, we were able to measure the relative amount of light scattering in each binding site by eye by viewing the digitized image on a computer screen. We also measured the scattered light intensity of the binding sites by the image analysis methods described herein (e.g. integrated light intensity, counting, summing individual particles intensities). We were very surprised at the extremely low level of non-specific binding and the reproducibility of the data. We were also very surprised that we could collect images very rapidly and by various image analysis methods measure the amount of binding in each site. In an alternative embodiment of detection, mechanical semi-automated or filly automated detection of the scattered light intensities can be used with a confocal or non-confocal instrument and methods. For example, the methods of Trulson et al. U.S. Pat. No. 5,578,832 and Fodor et. al. *Nature* 364: 555 (1993) can be used to detect the light scattering signals in the binding sites and these methods are incorporated by reference herein. We should note that the current laser scanning (confocal imaging or non-confocal imaging) methods currently used with fluorescence usually takes several minutes depending on the number of binding sites on the surface. Following detection, there are massive amounts of data that must be analyzed and this step takes an additional several minutes. Using our methods of photodetection with a CCD camera, we were able to collect the data for an entire chip in a second or less at low magnification. At higher magnifications, the chip was manually moved and different sections of the chip were photodetected and digitized. This procedure can be easily converted to being fully automated. We manually analyzed the digitized image with various image analysis methods as described herein. Once a chip design is fixed, a fully automated system for detection and analysis can be made based on the collection of digitized images and measurement by image analysis methods utilizing software as we have described. Thus, the present invention has great utility as a signal generation and detection system for oligonucleotide arrays and chips, and other types of arrays for rapid screening and detection of analytes and new pharmaceutical agents. Utilization of the present invention in these applications can substantially decrease the complexity and cost of procedures and instrumentation while increasing the throughput in the detection and analysis of the samples.

Gene Expression and Gene Expression Arrays

The study of gene expression is becoming very important in many different fields including disease diagnosis, pharmaceutical drug target and drug development, and biochemical research. In recent times, there has been much effort in the development of new methods and strategies to measure gene expression levels and to increase the rate at which information is gathered. For example, array-based methods that involve the attachment of multiple cDNAs onto glass or other substrates have been reported (Schena, et. al. *Science* (1995) 270:467-470; Shalon et. al. *Genome Research* 6:639-645). An alternative array method for measuring gene expression utilizes oligonucleotide arrays has also been described Lockhart et. al., *Nature Biotechnology* 14:1675-1680). These methods are incorporated by reference herein.

To determine the relative or absolute expression levels of any given gene, the concentration of the mRNA levels which exist in an organism or cell must be determined. There are many art known methods for determining the amounts of mRNAs present in a sample which in part use hybridization methods and these methods are incorporated by reference herein. Current art known gene expression array methods use fluorescence techniques and fluorescent labels to detect and measure the hybridization of a target nucleic acid sequence species to the array, the amount hybridization then being related to the amount of mRNA of a particular gene in a sample.

We now describe how a gene expression array assay can be performed with the present invention to assess, detect, and quantify the expression level of one or more genes in a sample. We have previously described how light scattering labels and various assay specific formats are incorporated into the nucleic acid assay system. An array of oligonucleotides, cDNAs, or other nucleic acid sequences is made. The sequences of nucleic acids used in the different binding sites of the array are specific (complementary to) a specific target mRNA, a cDNA produced from the mRNA target, or invitro transcribed sequences produced from a cDNA copy of the target mRNA. In the actual assay method, if the mRNA of the sample is being directly analyzed on the chip then the mRNA is the target nucleic acid sequence. In the cDNA and invitro transcription methods, the cDNA and the invitro transcribed nucleic acid sequences are the target nucleic acids being assayed for. One or more light scattering labels are attached to the target sequence. Once the target nucleic acid sequence has been labeled, the preparation is applied to the array and hybridization methods used. The array can then be washed or can be detected without washing using the methods of DLASLPD illumination and detection by the many different variations we have described herein.

In another embodiment, mRNA levels can be detected and measured directly in gene expression arrays or other formats by attaching oligo-dT nucleic acid sequences to light scattering particles to form a nucleic acid sequence-particle reagent that binds to Poly(A) sequences. It is well known in the art that most mRNA molecules contain a Polyadenylate sequence ("Poly(A)") at one end of the molecule. This Poly(A) tail is often made of use in the purification of mRNAs from samples with the use of a separation column containing oligo dT. To perform the assay an array chip is constructed which has nucleic acid sequences complementary to the mRNAs of interest immobilized on the surface in spatially different regions. The sample mRNA is collected and applied to the chip. The Poly dT-coated light scattering particles can be added to the sample prior to, during, or following hybridization. The Poly(dT)-coated light scattering particles become bound to the Poly(A) sequences contained on the mRNAs. The presence and amount of any given mRNA target in the sample is determined by measuring the amount of light scattering signal in the binding area of the chip that has the complementary nucleic acid sequence to that target mRNA.

In another embodiment of the present invention which is applicable both to the measurement of gene expression and nucleic acid detection and measurement, specific nucleic acid sequences, DNA binding proteins, or other molecular recognition agents are attached to light scattering particles and used to detect the presence and amount of a target nucleic acid sequence. For example, one or more Poly(A) sequences or another homopolymer pair of sequences such as Poly(I) and Poly(C) can be used to create a secondary binding pair for detection of the target nucleic acid sequence.

In an alternative method, a nucleic acid or DNA binding protein is attached to a light scattering particle and the nucleic acid binding protein-particle reagent is used as a detection probe for the presence of the target sequence. The sequence of the nucleic acid that the DNA binding protein binds to can be naturally occurring in the target sequence, or, it can be attached to a target or probe nucleic acid sequence involved in the assay procedure.

In an additional method, light scattering particles are attached to probe molecules which have specific binding properties for DNA-DNA duplexes, RNA-DNA duplexes, or even triple-stranded structures. For example, it is well known that there are many compounds which show specific binding properties for double-stranded nucleic acid structures. Ethidium bromide, dimers thereof, and other variations of this molecule bind to double-stranded nucleic acid structures. Thus, in this variation of the method, a light scattering particle-ethidium bromide reagent is prepared and added to the gene expression array following hybridization. The presence and amount of expression is determined from the amount of light scattering detected in the binding zone.

All of the art known methods for using secondary binding pairs in nucleic acid assays are incorporated by reference herein.

Examples of Light Scattering Detection Apparatus and Methods

For most types of nucleic acid arrays, and for any type of array-based method, there are several different types of instruments that can be used to detect and measure the light scattering signals with the present invention. In our disclosure of the detection and analysis of the AffyMetrix 1164 DNA Chip we described many different variations of the method for detection and analysis. Some of these methods can give rise to a simple instrument such as a detection light box. For example, a detection light box is made by providing a light source angled at the proper angle to illuminate the array and a stage, window or other platform to place the array upon to illuminate it and view. With this instrument, a physician, lab technician, researcher, or anyone places the array into the correct position on the holder and then manually interprets the array by eye observing the relative amounts of light scattering from each of the binding sites on the array. Overlay templates which are placed on top of the viewed array, or, diagnostic standard patterns of the appearance of the arrays which are related to a specific interpretation of the pattern of light scattering intensities observed on the chip can be used to assist in interpretation of the array. If more quantitative information is needed, an instrument based on imaging or non-imaging detection optics can be made as we have described. For example, if the array contains many binding sites and more quantitative measurements are needed, a semi-automated or automated image-analysis system instrument can be made. For example, an imaging instrument is constructed by using an appropriate collection lens and a photodetector which are perpendicular to the surface of the array and providing an illumination source which illuminates the array such that little or no light from the illumination source enters the collection optics to the photodetector. The collection optics can be confocal or non-confocal. Images, collected with a CCD chip or video camera can be analyzed using image analysis methods and appropriate algorithms specific for the test The signal detected can be analyzed by measuring the integrated scattered light intensity, counting of the individual particles, or the integrated light intensity of the counted particles, or some combination of these methods. One or more wavelengths of light can be analyzed depending on the nature of the illumination source.

Cell Identification and Measurement

The present invention can be used in many different forms to detect and measure specific cell types and organisms in a sample. We have already described how hybridization techniques can be used to detect the presence and amount of nucleic acid sequences attributable to an infectious disease or any organism. Other non-hybridization methods can also be used. For example, an organism or a specific type of cell can be detected in a sample by using immunochemical techniques, lectins, pharmaceutical agents, and other substances that bind specifically to certain types of cells. For example, a light scattering particle-antibody conjugate reagent is prepared where the antibody is specific for a cell surface antigen of a cell of interest. The light scattering particle-antibody conjugate reagent is applied to the sample, allowed to incubate, and then the cells are prepared for analysis. In one embodiment, we have been able to conduct a homogeneous (non-separation assay) for a particular cell type by using image analysis techniques. A human lymphocyte preparation was isolated, the red blood cells were lysed and the cells washed. An antihuman-IgG antibody-60 nm diameter gold particle conjugate reagent was prepared. The particle reagent was mixed together with the lymphocyte cell preparation and then an aliquot was placed on a microscope slide and viewed on a light microscope using DLASLPD methods with the appropriate collection optics. In this method the conjugate reagent was observed to become bound to only a select few of the cells in the lymphocyte preparation while many of the cells showed no binding of the particle reagent. We observed that about 1% of the cells became labeled with the particle reagent. This ratio of labeling of the lymphocyte population was about what is expected as it is known that about 5% of B-lymphocytes have the IgG antigen expressed and that the relative abundance of B-cells is about 20% of the non-RBC lymphocyte population. The individual particle conjugates could be observed moving in Brownian motion in the field of view and there was no need to wash out the unbound or free particles to make a determination as to which cells contained bound particle reagent and which ones did not. Also the number of bound particle conjugates could be easily quantified by counting the particle attached to each cell. We were also able to capture and digitize images with a CCD video camera and by image processing methods, determine which cells were labeled, the number of particle-conjugates per cell, and the relative amount of labeled cells in the sample. As described elsewhere, a microscope-based or other imaging instrument can be constructed for detection and analysis.

In another embodiment of the present invention, the identification and quantification of specific cells can also be detected and measured by using a flow cytometer or other flow-based apparatus. In this variation, one or more light scattering properties of the light scattering particles associated with the cell are detected. The illumination and detection optics are arranged to maximize the detection of the specific light scattering properties of interest.

In another embodiment of the present invention, particles are attached to the surface of a cell, or placed internally within the cell. The particle is used as an identification tag for the cell so that the cell can be followed and traced through a series of manipulations, or identified at a later date in a population of cells by detecting one or more light scattering properties of the light scattering particles associated with the cell.

Organism Detection and Measurement

The detection and measurement of organisms in a sample can be performed by utilizing one or more aspects of the present invention. The use of nucleic acid hybridization techniques has been discussed elsewhere. For example, specific light-scattering particle-antibody conjugates can be prepared which have specific binding properties for a surface antigen on the organism, a chemical or biological substance that is produced by the organism, as for example a toxin, or any other substance which is specific for the organism. In one embodiment, a sandwich immunoassay format is used. A particle-conjugate reagent is made which has specific binding properties for a known toxin molecule or surface antigen of a bacterium or virus. A microwell, plastic, glass or other solid-surface is coated with an antibody that can specifically bind to the surface analyte or toxin. The sample and particle-conjugate reagent can be mixed together prior to application to the solid-phase or, a two step approach is used. In the two step approach, the sample is applied to the container, washed, then the particle-conjugate is applied. In either approach, following incubation with the particle conjugate, the solid-phase is washed and the amount of organism in the sample is determined by the presence and amount of light scattering signal detected.

In a different embodiment, an aggregation format is performed in solution. Light scattering particles are coated with molecules of a specific binding agent. The particle-reagent is added to the sample and if the target organism is present, multi-particle aggregates will form. The number of multiparticle aggregates, or light scattering properties of the aggregates, or the decrease in particle-binding agent reagent can be used to detect and measure the amount of organism present. In a variation of the aggregation format, optical chromatography techniques can be used such as those described in Hatano, et. al., *Anal. Chem.* 69: 2711-2716 (1997) and Kanota et. al., *Anal. Chem.* 69:2701-2710 (1997). These methods are incorporated by reference herein.

In another embodiment, an array-based device which has cell specific antibodies, lectins, or other molecular recognition agents attached to the array in spatially distinct areas is used to capture the different cells into different areas of the array. A light scattering particle reagent is used to label the cells prior to or following the application of the sample to the array. In another example, a virus or bacterium is detected and measured by using the present invention and specific monoclonal or polyclonal antibodies which specifically recognize viral or bacterial antigens specific for the species and/or strain of the organism. On a solid-phase made of glass, plastic or other optically transparent medium, antibodies are coated onto the surface that are specific for the organism that is being detected. The solid-phase can be in a chip, dipstick or other form. One or more specific binding agents can be used on the surface of the solid-phase in discreet areas in an array or other pattern. The sample is applied to the solid-phase. During or following incubation and/or following washing, a solution containing light scattering particles attached to specific antibodies which bind to the viral or bacterial antigen is applied. The solid-phase is then removed from the solution containing the light scattering particle-antibody conjugate and can be washed prior to detection or measurement. The presence and/or amount of organism present is determined by detecting and/or measuring the amount of light scattering signal coming from the binding zones of the solid-phase. Detection and measurement can be done by the unaided or aided eye, or by imaging or non-imaging photodetection and analysis as described elsewhere herein. Multiple viruses or bacteria can be detected and measured in a similar fashion by using several different binding zones on the solid-phase where each binding zone contains a binding agent specific for a virus, bacteria, or antigens that are specific for a particular strain of the organism. These are only a few examples of the great utility of the present invention for the identification of cells and organisms. Those of average skill in the art recognize that there are many other different formats possible to utilize the present invention in one form or another to detect the presence and amount of cells or organisms in a sample.

Applications of the Present Invention to Combinatorial Chemistry, Pharmaceutical Target and Drug Identification and Characterization, and High Throughput Screening The present invention in one form or another has great utility in the field of pharmaceutical drug discovery and development. In recent years, there has been an explosion of new methods and techniques for drug discovery. Combinatorial chemistry methods have developed which allow for the rapid construction of synthetic, biological, or biosynthetic libraries consisting of many thousands of unique molecules which may have potential as pharmaceutical agents. A recent publication contains several articles as related to combinatorial chemistry and serves as a good source for background information (Chemical Reviews Volume 97, Issue 2 (1997)) and these methods are incorporated by reference herein. There is a diversity of combinatorial library methods. For example, biological library methods include those involving plasmid, polysomes, and phage display methods. Spatially addressable library methods include the multipin system, multiple synthetic techniques which use segmentable carriers, SPOT synthesis on cellulose paper or polymeric membrane, light-directed synthesis on glass surfaces, gene expression arrays, and diversomer technology. Additionally, the methods of positional scanning, orthogonal partition, and an iterative approach in general are art known. Also, the one-bead-one-compound combinatorial library method and synthetic solution library methods, affinity chromatography selection, and affinity capillary electrophoresis are also known. Brief descriptions and further detailed disclosures of these methods can be found in the publication of Lam et. al. Chemical Reviews 97: pp. 411-448 (1997). All of these methods and the references cited in the publication of Lam et. al are incorporated by reference herein.

All combinatorial methods usually consist of three main steps: (1) construction of a library;(2) screening of the library for pharmacological activity; arid (3) determination of the active substances identity at the molecular level. The present invention in many different forms can be used to detect and measure potential drug substances and drug targets including those made by combinatorial chemistry. Utilizing the present invention, many different types of screening assays can be developed. For example, screening and characterization assays can be developed with the present invention for (1) the identification and characterization of drug targets and (2)developing specific assays for screening of pharmaceutical agents where the target is the basis of the assay.

It is more than likely that many thousand of the approximately ~100,000 different human genes code for biological substances that are potential drug targets. As a result of the Human Genome Project and a high level of activity in the analysis of the human genome, many genes have already been identified. In addition, many genes of organisms responsible for human and animal diseases have also been identified. Functional genomics is the field of determining the function of these genes and the proteins that they code for. Gene expression and protein expression assays can be developed with the present invention to determine which of these may be targets. In addition, drug target-based screening assays can be developed to screen for new pharmaceutical agents. Drug targets are biological components, metabolic pathways, messenger pathways, or any other biological component or system upon which the pharmaceutical agent can modulate an effect.

The advent and development of combinatorial chemistry methods, the Human Genome Project, and functional genomics has created a great need for a detection system which can be used to screen thousands to hundreds of thousands of potential pharmaceutical agents very quickly. High sensitivity of detection, robustness, low cost, and adaptability to many different formats are all important criteria. To date, fluorescence labels and fluorescence techniques seem to be the method of choice for detection. Colorimetry, radioisotope, and chemiluminescence methods are also known. Some of these methods utilize an enzyme to achieve signal amplification (e.g. alkaline phosphatase).

For example, Colorimetric-based detection methods are generally limited to micromolar($10^{-6}$ M to $10^{-8}$ M)detection sensitivities. Fluorescence-based methods improve the detection sensitivity and have detection sensitivities in the nanomolar to subnanomolar ranges ($10^{-8}$ to $10^{-11}$ M). Problems associated with fluorescence labels and methods include photodecomposition and quenching phenomenon. In many instances, other agents in the sample can interact with fluorescent labels causing the signal being detected to vary. Chemiluminescence-based methods provide good detection sensitivities ($10^{-12}$ M and below) but require special reagents and careful handling techniques and the chemiluminescence reactions are susceptible to interferences from components in the sample. Radioisotope techniques are among the most sensitive known but require special handling procedures, they are hazardous materials, generally hard to use, and are expensive.

The present invention provides a new signal generation and detection system for pharmaceutical drug target and pharmaceutical drug agent discovery and development. Compared to the art known label and detection techniques used currently in the art of pharmaceutical drug discovery and drug target identification, the present invention has several advantages including improved detection sensitivity, greater ease of use, broader applicability, greater robustness, and is less costly. The present invention provides a very stable and easy to detect light scattering signal in many different types of drug target and drug agent assays. The present invention in many different variations is so sensitive and produces so much detectable signal that very small arrays or miniature reaction and sample vessels can be used for analysis. The miniaturization of the sample containers and arrays allows for a substantial decrease in the cost of the assays and time needed, and thus greatly accelerates the rate and cost efficiency at which many thousands of assays can be performed.

Many different types of invitro biochemical or cell-based assays can be developed with the present invention to test for potential pharmaceutical agents. Assays which utilize drug targets such as cell surface receptors, intra-cellular receptors, intra-cellular signaling proteins, G-protein coupled receptors, ion channels, enzymes including proteases and protein kinases, DNA binding proteins, nucleic acids, and hormones can be used to identify and characterize new pharmaceutical agents. The samples being analyzed can be individual or multiple cells, cellular lysates, tissue samples, membrane preparations or most any sample. Many of the assay formats that can be used with the present invention are similar to those assay formats used in biological, biochemical, and medical diagnostic assays. These include competitive and noncompetitive assays, homogeneous assays, solid-phase microwell and smaller wells, arrays, microfluidic chambers, and solution phase assays to detect and measure pharmaceutical agent binding activity and/or modulating effects upon a drug target system.

In order to perform the assay a particular assay format and drug target system is chosen. Light scattering particles are used as the entity that provides the detection signal. The light scattering particle may be attached to a receptor, an enzyme substrate, a hormone, a nucleic acid, monoclonal or polyclonal antibody of fragment thereof, peptide, protein or any agent that demonstrates some level of specific binding activity to the target substance being detected and measured. Illumination and detection methods based on DLASLPD methods are used to produce and detect the light scattering signal. One or more wavelengths of illumination and/or detection may be used depending on the nature of the assay. Homogeneous assays for nucleic acids and antigenic substances which do not need a separation or washing step can be performed by using the proper combination of binding agents as we have described elsewhere herein. In assay formats where two or more particles come into close proximity, the changes in light scattering intensities, polarization, angular dependence, wavelength, or other scattered light properties can be used to detect and measure the binding. Individual binding events can be detected and characterized by using the DLASSLPD methods incorporated into a light microscope or similar imaging system which can detect the individual particles.

New proteins and/or genes can be identified by using the present invention. For example, the method of "CD-Tagging" as described by Jarvik et. al., *BioTechniques* 20:896-94 (1996) is used in combination with one or more forms of the present invention to detect and measure. In the method of CD-Tagging, a specific tag is added to a gene, mRNA and protein in a single recombinatorial event. The tag is localized and identified with the present invention by using a specific binding agent for the tag which has a light scattering particle directly or indirectly attached to it.

The present invention can also be used to detect and measure protein expression and protein concentration levels in a sample. One or more light scattering particles are attached to an antibody, ligand, receptor, or other binding agent that has binding specificity for the protein being detected. Various art known assay formats or those assay formats described herein can be used. The presence and amount of protein present in the sample is determined by the detection and measurement of the light scattering signal.

Screening of Combinatorial Synthesized Molecule Libraries

A tremendous problem currently in the burgeoning field of combinatorial synthesis of important molecules is the lack of highly sensitive, practical, and easy to use signal and detection technology and assay formats to detect the few copies of newly synthesized combinatorial molecule(s).

We have determined that our signal and detection technology is easily used on solid-phases that contain spatially addressable sites such as 2-dimensional arrays or any spatially addressable solid-phase. Therefore, our methods in one form or another are directly applicable to the screening and detection of one or more than one class of combinatorial or biocombinatorial molecule(s) in this type of format. The assay method can be any of the known procedures in the art.

The invention as we have described herein can also be used to detect and quantify one or more specific combinatorial, biocombinatorial, or otherwise synthesized molecules that are not on a spatially addressable solid-phase. For example, it is well known in the art that a wide diversity of biocombinatorial and combinatorial molecules can be synthesized by using the methods of "split synthesis", "parallel synthesis", and related methods (all of these methods are incorporated herein). Typically, a wide diversity of combinatorial molecules are synthesized on small particles or other pieces of solid substrate where each particle or substrate piece contains one unique set of combinatorial synthesized molecules. There are problems of identifying and purifying those pieces or particles that contain the "active" sets of synthesized molecules in the art.

There are several ways to utilize our signal and detection system to purify and/or detect these specific and desirable combinatorial product(s). In one assay method, a binding agent(that is specific for the desired analyte) is coated on a selected type of metal-like particle. When the coated particle is added to the sample, it binds to the analyte. Alternatively, an indirect method involving the use of biotin labeled binding agent first binds the analyte, which is then detected by adding streptavidin coated metal-like particles prior to detection. The light scattering particle is bound in one form or another to the desired analyte of interest which resides on the synthetic solid phase. In this manner, the desired molecules are identified, isolated, and purified from the sample by filtration, centrifugation, dialysis or any other art known technique. Alternatively, light scattering particles labeled with binding agents can be added such that aggregates or networks are formed between the specific molecule-containing synthetic particles and the metal-like particles. Similar means as described above are used to identify and purify the desired molecules.

Multi-analyte analysis for different combinatorial synthesized molecules is accomplished by using two or more types of metal-like particles each coated with a different type of binding agent. Refractive index enhancement and DLASLPD video-enhanced contrast methods can also be used.

In another assay method, the metal-like particles also contain a composition of a ferro-electric or magnetic composition such that these particles can be manipulated in three dimensional space by using an applied EMF to the reaction container. In this manner, the substrate particles containing the "active" combinatorial molecules can be easily purified and detected from all the other material. It should be noted that a mixed composition of ferro-electric or magnetic and other metal-like compositions of specific particles are also very useful in many other fields including diagnostic assays, and for isolation and purification of desired molecules. The use of refractive index enhancement methods in combination with the above methods increases the sensitivity of detection.

Metal-like Particles Used as Solid-Phase Synthetic Supports

Metal like particles when coated with appropriate substances, are excellent substrates for conducting chemical or biochemical synthesis as for example, combinatorial synthesis. The specific coating of metal-like particles can be made to consist of for example, polymers, antibodies, proteins, nucleic acids, amino acids, reactive chemical groups, and the like. For example, metal-like particles are coated with a polyethylene glycol compound containing chemically reactive amine groups. Synthesis is then initiated on these amine groups which are numerous on the surface of metal-like coated particle. Other reactive chemical groups or groups that can be specifically activated can be used instead of the amine group. In another example, amino acids, or small peptides are coated directly on the surface of the metal or metal-like particle, or are chemically linked to polymer or other type of macromolecules that are coated on the surface of the metal-like particle. Synthesis is then initiated on these reactive groups which are attached to the metal-like coated particles. In yet another example, reactive groups on the surface of the particle can be also the metal-like particle so that protein, nucleic acid, chemical, or biochemical synthesis can be performed. The number of reactive groups on the surface of the particle can be also modified as follows. A mixture of polyethylene glycol compounds (MW 20,000) with and without reactive amine groups (or other reactive groups) are mixed in an appropriate ratio to achieve a desired number of reactive groups on the surface per particle. In this manner, the metal-like particle is coated with a specific amount of chemical synthetic sites, or binding sites per metal-like particle. The specific number of sites and the type of reactive groups sites can be varied to suit any particular need as for example, further chemical synthesis or for diagnostic reagent purposes. For example, for diagnostic-type applications, adding a discreet number of specific binding agent molecules per metal-like particle may be important to achieve the desired assay performance. In addition, two or more different types of reactive synthetic or binding sites can be placed on the same metal-like particle in specific amounts utilizing the same approach as described for the polyethylene compound above by mixing in appropriate ratios the desired substances (i.e. different binding agents or chemical groups, etc.). These types of coated particles may be useful for example, to isolate, purify and detect two or more different molecules using the same particle. The high densities (grams/cm$^3$) of many types of metal-like particles also offers many advantages in the purification, isolation, and identification of molecules of interest. MLSP type particles offer the further advantage of more easily manipulating the particles within the medium. The above examples are only a few of the many possible variations of this method. Other variations will be apparent to one skilled in the art.

Practice of Various Aspects of the Invention Outside the Field of Analytical Diagnostics The present invention features methods to detect one or more analytes in a sample by detection of the scattered light properties of a particle. It should be noted that various aspects of the invention as disclosed herein are directly applicable to many other specific applications outside of the diagnostic field. One skilled in the art or the art of other fields such as optical information and storage, image formation and processing, electrical-optical signal transduction and switches, telecommunications, information transducers, and many other related applications has been enabled by this disclosure to practice various aspects of the present invention specifically to solve problems and create new products in fields outside of analytic diagnostic assays.

One aspect of the current invention that is very useful for applications to other fields is the ability to identify specific metal-like particles of certain size, shape, composition, and homogeneity by a unique optical signature which is characteristic of that type of particle. Embodying such specific optical signatures in a very small structure allows for these particle signal agents to be used in numerous fields. For example, they can be used in industrial quality control, markers or labels to identify or trace any product, material, substance, or object that contains the particle. The particles in one form or another can be used as a means for identification and the like similar to the art known method of "barcoding". For example, a coating containing one or more types of particles can be applied to consumer products to identify the authenticity, date, or other relevant information. Similarly, paper currency, stock and bond certificates and the like can have coated on the surface or embedded within the paper material itself certain particle types that can be detected to determine the authenticity of the object.

Other examples include placing small amounts of a specific type of particle inside prescription or over the counter drugs to authenticate or trace of drug. In addition, the particles can be used as environmental, industrial, pharmaceutical, or biological tracers to study the physical properties of a system such as disposition of fluids, materials, and the like. One skilled in the art will recognize that these are just a few of the many possibilities.

Another aspect of the current invention which is directly applicable to other fields is the use of light scattering particles which can be physically manipulated by electric, magnetic, or related fields. We name such particles Manipulatable Light Scattering Particles (MLSP) and these are described in detail later. Such MLSP particles can be oriented into various arrangements in one-, two-, or three-dimensional space by using a magnetic, electric, or related electromagnetic field (EMF). In this way the unique light scattering properties of the particles can be used to form certain patterns, images, or colors. The specific orientations of one or more MLSP particles are used to store or transduce information via the light scattering properties of an individual particle, or the resulting light scattering information, that is, optical signature of two or more particles arranged in a particular orientation. For example, three different types of particles that scatter blue, red, and green light are placed inside a small area or volume such as a "pixel" in a screen that contains a specified number of pixels in a two-dimensional array. The screen forms a color or black and white image, or moving picture that is similar to the appearance of a television image, video image, motion picture image and the like when the screen is illuminated with white light. Each pixel or groups of pixels is spatially addressable by an electric or magnetic field (EMF) such that by applying the appropriate EMF, the individual particles that scatter blue, red, and green light are oriented to produce a specific color with a certain hue and intensity when appropriately illuminated. For example, at one applied EMF, the red and green particles are concentrated to a very tiny spot while the blue scattering particles are freely dispersed within the inner volume of the pixel. This pixel will then appear blue. A different EMF can then be applied to cause the same effect for the red or green light scattering particles. In this way, by specifically orienting the different particles in each pixel, the desired color image is produced. This method and apparatus offers many attractive advantages to the current cathode ray tube based image formation technology and the like.

In another example, MLSP particles are switched from one specific orientation to another by appropriately adjusting the EMF. For example, asymmetrical silver particles which can produce green or red scattered light and/or also have two different levels of intensity of scattered light are used as follows. One or more particles are placed in a specific location in either a liquid type or solid type of material where the particle is able to rotate, that is, re-orient itself an EMF field is applied to the material or device containing the particles. Depending on how many particles are used and the desired function of the device, the different orientations of the particles will signify different types of information. For example, in one orientation, the light scattering properties of the asymmetric MLSP particle(s) indicate the "off" or number 0 in a binary code system, while in a different position or orientation the light scattering properties indicate the "on" or number 1 in a binary numeric system. The orientation of the asymmetric MLSP particles is changed by varying the EMF to achieve the desired orientation of the particles in the material or device. When light interacts with the particles in a specific orientation, the properties of the scattered light signify a specific type of information as described above. In this manner, simple and multi-component optical switches that are useful in telecommunications and related fields can be made. Similarly, a series of these switches can be assembled in a serial or parallel fashion for more complex information storage and handling.

New types of information storage devices can be made by encrypting or storing the information by using different types and/or orientations of light scattering particles and MLSP particles. For example, an optical storage disk can be made that is similar to what is known in the art as a "Compact Disk" or "CD-ROM" Disk or the like. Instead of using bumps which project above the surface to encode the information, light scattering particles are used. The particles can be placed on or in any material from which the light scattering properties of the particles can be detected. In this manner much more specific information and storage of higher densities of information are possible. One skilled in the art will recognize the many different types of devices that can be built using various light scattering particles in a particular application. The above examples are just a few of the many ways such metal-like and MLSP particles are used outside the field of analytic and diagnostic detection. These applications are enabled by the disclosure herein and applicant hereby claims right to the practice of various parts of the invention as described herein to fields outside the field of diagnostic analytic assays.

Description of an Exemplary Spectrophotometer Instrument for Liquid Samples and Theory of Operation The exemplary photometer is a right angle photometer that measures the intensity of light which is scattered or emitted light at right angles to the exciting light beam. A schematic diagram of the instrument is given in FIG. 21. The light source is a microscope illuminator or any other type of light source. The instrument can be used with or without the monochromator. Adapters for connecting different light sources are provided with the photometer. Scattered or emitted light is detected by a photomultiplier (PM) tube. The photometer has a manual light shutter to keep light from reaching the PM tube while changing samples. Optical filters or polarizers are introduced in the incident or emitted light path as required. Cylindrical cuvettes (e.g. test tubes) of different diameters are used as sample cuvettes. However, any type of optically transmissive sample container may also be used with the appropriate holder. Test tubes of a diameter of 6 mm by 50 mm were used and a microscope illuminator with an infrared (heat) filter were used to obtain the data reported herein.

The illuminator can be connected directly to the spectrophotometer or through a monochromator. The monochromator used for the measurements reported herein is a diffraction grating monochromator. The illuminator is powered by a regulated DC power supply at 6 V and 3 Amps. In this paragraph we describe the optics of the instrument that we used without monochromator operation. A ×10 objective focuses the light from the illuminator unto the sample tube. A light collecting lens (23 mm focal length, 19 mm diameter), that is positioned at right angles to the exciting light beam (about 1.5 inches from center of sample cuvette), focuses an image of the sample tube at a distance of about 106 mm from the center of the sample tube. This distance allows a light shutter and filter holder to be placed between the collecting lens and the PM tube. A diaphragm with a 3.25 mm diameter hole (made with a #20 drill bit) is placed at the image plane. The PM tube is placed behind the diaphragm. The diaphragm blocks the light reflected from the walls of the cuvette and allows only light scattered from the center of the sample volume to reach the PM tube. The diaphragm, while reducing the amount of scattered light that reaches the PM tube, maximizes the signal to background ratio. In order to further minimize the detection of light reflected from the sample tube, the tube is positioned at an angle of about 40-50 degrees with respect to the vertical direction so that reflected light does not reach the collecting lens. Because of this angle and refractive index effects, the light emerging from the tube does not travel along the center axis of the collecting lens and the scattered light beam at the image plane is displaced downward from the center axis of the collecting lens. This requires that the 3.25 mm aperture and PM tube be displaced downwards from the collecting lens axis. The instrument is constructed such that the downward displacement can be manually adjusted for the most efficient scattered light detection.

When the monochromator is used, the optics are the same as above except that an additional lens (23 mm focal length, 19 mm diameter) is positioned between the 10× objective and the monochromator exit slit. The lens is 4 inches from the center of the sample cuvette. The exit slit of the monochromator is 5.6 inches from center of sample cuvette. The illuminator is connected to the adapter at the entrance slit of the monochromator.

Adjustment of the Photometer Optics a. Place a 60 nm, 4×10-12 M gold sol in a 6×50 mm culture tube in the sample holder of the spectrometer. Adjust the angle of the tube with respect to the vertical so that it is between 40 and 50 degrees. Position the angled tube so that the focused exciting light beam crosses through the center of the cuvette. Do not allow the exciting light to strike the front surface of the tube (surface towards collecting lens) as this will increase the amount of light reflected towards the detecting system.

b. The distance of the collecting lens from the center of the sample tube is adjusted so as to form a sharp image of the walls of the tube at a distance of 106 mm from the tube center. The image of the scattered light beam and the walls of the sample tube can be seen clearly on a piece of white paper placed at the distance of about 106 mm from the tube center. The tube image has a diameter of about 8 to 10 mm at the image plane. The lens should be positioned so as to obtain a sharp image of the walls of the cuvette. The scattered light beam appears a little fuzzy at the image plane because of its finite width. The best position of the lens is about 1.5 inches from the center of the sample cuvette. The exciting beam can clearly be seen as it crosses a scattering solution.

c. The above adjustments of the collecting lens position are performed with the structure that contains the shutter, filter holder and diaphragm holder removed from the instrument. After the lens is correctly positioned, the latter structure is replaced and the light blocking diaphragm with 3.25 mm opening is inserted. The PM tube is inserted into place.

d. After steps a, b, and c, the position of the aperture with respect to the collecting lens optics is adjusted as follows. Place a piece of white paper in the place where plane of the PM photocathode will be positioned when the PM is inserted. With light scattering gold particles in the sample compartment, adjust the position of the aperture until the maximum amount of light on the PM tube is seen. When the aperture is properly positioned, the light on the paper appears as a 0.32 inch (8 mm) diameter spot.

6. EXAMPLES

Examples 6.1 through 6.10 involve the measurement of light scattered from particles, or emitted from fluorescent molecules, or both. The instrument used to measure the light signal was a photometer built as described previously.

For examples 6.1 through 6.3 the polystyrene particles used for these measurements were NIST traceable certified nanospheres obtained from Duke Scientific Corp., Palo Alto, Calif. The gold particles were obtained from Goldmark Biologicals, Phillipsburg, N.J., a distributor for British Biocell Intl., Cardiff UK.

For examples 6.4 through 6.10 the fluorescein was obtained from Molecular Probes Inc., Eugene Oreg., the gold particles were obtained from Goldmark Biologicals, Phillipsburg, N.J., a distributor for British Biocell Intl., Cardiff UK., and the Polystyrene particles were obtained from Interfacial Dynamics Inc., Portland, Oreg.

The relative light scattering powers of particles of the same shape and size, but of different composition, can be directly compared by comparing the light scattering intensities at right angles to the path of the incident light. If the light scattering intensity measurement for a known concentration of each particle of interest is done at the right angle of observation, the light scattering intensities for identical concentrations of particles of the same size and shape but of different composition, can be directly compared and the relative total light scattering powers of the different particles determined.

Examples 6.1, 6.2, and 6.3

Calculated and Measured Relative Scattering Power of Comparable Polystyrene and Gold Particles The results are presented in Tables 6, 7, and 8. Calculations were performed using known light scattering relationships and our newly defined relationships as previously described. Experimental measurements were done for particles in water by detection of the light scattered by particles free in solution at a given illumination intensity and wavelength using the exemplary Photometer. The following steps were performed.

(a) Illuminate the control and comparable sized particle samples with the same incident light composition and intensity.
(b) Determine the light signal emitted from a control tube containing water but no particles.
(c) Determine the light signal emitted from a tube containing particles at known concentration.
(d) Subtract the control light signal value (b) from the light signal value of (c).
(e) Compare light signals from equal concentration of gold and polystyrene particles.

Example 6.4

Measured Relative Signal Generating Power of Fluorescein and Gold Particles-White Light Illumination.

The results are shown in Table 10. The same method of light detection was practiced to determine the light signal emitted from all samples in a 6 mm by 50 mm glass tube. No optical filters were used in the measurement of the light signal from either the gold particles or the fluorescein.

All measurements were made in water. The solution containing the fluorescein had a pH of 8-9. The light signal value of a tube containing only water was subtracted from the gold particle or fluorescein value in order to obtain the light signal due to just the fluorescein or gold particles.

The following steps were performed for the measurement of the light signal from particles.

A. (a) Illuminate all samples with the same incident light composition and intensity.
  (b) Determine the light signal emitted from a control tube containing water but no particles.
  (c) Determine the light signal emitted from a tube containing particles at known concentration.
  (d) Subtract the control light signal value (b) from the light signal value of (c).

The following steps were performed for the measurement of the light signal from fluorescein.

B. (a) Illuminate the samples with incident light of the same intensity and composition as above in
  (b) Determine the light signal emitted from the control tube.
  (c) Determine the light signal emitted form a known concentration of fluorescein in a tube.
  (d) Subtract the control light signal value (b) form the light signal value of (c).

C. (a) Compare light signals obtained from known concentrations of particles and fluorescein molecules.

Example 6.5

Measured Relative Signal Generating Power of Fluorescein and Gold Particles-Monochromatic Illumination The results are given in Table 11. These results have not been corrected for differences in incident light intensity. Monochromatic incident light at wavelengths where maximum light emission occurs from fluorescein (490 nm) and where maximum light scattering occurs form the gold particles was used. The incident light intensity at 490 nm was slightly lower than the intensities used for the gold particles and ranged from about 86 percent of the intensity at 520 nm to about 80 percent of the intensity used at 565 nm. On the other hand, the quantum efficiency of the photomultiplier tube ranged from 0.34 at the primary emission wavelength of fluorescein (520 nm) while it was about 0.18 at 560 nm.

Except for the incident wavelength, the same method of light detection was used on all samples in a 6 mm by 50 mm glass tube. No optical filters were used in the measurement of the light signal from either the gold particles or the fluorescein.

All measurements were made in water. The solution containing the fluorescein had a pH of 8-9. The light signal value of a tube containing only water was subtracted the gold particle or fluorescein value in order to obtain the light signal due to just the fluorescein or gold particles.

The following steps were performed for the measurement of the light signal from particles.

A. (a) Determine the light signal emitted from a control tube containing water but no particles.
  (b) the light signal emitted from a tube containing particles at known concentration.
  (c) Subtract the control light signal value (a) from the light signal value of (b).

The following steps were performed for the measurement of the light signal from fluorescein.

B. (a) Determine the light signal emitted from the control tube.
  (b) Determine the light signal emitted form a known concentration of fluorescein in a tube.
  (c) Subtract the control light signal value (a) from the light signal value of (b).

C. (a) Compare light signals obtained form known concentrations of particle sand fluorescein molecules.

Example 6.6

Measured Relative Signal Generating Power of Fluorescein, Polystyrene, Polystrene-fluorescent Compound, and Gold Particles The results are given in Table 12. These results have not been corrected for differences in incident light intensity.

All samples were illuminated with monochromatic incident light. The 100 nm diameter gold particle was illuminated with incident monochromatic light of a wavelength near where maximum light scattering form the particle occurs. The polystyrene-fluorescent compound particle sample was illuminated with monochromatic incident light of a wavelength where maximum fluorescence excitation occurred (490 nm). The maximum fluorescence emission for this fluorescent compound occurred at 515 nm. The incident light intensity at 490 nm was about 80 percent of that at 555 nm. The quantum efficiency of the photomultiplier tube at 555 nm was about 60 percent of that at 515 nm.

Except for the incident wavelength, the same method of light detection was used on all samples in 6 mm by 50 mm glass tubes. No optical filters were used in the measurement of the light signal from either the gold particles or the fluorescent particles. All measurements were made in water. The light signal value of a tube containing only water was subtracted form the gold particle or polystyrene particle value in order to obtain the light signal due to just the polystyrene or gold particles.

The following steps were performed for the measurement of the light signal from particles.

A. (a) Determine the light signal emitted from a control tube containing water but no particles.
  (b) Determine the light signal emitted from a tube containing particles at known concentration.
  (c) Subtract the control light signal value (a) from the light signal value of (b).

The following steps were performed for the measurement of the light signal from the fluorescent particles.

B. (a) Determine the light signal emitted form the control tube.
  (b) Determine the light signal emitted from a known concentration of fluorescent particles in a tube.
  (c) Subtract the control light signal value (a) from the light signal value of (b).

C. (a) Compare light signals obtained from known concentrations of particles.

Example 6.7

Detection of 59.6 nm Diameter Gold Particles and Fluorescein at High Serum Concentration The results are given in Table 17. The serum was obtained from Biowhittaker Inc., Walkerville, Md. The serum had been filtered through a one micron filter before sale and was clear and straw colored in appearance. For fluorescein measurements the serum was adjusted to about pH 9 to 9.5. The solution containing the gold particles was illuminated with monochromatic incident light of 543 nm wavelength, a wavelength near that where maximal light scattering from the particle occurs. The solution containing the fluorescein was illuminated at 490 nm where the maximal fluorescence excitation occurs.

Except for the incident wavelength, the same method of light detection was used for all samples in 6 mm by 50 mm glass tubes. No optical filters were used in the measurement of the light signal from either the gold particles or the fluorescein.

Measurements were made in the stated concentration of serum. The light signal value of a tube containing only serum at the proper concentration was subtracted from the gold particle or fluorescein value in order to obtain the light signal due to just the fluorescein or gold particles.

The following steps were performed for the measurement of the light signal from particles.

A. (a) Determine the light signal emitted from a control tube containing serum at the proper concentration but no particles.
 (b) Determine the light signal emitted from a tube containing particles at known concentration.
 (c) Subtract the control light signal value (a) from the light signal value of (b).

The following steps were performed for the measurement of the light signal from the fluorescent solution.

B. (a) Determine the light signal emitted from the control tube.
 (b) Determine the light signal emitted from a known concentration of fluorescein in a tube.
 (c) Subtract the control light signal value (a) from the light signal value of (b).

C. (a) Compare light signals obtained from known concentrations of particles.

Example 6.8

Lower Limit of Detection of Fluorescein Gold and Polystyrene Particles at 92.8% Serum Concentration The results are given in Table 18. For the fluorescein measurement, the light signal emitted from the sample containing fluorescein was passed through a Kodak No. 16 Wratten filter before encountering the photomultiplier tube. The maximum light intensity from the fluorescein solution was observed at an incident monochromatic wavelength of 498 nm, while the maximum light scattering from the gold particles was observed at 554 nm. No optical filters were used in the measurement of the light signal from the gold or polystyrene particles. For fluorescence measurements the pH of the serum was adjusted to about pH 9.

Except for the incident wavelength, the same method of light detection was used for all samples in 6 mm by 50 mm glass tubes. The serum is described in Example 6.7.

Measurements were made in the stated concentration of serum. The light signal value of a tube containing only serum at the proper concentration was subtracted from the gold particle or fluorescein value in order to obtain the light signal due to just the fluorescein or gold particles.

The following steps were performed for the measurement of the light signal from particles.

A. (a) Determine the light signal emitted from a control tube containing serum at the proper concentration but no particles.
 (b) Determine the light signal emitted from a tube containing particles at known concentration.
 (c) Subtract the control light signal value (a) from the light signal value of (b).

The following steps were performed for the measurement of the light signal from the fluorescent solution.

B. (a) Determine the light signal emitted from the control tube.
 (b) Determine the light signal emitted from a known concentration of fluorescein in a tube.
 (c) Subtract the control light signal value (a) from the light signal value of (b).

C. (a) Compare light signals obtained from known concentrations of particles.

Example 6.9

Detection Limits for Polystyrene, Polystyrene-fluorescent compound, and Gold Particles at High Serum Concentration The results are given in Table 19. Measurements were made in the stated concentration of serum. The light signal value of a tube containing only serum at the proper concentration was subtracted from the gold particle or polystyrene particle value in order to obtain the light signal due to just the polystyrene or gold particles. No optical filtration was done.

The following steps were performed for the measurement of the light signal from particles.

A. (a) Determine the light signal emitted from a control tube containing serum at the proper concentration but no particles.
 (b) Determine the light signal emitted from a tube containing particles at known concentration.
 (c) Subtract the control light signal value (a) from the light signal value of (b).
 (d) Compare light signals from known concentrations of particles.

Except for the incident wavelength, the same method of light detection was used for all samples in 6 mm by 50 mm glass tubes. The serum is described in Example 6.7.

Example 6.10

At Low concentrations of Gold Particles Serum has No Effect on Light Scattering Properties of the Gold Particles The results are presented in Table 20. The serum at 95.7 percent concentration is clear and straw colored and has an absorbance of 0.14 at one cm path length and incident light wavelength of 543 nm. The light scattering measurements were made in 6 mm by 50 mm glass tubes with an inner diameter of about 5 mm. On the basis of the difference in the absorption of both incident and scattered light of a wavelength of 543 nm the light scattering signal from gold particles present in the serum sample should be roughly 80 percent of the signal from the same concentration of gold particles present in water. No optical filters are used in this example.

The following steps were performed.
 (a) Illuminate all samples with the same incident light composition and intensity.
 (b) Determine the light signal emitted from a control tube containing water or a proper concentration of serum but no particles.
 (c) Determine the light signal emitted from a tube containing particles at a known concentration.

(d) Subtract the control light signal value (b) from the light signal value of (c).
(e) Compare light signals from equal concentrations of gold serum and water.

Example 6.11

Preparation of a 16 nm Gold Particle Suspension 2.5 ml of sterile water was added to 0.1 g $HAuCl_4 \cdot 3H_2O$ to form a 4% $HAuCl_4 \cdot 3H_2O$ solution. The solution was centrifuged to remove particulate matter. In a separate flask, 10 ml of sterile water was added to 0.1 g. of sodium citrate to form a 1% sodium citrate solution. The citrate solution was filtered through a 0.4 µ polycarbonate membrane filter to remove particulate matter. To a very clean 250 ml Erlenmeyer flask, 100 ml of sterile water and 0.25 ml of the 4% $HAuCl_4 \cdot 3H_2O$ was added. The flask was placed on a stir hot plate at a setting of 4 and covered with a 100 ml beaker. When the mixture started boiling, 2 ml of the 1% sodium citrate was added. The solution turned a black color within a minute after adding the citrate. It then turned purple and finally a deep red. The red color was achieved after about 2 minutes after adding the citrate solution. The mixture solution was boiled for 30 more minutes and then cooled to room temperature and sterile water was added to bring the total volume to 100 ml. The final gold concentration is about 0.005% and particle concentration is $1.2 \times 10^{12}$ particles/ml, assuming that all the gold salt was converted to gold particles.

Example 6.12

Stabilization of Metal Particles with Polyethylene Compound 1 gram of the PEG compound (MW 20,000) was added to 100 ml of sterile water to form a 1% PEG compound solution and the solution was filtered through a 0.4 µ polycarbonate filter using a 50 ml syringe. To stabilize a given volume of particles, add the volume of particle solution to a volume of 1% PEG compound solution that gives a final PEG concentration of 0.1%.

Example 6.13

Preparation of 30 nm Silver Coated Particles from 5 nm Diameter Gold Particles 10 ml of sterile water was brought to a boil in a 30 ml beaker. 2 mg of gelatin was then added slowly and the solution was allowed to continue to boil with stirring until all of the gelatin was dissolved. The solution was then cooled to room temperature. 2 ml of a 47% citrate buffer pH 5 was added. 0.18 ml of a solution containing 5 nm gold particles (at a concentration of about 0.005% gold, $3.8 \times 10^{13}$ gold particles/ml) was added followed by the addition of 3 ml of a 5.7% hydroquinone solution. The mixture was mixed well, followed by addition of sterile water for a final volume of 20 ml. 50 µl of a 4% silver lactate solution was added in 10 µl increments and the mixture was stirred rapidly by hand. The final silver concentration is about 0.005% and the final silver coated particle concentration was about $3.4 \times 10^{11}$ particles/ml. Assuming that all of the added silver had deposited equally on each gold particle, the particle size was calculated to be 30 nm. After the final addition, the sol appeared bright yellow in room lights. In bulk solution, the light scattered by a diluted volume of the sol contained in a 6×50 mm glass tube was blue when illuminated by a narrow beam of white light. When a dilution of the silver sol was examined microscopically with the SpectraMetrix microscope under DLASLPD conditions with a 10× objective and 12.5 eyepiece, a mixture of bright particles with different colors could easily be seen. The particles dominant in number were purple-blue particles. Yellow, green and red particles were also present. By adjusting the concentration of the 5 nm diameter gold particles that we use in the procedure described here, we made silver coated particles with diameters in the range 20 to 100 nm.

Example 6.14

Scattered Light Properties of Nonspherical Silver Particles Formed and Examined on a Microscope Glass Slide A small drop of a diluted, silver particle sol prepared as described in example 6.13 was placed on a microscope glass slide and covered with a cover glass to form a very thin film of sol between the cover glass and microscope slide. When a spot of the thin silver sol film was illuminated by a very narrow beam of light and viewed by the naked eye, at an angle which prevented the incident light from entering the eye, the illuminated spot had a blue scattered light appearance. The silver sol film was then examined microscopically with a light microscope under DLASLPD conditions with 10× objective and 12.5× eyepiece. It was observed that in a few minutes most of the particles became attached to and immobilized on the surface of the glass slide and cover glass. Blue colored particles were the most abundant. We then discovered that when a point on the cover glass was pressed with the point of a fine needle probe, the particles in the pressed area permanently changed color from their original blue (scattered light detection). At the center of the pressed area the particles were red. This center spot was surrounded by concentric circles of different colors. From the center on out, the colors changed from red, to green to yellow to blue. The red, green and yellow particles were very bright. Theoretical calculations which we have done indicate that small silver particles have a blue color. The effect of pressing seems to be to change the shape of the particles. Our results therefore show that small silver particles can be converted from their original blue scattered light color to other colors of scattered light by changing their shapes. By moving the cover glass we found that we could disperse the differently colored particles in the pressed area into the liquid phase. In this phase the particles underwent Brownian motion and the light scattered by green and red particles flickered, which is expected for nonspherical particles.

Example 6.15

Preparation of Larger Diameter Gold Particles from 16 nm Diameter Particles

A 2.4% solution of hydroxylamine hydrochloride was made by adding 24 mg. of hydroxylamine hydrochloride to 1 ml of sterile water, mixing and then filtering through a 4 µ polycarbonate membrane filter attached to a 10 ml syringe. A solution of 4% $HAuCl_4 \cdot 3H_2O$ was made by adding 2.5 ml of sterile water to 0.1 g $HAuCl_4 \cdot 3H_2O$ in a test tube mixing and then centrifuging to remove particulate matter. 25 ml of sterile water was added to a 250 ml Erlenmeyer flask, followed by addition of the volume of 16 nm gold particles shown in Table 1 depending on the desired particle size. Next we added the volume of the 4% $HAuCl_4 \cdot 3H_2O$ solution specified in Table 1. Finally we added sterile water to bring the total volume to 100 ml. Then the volume of the hydroxylamine hydrochloride solution specified in Table 1 was added with rapid hand stirring and the mixture was allowed to sit for 30 minutes. Within seconds after adding the hydroxylamine hydrochloride solution, the solution turned from a clear, slightly pink color to a final clear red or murky brown color, depending on particle size. The smaller sizes give red colored solutions.

TABLE 1

| Desired Au Particle Diameter, nm | 16 nm Gold Sol, ml | $HAuCL_4 \cdot 3H_2O$ solution, ml | Hydroxyl-amine solution ml |
|---|---|---|---|
| 40 | 6.4 | 0.234 | 1.25 |
| 60 | 1.9 | 0.245 | 1.25 |
| 80 | 0.8 | 0.248 | 1.25 |
| 100 | 0.41 | 0.249 | 1.25 |

Larger diameter particles were prepared following the same procedure as described above, but using the specified volumes of solutions as described in Table 2 and using the 100 nm diameter Au particle solution instead of the 16 nm gold solution.

TABLE 2

| Desired Au Particle Diameter, nm | 16 nm Gold Sol, ml | 4% $HAuCL_4 \cdot 3H_2O$ Solution, ml | Hydroxylamine Solution ml |
|---|---|---|---|
| 200 | 12.5 | 0.219 | 1.25 |
| 400 | 1.56 | 0.246 | 1.25 |
| 600 | 0.436 | 0.249 | 1.25 |
| 800 | 0.195 | 0.25 | 1.25 |
| 1000 | 0.1 | 0.25 | 1.25 |
| 2000 | 0.012 | 0.25 | 1.25 |

Example 6.16

Preparation of a Silver Coated Particle from 16 nm Gold Particles 25 ml of sterile water was added to a 250 ml Erlenmeyer flask followed by the addition of 6.4 ml of a 0.005% 16 nm gold particle sol and the resulting solution was mixed. 0.234 ml of a 40 mg/ml L(+) Lactic Acid silver salt solution was then added. A deep purple color was immediately seen. Enough sterile water was then added to bring the total volume to 100 ml. While rapidly stirring by hand, 1.25 ml of a 24 mg/ml solution of Hydroxylamine Hydrochloride was added and the resulting sol appeared lavender silver in color. A small drop of the sol was placed on a glass slide, covered with a cover glass and examined with a light microscope under DLASLPD conditions. Red, green, purple, and yellow particles were seen. The scattered light color of a dilute solution of these particles in a test tube with white light illumination was ice blue.

Example 6.17

Preparing BSA Coated Glass Slides

A model system was setup to study the signal and detection parameters for various combinations of particles and illumination and detection methods for detecting particles on a solid phase as in a solid phase assay.

This system involved first coating glass slides with bovine serum albumin (BSA) and then depositing different amounts of gold particles in specified areas to study the parameters. Here we discuss the method which we use to coat the slides with BSA.

A 10% BSA in water solution was made by adding 1.5 g BSA to 15 ml of sterile ultrapure water mixing and then filtering the solution with a 0.44 mm polycarbonate membrane. A 0.02% BSA (200 µg BSA/ml) solution was made by adding 20 µl of the 10% BSA solution to 10 ml of sterile water and filtering the BSA solution through a 0.4 mm polycarbonate membrane.

Ordinary microscope glass slides were cleaned by scrubbing with a brush dipped in methanol. After brushing, the slide was then cleaned by squirting the slide with sterile water using a plastic squirt bottle. A glass slide was coated with BSA by submerging the slide in a beaker containing 0.02% BSA in sterile water and incubating for 1 hour. The slide was then removed from the beaker and rinsed by squirting sterile water from a squirt bottle. Both sides of the slide were rinsed. The slide was then submerged in 150 ml beaker full of sterile water for about 10 min. It was rinsed again by squirting water. It is most important to remove free BSA from the slide because free BSA hinders the binding of metal particles to the coated slide. The BSA coated glass slide is then dried and stored dry in a clean plastic box.

Example 6.18

Depositing Gold Particles on a BSA Slide

Small circles (about 8 mm diameter) were scribed on the BSA coated glass slides using a diamond scriber to mark the areas where gold particles were to be deposited. 3 µl of an unprotected gold particle solution with the desired gold particle concentration is deposited on one of the marked areas of the slide. The gold particle solution is deposited on the opposite side of the actual scribe marks to prevent interaction of the gold particle solution with the scribe marks.

To prepare a series of patches of gold particles, on a glass slide, in which the gold particle density is systematically decreasing, it is desirable to have the series of patches on a line in the center of the slide. To achieve this alignment we mount the slide on a holder, which we made, which allows us to deposit the gold patches in the correct alignment. It should be noted that the patches cannot be seen in room lights (that is, the particle density is so low that they have no color in room lights). We thus make a mark on the side of the slide to identify the position of the patches. The marks are made as we deposit the particles. To form a patch of particles, we deposit 3 µl of the unprotected gold solution diluted to the desired gold particle concentration. The slide is then incubated for a specified time in a closed plastic box. The interior walls and bottom of the box are covered with a wet paper towel to prevent evaporation of the gold sol on the slide. The slide is then removed and rinsed by squirting sterile water with a pasteur pipette. We have found that for the most efficient binding of gold particles to the BSA on the slide, the pH of the gold particle solution should be adjusted to the pI of BSA (pI=4.58-5.45).

Example 6.19

Microarray Analytical Assay-Binding 60 nm Diameter Gold Particles Coated with BSA-Biotin to Discreet Individual 80 Micron Diameter Streptavidin Patches on a Plastic Substrate The following solutions were prepared. A 1 mg/ml BSA-Biotin solution was made by adding 2 mg of BSA-Biotin to 2 ml of sterile water and dialyzing against distilled water in a 500 ml Erlenmeyer flask for several hours at room temperature. The water was changed 4 times. The last water change was sterile water. A 20 mM Tris-Saline, 0.1% PEG Compound, 0.02% Na Azide pH 7.4 buffer was also prepared. All solutions were filtered through a 0.4 µ polycarbonate membrane filter. Polystyrene test tubes were washed very well with sterile water using a squirt bottle and filled with 4 ml of the 60 nm diameter gold particle solution and centrifuged in the clinical centrifuge for half an hour.

The particles were then washed as described elsewhere. The soft pellets were resuspended in 10 ml of sterile water. The pH of the gold particle solution was adjusted as follows: 100 µl of 1% PEG compound solution was added to a clean polycarbonate test tube. To this 1 ml of the 60 nm gold sol was added and incubated for 2 minutes. 0.02M $K_2CO_3$ was added to the gold sol in increments of 2 µl until pH 6.6 was achieved. The number of µl of 0.02M $K_2CO_3$ needed to adjust the pH is then calculated to add to the remaining ml of the gold sol, in this case it was 80 µl. 9.5 ml of the pH 6.6 gold sol was then added to 1.15 ml of a 1 mg/ml BSA-Biotin solution in a polycarbonate tube, and incubated for 5 minutes at room temperature. The solution was then centrifuged for half an hour in the clinical centrifuge and the supernate was then decanted. The remaining soft pellet was resuspended in 3 ml of sterile water and then centrifuged as previously described, supernate decanted, and then resuspended in 0.1% PEG compound solution and centrifuged again. The supernate was decanted and the pellet was resuspended in 20 mM Tris-Saline, 0.1% PEG compound solution and centrifuged The supernate was then decanted leaving behind about a 200 µl soft pellet. 50 µl of this solution was added to the plastic wells that contained the 80µ diameter streptavidin spots and the wells were incubated overnight in a humid chamber. The wells were then washed several times with sterile water using a pasteur pipette to squirt and remove water from the well. For detection with the microscope the wells were filled with 60 µl of sterile water.

Example 6.20

Detection of Bound 60 nm diameter Gold Particles Coated with BSA-biotin to a Microarray of 80 Micron Diameter Streptavidin Coated Binding Site Spots A suspension of the BSA-biotin-Au binding agent(60 nm diameter gold particle) was added to plastic wells which contain the microarray of streptavidin 80µ diameter spots on the bottom surface of the well. After a suitable incubation time, the wells were washed and viewed with our developed light microscope system under DLASLPD conditions. We observed the BSA-biotin-Au labeled particles bound to the individual 80u individual spots. The 80µ streptavidin spots which were not visible prior to the addition of the particles, appeared as bright fairly circular spots. Individual spots containing different BSA-biotin-Au particle surface densities were obtained by incubating for different times or by using different BSA-biotin-Au concentrations. We were easily able to detect by eye with our microscope at magnification of about 200×, individual particles bound to the streptavidin spots at low binding densities. To automate the counting and integrated light intensity measurements from individual 80 u spots, we tested video image processing software which we had on 24 hour loan from a Company here in San Diego. We captured video images using an inexpensive black and white video camera, a video frame grabber, and a simple desktop computer images which contained the 25 individual spots that were in the array device well. The software was able to measure the integrated light intensity of each spot as well as the number of particles per individual spot. For example, a streptavidin spot that was labeled with a low density of BSA-biotin-Au binding agent was analyzed with the video imaging system using a particle counting mode. To get some idea of the signal to background, an 80u diameter spot of solid-phase area not coated with streptavidin was analyzed to determine the background. In this preliminary model system, the signal/background was 317/25~13 with a labeling density on the spot of about 0.06 particles/$u^2$ under non-optimized illumination and detection conditions. Based on this non-optimized preliminary data, these data imply that at a signal/background of 3/1 particle densities of 0.015 particles/$u^2$ are detectable. Under more optimized conditions, the lower level of sensitivity may be much lower.

Example 6.21

Detection Sensitivity of Gold Particles in Thin Films

A 60 nm amount of gold sol was diluted by factors of 10 and 20 µl of each dilution was deposited as spots on a BSA coated slide. The slide, with no cover glass was then placed on a Porro prism with immersion oil. Each gold sol spot had a diameter of about 4 mm. The following table gives pertinent information on each spot.

| Au Sol M | Particles/ml | SPOT Diameter (mm) | # of Particles | Observation* |
|---|---|---|---|---|
| $3 \times 10^{-11}$ | $2.3 \times 10^{10}$ | 12.4 | $4.6 \times 10^8$ | Very Intense Yellow |
| $3.8 \times 10^{-12}$ | $2.3 \times 10^9$ | 12.8 | $4.6 \times 10^7$ | Intense Yellow Green |
| $3.8 \times 10^{-13}$ M | $2.3 \times 10^8$ | 11.4 | $4.6 \times 10^6$ | Weak but detectable green |

*As detected by eye

The table below expresses the above data in units that are more meaningful in clinical assay applications. The height of the liquid in the spot can be calculated with the expression $h = V/A$ where V is the volume of liquid in the spot (20 ml=0.02 $cm^3$) and A is the area (in $cm^2$) of the spot. Using A=1.2 $cm^2$ we get h=0.016 cm=160 m. This height is much smaller than the depth of field of the eye or our electronic and optical methods of detection and thus each spot behaves (from a geometrical point of view) as if all of the particles were on the surface of the slide and the sensitivity reported in the table are similar to the sensitivities expected for particle deposited on the surface.

| Au M | Spot Area, $cm^2$ | Spot Area, $\mu^2$ | Particles per Spot | #Particles per $\mu^2$ | *Intensity of Spot |
|---|---|---|---|---|---|
| $3.8 \times 10^{-11}$ | 1.2 | $1.2 \times 10^8$ | $4.6 \times 10^8$ | 3.83 | Very Intense, Yellow |
| $3.8 \times 10^{-12}$ | 1.3 | $1.3 \times 10^8$ | $4.6 \times 10^7$ | 0.35 | Intense Yellow Green |

-continued

| Au M | Spot Area, $cm^2$ | Spot Area, $\mu^2$ | Particles per Spot | #Particles per $\mu^2$ | *Intensity of Spot |
|---|---|---|---|---|---|
| $3.8 \times 10^{-13}$ | 1.2 | $1.2 \times 10^8$ | $4.6 \times 10^6$ | 0.038 | Weak but Detectable green |

*As detected by eye
This column was calculated by dividing the number of particles per spot by the area of the spot.

Example 6.22

60 nm Gold Particles Deposited on the Surface of a BSA Coated Glass Slide

A series of 60 nm gold particle solution dilutions were formed and 3 µl of each dilution was deposited as a small spot on a BSA coated slide. The spots were in a row on the same slide. The slide was incubated in a humid chamber for 6.5 hours, then rinsed with sterile water. The particle density on each spot was determined by particle counting under DLASLPD conditions in a light microscope which has an eyepiece with a calibrated reticle. The following table shows our results.

| Area Number | Deposit concentration* particles/ml | Total number of particles deposited | #Particles per 100 $micron^2$ |
|---|---|---|---|
| 1 | $2.3 \times 10^{10}$ | $2.3 \times 10^8$ | 460 |
| 2 | $2.1 \times 10^9$ | $2.1 \times 10^7$ | 41.8 |
| 3 | $7 \times 10^8$ | $7 \times 10^6$ | 13.9 |
| 4 | $3.5 \times 10^8$ | $3.5 \times 10^6$ | 7 |
| 5 | $1.75 \times 10^8$ | $1.75 \times 10^6$ | 3.48 |
| 6 | $8.75 \times 10^7$ | $8.75 \times 10^5$ | 1.74 |

*Deposit concentration is the concentration of unprotected gold sol solution that was placed on top on a spots.
Particles per $micron^2$ - This gives the number of particles per 100 micron square if all of the particles in the solution deposited on a specified are became attached to the slide. The area covered by the solution has a diameter of about 8 mm. The area is A = 3.1416 * (.4)$^2$ $cm^2$ = 0.5 $cm^2$ = 0.5 × $10^8$ $micron^2$.

After 6.5 hours, the slide was washed by gently squirting sterile water on each gold containing area on the slide. The slide was dried with heat gun on cold setting. The dried slide was viewed under DLASLPD conditions with a light microscope and the particle density in each area was determined using the calibrated reticle in the microscope eyepiece to count particles/reticle square. The following table shows the results.

| Sample | Eye* | Particles deposited/ 100 $micron^2$ | Particles counted using reticle (area, $micron^2$)# | Particles counted per 100 $micron^2$ |
|---|---|---|---|---|
| 1 | Very intense yellow green | 460 | 20** (39) | 51.2 |
| 2 | Intense yellow green | 41.8 | 7 (39) | 18 |
| 3 | Fairly Intense yellow green | 13.9 | 13 (100) | 13 |
| 4 | No intensity detected | 7 | 0 | 0 |
| 5 | No intensity detected | 3.48 | 0 | 0 |
| 6 | No intensity detected | 1.74 | 0 | 0 |

*Eye - This is the light intensity excited by the microscope illuminator under DLASLDP conditions and viewed by eye from the gold on the specified area of the slide.
**The particles in this area were too numerous to count and the count listed here may be in error by as much as 2x.
The area listed in parenthesis is the area of 1 reticule square for the objective and optovar setting used to count particles.

| Sample | Particles counted per $micron^2$ | Eye* |
|---|---|---|
| 1 | 0.512 | Very intense yellow green |
| 2 | 0.18 | Intense yellow green |
| 3 | 0.13 | Fairly intense yellow green |
| 4 | 0 | No intensity detected |
| 5 | 0 | No intensity detected |
| 6 | 0 | No intensity detected |

Example 6.23

Sensitivity for Visual Detection of Intensity from a Small Liquid Spot of 60 nm Gold Particle Two dilutions of $3.4 \times 10^{-12}$ M (0.005% gold) 60 nm gold sols were prepared and 2 mL of each dilution was deposited in a separate spot on a glass slide. Each spot had a diameter of about 4 mm (Area=$6.28 \times 10^6$ $m^2$). The different spots were in a row in the middle of the same slide. Particle concentrations and densities in each spot are shown in the following table.

| Gold Sol M | Particles/ml | Particles/µl | Particles/$\mu^2$ |
|---|---|---|---|
| $3.4 \times 10^{-12}$ M | $2.1 \times 10^9$ | $2.1 \times 10^6$ | 0.31 |
| $1.05 \times 10^{-12}$ M | $1.05 \times 10^9$ | $1.05 \times 10^6$ | 0.155 |
| $0.5 \times 10^{-12}$ M | $0.5 \times 10^9$ | $0.5 \times 10^6$ | 0.077 |
| $0.25 \times 10^{-12}$ M | $0.25 \times 10^9$ | $0.25 \times 10^6$ | 0.0385 |

To determine the lowest particle density from scattered light intensity as detected by the unaided eye, we placed the slide on a Porro prism by means of immersion oil. Each spot, still in liquid form, was sequentially illuminated by light from the Baush-Lomb Illuminator with a ×10 objective at the end of the fiber. The spot produced by the illuminator was about 4 mm in diameter. In the dark room, at night, we could see down to 0.0385 although the latter could just barely be seen.

Example 6.24

Sensitivity for Photodiode Detection of 60 nm Gold Particles (in Suspension) at Different Concentrations in Immulon Plastic Microtiter Wells Different dilutions of 60 nm gold sol were placed in different Immulon Wells (200 µl in each well). To measure scattered light intensity, the bottom of a well was illuminated with white light from a Leica Microscope Illuminator that was equipped with ×10 objective. The bottom of the well was a few mm from the objective. The light from the objective produced a beam that was focused on the center of the well. The beam diameter at the focal point was about 5 mm. Scattered light was detected by a photodiode that was positioned to detect light through the side wall of the well (right angle detection). The scattered light was detected through a small hole (diameter about 1 mm) that was positioned in front of the photodiode to limit background light detection. The wells containing the different gold sol dilutions were attached to each other and each well can be sequential positioned in the illumination and detection paths. The output of the photodiode is measured with an operational amplifier that is operated in the current mode. The feedback resistor of the op amp determines the sensitivity of the amplifier. The photodiode is operated in the photovoltaic mode. Two sets of 60 nm gold dilutions were prepared and the intensities measured with the photodiode.

a. First Set of Dilutions

The master solution ($3.8\times10^{-11}$ M) was diluted by factors of two. The following readings were obtained. Readings were made with a 5 megohm resistor in the feedback loop of the op amp.

| Gold Particle Concentration | Intensity (Volts) |
| --- | --- |
| $1.9 \times 10^{-11}$ M | 3.27 |
| $0.95 \times 10^{-11}$ M | 1.6 |
| $4.75 \times 10^{-12}$ M | 0.89 |
| $2.38 \times 10^{-12}$ M | 0.44 |
| $1.2 \times 10^{-12}$ M | 0.24 |
| 0 | 0.075 | b. Second Dilution

A ×11 dilution solution ($3.4\times10^{-12}$ M) was diluted by factors of ×2. Results are as follows.

| Gold Particle Concentration | Intensity (Volts) |
| --- | --- |
| $3.4 \times 10^{-12}$ M | 0.614 |
| $1.7 \times 10^{-12}$ M | 0.378 |
| $8.5 \times 10^{-13}$ M | 0.198 |
| $4.25 \times 10^{-13}$ M | 0.147 |
| $2.13 \times 10^{-13}$ M | 0.100 |
| $1.06 \times 10^{-13}$ M | 0.086 |
| 0 | 0.075 |

The above results show that, in wells, we can detect 60 nm diameter gold particles in the range $1.9\times10^{-11}$ M to $1\times10^{-13}$M. The upper range can be extended.

Example 6.25

Reproducibility for Depositing and Visually Detecting (Integrated Scattered Light Intensity) 60 nm Gold Particles Deposited on a BSA Coated Glass Slide 3 µl of a 2× dilution of 0.005% gold (60 nm) solution was deposited in each of 5 spots on a BSA coated slide. The slide was incubated for five minutes and then introduced into a beaker containing 150 ml of distilled water. The water washed the unbound gold off the slide. The spots were then illuminated with our illuminator (white light SpectraMetrix Illuminator). The gold particles in each spot were in the form of a ring (that is the particles were not homogeneously distributed in the spot but were confined to a ring) which scattered green light and could be clearly seen in the dark room with the unaided eye.

The experiment was repeated with a newly coated BSA slide except that during the incubation of the gold dots, the slide was gently tapped on the side with the finger so as to stir the liquid in the gold particle spots. After 5 minutes, the slide was introduced into 150 ml of sterile water in a beaker and the light scattered by each spot was viewed alternatively using the white light SpectraMetrix Illuminator. The illuminator produced a spot of light of about 5 mm diameter on the slide. Gold spots could clearly be seen through scattered light where the gold sol was deposited. The spots were viewed with the slide submerged in water which reduced scattering by imperfection on the slide. All of the spots scattered green light and had about the same intensity as evaluated by visual detection. A small, non-light scattering spot (dark spot) appeared in the center of each spot.

Example 6.26

Color of Light Scattered by 60 nm Gold Sols at Different Gold Particle Concentrations Six 8×50 mm (1.6 mL) polystyrene tubes were washed by rinsing with sterile from a squirt bottle. Excess water was removed from each tube by shaking but the tubes were not dried. A gold particle solution (60 nm, 0.005%) was then serially diluted by factors of 1,2,4,8,16 and 32. Each tube had 500 mL of gold particle solution. The diluted gold sol was stable (scattered light did not change color on standing) in the polystyrene tubes. No evidence of aggregation. The light scattered by the different dilutions had the following colors. The gold sol used in these observations had been washed several times with sterile water to remove salts (that are used to form the gold sol) which seem to destabilize the gold particles.

| Dilution | Color |
| --- | --- |
| 1 | yellow green |
| 2 | yellow green |
| 4 | light green |
| 8 | light green |
| 16 | light green |
| 32 | light green |

Example 6.27

Stabilization of Gold Particles with BSA

We found that 900 mg of BSA were required per ml of 60 nm, 0.005% gold sol to stabilize the gold sol against agglutination by 1% NaCl.

Example 6.28

Deposition of 60 nm Gold Particles at High Particle Densities on BSA Coated Glass Slides This example shows how to deposit spots of different surface densities (25 to 100 particles/$\mu^2$) of gold particles on a glass slide. These spots are used in examples 30 and 31 to determine the intensity, color and homogeneity of light scattered from these spots (white light illumination) as seen by the naked eye and in a light microscope using DLASLPD methods.

4 ml of 60 nm gold sol (0.005%, $3 \times 10^{10}$ particles per ml) were centrifuged in the clinical centrifuge at maximum speed until all of the gold particles sedimented to the bottom of the tube (about 30 min). The supernatant was removed and the soft pellet was diluted by factors of 1, 2 and 4. We estimate that the soft pellet had a particle concentration of about $3 \times 10^{11}$ particles per ml. 4 ml of each dilution was deposited on separate spots on a BSA coated glass slide and the liquid in each spot was allowed to evaporate at room Temperature. The number of particles deposited in each spot (assuming that the ×1 gold sol had a concentration of $3 \times 10^{11}$ particles per ml) is shown in the following table. It should be noted that the maximum particle density which can be achieved with 60 nm particles (saturated monolayer of particles) is 354 particles/$\mu^2$.

| Dilution | Particles Deposited[#] | Particles/$\mu^2$* |
|---|---|---|
| 1 | $1.2 \times 10^9$ | 100 |
| 2 | $6 \times 10^8$ | 50 |
| 4 | $3 \times 10^8$ | 25 |

*Particle Density in particles/$\mu^2$ is calculated for a spot with a diameter of 4 mm ($4 \times 10^3 \mu$) and area of $12.6 \times 10^6 \mu^2$.
[#]Calculated for a deposit of 4 µl of a $3 \times 10^{11}$ particles per ml 60 nm gold sol.

After solvent evaporation, each spot was examined for its appearance in room lights and under DLASLPD illumination (as viewed with unaided eye). DLASLPD illumination was with a Leica microscope illuminator that had a ×10 objective focusing lens and produced a narrow beam of light that focused to a small spot at a distance of about 10 mm from the objective. The spots were also examined by light microscopy using DLASLPD methods with ×2.5, ×10, ×25 and ×40 objectives and plus additional magnification of ×1.25, ×1.6, and ×2. Only a small area of each spot could be seen at a time with the ×10 and ×20 objectives. However, the whole spot could be seen with the ×2.5 objective. To determine the particle surface density on each spot, we counted the particles seen through the microscope on a given area and divided by this number by the area. The area was determined with a reticle positioned in the ocular of the microscope which had been calibrated with slide micrometer. As an example, when particle counting was done with the ×40 objective and additional magnification of 1.25 and 2 (before the ocular), the unit square in the ocular reticle used for particle counting were respectively 6.25 µ×6.25 µ (area of square=39.1 $\mu^2$) and 10 µ×10 µ (area=100 $\mu^2$). These are the areas in the object plane.

Example 6.29

Observations of High Surface Density Gold Particle Spots in Air

In this example, the gold particle spots prepared as described in example 6.29 are examined visually and microscopically using DLASLPD illumination. The spots were dry and the gold particles were thus in air.

a. ×1 Dilution Spot

In room lights the spot has a dark purple appearance with a lighter spot of less than 1 mm diameter in the center. Under DLASLPD illumination the spot had a rather uniform whitish orange appearance. The spot was highly intense. Under DLASLPD conditions in the microscope (×10 objective, extra magnification ×2, 12.5 ocular) the spot as viewed through the ocular had a highly intense orange color. Individual particles could easily be seen. Some particles could be seen very close to each other or even overlapping. The majority or particles are orange but some are green. Two or more particles which are separated from each other by less than about the spatial resolution of the microscope appear as single particles. If the space between the particles are close enough to perturb their light scattering properties, the particle group appears as a single particle of a color that is different than that of the single particle. At high particle density, it is expected from theoretical calculations that many particles will be separated by distances which are smaller than the resolution of the microscope. The appearance of the spot did not change much when viewed with a ×10 or ×20 objective. The area on the slide which is outside of the spot (background) was very dark compared to the intense spot. With the ×2.5 objective, the whole spot could be seen. It had an intense orange appearance with a small green ring at the periphery. The color seemed to be fairly uniform in the orange area although same patches seemed to be lighter than others. The particle surface density in the green ring was much lower than in the orange area.

b. ×2 Dilution Spot

In room lights, the spot has a medium purple outer ring with a dark purple spot of about 2 mm in the center. Under DLASLPD illumination the spot had a rather uniform whitish yellow appearance. The spot was highly intense. Under DLASLPD conditions in the light microscope (×10 and ×20 objectives, ×2 extra magnification, 12.5 ocular) the spot as seen through the ocular had a highly intense orange color but the color was not as uniform as ×1 dilution. There are patches which have a greenish appearance. Very closely spaced particles could be seen. The majority of the particles are orange but there are some green which are in high abundance in the green patches. The appearance of the spot did not very much when viewed with a ×10 or ×20 objective. The area outside of the spot was very dark compared to the intense spot. With the 2.5 objective the whole spot could be seen. It had an intense orange appearance with a small green ring at the periphery. The color seemed to be fairly uniform in the orange area although same patches seemed to be lighter than others. Some of this non-uniformity is due to inhomogeneities in the illuminating system which had not been optimized.

c. ×4 Dilution Spot

In room lights, the spot had a very light purple color with a small dark spot (about 1 mm diameter) displaced to one side of the circle. Under DLASLPD illumination the spot had a rather uniform whitish green appearance. The spot was highly intense. Under DLASLPD conditions in the light microscope (×10 objective, ×2 extra magnification, 12.5 ocular) the spot appeared to be highly non-uniform probably to uneven evaporation of solvent. The center of the spot had a highly intense orange or lavender color. Particles are very close to each other or even overlapping in this central area, with most particles having an orange color and some a green color. Away from the center, the spot had a greenish appearance with a predominance of green particles with some orange particles. There are alternating rings of green and yellow color as one goes from the center of the spot to the periphery. The area outside of the spot (background) was very dark compared to the intense spot. The whole spot can be seen with ×2.5 objective. The spot had an oval appearance with a orange or lavender spot (about 1.5 mm diameter) towards the center. This was surrounded by intense circles of alternating yellow green and green area. A small ring at the periphery had a less intense (but still intense) color which was distinctly green. In this peripheral area, almost all of the particles are green particles and could be counted with ×40 objective, extra magnification ×2. The particle surface density in the green particle area was about 20 particles/39.1 $\mu^2$ or 0.5 particles per/$\mu^2$. At the very periphery the particle count dropped rapidly and we counted about 7 particles per 100 $\mu^2$ or 0.07 particles/$\mu^2$. The gradient of particles on this spot allows us to count the particles up to the counting limit of about 1 particle/$\mu^2$.

Conclusions for Immobilized Particles in Air a. The procedure described above allows us to deposit gold particles at high surface densities on small (4 mm) spots. The deposits are not completely uniform when viewed in room lights as expected for the evaporation process which we use to form the spots.

b. Under DLASLPD conditions in the light microscope, the ×1 and ×2 dilution spots are fairly uniform. For the ×4 dilution, the spot displayed more non-uniformity.

c. The particle density of the spots seems too high for particle counting to be meaningful (particles to close to be resolved as individual particles). However, at the periphery of the ×4 dilution spot the particles could be counted and the density here was around 0.5 particles/$\mu^2$. This particle density is close to the maximum particle density which can be counted with the resolution of our microscope.

Example 6.30

Observations with High Surface Density Gold Particle Spots in Water

The slide used in example 6.30 was submerged in 150 ml of sterile water in a beaker. The particles did not seem to come off the slide. Using the microscope illuminator with 10× objective, the gold spots in the submerged slide could each be separately illuminated with a narrow beam of light. The color of the spots (observation with unaided eye) did not seem to change in going from air to water. The glass slide was removed from the beaker of water and covered with a cover glass. A thin film of water surrounded the gold particles. Microscope observations were as follows.

a. ×1 Dilution Spot

When viewed under DLASLPD conditions with a light microscope with ×2.5 objective, ×1.25 extra magnification and ×12.5 ocular, the spot had a fairly uniform orange lavender appearance. The periphery of the spot contained bright, yellow green particles. The particles at the periphery can be easily seen with 10×to 40×objectives. The particle surface density was very high throughout the spot even at the periphery except at a very thin ring at the very periphery where the individual particles can easily be seen as bright objects.

b. ×2 Dilution Spot

The whole spot could be seen through the 12.5 ×ocular using the ×2.5 objective and ×1.25 extra magnification. The spot had a very intense yellow color overall and seemed fairly uniform. Most of the spot was yellow but towards the periphery the spot had a yellow green color. With a ×40 objective and ×1.25 extra magnification, the particles at a very high surface density could be seen Most of the particles have a yellow green color. A few have a green or red color. The spot had a very fairly uniform intensity except at the periphery where the particle density drops off very rapidly to zero (dark background). The individual particles with dark spaces between then can easily be seen and counted at the periphery where the particle surface density is low.

c. ×4 Dilution Spot

The whole spot could be seen with the 2.5 ×objective plus 1.25×extra magnification. The spot had a very intense yellow green color and the color was very uniform in contrast to the observations in air where the spot had many green patches. Individual particles could easily be seen with ×40 objective and ×1.25 extra magnification. The particles in water are much more intense or brilliant than in air. The particles at the periphery were not predominantly green but in water most of the particles were yellow green with some red and orange particles. Most of the spot had a very intense yellow color. Individual particles can be seen with ×40 objective but the particles are very dense and overlap. In the most intense area of the spot, the particles seen with ×40 objective and ×2 extra magnification, were at a density of about 25 particles/39.1 $\mu^2$ or about 0.6 particle/$\mu^2$. This number may not represent the true particle surface density because of limitations microscope resolution.

Conclusions for Immobilized Particles Covered by Water

Placing the gold spots in water seems to give them a more uniform appearance. Spots ×2 and ×4 dilutions seem to both have a yellow color when viewed by the unaided eye with the illumination of the light microscope under DLASLPD conditions (slide sitting on prism and coupled to the prism with immersion oil). The ×1 dilution spot appears to be orange to the eye.

Example 6.31

Binding of 60 nm Gold-BSA-biotin Reagent to Magnetic Beads

This example demonstrates our ability to detect and quantify the specific binding of gold particles to magnetic beads by light scattering intensity measurements in suspension and to detect individual gold particles bound to magnetic beads by light microscopy under DLASLPD conditions.

60 nm gold particles were coated with BSA that had been covalently labeled with biotin (BSA-biotin-Au). 500 µl of a phosphate buffered saline solution, pH 7.4, containing 0.1% BSA solution was added to each of 5 microcentrifuge tubes. The tubes were labeled 0, 1, 2, 3, 4. A solution of BSA-biotin-Au at a gold particle concentration of $3.8 \times 10^{-11}$ M was added to each tube and the tubes were shaken. Additional amounts of the BSA-biotin-Au solution were added to bring the concentration of gold BSA-biotin particles $=8 \times 10^{-13}$ M in each tube. The following amounts in µl of Dyna beads M280 Streptavidin (2.8 µ diameter beads with streptavidin covalently attached to the surface of the bead) suspension containing $6.7 \times 10^8$ Dyna beads/ml (10mg/ml) or about $1 \times 10^{-12}$ M bead molar concentration, dissolved in phosphate buffered saline (PBS), pH 7.4, containing 0.1% BSA and 0.02% $NaN_3$ was added to each tube:

| Tube # | μl | Conc. of mag. beads | Conc. of biotin | Gold BSA-Biotin Conc. |
|---|---|---|---|---|
| 0 | 0 | 0 | 0 | 0 |
| 1 | 5 | $1 \times 10^{-14}$ M | $3 \times 10^{-8}$ M | $8 \times 10^{-13}$ M |
| 2 | 10 | $2 \times 10^{-14}$ M | $6 \times 10^{-8}$ M | $8 \times 10^{-13}$ M |
| 3 | 15 | $3 \times 10^{-14}$ M | $9 \times 10^{-8}$ M | $8 \times 10^{-13}$ M |
| 4 | 20 | $4 \times 10^{-14}$ M | $12 \times 10^{-8}$ M | $8 \times 10^{-13}$ M |

The tubes were incubated for 30 minutes at room temperature and then were placed, one at a time starting with tube zero, in a MPC-E/E-1 magnetic particle concentrator to separate magnetic beads from solution. After 2 minutes the supernatant solution was carefully removed with the tube still in the magnetic separator. The supernatant was placed in a 1 ml microculture tube. Tube 5 was left for 5 minutes in the magnetic concentrator while the other tubes were left for 2 minutes. The scattered light intensity of the supernates were then measured in the SpectraMetrix photometer with the following settings: Resister PM out=0.1 Meg ohm, Filter on excitation side=orange filter CS 3-67, ×10 neutral density attenuator=out.

The following scattered light intensities were measured:

| Tube # | Intensity |
|---|---|
| 0 | 1.21 Volts |
| 1 | 1.04 |
| 2 | 0.644 |
| 3 | 0.49 |
| 4 | 0.362 |

The supernatants were returned to their respective tubes containing the magnetic beads and allowed to incubate for an additional 2 hours. After 2 hours the tubes were then processed as previously described and the following scattered light intensities for the supernates were obtained:

| Tube # | Intensity (Volts) | Normalized Intensity | Frac. of Gold Particle Bound |
|---|---|---|---|
| 0 | 0.855 | 1.21 | 0 |
| 1 | 0.604 | 0.85 | 0.3 |
| 2 | 0.382 | 0.54 | 0.55 |
| 3 | 0.326 | 0.46 | 0.61 |
| 4 | 0.206 | 0.29 | 0.76 |

The 2 hour extra incubation did not result in greater binding of gold BSA-Biotin to magnetic beads.

A drop of the magnetic beads with attached gold particles was deposited on a microscope glass slide and covered with a cover glass. The slide was then examined under DLASLPD conditions with a light microscope. The magnetic beads could easily be seen as strongly scattering objects but the gold particles on the beads were more difficult to see because of the strong scattering by the large magnetic beads. However, if the water medium was replaced by a bathing medium with a refractive index around 1.4 to 1.5, the particles could be seen more clearly. Also if the illuminating light beam was inclined at a higher angle with respect to a line perpendicular to the slide, the gold particles could be seen more clearly.

Example 6.32

Detection of Nucleic Acid Hybridization With Nucleic Acid-Labeled 40 nm Diameter Gold (Au) Particles 1. Preparation of Chemically Activated Polyethylene Glycol-Amine Coated Au Particles Reactive amine groups for conjugation of nucleic acids to the Au particles was accomplished as follows. 40 nm Au particles were coated with bis(Polyoxyethylene bis[3-Amino-2-hydroxypropyl]) Polyethylene compound using the procedure described in Example 6.12. This results in 40 nm diameter Au particles with a thin coat of polyethylene compound that has several chemically reactive amine groups for conjugation of the nucleic acids to the particles.

2. Preparation of Nucleic Acids for Conjugation to the 40 nm Diameter Au Particles Homopolymers of polycytidylic acid(Poly (C)) and polyinosinic acid (Poly(I)) were chemically modified as follows. 0.8 mg and 1.3 mg of Poly(I) and Poly(C) were placed in separate tubes. To each of the tubes was added 1.0 ml of a 0.1M solution of 1-ethyl-3,3-dimethylaminopropylcarbodiimide (CDI) in imidizole buffer pH 8.5 and incubated for one hour. The nucleic acids were then precipitated by ethanol precipitation and resuspended in hybridization buffer (20 mM Tris-HCl, 100 mM NaCl, 1 mM EDTA pH 7.6).

3. Conjugation of Activated Nucleic Acids to Activated Au Particles

The same protocol was used for both the Poly(I) and Poly(C) preparations. To 50 ul of nucleic acid solution was added 20 ul of 40 nm-Au-PEG activated particle solution, and 100 ul of Hepes 0.2 M pH 8.0 and incubated for 1 hour at 50° C. Following the reaction, the Poly(C) and Poly(I) 40 nm Au-nucleic acid conjugates were collected by centrifugation, washed, and resuspended in hybridization buffer.

4. Hybridization Experiments

The hybridization properties of the nucleic acid-40 nm Au particle conjugates (40 nm diameter gold particles with nucleic acids covalently attached to the polymer coated surface of the particle) were studied as follows. A light microscope using DLASLPD methods was used. The glass slide-liquid-cover slip experimental setup as shown in FIG. 9 was used. A drop of the Poly(C)-Au particle conjugate preparation was placed on the slide and covered with a cover slip. A drop of immersion oil was placed on the microscope condenser and the slide then placed on top of the condenser. The 10× objective was used. The solution appeared fairly homogeneous, and the Poly(C)-Au particle conjugates could be seen floating across the field. Their brownian motion appeared to be less than what we have previously observed for 40 nm Au particles not labeled with nucleic acids. A few Poly(C)-Au particles appeared to be stuck to the surface of the glass slide. There were a few aggregates of Poly(C)-Au particles, mostly of two to four Poly(C)-Au particles. These aggregate structures moved as one unit as they floated across the field of view. We noticed that the particle density of Poly(C)-Au particles attached to the surface of the slide was increasing as we observed this slide for several minutes. The color of the scattered light coming from the Poly(C)-Au particles was green. The cover slide was removed, and a drop of the Poly(I)-Au preparation was then placed next to the wet area of the slide containing the Poly(C)-Au drop. Contact between the two spots was achieved by using a metal probe to drag a line of liquid from the Poly(I)-Au drop to the wet part of the slide containing the poly(C)-Au. A cover slide was then placed on top, and the slide was then placed back on the microscope and viewed. We observed the formation of increasing numbers of multiple Poly(I)-Au-Poly(C)-Au particle aggregates over time. After about 20 minutes, we scanned the slide and observed that there were very few single particles, and most of the particles were in aggregates of several particles, many of them stuck to the glass slide. The aggregates appeared to have defined shapes, that is, there seemed to be a particular way these particle aggregates were assembled, some appearing as a spool of randomly wound up string, and others appeared as branched chain networks. The appearance of these multiple aggregates was very different as compared to the few aggregates we observed on the control Poly(C)-Au slide. We switched to the 40× objective and in some of the aggregates, some of the particles appeared more yellow in color than green. We then removed the cover slip of the slide containing the Poly(Au)-Poly(I)-Au reaction and added a drop of $10^{-5}$ M ethidium bromide onto the slide and covered with a cover slip. We observed a faint orange color coming from the aggregates of particles on the slides, that is, it appeared like the green and yellow-green color of the particles was placed on a background of a faint orange color. No orange color was observed in the areas away from the aggregates. This faint orange color indicated to us that there was double-stranded structures of nucleic acids near and within the particle aggregates. We interpret this as the hybridization of the Poly(C)-Au conjugates to Poly(I)-Au conjugates. This slide was removed and a control slide containing a drop of the Poly(I)-Au was observed under the microscope. We made similar observations as compared to the control Poly(C)-Au slide but that this Poly(I)-Au preparation seemed to have about twice as many small aggregates as compared to the Poly(C)-Au control slide. The color of scattered light appeared green with some aggregates appearing yellow-green.

In this particular format, both of the complementary strands were labeled with gold particles. As the complementary strands hybridize, more particle aggregates appeared. The binding of nucleic acids can be detected by detecting the scattered light from gold or similar particles. It also appears that when two or more Au particles are in close proximity to each other, the color of the scattered light can change. This change in color of the scattered light can be used also as a way to detect a binding event. It should be noted that the Au particles, or any other particle which scatters light sufficiently can be used in numerous formats to detect the binding of nucleic acids or any other ligand-receptor pair in a separation or non-separation assay format.

Example 6.33

Detection of Bound Gold Particles to Large Polystyrene Beads

We placed a drop of a solution of spherical polystyrene particles of about 2 microns in diameter coated with biotin on a glass microscope slide and viewed in the light microscope under DLASLPD conditions. The polystyrene particles were easily seen as bright white light point sources. We then place a drop of a preparation of 60 nm gold particles coated with streptavidin onto the drop of polystyrene particles and viewed this preparation in the microscope. The bright white polystyrene particles could be seen and a faint halo of yellow-green color was observed surrounding the polystyrene particle. We evaporated the solution from the slide and then placed a drop of microscope immersion oil on the preparation and then viewed under the microscope. Individual gold particles and large circular ring areas of yellow-green gold particles were easily visible. The polystyrene particles appeared as almost a dark or black spot surrounded by a halo or ring of yellow-green color. This method can be used to detect bound gold particles or other metal-like particles to the surface of solid particulate matter and small solid-phases such as glass or other beads, and biological cells and the like.

Example 6.34

Light Scattering Properties of Gold Particles Coated with Polyethylene Compound

Gold particles approximately 100 nm in diameter made by the citrate procedure were used. A portion of this solution was placed in a separate container and the particles were coated with polyethylene glycol compound(MW=20,000) using the procedure described elsewhere.

For scattered light comparisons of coated and uncoated particles, the samples were diluted in water until each solution had a faint tinge of pinkish-red color. The scattered light intensity versus incident wavelength profiles for the samples were collected using the SpectraMetrix Photometer.

For these measurements, a monochromator was placed between the light source and sample Scattered light data was collected at 10 nm increments from 400 nm to 700 nm by adjusting the monochromator setting. The data were corrected for wavelength dependent monochromator and photodetector variation as a function of wavelength using a calibration graph that was made by using 12 nm silica particles. The data was analyzed using the calibration graph. The data are shown in FIG. 16.

The data show that the coated and uncoated 100 nm gold particles have very similar scattered light intensity vs. Incident wavelength profiles. Therefore, many different types of macromolecular substances such antibodies, nucleic acids, receptors, or similar can be coated on the surface of the particles without significantly altering the scattered light properties.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The particle compositions and sizes described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, use of various compositions and sizes of particles, and detection orientations and apparatus are all within the scope of the present invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In cases where a range of integer values is stated in connection with any feature, each and every integer member of that range, including endpoints, is specifically and individually included, as are subranges defined by taking any two different integer values within the range, including endpoints, unless clearly stated to the contrary. Thus, for example, the range 1-4 is equivalent to individually specifying 1, 2, 3, and 4, and includes sub-ranges, for example, 1-3 and 2-4.

In addition, where features or aspects of the invention are described in terms of Markush groups or other grouping of alternatives, those skilled in the art will recognize that the invention is also thereby described in terms of any individual member or subgroup of members of the Markush group or other group. For example, if there are alternatives A, B, and C, all of the following possibilities are included: A separately, B separately, C separately, A and B, A and C, B and C, and A and B and C.

Thus, additional embodiments are within the scope of the invention and within the following claims

What we claim is:

1. A method for providing an extended dynamic range in an analyte assay that uses scattered light from light scattering particles at one or more assay sites as signals, said method comprising:
    (a) detecting a first set of integrated scattered light intensity signals from light scattering particles at one or more assay sites with a sensor having a dynamic range, wherein the integrated scattered light intensity signal collected from at least one assay site exceeds the dynamic range of the senor;
    (b) applying at least one optical filter having an optical density to provide a reduced-intensity integrated scattered light signal that does not exceed the dynamic range of the sensor, said reduced intensity scattered light signal is from the at least one of said one or more assay sites in (a) that produced an integrated light scattering signal that exceeded the dynamic range of the sensor;
    (c) detecting a second set of integrated scattered light intensity signals from the light scattering particles at said one or more assay sites in (a) with the sensor, said second set comprising the reduced-intensity integrated scattered light signals of step (b);
    (d) converting the reduced-intensity integrated scattered light signals in (c) to a scaled signal using a predetermined conversion factor related to the optical density of the optical filter; and
    (e) combining the scaled signal with the first set of integrated scattered light intensity signals to provide an extended dynamic range.

2. The method of claim 1, wherein the conversion factor is determined from a transmission curve for the filter based on the measurements of transmission of light from a white light source through the filter.

3. The method of claim 2, wherein the transmission curve for the filter is wavelength-dependent.

4. The method of claim 1, wherein converting the one or more reduced-intensity signals in (c) to one or more scaled signals comprises the step of multiplying the one or more reduced intensity signals by the conversion factor of the at least one filter.

5. The method of claim 1, wherein the at least one filter is selected from the group consisting of longpass filters, shortpass filters, bandpass interference filters, filter wheels, neutral density filters, color filters, notch filters, super notch filters, supernotch plus filters, and filter monochromers.

6. The method of claim 1, wherein an amount of light transmitted by the at least one filter is selected from the group consisting of 1%, 3.2%, 6.3%, 10%, 13%, 16%, 20%, 25%, 32%, 40%, 50%, 63%, 70%, and 80% of the light entering the filter.

7. The method of claim 1, wherein the integrated scattered light intensity signals from the light scattering particles comprise light scattered by the light scattering particles, light emitted by fluorescent entities on the light scattering particles, or both.

8. The method of claim 1, wherein the extended dynamic range comprises integrated scattered light intensity signals quantified over at least four, five, six, or seven orders of magnitude.

9. The method of claim 1, wherein the dynamic range is extended by at least one order of magnitude over the dynamic range of an assay without the extension of dynamic range and the extended dynamic range is linear.

10. The method of claim 1, further comprising the step of:
(f) forming an image of one or more of the one or more assay sites with the combined scaled signal and first set of integrated scattered light intensity signals from step (e).

11. The method of claim 10, wherein forming the image comprises the steps of identifying background portions of the image, and removing signals corresponding to the background portions of the image.

12. The method of claim 1, wherein the sensor is selected from the group consisting of a camera, a photographic film, a video camera, a charged-coupled device, a charged injection device, a photodiode, a photodiode array, and a photomultiplier tube.

13. The method of claim 1, wherein said at least one or more assay sites are separately addressable assay sites.

14. The method of claim 1, wherein said at least one or more assay sites are associated with a physical form selected from the group consisting of a slide, a membrane, a filter, a test tube, a vial, a microtiter plate, a microarray, a small volume device, and a gel.

15. The method of claim 1, wherein said at least one or more assay sites are present in a sample selected from the group consisting of a tissue, a tissue section, a cell culture, a cell, a cell organelle, a chromosome preparation, and a chromosome.

16. The method of claim 1, further comprising, after step (c) repeating: applying at least one optical filter having an optical density that is different than the at least one optical filter in step (b) to provide a second reduced-intensity integrated scattered light signal that does not exceed the dynamic range of the sensor, said second reduced-intensity scattered light signal is from at least one of said at least one assay site that produced an integrated light scattering signal that exceeded the dynamic range of the sensor; and detecting a third set of integrated scattered light intensity signals from the light scattering particles at said one or more assay sites with the sensor, said third set comprising the second reduced-intensity integrated scattered light signals of the repeated step (c).

* * * * *